United States Patent
Despres et al.

(10) Patent No.: US 9,546,380 B2
(45) Date of Patent: Jan. 17, 2017

(54) MGMT-BASED METHOD FOR OBTAINING HIGH YIELDS OF RECOMBINANT PROTEIN EXPRESSION

(71) Applicant: INSTITUT PASTEUR, Paris (FR)

(72) Inventors: Philippe Despres, La Garenne-Colombes (FR); Sylvie Paulous, Sarcelles (FR); Elodie Crublet, L'Albenc (FR)

(73) Assignee: INSTITUT PASTEUR, Paris (FR)

( * ) Notice: Subject to any disclaimer, the term of this patent is extended or adjusted under 35 U.S.C. 154(b) by 0 days.

(21) Appl. No.: 14/811,079

(22) Filed: Jul. 28, 2015

(65) Prior Publication Data
US 2016/0017367 A1    Jan. 21, 2016

Related U.S. Application Data

(62) Division of application No. 13/824,476, filed as application No. PCT/EP2011/072387 on Dec. 9, 2011, now Pat. No. 9,109,219.

(60) Provisional application No. 61/505,694, filed on Jul. 8, 2011.

(30) Foreign Application Priority Data

Dec. 9, 2010 (EP) .................................... 10306389

(51) Int. Cl.
| | |
|---|---|
| *C12N 15/00* | (2006.01) |
| *C12N 9/96* | (2006.01) |
| *C12N 5/07* | (2010.01) |
| *C12N 15/85* | (2006.01) |
| *C12N 9/10* | (2006.01) |
| *C12N 15/62* | (2006.01) |

(52) U.S. Cl.
CPC ............. *C12N 15/85* (2013.01); *C12N 9/1007* (2013.01); *C12N 9/96* (2013.01); *C12N 15/625* (2013.01); *C12Y 201/01063* (2013.01); *C07K 2319/00* (2013.01); *C07K 2319/055* (2013.01); *C07K 2319/20* (2013.01); *C07K 2319/21* (2013.01); *C07K 2319/50* (2013.01)

(58) Field of Classification Search
CPC ...................... C07K 2319/00; C07K 2319/055; C07K 2319/21; C07K 2319/50; C07K 2319/20; C12N 9/1007; C12N 15/85; C12N 9/96; C12N 15/625; C12Y 201/01063
USPC ............ 435/455, 188, 320.1, 348, 360, 361, 362, 435/365.1
See application file for complete search history.

(56) References Cited

U.S. PATENT DOCUMENTS

| | | | |
|---|---|---|---|
| 6,252,048 B1 * | 6/2001 | Kelley ................ | C12N 9/1007 435/183 |
| 7,662,584 B2 | 2/2010 | Penttila et al. | |
| 7,846,722 B2 | 12/2010 | Williams et al. | |
| 9,109,219 B2 * | 8/2015 | Despres ............... | C12N 9/1007 |
| 2008/0220456 A1 | 9/2008 | Williams et al. | |
| 2010/0196889 A1 * | 8/2010 | Bankaitis-Davis .. | C12Q 1/6886 435/6.14 |
| 2011/0034368 A1 | 2/2011 | Carson et al. | |
| 2012/0009599 A1 | 1/2012 | Zwier et al. | |

FOREIGN PATENT DOCUMENTS

| | | |
|---|---|---|
| EP | 1 132 479 A1 | 9/2001 |
| WO | 2004/031404 A1 | 4/2004 |
| WO | 2006/114409 A1 | 11/2006 |
| WO | 2008/106551 A2 | 9/2008 |

OTHER PUBLICATIONS

Brecht et al., Snap-Tag(TM): Self-Labeling Protein tag for medium throughput and HTS assay formats, Poster P7016 Booth 345, Sep. 19, 2006, SBS 12th Annual Conference and Exhibition Advancing Drug Discovery: From Better Hits to Better Candidates Sep. 17-21, 2006, Seattle, WA, USA.
Brehin et al., Production and characterization of mouse monoclonal antibodies reactive to Chikungunya envelope E2 glycoprotein, Virology 371 (2008) 185-195.
Erhardt et al., Genome-wide analysis reveals a cell cycle—dependent mechanism controlling centromere propagation, J. Cell Biol. vol. 183 No. 5 805-818 (2008).
Johnsson K., Snap-tag Technologies: Novel Tools to Study Protein Function, NEB expressions, Dec. 1, 2008, pp. 1-8.
Juillerat et al., Directed Evolution of 06-Alkylguanine-DNA Alkyltransferase for Efficient Labeling of Fusion Proteins with Small Molecules In Vivo, Chemistry and Biology, Current Biology, vol. 10, 2003, pp. 316-317.
Keppler et al., Labeling of fusion proteins with synthetic fluorophores in live cells, Proceedings of the National Academy of Sciences of USA, vol. 101, No. 27, 2004, pp. 9955-9959.
Keppler et al., Labeling of fusion proteins of 06-alkylguanine-DNA alkyltransferase with small molecules in vivo and in vitro, Methods : A Companion to Methods in Enzymology, vol. 32, No. 4, 2004, pp. 437-444.
Wu et al., Expression of Human O6-Methylguanine-DNA Methyltransferase in Chineses Hamster Ovary Cells and Restoration of Cellular Resistance to Certain N-Nitrosos Compounds, Molecular Carcinogenesis 4: 482-488, 1991.
Barash et al., Human secretory signal peptide desciption by hidden Markov model and generation of a strong artificial signal peptide for secreted protein expression, BBRC 294: 835-842, 2002.

(Continued)

*Primary Examiner* — Ganapathirama Raghu
(74) *Attorney, Agent, or Firm* — Law Office of Salvatore Arrigo and Scott Lee, LLP

(57) ABSTRACT

The present invention relates to a novel enhancer of protein production in host cells. It discloses a vector for expressing recombinant proteins in these cells, comprising a nucleotide sequence encoding a) a secretion peptidic signal, b) a 6-methylguanine-DNA-methyltransferase enzyme (MGMT, EC 2.1.1.63), a mutant or a catalytic domain thereof, and c) a recombinant protein. Said MGMT enzyme is preferably the so-called SNAP protein.

22 Claims, 41 Drawing Sheets

(56) References Cited

OTHER PUBLICATIONS

Figure 1:
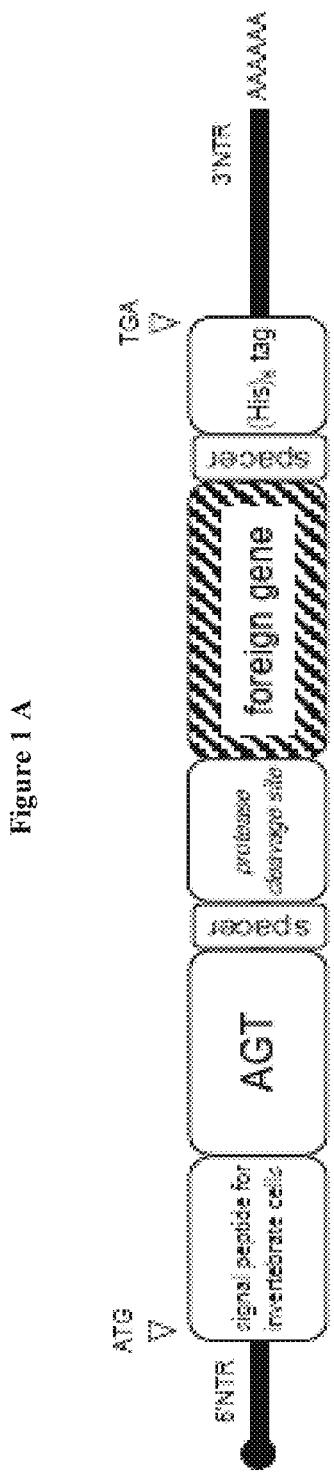

Broun et al., Catalytic plasticity of fatty acid modification enzymes underlying chemical diversity of plant lipids. Science, 1998, vol. 282: 1315-1317.
Chica et al., Semi-rational approaches to engineering enzyme activity: combining the benefits of directed evolution and rational design. Curr. Opi. Biotechnol., 2005, vol. 16: 378-384.
Devos et al., Practical limits of function prediction. Proteins: Structure, Function, and Genetics. 2000, vol. 41: 98-107.
Kisselev L., Polypeptide release factors in prokaryotes and eukaryotes: same function, different structure, Structure, 2002, vol. 10: 8-9.
Lemos et al., Rabies virus glycoprotein expression in *Drosophila* S2 cells. I: Design of expression/selection vectors, subpopulations selection and influence of sodium butyrate and culture medium on protein expression. J. Biotechol., 2009, vol. 143: 103-110.
Schamabach et al., Vector design for expression of O-methylguanine-DNA-methyltransferase in hematopoietic cells. DNA Repair, 2007, vol. 7: 1187-1196.
Seffernick et al., Melamine deaminase and Atrazine chlorohydrolase: 98 percent identical but functionally different. J. Bacteriol., 2001, vol. 183 (8): 2405-2410.
Sen et al., Developments in directed evolution for improving enzyme functions. Appl. Biochem. Biotechnol., 2007, vol. 143: 212-223.
Whisstock et al., Prediction of protein function from protein sequence. Q. Rev. Biophysics., 2003, vol. 36 (3): 307-340.
Witkowski et al., Conversion of b-ketoacyl synthase to a Malonyl Decarboxylase by replacement of the active cysteine with glutamine. Biochemistry, 1999, vol. 38: 11643-11650.

\* cited by examiner

```
g tat ctg ctg cag ttc tcc cgg gtc atc aac cca aac ctc cga ggt aga aca aaa gag gag gtt gct gca acg ttc acg cag cca atg aat gca gtg  < 1200
  Y   L   L   Q   F   S   R   V   I   N   P   N   L   R   G   R   T   K   E   E   V   A   A   T   F   T   Q   P   M   N   A   A   V
                      1110                    1120                    1130                    1140                    1150                    1160                    1170                    1180                    1190 aat agc aac ttt ata agc cat gag aag agg aag gaa ttc ttg aaa gcc ttt gga gat tcc aat ggg tca gct gtc gca gcc g  < 1300
  N   S   N   F   I   S   H   E   K   R   K   E   F   L   K   A   F   G   D   S   N   G   K   P   S   A   A   V   M   A   A   A
                      1210                    1220                    1230                    1240                    1250                    1260                    1270                    1280                    1290 ct cag gct tac aag aca gca gcc ggt gga agt cat cat cat cat cat cat tgaccggt  < 1361
  Q   A   Y   K   T   A   A   G   G   S   H   H   H   H   H   H   *
                      1310                    1320                    1330                    1340                    1350
```

```
c acg gcc aac gct aag gtc ctg att gaa ttg gaa cca ccc ttt gga gac tca tac ata gtg ggc aga gga gaa caa gaa att aat cac cat tgg cac  < 1200
    T  A  N  A  K  V  L  I  E  L  E  P  P  F  G  D  S  Y  I  V  G  R  G  E  Q  E  I  N  H  H  W  H
   1110            1120           1130          1140           1150          1160          1170           1180          1190 aag tct gga agc agc att ggc aaa gcc ttt aca acc ctc aaa aca acc gct cta gga gcc gct cta gga gac aca gct cta gga gac aca gct ctg gac aca gct cta gga tca gtt g  < 1300
 K  S  G  S  S  I  G  K  A  F  T  T  L  K  T  T  A  L  G  A  A  L  G  D  T  A  L  G  D  T  A  V
   1210           1220           1230          1240          1250          1260           1270          1280          1290 ga ggg gtg ttc acc tca gtt cgg aag gct gtg ccg ctg cac gag atc ttt aag ctg ctg ggg aaa atg tgc gaa gac atg aag cgc acc ctg gat agc cct ctg ggc aa   < 1400
   G  V  F  T  S  V  R  K  A  V  P  L  H  E  I  F  K  L  L  G  K  M  C  E  D  M  K  R  T  L  D  S  P  L  G  K
      1310           1320          1330          1340           1350          1360          1370          1380           1390 g ctg gaa ctg tct ggg tgc gaa gag cca gag atg cag gag agc ttc cag gag atc aag ctg ctg ggg aca tct gcc gcc gga gca gat gcc gtg gaa gag ttc cct gtc gag gcc atc gag cct gtg ccg ctg cac gag atc  < 1500
    L  E  L  S  G  C  E  E  Q  G  L  H  M  Q  E  S  F  I  K  L  L  G  K  G  T  S  A  A  D  A  V  E  E  F  P  V  E  A  I  E
      1410           1420           1430          1440          1450          1460          1470          1480          1490 gtg ctg ggc gga cca gag cca ctg atg cag gag gag cca gag cca ctg atg cag gag cgc cag gag atc ttc ctc gag gag gag gtg aag ttc ggt gag gag ttc cct gtg ccg ctg cac gag atc ttc cgg ctg c < 1600
 V  L  G  G  P  E  P  L  M  Q  E  E  P  E  A  I  E  R  Q  E  I  F  L  E  E  V  K  F  G  E  E  F  P  V  P  A  L  H
   1510          1520           1530          1540          1550           1560          1570          1580          1590 ac cac cca gag ttc cag cag gag agc ttc acc cgg cag gtg ctc tgg aaa cgg ctg aaa gtg ctg tgg aaa cgg ctg aaa gtg aag ttc ggt gag gag ttc cct gtc gag gcc atc ctg ccc att ctg ccc gtg ccg ctg cac gag atc < 1700
 H  H  P  E  F  Q  Q  E  S  F  T  R  Q  V  L  W  K  R  L  K  V  V  K  F  G  E  E  V  I  S  Y  Q  Q  L  H
   1610           1620          1630          1640           1650          1660          1670          1680          1690 c ggc ctg gcc aat ccc gcc gcc acc acc gcc gcc gtg aag acc aag aca gag cgc acc ctg gat cct ctg gga cat cat gct cta ctg gag cac gag cca cta cag gac tga tga gcc aag cct gtc gag cct gct gcc aag < 1800
    A  L  A  N  P  A  A  T  T  A  L  S  G  N  P  V  P  I  L  I  P  C  H  R  V  V  S  G  G  P  L  A  A  L  A
      1710          1720          1730           1740           1750          1760           1770          1780          1790 tct gcc ggc gcc gcc ggg tac gag ggg gtg ctc gcc gtg aaa gag tgg ctg cta gca cac gag tgg ctg ttg gcc aag cct gtc gcc tgt gcc tgg aag cct gtc gag gcc aag cct ctg cca gag cct gga g < 1900
 S  A  V  G  G  Y  E  G  V  L  A  V  K  E  W  L  L  A  H  E  G  H  R  L  G  K  P  G  L  G  P  A  G
   1810          1820          1830          1840          1850          1860          1870          1880          1890 gt ata ggc gcg ggg tcc ctg gag cat cat cat cat cat tga tga cgg gcc c
    I  G  A  P  G  S  L  E  H  H  H  H  H  H  *  *
   1910           1920          1930          1940          1950
```

Figure 3 B

WN.sE-SNAP

Cd²⁺ 10 days

MW  + −

100kDa
70kDa

Antibody to hexa-His$_{tag}$

Figure 4B

Figure 4:
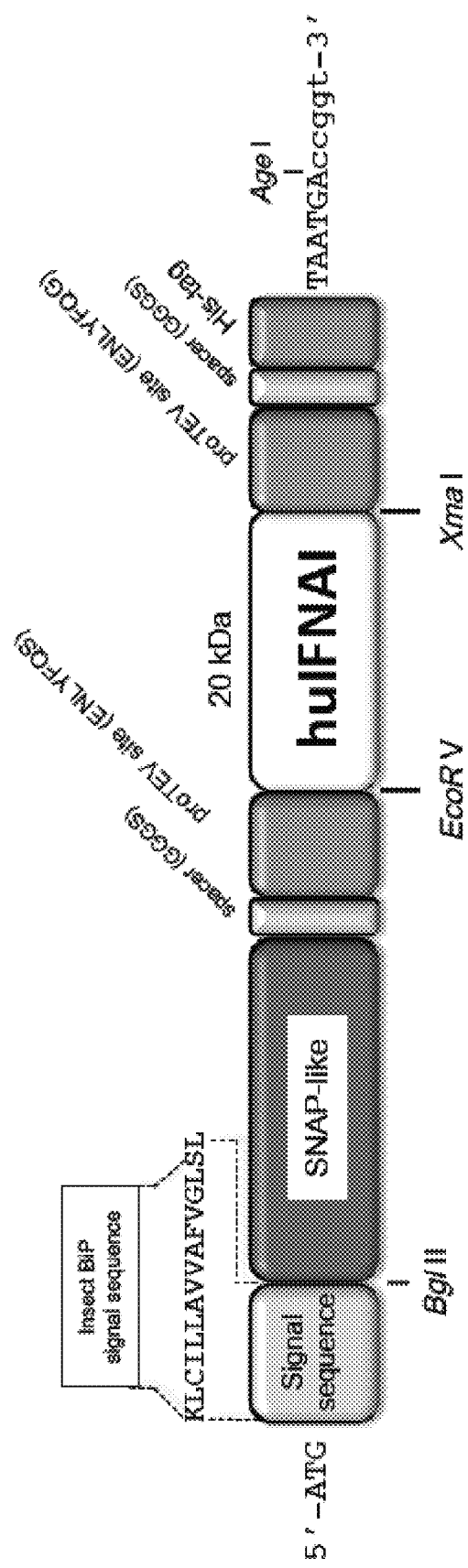
Figure 4D:
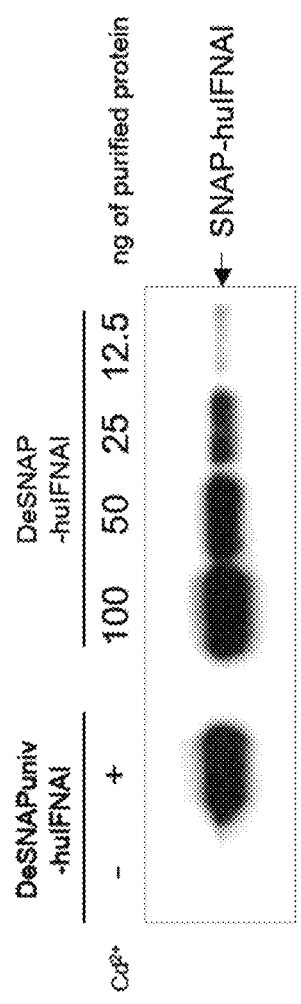
Figure 4:
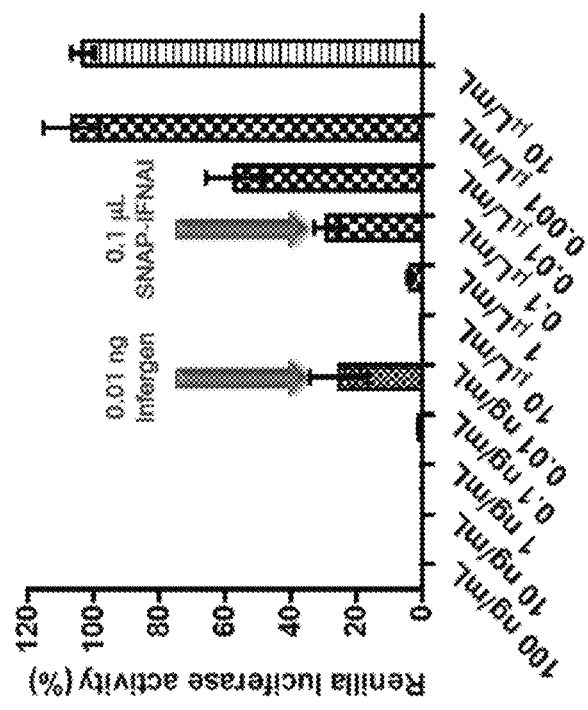

Figure 4B (continued)

```
gag gac ctc cta gac aaa ttc tgc acc gaa ctc tac cag cag ctg aat gac ttg gaa gcc tgt gtg atg cag gag agg gtg gga gaa act ccc ctg a  < 1000
 E   D   L   L   D   K   F   C   T   E   L   Y   Q   Q   L   N   D   L   E   A   C   V   M   Q   E   R   V   G   E   T   P   L   M
        910                 920                 930                 940                 950                 960                 970                 980                 990 tg aat gcc gac atc tcc att ctg gct gtg aag tac ttc cga aga atc act ctc tat ctg aca gag aag aaa tac agc cct tgt gcc tgg gag gtt gtc ag  < 1100
 N   A   D   I   S   I   L   A   V   K   Y   F   R   R   I   T   L   Y   L   T   E   K   K   Y   S   P   C   A   W   E   V   V   R
        1010                1020                1030                1040                1050                1060                1070                1080                1090 a gca gaa atc atg aga tcc ctc tct tta tca aca aca ttg caa gaa aga tta agg agg ggc aag tgg ggt gga agt cat cat cat cat cat cat  < 1200
 A   E   I   M   R   S   L   S   L   S   T   N   L   Q   E   R   L   R   R   K   E   G   K   W   G   G   S   H   H   H   H   H   H
        1110                1120                1130                1140                1150                1160                1170                1180                1190

AgeI
    |
cat tga ccg gt  < 1211
 H   *
```

Figure 4 C

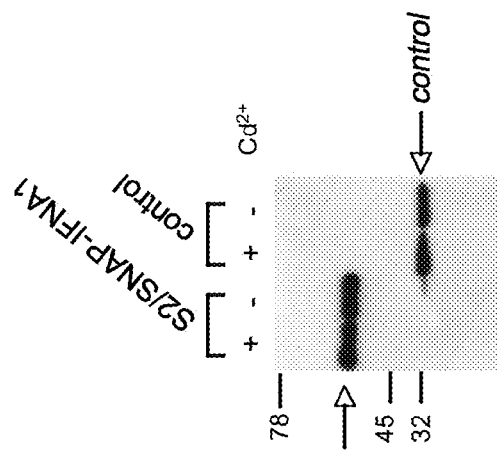

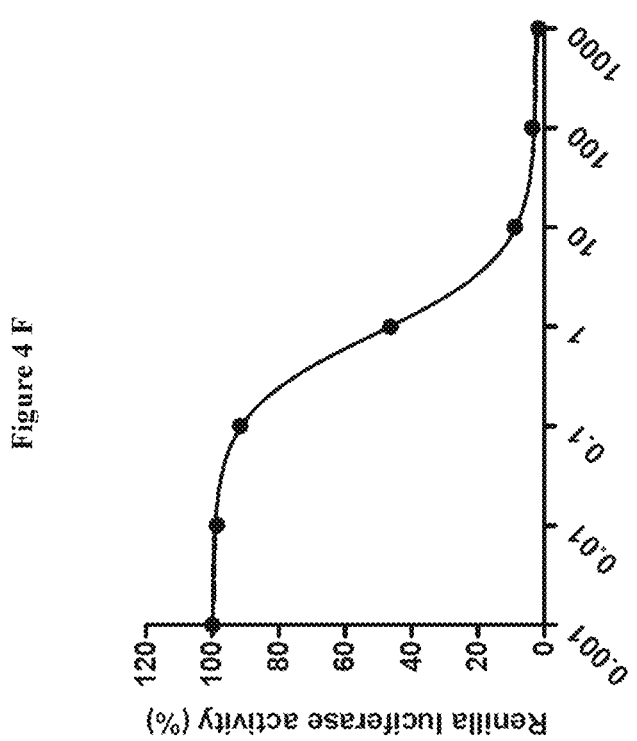

```
>ArsI
                                                        EcoNI
                    HpyCH4IV                BstEII           PvuI      XmaI
                    TaiI     PfoI           <NgoAVIII        <ApyPI   SmaI
G  D  S  G  G  P  L  V  C  G  R  V  L  A  G  V  L  S  F  S  S  R  V  C  T  D  I  F  K  P  P  V
gat ... (sequence) ... < 1300
1210   1220   1230   1240   1250   1260   1270   1280   1290
                                                                        <MboII
                                                                                    His-tag
                                                              ccg ggc ggt gga agt cat cat cat cat cat cat cat tga ccg gt < 1400
A  T  A  V  A  P  Y  V  S  W  I  R  K  V  T  G  R  S  A  P  G  G  G  S  H  H  H  H  H  H  *
1310   1320   1330   1340   1350   1360   1370   1380   1390
```

Figure 7:
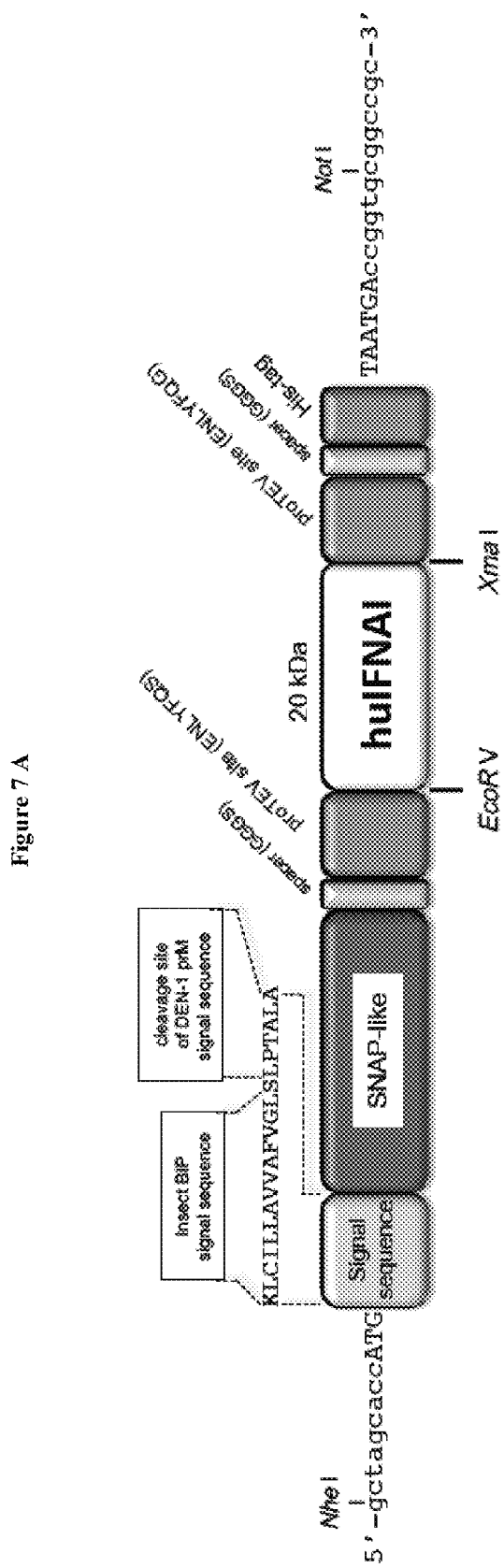
Figure 7:
Figure 7:
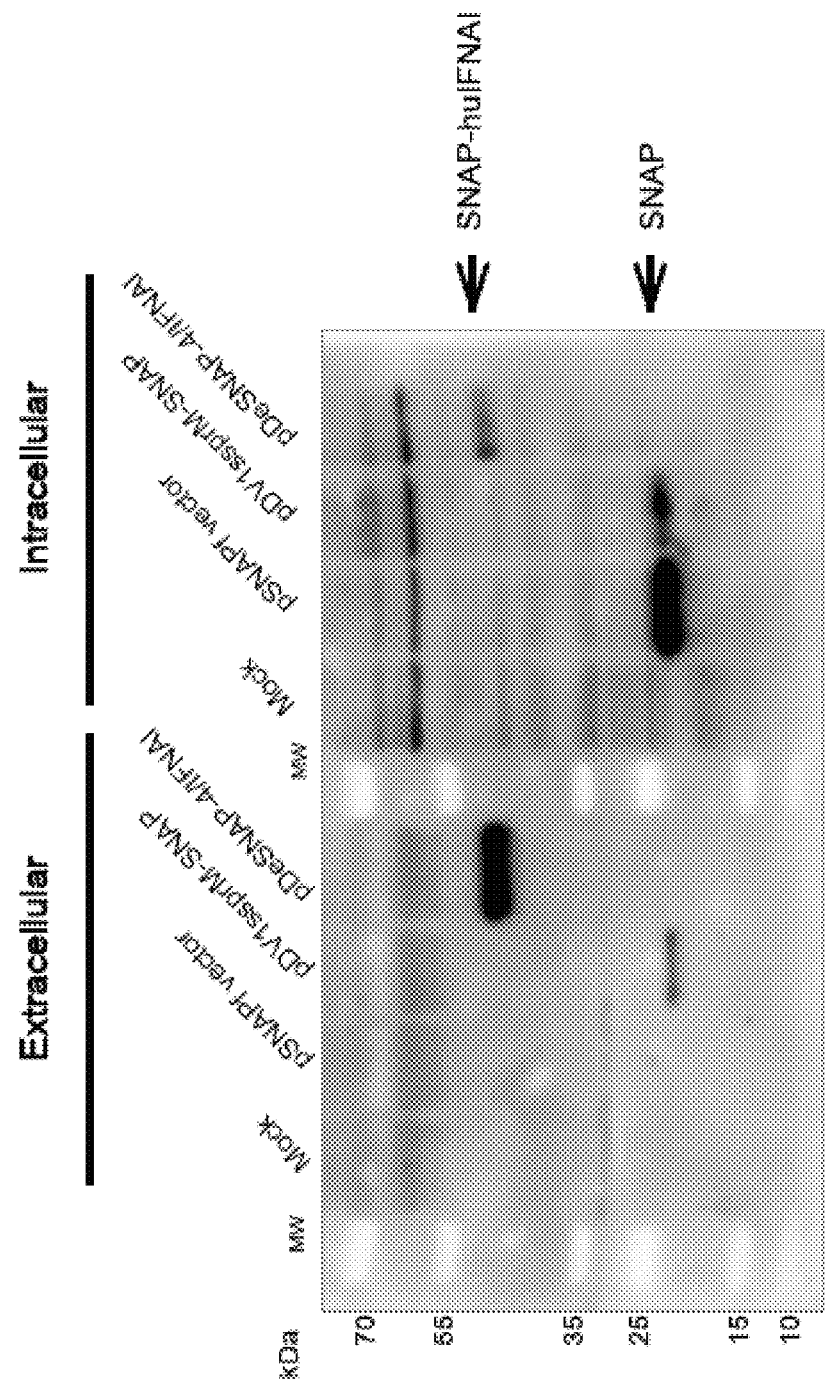

Figure 7 B (continued)

```
                >RleAI
                <BsmAI
                <BsaI
                  |
gt gat ctc cct gag acc cac agc ctg gat aac agg agg acc ttg atg ctc ctg gca caa atg agc aga atc tct cct tcc tcc tgt ctg atg gac aga ca <  800
   D   L   P   E   T   H   S   L   D   N   R   R   T   L   M   L   L   A   Q   M   S   R   I   S   P   S   S   C   L   M   D   R   H
   710                     720                 730                 740                 750                 760                 770                 780                 790
                                                                        <BsmI
                                                                          |
t gac ttt gga ttt ccc cag gag gag ttt gat ggc aac cag ttc cag aag gct cca gcc atc tct gtc ctc cat gag ctc atc cag cag att ttc aac ctc <  900
   D   F   G   F   P   Q   E   E   F   D   G   N   Q   F   Q   K   A   P   A   I   S   V   L   H   E   L   I   Q   Q   I   F   N   L
    810                 820                 830                 840                 850                 860                 870                 880                 890
                <Tth111I
                  |
ttt acc aca aaa gat tca tct gct gct tgg gat gag gac cta gac aaa ttc tgc acc gaa ctc tac cag cag ctg aat gac ttg gaa gcc tgt gtg a <  1000
   F   T   T   K   D   S   S   A   A   W   D   E   D   L   D   K   F   C   T   E   L   Y   Q   Q   L   N   D   L   E   A   C   V   M
    910                 920                 930                 940                 950                 960                 970                 980                 990
                                           >BsmI                XmnI
                                             |                  >FalI
                                                                  |
tg cag gag agg gtg gga gaa act ccc ctg atg aat gcg gac tcc atc ttg gct gtg aaa aag tac ttc cga aga atc act tat ctc tta aca gag aa < 1100
   Q   E   E   R   V   G   E   T   P   L   M   N   A   D   S   I   L   A   V   K   K   Y   F   R   R   I   T   Y   L   L   T   E   K
   1010                1020                1030                1040                1050                1060                1070                1080                1090
                                                                                                                              XmaI
                                                                                                                              AvaI
                                                                                                                              SmaI
                                                                                                                              Nli3877I
                                                                                                                                |
g aaa tac agc cct tgc gcc tgg gag gtt gtc aga gca gaa atc atg aga tcc ctc tct tta tca aca gaa aga ttg caa gag aga tta agg aag ggc < 1200
   K   Y   S   P   C   A   W   E   V   V   R   A   E   I   M   R   S   L   S   L   S   T   N   L   Q   E   R   L   R   R   K   E   G
   1110                1120                1130                1140                1150                1160                1170                1180                1190
            PspOMI                                                                              EagI
            ApaI      >CdpI                                                          AgeI      NotI        HindIII
              |         |                                                              |         |            |
ccg ggA GAG AAT CTA TAT TTT CAA GGG CCC GGA GGT AGT CAC CAT CAC CAT CAC TAA TGA CCG GTG CGG CCG CAA GCT T < 1285
 P   G   E   N   L   Y   F   Q   G   P   G   G   S   H   H   H   H   H   H   *   *
              1210               1220               1230                1240                1250                1260
```

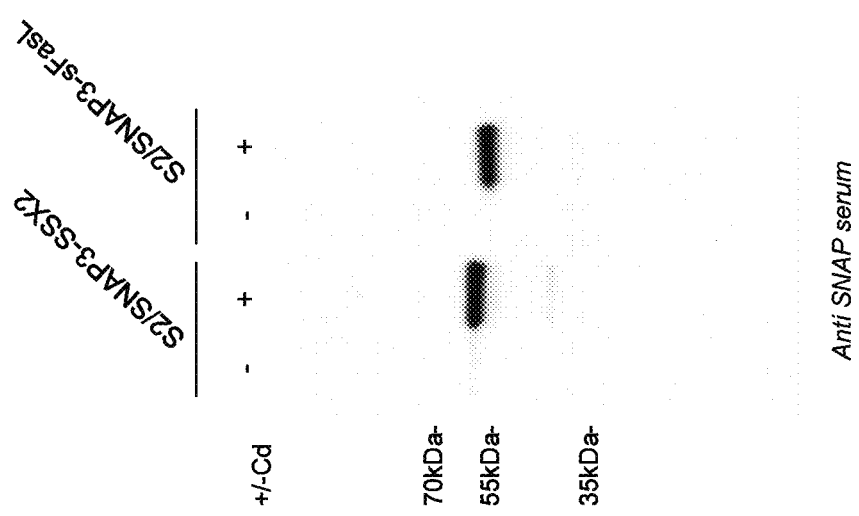

Figure 12:
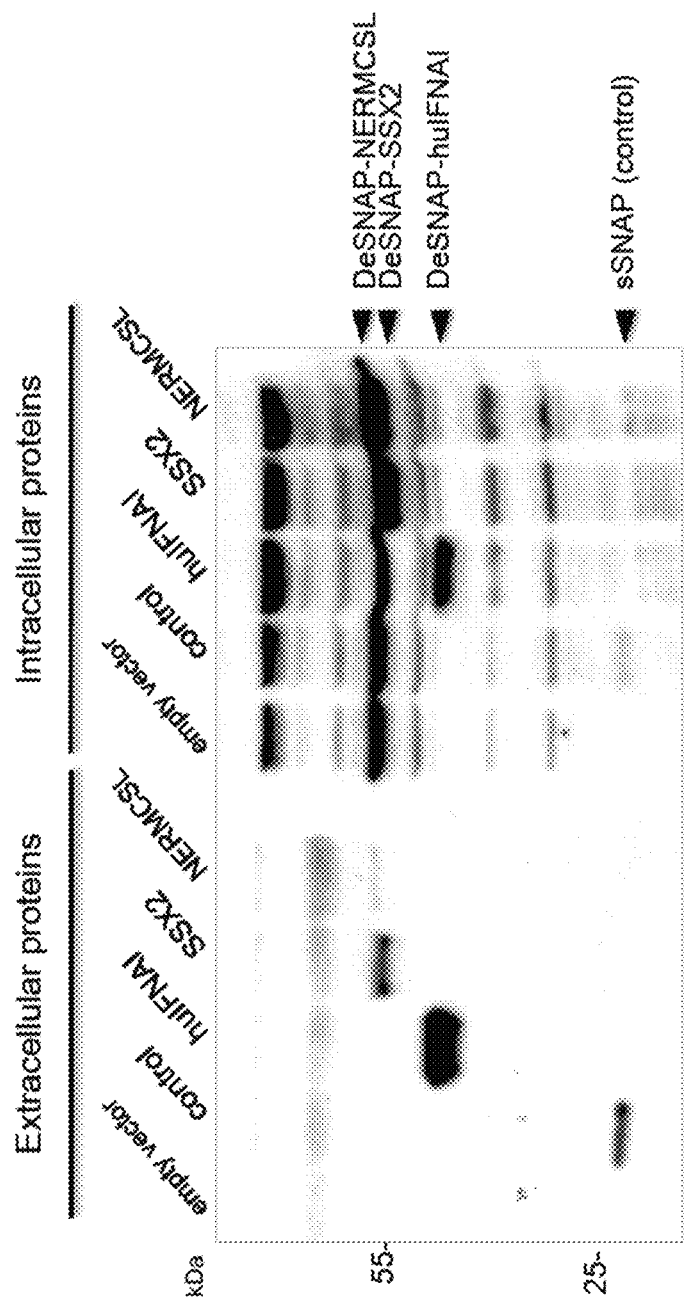

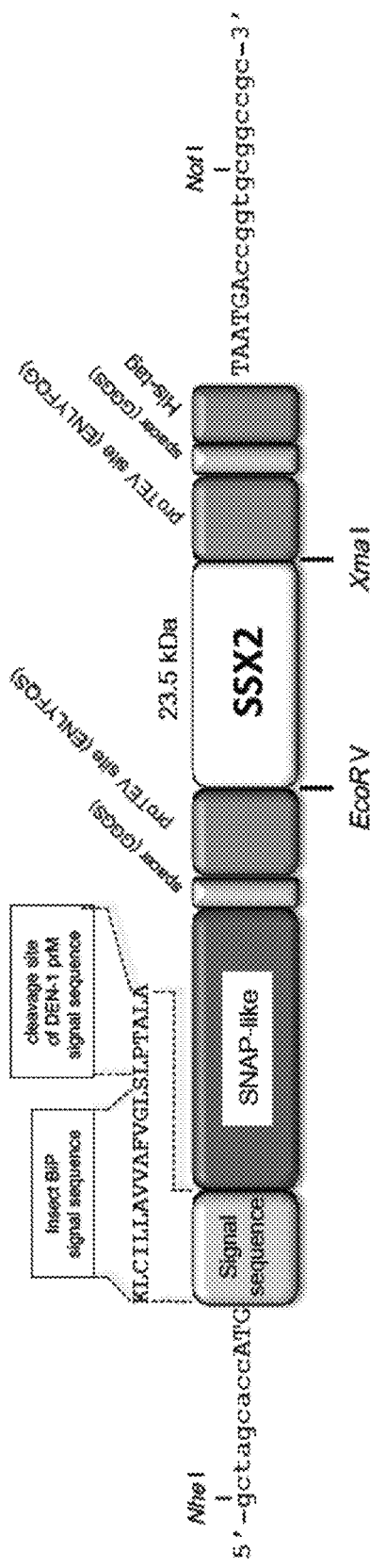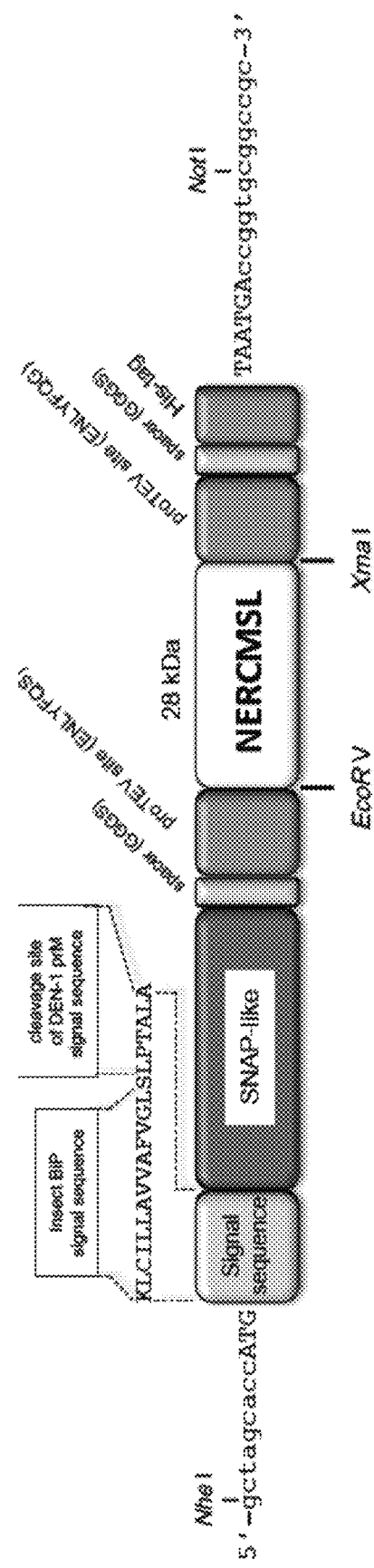
Figure 12 A
Figure 12 B

Figure 13:
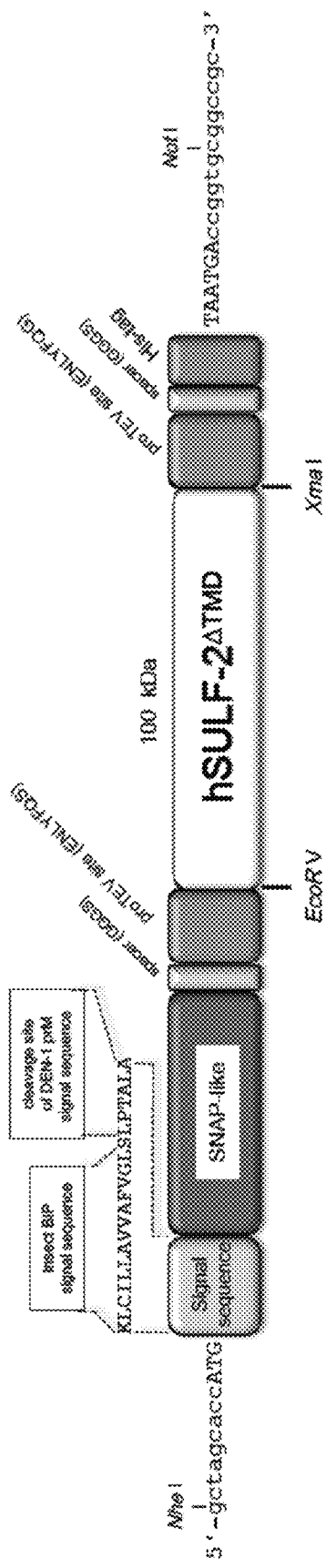
Figure 13:
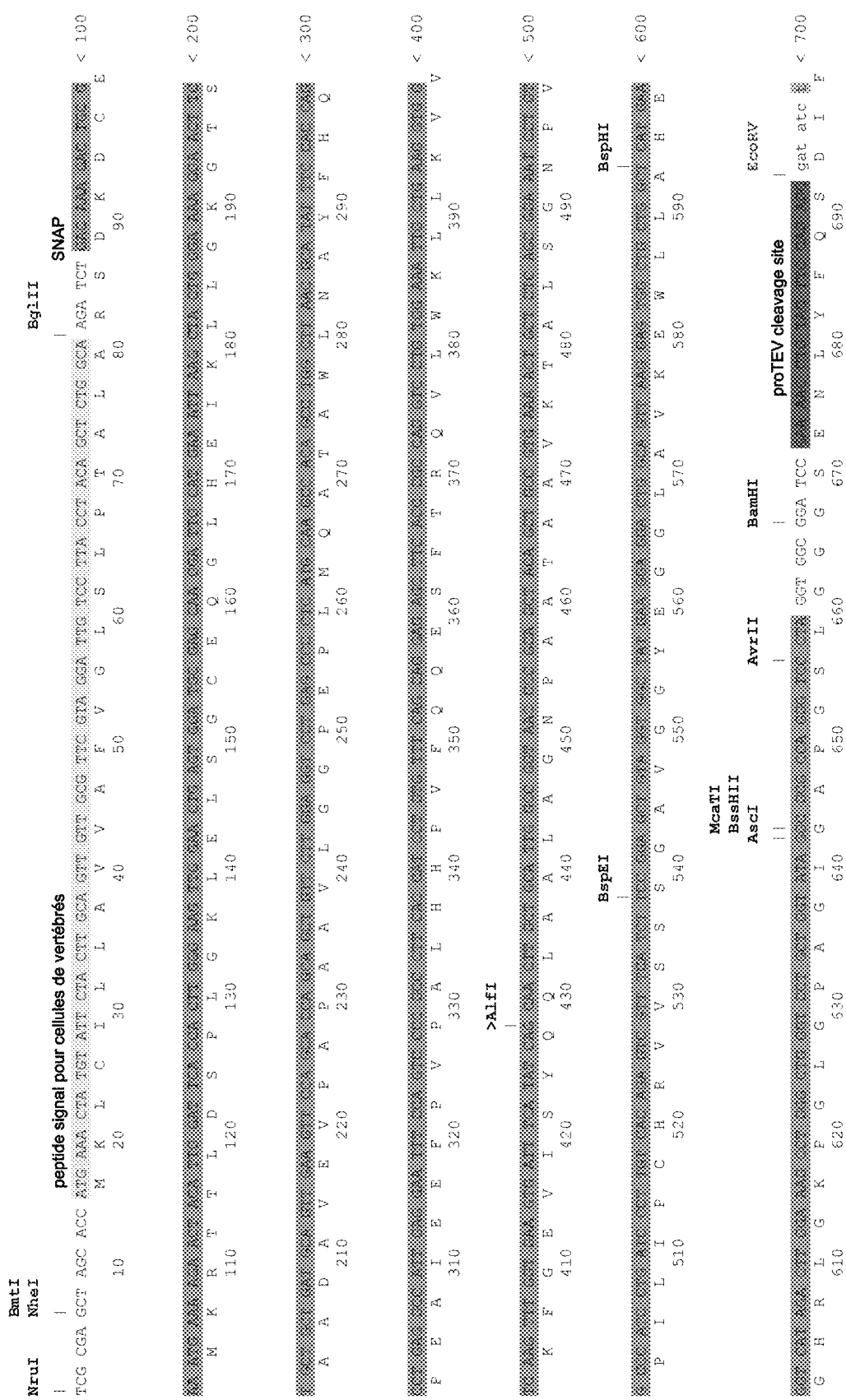
Figure 13:
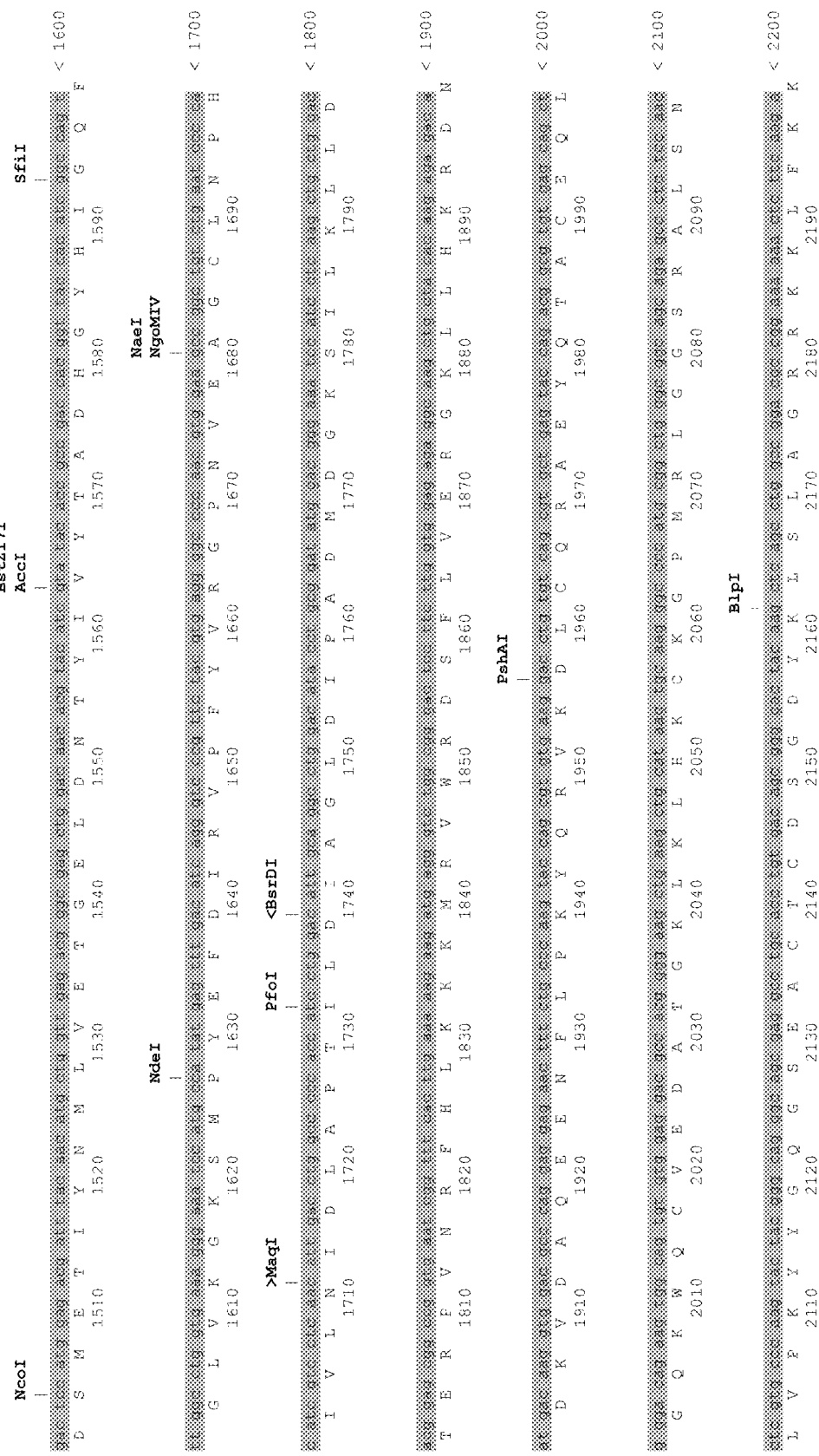
Figure 13:
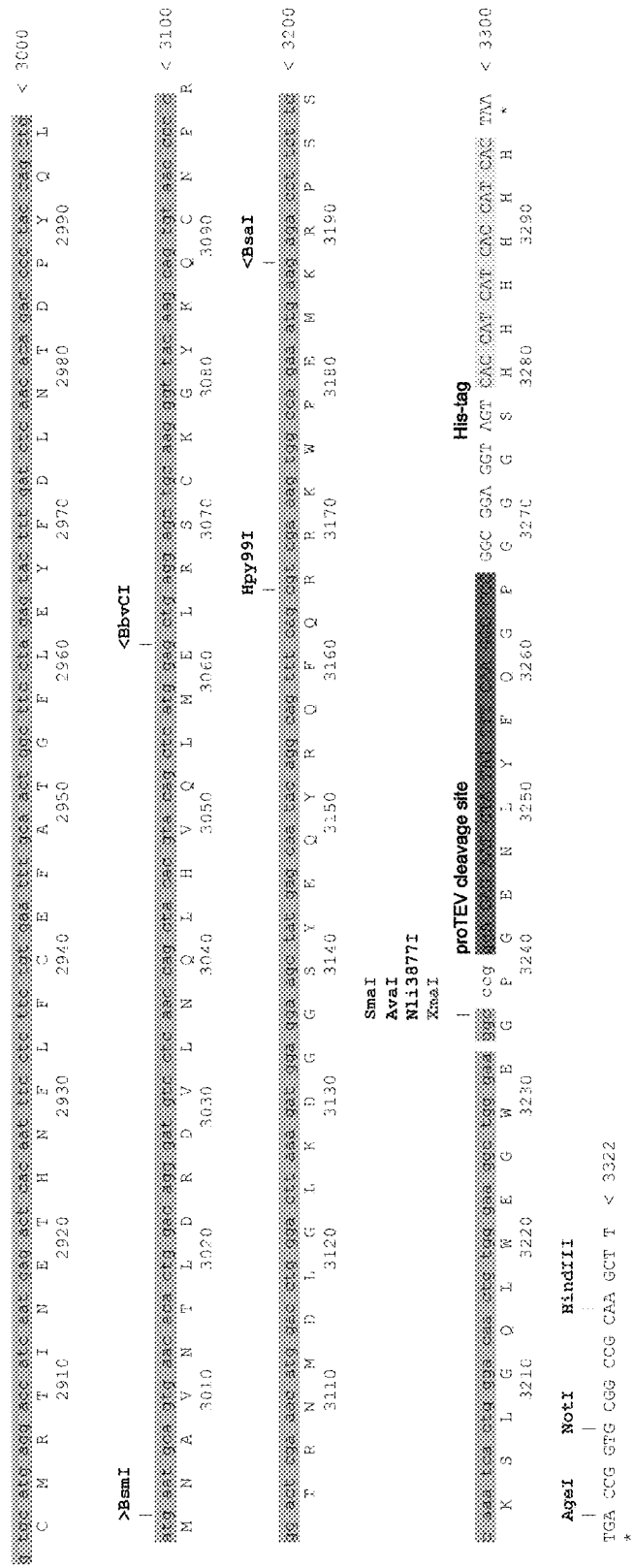

Figure 13 B (continued)

hSULF2

L S H H R L K G R F Q R D R R N I R P N I L V L F D D Q D V E L
710        720        730        740        750        760        770        780        790        <800
<AarI

G S M Q V M N K T R R I M E Q G G A H F I N A F V T P M C C P S
810        820        830        840        850        860        870        880        890        <900
                                                                              >PpiI
                                                                              >BpiI

R S S I L T G K K Y V H N H N T Y T N N E N C S S P S W Q A Q H E S R
910        920        930        940        950        960        970        980        990        <1000

T F A V Y L N S T G Y R T A F F G K Y L N E Y N G S Y V F P G W K
1010       1020       1030       1040       1050       1060       1070       1080       1090       <1100
                         PsiI    DraIII

B W V G L L K N S R F Y N Y T L C R N G V K E K H G S D Y S K D Y
1110       1120       1130       1140       1150       1160       1170       1180       1190       <1200
                                        >BmgBI

L T D L I T N D S V S F F R T S K K K M Y P H R P V L M V I S H A A P
1210       1220       1230       1240       1250       1260       1270       1280       1290       <1300
     SspI                                                              >NmeAIII

H G P E D S A P Q Y S R L F P N A S Q H I T P S Y N Y A P N P D K
1310       1320       1330       1340       1350       1360       1370       1380       1390       <1400
                                       EcoRI                               AfeI

H W I M R Y T G P M K P I H M E F T N M L Q R K K R L Q T L M S V D
1410       1420       1430       1440       1450       1460       1470       1480       1490       <1500

Figure 13 B (continued)

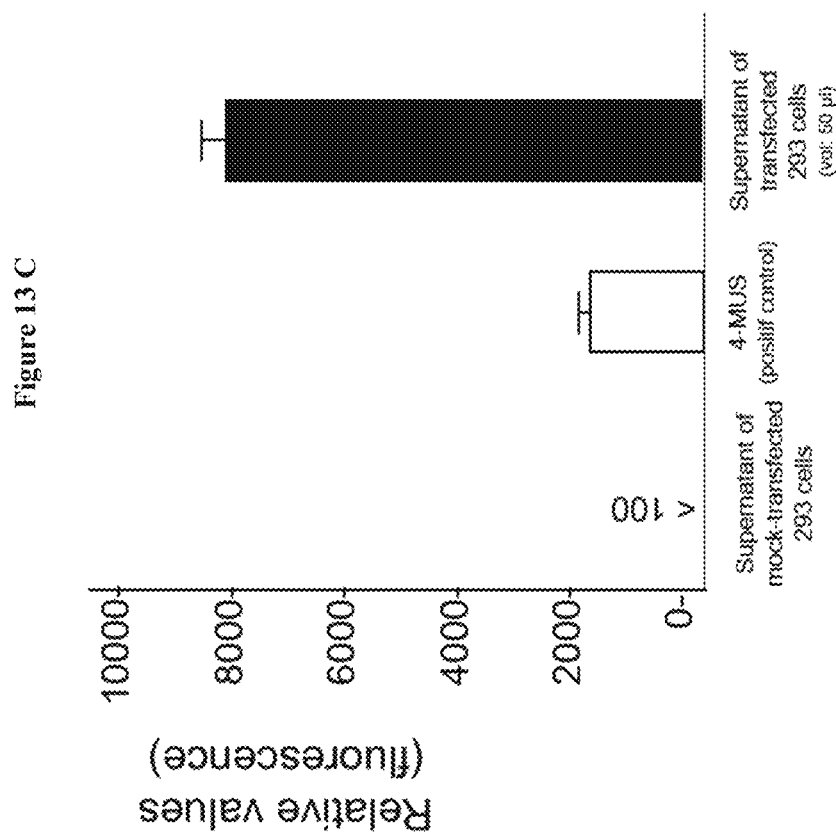

MGMT-BASED METHOD FOR OBTAINING HIGH YIELDS OF RECOMBINANT PROTEIN EXPRESSION

This application is a divisional of U.S. Ser. No. 13/824,476 (now U.S. Pat. No. 9,109,219), which is the U.S. Natl. Stage of International Application PCT/EP2011/072387, filed Dec. 9, 2011, which claims the benefit of U.S. Provisional Appln. 61/505,694, filed Jul. 8, 2011, and European Appln. EP 10306389.7, filed Dec. 9, 2010, all of which are hereby incorporated by reference.

The present invention relates to the field of genetic engineering and molecular biology. In particular, the present invention relates to a novel enhancer of protein production in host cells. Furthermore, the present invention relates to vectors containing the DNA sequence encoding said enhancer protein and also their use for expressing recombinant proteins, such as industrial enzymes or proteins for pharmaceutical use including eukaryotic (e.g. mammalian, such as human) and viral proteins.

BACKGROUND OF THE INVENTION

Protein production systems, in which polypeptides or proteins of interest are produced in recombinant organisms or cells, are the backbone of commercial biotechnology.

The earliest systems, based on bacterial expression in hosts such as *E. coli*, have been joined by systems based on eukaryotic hosts, in particular mammalian cells in culture, insect cells both in culture and in the form of whole insects, and transgenic mammals such as sheep and goats.

Prokaryotic cell culture systems are easy to maintain and cheap to operate. However, prokaryotic cells are not capable of post-translational modification of eukaryotic proteins. Moreover, many proteins are incorrectly folded, requiring specific procedures to refold them, which adds to the cost of production.

Eukaryotic cell culture systems have been described for a number of applications. For example, mammalian cells are capable of post-translational modification, and generally produce proteins which are correctly folded and soluble. The chief disadvantages of mammalian cell systems include the requirement for specialised and expensive culture facilities, the risk of infection, which can lead to loss of the whole culture, and the risk of contaminating the end product with potentially hazardous mammalian proteins. Insect cells are alternatively used for polypeptide expression. The most widespread expression system used in insect cells is based on baculovirus vectors. A baculovirus expression vector is constructed by replacing the polyhedrin gene of baculovirus, which encodes a major structural protein of the baculovirus, with a heterologous gene, under the control of the strong native polyhedrin promoter. Cultured insect host cells are infected with the recombinant virus, and the protein produced thereby can be recovered from the cells themselves or from the culture medium if suitable secretion signals are employed.

Both systems, however, suffer from problems associated with reproducibility of recombinant protein expression level and quality, infection of the culture, and may require specialised culture facilities. Furthermore, baculovirus stocks, which for the production of certain proteins may have to be made under GMP conditions, are not always stable over time.

*Drosophila* cells, in particular *Drosophila melanogaster* S2 cells, for protein expression have been disclosed in U.S. Pat. No. 5,550,043, U.S. Pat. No. 5,681,713 and U.S. Pat. No. 5,705,359. In contrast to the Baculovirus system of the prior art, in which the protein of interest is provided only upon lysis of the infected insect cells, the method based on S2 cells provides a continuous cell expression system for heterologous proteins and therefore leads to higher expression levels.

Several other means have been suggested for enhancing the expression of heterologous protein in host cells: for example, U.S. Pat. No. 5,919,682 describes a method of overproducing functional nitric acid synthase in a prokaryote using a pCW vector under the control of tac promoter and co-expressing the protein with chaperons. Also, U.S. Pat. No. 4,758,512 relates to the production of host cells having specific mutations within their DNA sequences which cause the organism to exhibit a reduced capacity for degrading foreign products. These mutated host organisms can be used to increase yields of genetically engineered foreign proteins.

Vertebrate cells, in particular mammal cells, have also been widely used in the expression of recombinant proteins. The quantity of protein production over time from the cells growing in culture depends on a number of factors, such as, for example, cell density, cell cycle phase, cellular biosynthesis rates of the proteins, condition of the medium used to support cell viability and growth, and the longevity of the cells in culture (i.e., how long before they succumb to programmed cell death, or apoptosis). Various methods of improving the viability and lifespan of the cells in culture have been developed, together with methods of increasing productivity of a desired protein by, for example, controlling nutrients, cell density, oxygen and carbon dioxide content, lactate dehydrogenase, pH, osmolarity, catabolites, etc.

Other host cells can be used for producing heterologous recombinant proteins, notably plant cells and yeast cells.

Many pharmaceutical proteins of mammalian origin have been synthesized in plants. These range from blood products, such as human serum albumin for which there is an annual demand of more than 500 tonnes, to cytokines and other signalling molecules that are required in much smaller amounts. Most plant-derived proteins have been produced in transgenic tobacco and extracted directly from leaves. Generally, these proteins are produced at low levels, typically less than 0.1% of the total soluble protein. This low level of production probably reflects a combination of factors, with poor protein folding and stability among the most important. More recently, the tobacco chloroplast system has been used to express human proteins at much higher levels (MA JKC et al, 2004).

Yeast systems have been a staple for producing large amounts of proteins for industrial and biopharmaceutical use for many years. Yeast can be grown to very high cell mass densities in well-defined medium. Recombinant proteins in yeast can be over-expressed so the product is secreted from the cell and available for recovery in the fermentation solution. Proteins secreted by yeasts are heavily glycosylated at consensus glycosylation sites. Thus, expression of recombinant proteins in yeast systems historically has been confined to proteins where post-translations glycosylation patterns do not affect the function of proteins. Several yeast expression systems are used for recombinant protein expression, including *Sacharomyces, Scizosacchromyces pombe, Pichia pastoris* and *Hansanuela polymorpha*. Recently, a novel system with the capability of producing recombinant glycoproteins in yeast has emerged with glycosylation sequences similar to secreted human glycoproteins produced in mammalian cells. The glycosylation pathway of *Pichia pastoris* was modified by eliminating endogenous enzymes, which add high mannose chains to N-glycosylation intermediates. In addition, at least five active enzymes, involved in synthesizing humanized oligosaccharide chains, were specifically transferred into *P. pastoris*. The ability to produce large quantities of humanized glycoproteins in yeast offer advantages in that glycosylated structures could be highly uniform and easily purified. In addition, cross-contamination with mammalian viruses and other mammalian host glycoproteins may be eliminated by using fed-batch production in yeast with much shorter fermentation times than mammalian cells.

However, by using these systems, heterologous proteins are produced at approximately 1-2 mg/L in the supernatant of the cultured cells, what is quite low as compared to the goals of industrial production.

There is thus an urgent need of providing a system enabling to reach significantly higher level of heterologous protein expression.

The present invention answers this need and provides protein expression methods reaching a production level until 100 times higher than the existing means of protein production (that is, until 200 mg/L of proteins in the supernatant).

The present inventors have indeed demonstrated that the use of a nucleotide vector encoding a protein derived from the human 6-methylguanine-DNA-methyltransferase (hMGMT) protein, said hMGMT derived protein being linked, directly or not, with a protein of interest enhances the production of said protein of interest to a yield of 40 mg/L to 200 mg/L in average.

FIGURE LEGENDS

Figure 1B:
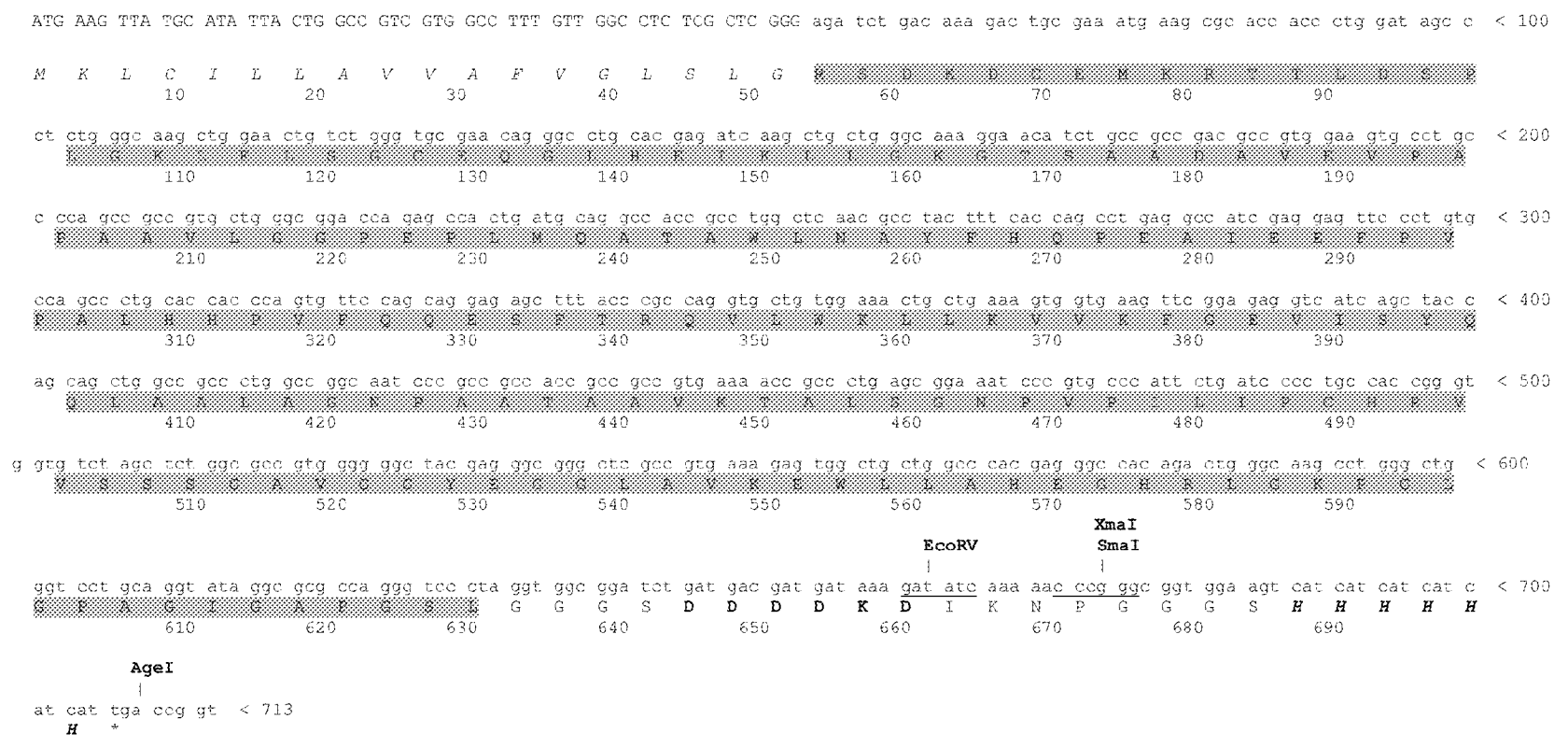

FIG. 1A-B discloses (A) a schematic view of a mRNA encoding a MGMT fusion protein sequence of the invention, containing, from 5' to 3', a signal peptide, the MGMT mRNA sequence, a spacer, a protease cleavage site, a recombinant protein gene (foreign gene), a spacer, and a label a (His6)-tag and (B) the DNA and amino acid sequences of the same part of the vector, comprising i) the insect ssBiP signal peptide (in italic), ii) the SNAP-encoding enhancer sequence (in grey), iii) a DNA spacer sequence, iv) the enterokinase site-encoding sequence (in bold), v) the cloning sites EcoRV/XmaI (underlined) and vi) the DNA encoding the Histag label (bold italic) (see also SEQ ID NO:5).

Figure 2A:
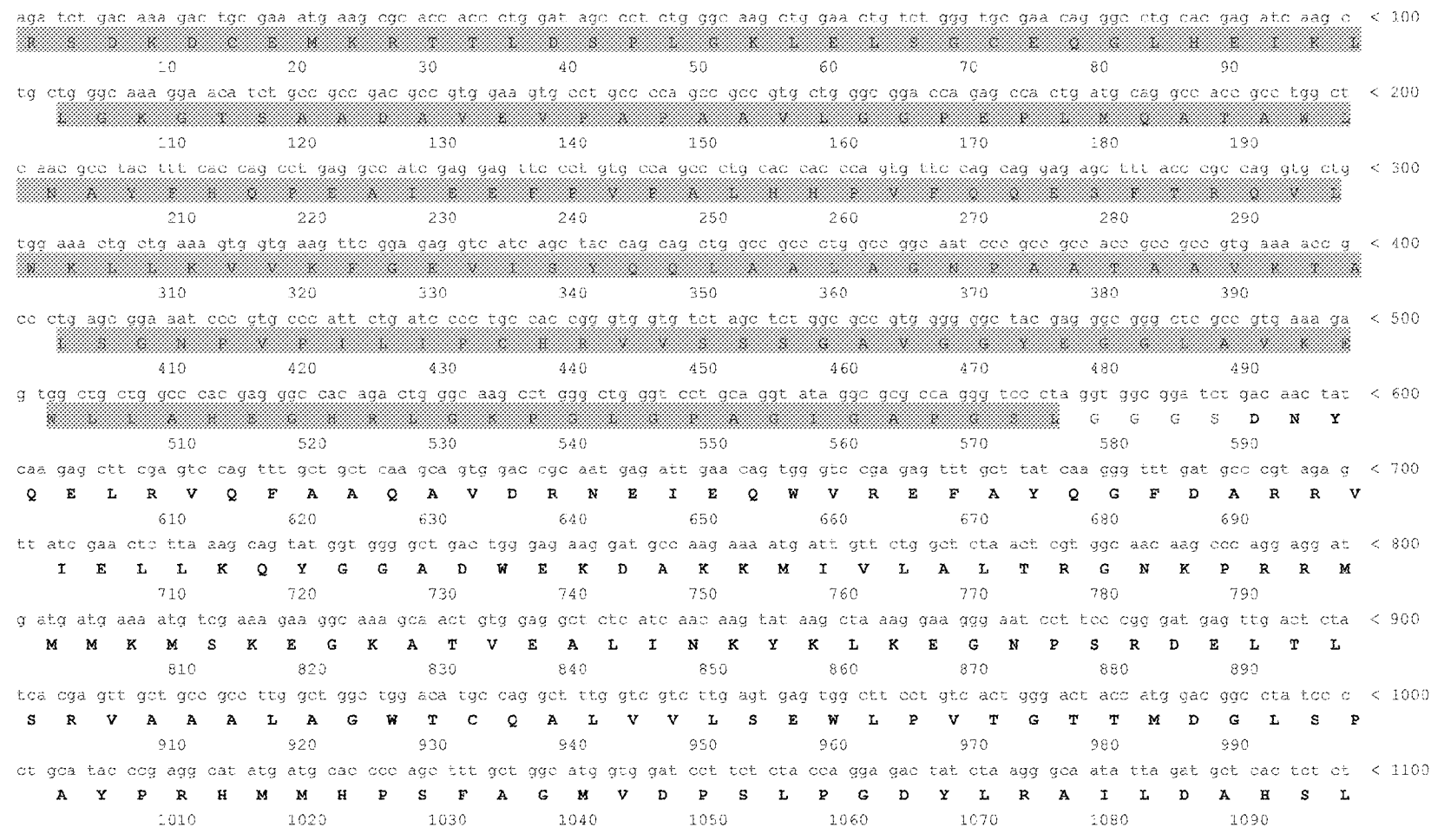
Figure 2C:
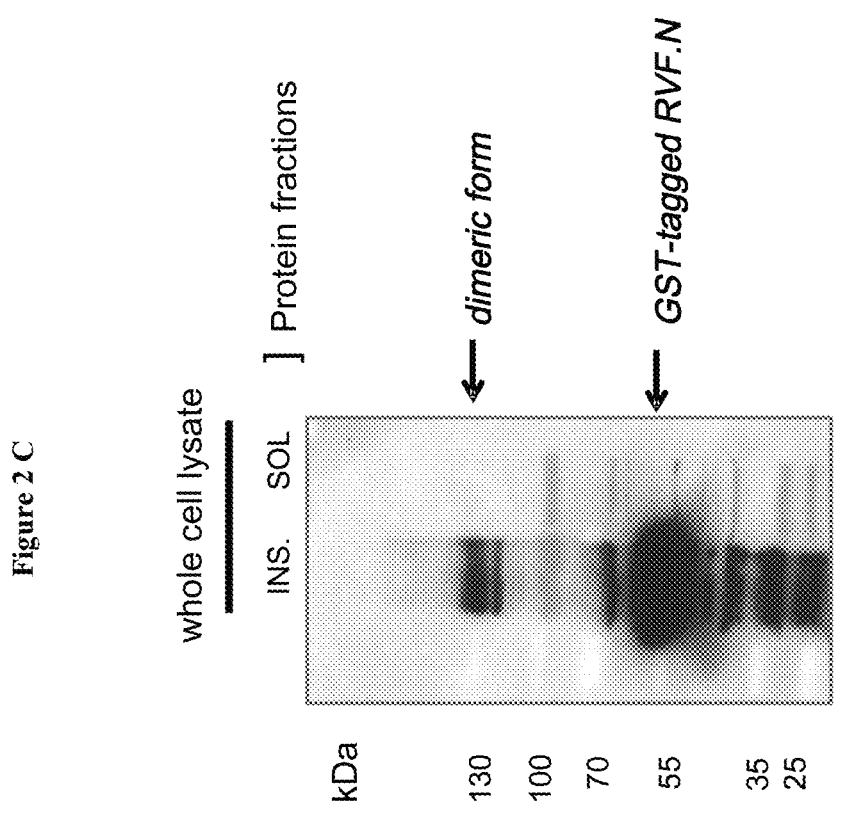
Figure 2D:
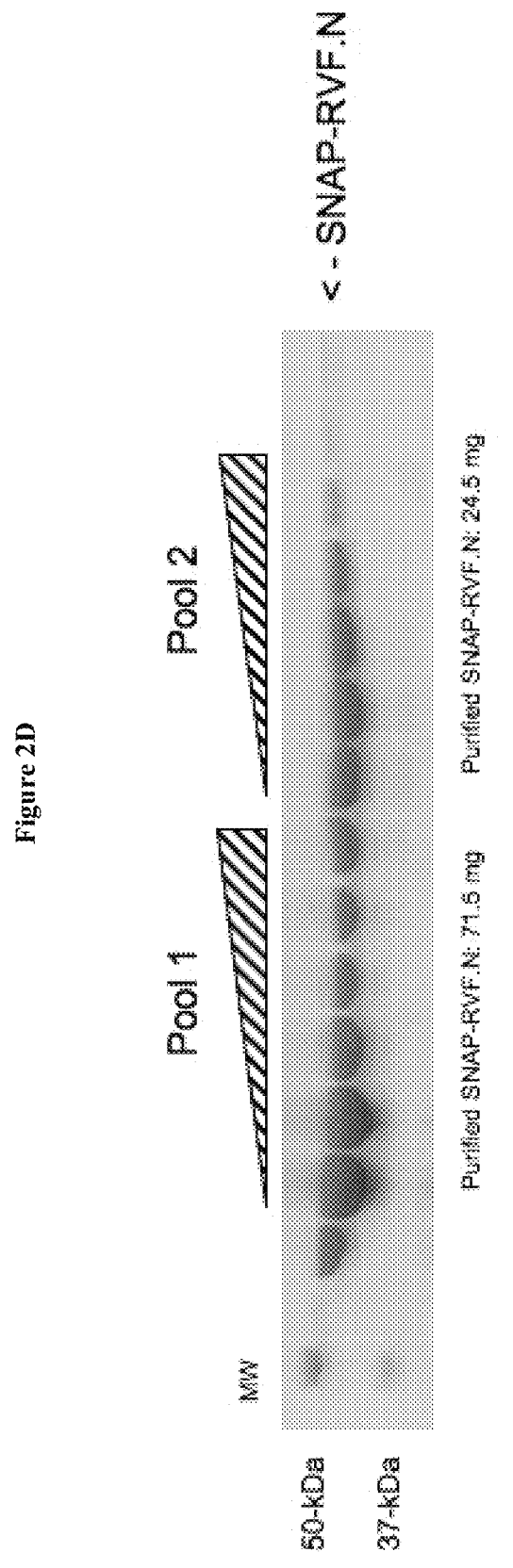

FIG. 2A-D discloses (A) the amino acid sequence of the fusion protein SNAP (in grey) and the N nucleoprotein of the Rift Valley Fiever virus (RVF.N, bold) linked to a Histag label, both proteins being separated by a spacer GGGS, (B) immunoblots assay on cell supernatant of S2 cells transfected by the DNA vector of SEQ ID NO:19 (SNAP-RVF) stimulated or not with cadmium for 10 days, using anti-His$_{tag}$ antibodies, and (C) an immunoblot assay performed with anti-His antibodies, on insoluble (INS) or soluble (SOL) protein fractions of *E. Coli* B21 lysates, said bacteria bearing a pET302/RVF.N+proTEV+GST plasmid. (D) an immunoblot assay showing the amount of SNAP-RVF.N in the successive fraction samples obtaining after a two-step purification of secreted chimeric protein SNAP-RVF.N from 10-days stimulated S2 cells, using Talon and Superdex 75 columns.

FIG. 3A-B discloses (A) the DNA and the amino acid sequences of the fusion protein SNAP (italic) and the soluble form of the envelop protein E from the West Nile virus (in grey), linked to a Histag label (bold), the proteins being separated by a spacer GGGS (SEQ ID NO:20) and (B) immunoblot assay with anti-His-tag antibodies, showing the secretion of the soluble form of the envelop protein E protein of the West-Nile virus in the supernatant of S2 cells transfected with the DNA vector of the invention encoding SNAP-WNsE (SEQ ID NO:20), and stimulated or nor with cadmium for 10 days.

FIG. 4A-F discloses (A) a scheme of the DNA cassette containing a BiP peptide signal, a MGMT-like encoding sequence (SNAP-like), two pro-TEV clivage sites at each side of the IFNα sequence (huIFNAI), and a Histag label, (B) the DNA (SEQ ID NO:5) and amino acid (SEQ ID NO:34) sequences of the fusion protein SNAP (in grey, preceded with an insect peptide signal in italic) and IFNα (in bold), followed by a Histag label (in bold italic), the SNAP and IFNα proteins being separated with the enterokinase cleavage site (underlined) and a spacer sequence GGGS. (C) Immunoblots assay using anti-Histag antibodies, to detect the expression of IFNα in the supernatant of S2 cells being transfected either by the vector of the invention encoding IFNα (S2/SNAP-IFN) or a control vector, stimulated or not with $Cd^{2+}$. (D) Immunoblots assay using anti-SNAP antibodies on 10 μL of supernatant of S2/DeSNAPuniv-IFNα cells induced for 10 days with Cadmium or not (E) Luciferase activity in HeLa cells infected with Chikungunya virus expressing a *Renilla luciferase*, said cells being treated with different doses of IFNα, either from commercial source (Intergen) or the IFNα produced by the method of the invention. (F) Luciferase activity in HeLa cells infected with Chikungunya virus expressing a *Renilla luciferase*, said cells being treated with different doses of the SNAP-IFNα protein obtained by the production process of the invention.

Figure 5:
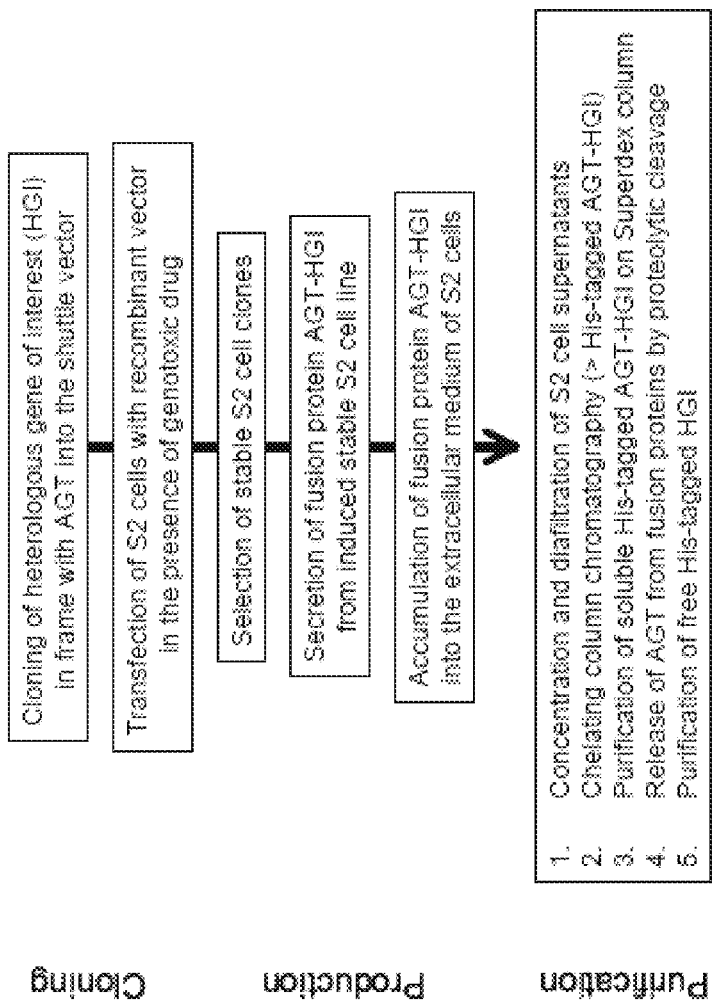

FIG. 5 represents the different steps of the recombinant protein production process of the invention.

FIG. 6A-C discloses (A) the DNA and amino acid sequences of the fusion protein SNAP (in grey, preceded with an insect peptide signal) and Granzyme M, followed by a Histag label, the SNAP and Granzyme M proteins being separated with the enterokinase cleavage site and a spacer sequence GGGS. (B) schematic view of the chimeric fusion protein SNAP-GrM, highlighting the three potential cleavage sites of the GrM protease in SNAP (C) Immunoblots assay using anti-SNAP or anti-Histag antibodies, to detect the expression of SNAP-GrM in the supernatant of S2 cells being transfected by the vector of the invention encoding GrM (S2/SNAP-GrM, SEQ ID NO:55).

FIG. 7A-C discloses (A) a scheme of the universal DNA cassette containing a BiP-like peptide signal, a MGMT encoding sequence, two pro-TEV cleavage sites at each side of the IFNα sequence (huIFNAI), and a Histag label, (B) the DNA (SEQ ID NO:57) and amino acid (SEQ ID NO:58) sequences of the fusion protein SNAP (in grey, preceded with an insect BiP-like peptide signal) and human IFNα1 (amino acids in bold), followed by a Histag label, the SNAP and IFNα proteins being separated with the proTEV cleavage site and a spacer sequence GGGS. (C) Immunoblot assay using anti-SNAP antibodies, to detect the expression of SNAP-IFNα in the supernatant of HeLa cells being transfected by either a vector encoding SNAP alone without peptide signal (pSNAPf vector), or a vector encoding SNAP alone, preceded with the peptide signal of the Dengue virus (pDV1ssprM-SNAP), or the vector of the invention encoding IFNα, comprising the DNA sequence as defined in (A) (pDeSNAP-4/SNAP-IFNA1, SEQ ID NO:57).

Figure 8A:
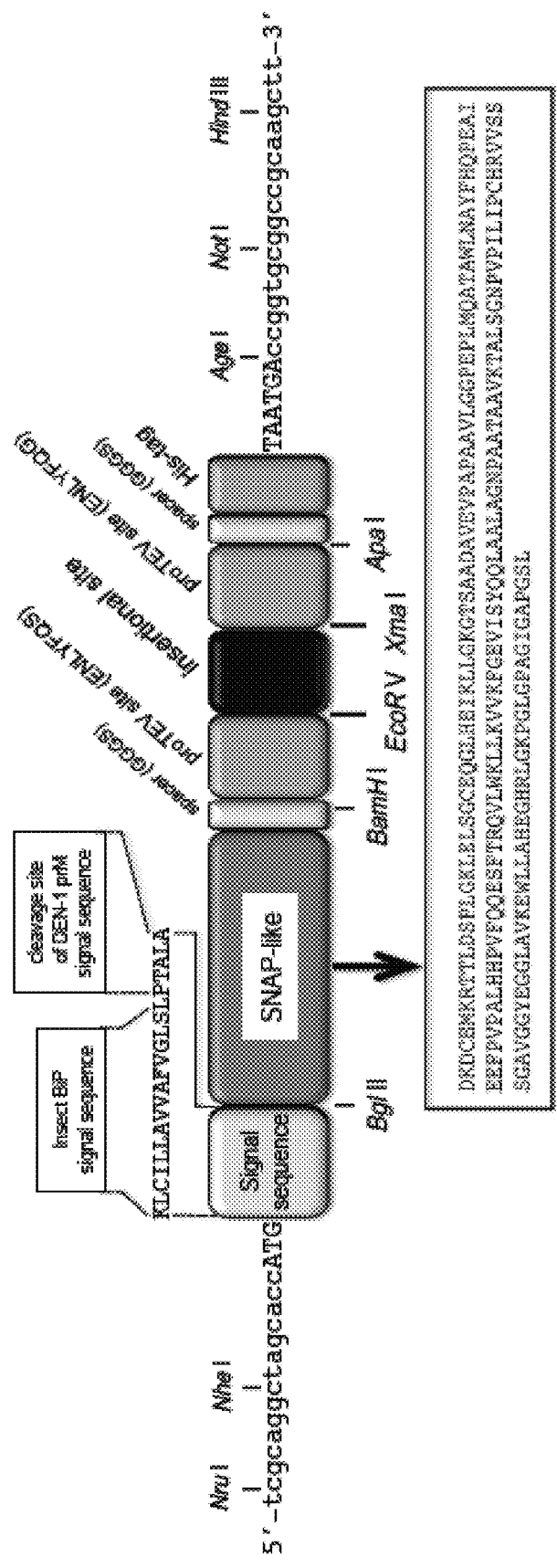

FIG. 8A-B discloses (A) the universal DNA cassette containing a BiP-like peptide signal, a SNAP encoding sequence, two pro-TEV clivage sites, a Histag label, four unique cloning sites BamH1, Eco RV, Xma I, and Apa I for cloning a gene of interest, and a spacer sequence GGGS (DeSNAP univ, SEQ ID NO:59 and 60). The unique sites at the 5' end Nhe I and 3' end Not I/Hind III are required for the sub-cloning step in mammalian expression vectors (e.g. plasmids pcDNA3 or pCI-neo), and the unique sites Bgl II at the 5' end and Age I at the 3' end are required for the subcloning step in non-vertebrate DES system. The scheme in (B) discloses the universal DNA cassette containing a BiP-like peptide signal, a MGMT encoding sequence, two pro-TEV clivage sites, a Histag label, four unique cloning sites BamH1, Eco RV, Xma I, and Apa I for cloning a gene of interest, and a spacer sequence GGGS (DeMGMT univ, SEQ ID NO:69 and 70).

Figure 9:
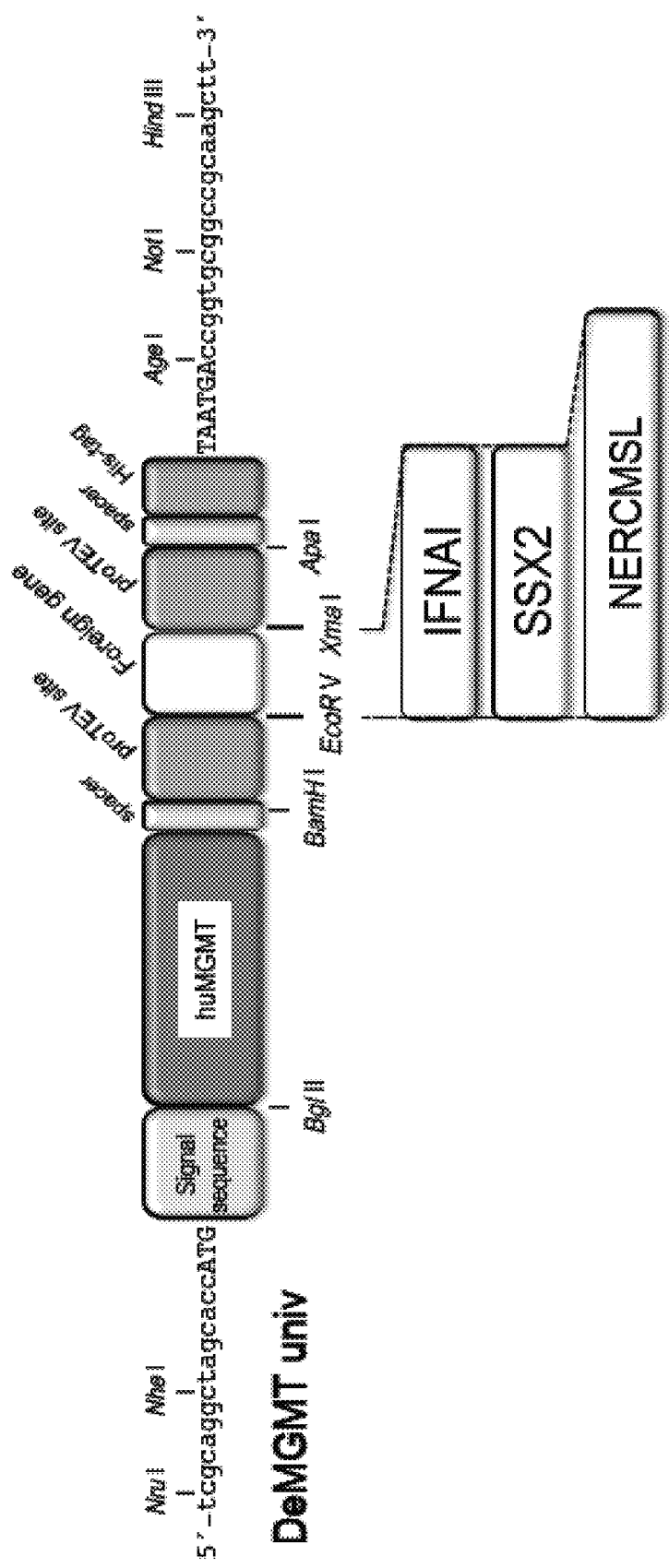

FIG. 9 discloses a means to insert a foreign gene of interest into DeMGMT Univ. (SEQ ID NO:69 and SEQ ID NO:70).

FIG. 10A-B discloses the thermostability of SNAP fusion proteins CHIK.sE2-SNAP, SNAP-WN.EDIII and SNAP-IFNαI) incubated 4 days at −80° C., 4° C., 25° C. or 37° C. (A) or two months at −80° C., 4° C., 25° C. or 37° C. (B).

Figure 11B:
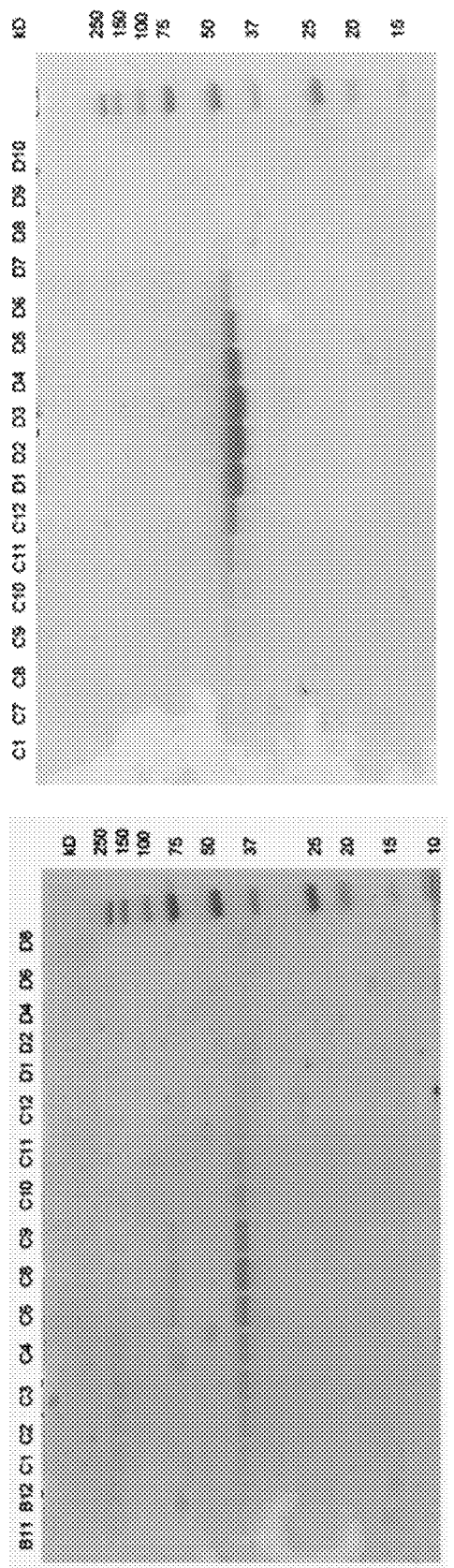

FIG. 11A-B discloses the production of the fusion proteins SNAP-SSX2 and SNAP-sFasL by the vectors of the invention introduced in S2 cells, after 10 days of cadmium induction (+) or without (−) in whole supernatant (A) or in the different fractions (B).

FIG. 12A-C discloses (A) a scheme of the universal DNA cassette containing a BiP-like peptide signal, a MGMT encoding sequence (SNAP-like), two pro-TEV cleavage sites, at each side of the SSX2 cancer antigen, and a Histag label (SEQ ID NO:69 and SEQ ID NO:70), (B) a scheme of the universal DNA cassette containing a BiP-like peptide signal, a MGMT encoding sequence, two pro-TEV cleavage sites at each side of the NERMCSL protein, and a Histag label (SEQ ID NO:96) and (SEQ ID NO:97, (C) an immunoblot assay on transient transfected HeLa cells for two days using mouse anti-SNAP antibodies, showing the extracellular or intracellular production of IFNα, SSX2 and NERMCSL.

FIG. 13A-C discloses (A) a scheme of the universal DNA cassette containing a BiP-like peptide signal, a MGMT encoding sequence (SNAP-like), two pro-TEV cleavage sites, at each side of the hSULF-2$^{\Delta TMD}$ polypeptide, and a Histag label, (B) the DNA (SEQ ID NO:96) and amino acid (SEQ ID NO:97) sequences of the fusion protein SNAP (in dark grey, preceded with an insect BiP-like peptide signal) and hSULF-2$^{\Delta TMD}$, followed by a Histag label, the SNAP and hSULF-2$^{\Delta TMD}$ proteins being separated with the pro-TEV cleavage site and a spacer sequence GGGS and (C) the enzymatic activity of secreted chimeric DeSNAP-hSULF-2$^{\Delta TMD}$ secreted by HEK 293 cells transiently transfected for two days with pcDNA3/DeSNAPuniv-hSULF-2$^{\Delta TMD}$.

Figure 14:
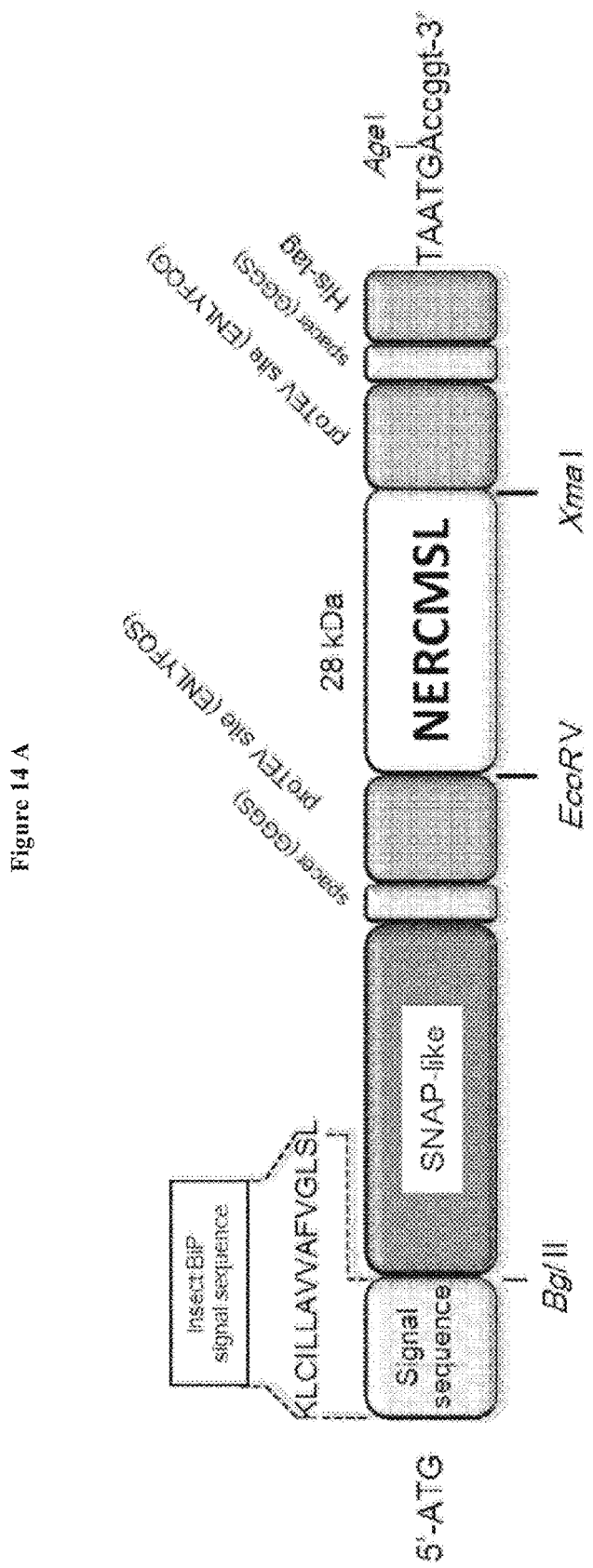
Figure 14:
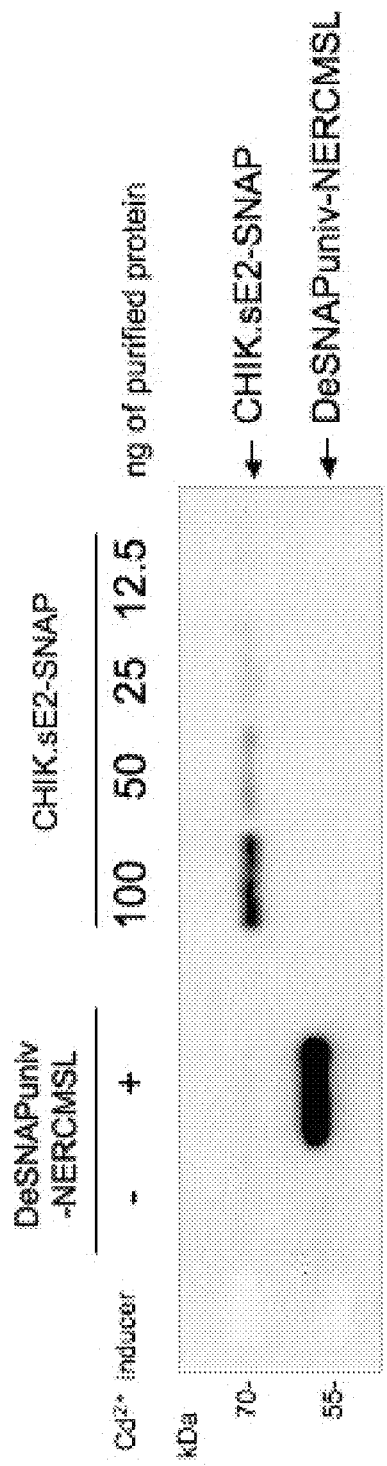

FIG. 14A-B discloses (A) a scheme of the DNA cassette containing a BiP peptide signal, a MGMT encoding sequence (SNAP-like), two pro-TEV clivage sites at each side of the NERMCSL protein, and a Histag label, and (B) Immunoblot assay using anti-SNAP antibodies, to detect the expression of the NERMCSL protein in the supernatant of S2 cells being transfected either by the vector of the invention encoding the NERMCSL protein (S2/SNAP-NERMCSL) or by a vector encoding the soluble protein E2 of the Chikungunya virus (CHIK.sE2-SNAP), stimulated or not with $Cd^{2+}$.

DETAILED DESCRIPTION OF THE INVENTION

The present inventors observed that co-expression of the 6-methylguanine-DNA-methyltransferase enzyme (MGMT) together with a recombinant protein of interest greatly improves the production of said recombinant protein in insect cells such as S2 cells, as well as in mammal cells, such as in HeLa cells.

The 6-methylguanine-DNA-methyltransferase enzyme (MGMT, also known as ATase or AGT, and hereafter referred to as "MGMT") is numbered EC 2.1.1.63 in the IUBMB enzyme nomenclature. It is a 6-alkylguanine-DNA-alkyltransferase DNA repair enzyme of 207 amino acid residues whose function in the cells is to repair alkylated DNA. More precisely, MGMT acts on $O^6$-methylated guanine in DNA by transferring the methyl group in an S2 reaction to a reactive cysteine residue (Cys 145). The repair mechanism is unusual, as the protein is irreversibly inactivated (Pegg A. E. et al, *Mutat. Res.* 2000; 462, 82-100). This enzyme is currently used in molecular biology for labelling proteins in vivo with reporter molecules, through an irreversible labelling reaction with $O^6$-benzylguanine derivatives (Juillerat A. et al, *Chemistry & Biology*, vol. 10, 313-317, 2003 and WO 2005/085470).

Different enzymes derived from MGMT have been described so far (Lim A. et al, *EMBO J.* 15: 4050-4060, 1996; Daniels D. S. et al, *EMBO J.* 19: 1719-1730, 2000; Juillerat A. et al, *Chemistry & Biology*, vol. 10, 313-317, 2003, WO 2005/085470, WO 2004/031405). In particular, a mutant protein of 20 kDa containing the mutations Cys62Ala, Lys125Ala, Ala127Thr, Arg128Ala, Gly131Lys, Gly132Thr, Met134Leu, Arg135Ser, Cys150Ser, Asn157Gly, Ser159Glu truncated at amino acid 182 has been obtained (the so-called "AGT26" mutant in WO 2005/085470, also called "SNAP 26" in WO 2006/114409). The particular mutant "SNAP26" has been shown to have enhanced labelling activity. However, it has never been shown nor suggested that it might enhance the expression of recombinant proteins to which it is coupled.

The present Inventors propose here for the first time the use the MGMT enzyme (EC 2.1.1.63), a mutant, a catalytic domain thereof or sub-fragments thereof, for enhancing the protein production in host cells, in particular in non-vertebrate and vertebrate host cells. The enhancing effect is observed when the host cells express a fusion polypeptide comprising at least i) a peptide secretion signal which is functional in said host cells, ii) the MGMT enzyme, mutant, catalytic domain or sub-fragments thereof, and iii) the protein of interest. For the enhancing effect to occur, the MGMT enzyme has to be physically linked, directly or indirectly (spacers and other amino acids might be introduced), to the protein of interest. Without being bound to the theory, it is contemplated that the MGMT enzyme can serve as chaperone protein, for example by favouring the secretion from the host cell and stabilising the synthesised fusion polypeptide in the supernatant of the host cells, or for preventing it to be metabolised during and after its synthesis and secretion from the host cells.

In addition, it has been observed that MGMT has a 3D globular structure comprising a helix (Wibley J. E. A. et al, 2000), which is compatible with a scaffolding role of MGMT.

In the context of the present invention, "host" cells are any cells which can be used for producing recombinant proteins, such as "non-vertebrate" (or invertebrate) cells, vertebrate cells, plant cells, yeast cells, or prokaryote cells. They are preferably non-vertebrate and vertebrate cells.

Non-vertebrate (also known as invertebrate) comprises different phyla, the most famous being the Insect, Arachnida, Crustacea, Mollusca, Annelida, Cirripedia, Radiata, Coelenterata and Infusoria. They are now classified into over 30 phyla, from simple organisms such as sea sponges and flatworms to complex animals such as arthropods and molluscs. In the context of the invention, non-vertebrate cells are preferably insect cells, such as *Drosophila* or Mosquito cells, more preferably *Drosophila* S2 cells.

Examples of cells derived from vertebrate organisms that are useful as host cell lines include non-human embryonic stem cells or derivative thereof, for example avian EBX cells; monkey kidney CVI line transformed by SV40 sequences (COS-7, ATCC CRL 1651); a human embryonic kidney line (293); baby hamster kidney cells (BHK, ATCC CCL 10); Chinese hamster ovary cells (CHO); mouse sertoli cells [TM4]; monkey kidney cells (CVI, ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL51); rat hepatoma cells [HTC, M1.5]; YB2/0 (ATCC n° CRL1662); NIH3T3; HEK and TRI cells. In the context of the invention, vertebrate cells are preferably EBX, CHO, YB2/O, COS, HEK, NIH3T3 cells or derivatives thereof.

Plant cells which can be used in the context of the invention are the tobacco cultivars Bright Yellow 2 (BY2) and *Nicotiana Tabaccum* 1 (NT-1).

Yeast cells which can be used in the context of the invention are: *Saccharomyces cerevisiae, Schizosaccharomyces pombe*, and *Hansenula polymorpha*, as well as methylotropic yeasts like *Pichia pastoris* and *Pichia methanolica*.

Prokaryote cells which can be used in the context of the invention are typically *E. Coli* bacteria or *Bacillus Subtilis* bacteria.

The present invention thus discloses a nucleotide expression vector encoding at least a) a peptidic secretion signal, which is preferably functional in non-vertebrate cells or vertebrate cells, and b) a 6-methylguanine-DNA-methyltransferase enzyme, a mutant, a sub-fragment or a catalytic domain thereof.

The term "vector" herein means the vehicle by which a DNA or RNA sequence of a foreign gene can be introduced into a host cell so as to transform it and promote expression of the introduced sequence. Vectors may include for example, plasmids, phages, and viruses and are discussed in greater detail below. Indeed, any type of plasmid, cosmid, YAC or viral vector may be used to prepare a recombinant nucleic acid construct which can be introduced to a host cell where expression of the protein of interest is desired. Alternatively, wherein expression of the protein of interest in a particular type of host cell is desired, viral vectors that selectively infect the desired cell type or tissue type can be used. Also important in the context of the invention are vectors for use in gene therapy (i.e. which are capable of delivering the nucleic acid molecule to a host organism).

For example, viral vectors, such as lentiviruses, retroviruses, herpes viruses, adenoviruses, adeno-associated viruses, vaccinia virus, baculovirus, and other recombinant viruses with desirable cellular tropism. Methods for constructing and using viral vectors are known in the art (see, Miller and Rosman, *BioTechniques*, 7:980-990, 1992).

Viral vectors that are actually preferred in the present invention are those that are well suited for use in vertebrate and non-vertebrate cells.

For non vertebrate cells, preferred vectors are the arboviruses, the West Nile virus being particularly preferred, which are arthropod vectors. Other vectors that are known to efficiently be expressed in non-vertebrate cells are the baculoviruses.

For vertebrate cells, lentiviral, AAV, baculoviral and adenoviral vectors are preferred. The vectors suited for expression in mammalian host cells can also be of non viral (e.g. plasmid DNA) origin. Suitable plasmid vectors include, without limitation, pREP4, pCEP4 (Invitrogene), pCI (Promega), pCDM8 and pMT2PC, pVAX and pgWiz.

For prokaryote cells, plasmid, bacteriophage and cosmid vectors are preferred. Suitable vectors for use in prokaryote systems include without limitation pBR322 (Gibco BRL), pUC (Gibco BRL), pBluescript (Stratagene), p Poly, pTrc; pET 11d; pIN; and pGEX vectors.

For plant cells, plasmid expression vectors such as Ti plasmids, and virus expression vectors such as Cauliflower mosaic virus (CaMV) and tobacco mosaic virus TMV are preferred.

Expression of recombinant proteins in yeast cells can be done using three types of vectors: integration vectors (YIp), episomal plasmids (YEp), and centromeric plasmids (YCp): Suitable vectors for expression in yeast (e.g. *S. cerevisiae*) include, but are not limited to pYepSec1, pMFa, pJRY88, pYES2 (Invitrogen Corporation, San Diego, Calif.) and pTEF-MF (Dualsystems Biotech Product code: P03303).

Vectors which can be used for gene therapy are well-know in the art. They are for example lentivirus, retrovirus, adenovirus, poxvirus, herpes virus, measle virus, foamy virus or adeno-associated virus (AAV). Viral vectors can be replication-competent, or can be genetically disabled so as to be replication-defective or replication-impaired. Preferred gene therapy vector are the DNA Flap vectors as described in WO 1999/055892, U.S. Pat. No. 6,682,507 and WO 2001/27300.

A sequence "encoding" an expression product, such as a RNA, polypeptide, protein or enzyme, is a nucleotide sequence that, when expressed, results in the production of that
RNA, polypeptide, protein or enzyme; i.e., the nucleotide sequence "encodes" that RNA or it encodes the amino acid sequence for that polypeptide, protein or enzyme.

In the context of the invention, the "catalytic domain" of an enzyme means the active site of the enzyme, or, in other words, the part of an enzyme molecule at which catalysis of the substrate occurs (here the transfer of the methyl group in an $S_N2$ reaction to a reactive cysteine residue). The term "a catalytic domain thereof" therefore designates any fragment or homologous sequence of the MGMT polypeptide, preferably having at least 80% of the catalytic activity of the native MGMT enzyme. These fragments (also called "sub-fragments") can comprise between 20 and 180, preferably between 30 and 100 amino acids.

The homologous sequence of said catalytic domain can have one or more mutations resulting in the partial or total lost of said catalytic activity.

In the context of the invention, the MGMT enzyme can be the human MGMT (referenced as NP_002403.2) of sequence SEQ ID NO:4, the mouse MGMT identified as NP_032624.1 (SEQ ID NO: 45), the rat MGMT identified as NP_036993.1 (SEQ ID NO:46) or an homologous sequence thereof.

The term "homologous" refers to sequences that have sequence similarity. The term "sequence similarity", in all its grammatical forms, refers to the degree of identity or correspondence between nucleic acid or amino acid sequences. In the context of the invention, two amino acid sequences are "homologous" when at least about 80%, alternatively at least about 81%, alternatively at least about 82%, alternatively at least about 83%, alternatively at least about 84%, alternatively at least about 85%, alternatively at least about 86%, alternatively at least about 87%, alternatively at least about 88%, alternatively at least about 89%, alternatively at least about 90%, alternatively at least about 91%, alternatively at least about 92%, alternatively at least about 93%, alternatively at least about 94%, alternatively at least about 95%, alternatively at least about 96%, alternatively at least about 97%, alternatively at least about 98%, alternatively at least about 99% of the amino acids are similar. Preferably the similar or homologous polypeptide sequences are identified by using the algorithm of Needleman and Wunsch.

Preferably, the homologous sequence to the 6-methylguanine-DNA-methyltransferase enzyme shares at least 64% amino acid sequence identity, preferably at least about 65% amino acid sequence identity, alternatively at least about 66% amino acid sequence identity, alternatively at least about 67% amino acid sequence identity, alternatively at least about 68% amino acid sequence identity, alternatively at least about 69% amino acid sequence identity, alternatively at least about 70% amino acid sequence identity, alternatively at least about 71% amino acid sequence identity, alternatively at least about 72% amino acid sequence identity, alternatively at least about 73% amino acid sequence identity, alternatively at least about 74% amino acid sequence identity, alternatively at least about 75% amino acid sequence identity, alternatively at least about 76% amino acid sequence identity, alternatively at least about 77% amino acid sequence identity, alternatively at least about 78% amino acid sequence identity, alternatively at least about 79% amino acid sequence identity, alternatively at least 80% amino acid identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity with SEQ ID NO:4. In a preferred embodiment, the homologous sequence of SEQ ID NO:4 is at least 64%, preferably 70%, and more preferably 80% identical to SEQ ID NO:4.

A more preferred homologous MGMT sequence contains the mutations described in WO 2005/085470, whose positions can be easily transposed in view of SEQ ID NO:4, the starting Methionine residue of SNAP26 corresponding to the Methionine residue in position 32 of SEQ ID NO:4 (31 amino acids should therefore be added to the positions disclosed in WO 2005/085470 so as to obtain the corresponding ones in SEQ ID NO:4).

Preferably, the MGMT homologous sequence useful in the invention corresponds to the wild-type MGMT sequence of SEQ ID NO:4, in which between 1 and 30, preferably between 6 and 25, and in particular 14, 15, 16, 17, 18, 19, 20, 21, 22, or 23 amino acids are substituted by other amino acids, and/or 1 to 40, preferably 1 to 20, in particular 10 to 20 amino acids, more preferably 15 amino acids at the C-terminus are deleted.

In a preferred embodiment, the MGMT homologous sequence contains the following mutations as compared with SEQ ID NO:4:

(A) Lys31 replaced by Arg, or Met32 replaced by Ser, or Cys93 replaced by Ala, or Lys156 replaced by Ala, or Ala158 replaced by Thr, or Arg159 replaced by Ala, or Gly162 replaced by Lys, or Gly163 replaced by Thr, or Met165 replaced by Leu, or Arg166 replaced by Ser, or Cys181 replaced by Ser, or Asn188 replaced by Gly, or Ser190 replaced by Glu, or Gly214 replaced by Pro, or Ser215 replaced by Ala, or Ser216 replaced by Gly, or Gly217 replaced by Ile, or Leu218 replaced by Gly, or Gly220 replaced by Pro, or Ala221 replaced by Gly, or Trp222 replaced by Ser, or (B) Lys31-Met32 replaced by Arg-Ser, or Ala158-Arg159 replaced by Thr-Ala, or Gly162-Gly163 replaced by Lys-Thr, or Met165-Arg166 replaced by Leu-Ser, or Gly162-Gly163/Met165-Arg166 replaced by Lys-Thr/Leu-Ser, or Asn188/Ser190 replaced by Gly/Glu, or Gly214-Ser215-Ser216-Gly217-Leu218 replaced by Pro-Ala-Gly-Ile-Gly, or Gly220-Ala221-Trp222 replaced by Pro-Gly-Ser, preferably in combination with any other amino acid replacements cited in (A), or (C) Truncation after Leu223 (amino acids 224-238 are deleted), preferably in combination with any other amino acid replacement cited in (A) or (B).

Preferred MGMT homologous sequences are those being truncated after Leu223.

Preferred MGMT homologous sequences are those wherein two out of the modifications (B) are present, and optionally truncation after Leu223.

Preferred MGMT homologous sequences are those wherein three out of the modifications (B) are present, and optionally truncation after Leu223.

Preferred MGMT homologous sequences are those wherein four out of the modifications (B) are present, and optionally truncation after Leu223.

Preferred MGMT homologous sequences are those wherein five out of the modifications (B) are present, and optionally truncation after Leu223.

Preferred MGMT homologous sequences are those wherein six out of the modifications (B) are present, and optionally truncation after Leu223.

Other preferred MGMT homologous sequences are those containing a combination of 2, 3, 4, 5, 6, 7, 8, 9, 10, 11, 12, 13, 14, 15, 16, 17, 18, 19, or 20 mutations chosen among the modifications disclosed in (A), and optionally truncated after Leu223.

Particularly preferred are homologous sequences containing the mutations Lys31Arg, Met32Ser, Cys93Ala, Lys156Ala, Ala158Thr, Arg159Ala, Gly162Lys, Gly163Thr, Met165Leu, Arg166Ser, Cys181Ser, Asn188Gly, Ser190Glu, Gly214Pro, Ser215Ala, Ser216Gly, Gly217Ile, Leu218Gly, Gly220Pro, Ala221Gly, Trp222Ser and truncation after Leu223 (that is, the SNAP sequence of SEQ ID NO:2).

In an even more preferred embodiment, the MGMT enzyme is the SNAP mutant protein of SEQ ID NO:2 or a homologous thereof. The SNAP mutant of SEQ ID NO:2 shares 77% homology with the amino acid sequence of the human 6-methylguanine-DNA-methyltransferase (NP_002403.2, SEQ ID NO:4), and 70% homology with the amino acid sequence of the mouse 6-methylguanine-DNA-methyltransferase (NP_032624.1, SEQ ID NO:45).

Preferably, said homologous sequence to the SNAP protein is at least identical at more than 80%, preferably 81%, more preferably 82%, more preferably 83%, more preferably 84%, more preferably 85%, preferably 86%, more preferably 87%, more preferably 88%, more preferably 89%, more preferably 90%, more preferably 91%, more preferably 92%, more preferably 93%, more preferably 94%, more preferably 95%, more preferably 96% to the and even more preferably 97% to the SNAP protein of sequence SEQ ID NO:2.

Preferably, the nucleotide expression vector of the invention further comprises cloning sites enabling the in frame insertion of an heterologous DNA sequence encoding a protein of interest.

As meant in the present invention, the term "peptidic secretion signal" designates a short (3-60 amino acids long) peptide chain that directs the transport of a protein.

Examples of secretion signals appropriate for the present invention include, but are not limited to, the signal peptide sequences of the mating factor (MF) alpha (U.S. Pat. No. 5,879,926); invertase (WO84/01153); PHO5 (DK 3614/83); YAP3 (yeast aspartic protease 3; WO95/02059); and BAR1 (WO87/02670).

In the context of the invention, this peptidic secretion signal is preferably functional either in non-vertebrate cells or in vertebrate cells, or both.

Examples of peptidic secretion signals which are functional in insect cells are: the insect ssBiP (SEQ ID NO: 48, for example having the DNA sequence SEQ ID NO:11), the BiP-like peptide signal of SEQ ID NO: 51 (for example having the DNA sequence SEQ ID NO:50) and any peptide signal present in an arbovirus, for example the envelop E protein of the West-Nile virus (SEQ ID NO: 15).

Interestingly, the above-mentioned BiP-like peptide signal is functional in both non-vertebrate and vertebrate cells. This BiP-like signal corresponds to the BiP peptide signal of SEQ ID NO:48 in which the last Glycine amino acid has been replaced by the amino acid sequence Pro Thr Ala Leu Ala (SEQ ID NO:61) which corresponds to the cleavage site of the E protein of the Dengue virus. Accordingly, the BiP-like signal will be advantageously cleaved once the protein will be translated and secreted in the supernatant of the host cells.

A variety of secretion signals are also available for expression in yeast host cells, e.g. in S. cerevisiae. These include the Prepro alpha factor, HSp150, PHO1, SUC2, KILM1 (killer toxin type 1), and GGP1.

A cloning site is a sequence which facilitates cloning of a gene encoding a protein of interest into the expression system. It contains restriction sites, or restriction recognition sites, i.e. locations on a DNA molecule containing specific sequences of nucleotides, which are recognized by restriction enzymes (see for example in the figures). These are generally palindromic sequences (because restriction enzymes usually bind as homodimers), and a particular restriction enzyme may cut the sequence between two nucleotides within its recognition site, or somewhere nearby. The cloning sites are well known for the man skilled in the art.

More preferably, the nucleotide expression vector further comprises a heterologous DNA sequence encoding an heterologous protein of interest or an heterologous polypeptide inserted at said cloning sites.

The term "heterologous" refers to a combination of elements not naturally occurring.

For example, the present invention includes "heterologous DNA sequences" encoding "protein/polypeptides of interest", these DNA sequences being not naturally located in, or within a chromosomal site of, the host cell which is used for protein expression.

When a heterologous DNA sequence encoding an heterologous protein or polypeptide of interest is inserted in the nucleotide vector of the invention, it is preferably requested that it encodes a fusion polypeptide comprising said peptidic signal, said MGMT enzyme, mutant or homologous thereof, and said heterologous protein/polypeptide of interest.

In a preferred embodiment of the invention, the DNA sequence encoding said MGMT enzyme is located in 5' or in 3' of the DNA sequence encoding said heterologous protein of interest, preferably in 5'. Therefore, the MGMT enzyme is directly or indirectly linked to the heterologous protein/polypeptide of interest, and preferably located at the N-terminal end of the heterologous protein/polypeptide of interest.

It is particularly preferred that the DNA sequence encoding said MGMT enzyme thereof is located in 5' of the DNA sequence encoding said heterologous protein/polypeptide of interest, when the activity domain of the heterologous protein/polypeptide of interest is located at its C-terminal part, such as IFNα. In a same manner, it could be particularly preferred that the DNA sequence encoding said MGMT enzyme is located in 3' of the DNA sequence encoding said heterologous protein/polypeptide of interest, when the activity domain of the heterologous protein/polypeptide of interest is located at its N-terminal part.

More precisely, in a first aspect, the present invention is drawn to a vector for expressing recombinant proteins in host cells, preferably in non-vertebrate and/or vertebrate host cells, more preferably in insect cells, comprising a nucleotide sequence encoding in a single open reading frame, from 5' to 3':

a) a peptidic secretion signal which is functional in said host cell, b) the 6-methylguanine-DNA-methyltransferase enzyme (MGMT, EC 2.1.1.63), a mutant or a catalytic domain thereof, and c) a recombinant protein.

In the context of the invention, the term "recombinant protein" or "protein of interest" designate gene products or polypeptides that are foreign to the protein producing cell, and which are preferably selected from the group consisting of diagnostic and therapeutic protein(s) or polypeptide(s).

More preferably, said diagnostic and therapeutic protein(s) or polypeptide(s) is (are) selected from the group consisting of:

bacterial or viral immunogenic proteins, more preferably (infectious, pathogenic) viral proteins, for example the EMI protein from the Dengue, Japanese Encephalitis, Tick-Born Encephalitis, Yellow Fever, Usutu, Rocio, Murray Encephalitis, Wesselbron, Zika or West Nile viruses, or the nucleoprotein N from Rift Valley Fever or Toscana viruses, or the soluble form of the E2 envelope protein from the Chikungunya virus, or the soluble form of the E envelope protein of the West-Nile virus, and blood factors, anticoagulants, growth factors, hormones, vaccines, therapeutic enzymes, monoclonal antibodies and cytokines (such as IFNα, Granzyme M and FasL), antigens, e.g. cancer antigens such as the cancer testis antigen SSX2, or the N-terminal region of the ERC/Mesotheline (NERCMSL), anti-tumoral proteins, e.g. FasL, or the heparan-sulfate 6-O-endosulfatases (hSULF), microbial, viral and/or parasite polypeptides, any other useful proteins (e.g. contactins).

The protein FasL is a pro-apoptotic protein which can be used as anti-tumor agent. It is encoded for example by SEQ ID NO:88.

The hSulf proteins (or hSULF) are heparan-sulfate 6-O-endosulfatases which regulate heparin sulfate structure and have a dramatic impact on the growth and progression of malignant cells in vivo (Dai et al, 2005). In the context of the invention, it is preferably the hSulf2 protein, and more preferably the hSulf-$2^{\Delta TMD}$, in which the transmembrane domain (TMD) has been deleted so as to enhance its solubility, this mutant having the amino acid sequence SEQ ID NO:95 and being encoded for example by SEQ ID NO:94.

The vector of the invention can also be used to express and purify peptides and/or polypeptides of interest. In the context of the present invention, the terms "peptides" and "polypeptides" are meant to be synonymous, designating short polymers of amino acid monomers (also called "residues") linked by peptide bonds. These polymers preferably contain less than 100 residues, more preferably less than 50 residues.

In particular, the vector of the invention can be used to express and purify diagnostic microbial polypeptides, such as bacterial, viral or parasite polypeptides. Examples of such polypeptides are antigenic peptides, mucins, and/or toxins secreted or expressed by bacteria, viruses or parasites. Preferably, said antigenic peptide is expressed by the Influenza virus, the hepatitis A virus, the hepatitis B virus, the hepatitis C virus, the hepatitis G virus, the HIV virus, the Yellow fever virus, the Dengue virus, the Japanese Encephalitis virus, the Tick-Born Encephalitis virus, the Usutu or West Nile viruses, the Rift Valley Fever or Toscana viruses, the Chikungunya virus, the Respiratory Synticial virus, the Rocio virus, the Murray Encephalitis virus, the Wesselbron virus, the Zika virus, the Lymphocytic Choreomeningitis virus, a human parvovirus, a human papillomavirus, the human cytomegalovirus, or any identified virus. Preferably, said antigenic peptide is expressed by parasitic protozoa (such as *Entamoeba histolytica* or *Giardia lamblia*), worms (such as nematodes, cestodes, or trematodes), or arthropods (such as crustaceans, insects, arachnids).

Preferably, said antigenic peptide is expressed by infectious bacteria, for example of the genera *Streptococcus, Staphylococcus*, and *E. Coli*. Infectious toxins are well known in the art. One can cite, as examples, the botulinum neurotoxins, the *Clostridium perfringens* epsilon toxin, ricin, saxitoxin, shigatoxin, tetrodotoxin, staphylococcal enterotoxins, etc. Mucins are also well known in the art. MUC5AC, MUC5B and MUC2 are examples thereof. These examples are not limiting and any peptide/polypeptide can be expressed by the method of the invention.

Contactins are a subgroup of molecules belonging to the immunoglobulin superfamily that are expressed exclusively in the nervous system (see the review of Shimoda and Watanabe, 2009). They have been involved in psychiatric disorders, in particular in autism. Preferred contactins to be produced by the system of the invention are contacting 2 and 4. Contactin 4 (CNTN4) is encoded for example by SEQ ID NO:91 (corresponding to amino acids 19-990 of the full protein NP_783200.1).

Numerous cancer antigens are known to be efficient vaccine targets for treating cancer. The production of high amount of such polypeptides (see the lists in Cheever et al, 2009) appears to be very important in order to obtain efficient cancer vaccine. Interestingly, the vectors of the invention enable to obtain high level of recombinant cancer antigen which can be used in immunotherapy, or to produce antibodies, or in cancer diagnostic methods.

SSX2 and NERCMSL are two examples of cancer antigens. The SSX2 cancer antigen is encoded by the DNA having SEQ ID NO:76 (Genebank: NM_175698). The N-terminal region of the ERC/Mesotheline (NERCMSL) is encoded by SEQ ID NO:83. This antigen is commonly used as a detection antigen in patients suffering of malign mesothelium.

Any protein can be produce by the methods of the invention.

Yet, preferred proteins are the therapeutic proteins such as insulin, IFN, FasL, Mesotheline, hSULF or contactins.

More generally, preferred proteins are those which have been difficult to produce in high amounts so far. Such proteins are for example FasL, Granzyme M, hSULF, Mesotheline and contactins.

The DNA sequence encoding the fusion polypeptide comprising said peptidic signal, said MGMT enzyme, mutant or catalytic domain, and said recombinant protein of interest, can be operatively associated with an inducible promoter which is functional in the same host cells as the peptidic signal is.

More preferably, in the vector of the invention, said open reading frame is operatively associated with an inducible promoter which is functional in the same host cell as the peptidic signal is.

A coding sequence is "operatively associated with" an expression control sequence (i.e. transcriptional and translational control sequences) in a cell, when RNA polymerase transcribes the coding sequence into RNA, which is then trans-RNA spliced (if it contains introns) and, if the sequence encodes a protein, is translated into that protein.

A "promoter" is a sequence of nucleotides from which transcription may be initiated of DNA operably linked downstream (i.e. in the 3' direction on the sense strand of double-stranded DNA). Within the promoter sequence will be found a transcription initiation site (conveniently found, for example, by mapping with nuclease S1), as well as protein binding domains (consensus sequences) responsible for the binding of RNA polymerase.

Promoters which may be used to control gene expression in the context of the present invention are for example the one that are functional in non-vertebrate cells or in vertebrate cells. For example, for non-vertebrate cells, the regulatory sequences of the metallothionein gene can be used (Brinster et al., *Nature,* 296:39-42, 1982).

Preferably, the inducible promoter which is present in the vector of the invention has a promoter activity in an insect cell, and more preferably in a *Drosophila* cell. It is for example the *Drosophila* metallothionein promoter (Lastowski-Perry et al, *J. Biol. Chem.* 260:1527 (1985)), which directs high level transcription of the gene in the presence of metals, e.g. $CuSO_4$. Alternatively, the *Drosophila* actin 5C gene promoter, which is a constitutive promoter and does not require addition of a metal, can be used (B. J. Bond et al, *Mol. Cell. Biol.* 6:2080 (1986)) Examples of other known *Drosophila* promoters include, e.g. the inducible heatshock (Hsp70) and COPIA LTR promoters. The SV40 early promoter gives lower level of expression than the *Drosophila* metallothionein.

Preferably, the inducible promoter which is present in the vector of the invention has a promoter activity in a *Drosophila melanogaster* cell, preferably in *Drosophila* S2 cells. It is for example the methallothionein promoter which is thoroughly described in Lastowski-Perry et al, *J. Biol. Chem.* 260:1527 (1985).

Promoters suitable for constitutive expression in mammalian cells include the cytomegalovirus (CMV) immediate early promoter, the adenovirus major late promoter, the phosphoglycero kinase (PGK) promoter, and the thymidine kinase (TK) promoter of herpes simplex virus (HSV)-1. Inducible eukaryotic promoters regulated by exogenously supplied compounds, include without limitation, the zinc-inducible metallothionein (MT) promoter, the dexamethasone (Dex)-inducible mouse mammary tumor virus (MMTV) promoter, the T7 polymerase promoter system (WO 98/10088), the ecdysone insect promoter, the tetracycline-repressible promoter, the tetracycline-inducible promoter, the RU486-inducible promoter and the rapamycin-inducible promoter.

Preferably, the promoter which is present in the vector of the invention has a promoter activity in a mammal cell, preferably in HeLa cells. It is for example the SV 40 promoter.

A range of yeast promoters is available for protein expression in yeast host cells. Some like ADH2, SUC2 are inducible and others like GAPDH are constitutive in expression. Other promoters suitable for expression in yeast include the TEF, PGK, MF alpha, CYC-1, GAL-1, GAL4, GAL10, PHO5, glyceraldehyde-3-phosphate dehydrogenase (GAP or GAPDH), and alcohol dehydrogenase (ADH) promoters.

For use in plant cells, the most commonly used promoter is the cauliflower mosaic virus (CaMV)35S promoter or its enhanced version, but a number of alternative promoter can be used, such as the hybrid (ocs)3mas promoter or the ubiquitin promoter from Maize and *A. Thaliana*. In contrast to these constitutive promoters, the rice α-amylase RAmy3D promoter is induced by sugar deprivation (Hellwig S et al, 2004).

Promoters suitable for expression in *E. coli* host cell include, but are not limited to, the bacteriophage lamba pL promoter, the lac, TRP and IPTG-inducible pTAC promoters.

It is preferred that the peptidic secretion signal and the inducible promoter are functional in the same host cell.

More preferably, the peptidic secretion signal and the inducible promoter are functional in both *Drosophila* S2 cells and vertebrate cells.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

Once an appropriate vector has been constructed and transfected into the selected host cell, preferably a *Drosophila* cell line, the expression of an heterologous protein is induced by the addition of an appropriate inducing agent for the inducible promoter. For example cadmium or copper are inducing agents for the Hsp70 promoter. For constitutive promoters, such as the actin 5C promoter, no inducing agent is required for expression.

The human MGMT enzyme of the invention is preferably encoded by the human MGMT gene sequence NM_002412.3, gene ID 4255 (SEQ ID NO:3) or by the optimised sequence SEQ ID NO: 68 (comprising only 50% of G/C). Nevertheless, any homologous sequence thereof can be used in the context of the invention, provided that it encodes a functional MGMT enzyme, mutant or catalytic domain thereof, preferably SEQ ID NO: 4 or SEQ ID NO:2.

Preferred DNA sequences encoding said MGMT mutant are the SNAP DNA sequence SEQ ID NO:1, or the DNA sequences SEQ ID NO:47 or SEQ ID NO:67 encoding the SEQ ID NO:2 but having a G/C content of 51%.

In another embodiment of the invention, the nucleotide vector of the invention encodes at least a fragment of the MGMT enzyme (for example a fragment of SEQ ID NO:4), or a fragment of an homologous thereof (for example a fragment of the MGMT mutant of sequence SEQ ID NO:2), that retains the biological activity of increasing the expression of the protein of interest by a factor of at least 0.5 times the level obtained with the full-length enzyme from which it is a fragment. As an example, if the production level is of 100 mg/L with the full-length enzyme of SEQ ID NO:4, then any fragments of SEQ ID NO:4 having a production level of at least 50 mg/L (in the same experimental conditions as for the full-length enzyme of SEQ ID NO:4) are encompassed within the present invention.

In another embodiment of the invention, the nucleotide expression vector encodes at least one peptidic cleavage site, which is preferably located between the MGMT enzyme or its catalytic domain and the recombinant protein of interest.

A peptidic cleavage site (also called "peptide cleavage site") is an amino acid sequence which is recognized by at least one protease enzyme (for example serine protease, cysteine protease, among others). An example of a peptidic cleavage site is the enterokinase cleavage site of SEQ ID NO:62 (AspAspAspAspLys/Asp), for example encoded by the DNA sequence SEQ ID NO:12. The enterokinase is a serine protease enzyme (EC 3.4.21.9) which is known to convert inactive trypsinogen into active trypsin by cleavage at the C-terminal end of the sequence: Val-(Asp)$_4$-Lys-Ile-Val~ (trypsinogen)→Val-(Asp)$_4$-Lys (hexapeptide)+Ile-Val~(trypsin). Enterokinase cleaves after Lysine if the Lys is preceded by four Asp and not followed by a Proline residue.

Another useful peptidic cleavage site is the cleavage site of the so-called "TEV protease", having the amino acid sequence SEQ ID NO:53 or SEQ ID NO: 65 (Glu Asn Leu Tyr Phe Gln Gly or Ser), and which is for example encoded by the DNA sequence SEQ ID NO:52 or SEQ ID NO:66. TEV protease is the common name for the 27 kDa catalytic domain of the nuclear inclusion a protein encoded by the tobacco etch virus. It is commercially available (Invitrogen).

The cleavage site from the membrane precursor prM from Dengue virus serotype 1 (SEQ ID NO:61) may also be used in the vector of the invention.

In another embodiment, the nucleotide expression vector of the invention further encodes a label, preferably located at the C terminal end of the recombinant protein in the fusion polypeptide of the invention (comprising the peptidic signal, the MGMT protein or homologous thereof, and the recombinant protein).

In the context of the invention, a "label" is dedicated to facilitate the recovery of the polypeptide from the crude lysate of the host cell, and is preferably selected from the group comprising: fluorescent proteins, poly-histidine (poly-his) or poly-histidine-glycine (poly-his-gly) tags; flu HA tags; c-myc tag Herpes Simplex virus glycoprotein D (gD) tags, Flag-peptides, alpha-tubulin epitopes, or T7 gene 10 protein peptide tags. However, any other label might be use. In a preferred embodiment of the invention, the vectors comprise the DNA encoding a hexa-hystidine tag which has the SEQ ID NO:14.

In another embodiment, the nucleotide expression vector of the invention further encodes spacer sequence(s), located preferably between the MGMT enzyme (or its catalytic domain) and the recombinant protein of interest and/or between the recombinant protein of interest and the label.

In the context of the invention, a spacer sequence is an amino acid sequence comprising at least three amino acids, dedicated to spatially separate two linked polypeptides (these polypeptides being then indirectly linked). Such spacer can be for example the amino acid sequence Glycine-Glycine-Glycine-Serine (GGGS, SEQ ID NO:63) and the DNA spacer sequence encoding it can be SEQ ID NO:13. In the context of this invention, this DNA sequence is hereafter designated as "DNA spacer sequence" and is located between the DNA encoding MGMT or its catalytic domain, and the recombinant DNA sequence, preferably upstream from the DNA sequence encoding the peptidic cleavage site.

Nucleotide expression vector that are disclosed by the present invention can have the sequence SEQ ID NO:9, the sequence SEQ ID NO:10 or the SEQ ID NO: 64 (corresponding to empty vectors without recombinant gene of interest inserted in the cloning sites). In a particular embodiment, the vector of the invention can encode:
- a peptidic BiP insect signal (which is preferably functional in S2 *drosophila* cells) or a BiP-like signal as defined above,
- a MGMT protein of SEQ ID NO:4 or a SNAP protein of SEQ ID NO:2,
- a recombinant protein of interest,
- an enterokinase peptidic cleavage site or a proTEV cleavage site as defined above,
- a poly-Histidine label, and,
- two spacer sequences having the amino acid sequence Glycine-Glycine-Glycine-Serine (GGGS, SEQ ID NO:63).

In a more preferred embodiment, the expression vector of the invention encodes:
- a peptidic BiP insect signal of SEQ ID NO:48,
- a MGMT protein of SEQ ID NO:4 or a SNAP protein of SEQ ID NO:2,
- a recombinant protein of interest,
- an enterokinase peptidic cleavage site of SEQ ID NO:62,
- a poly-Histidine label, and,
- two spacer sequences having the amino acid sequence Glycine-Glycine-Glycine-Serine (GGGS).

In another preferred embodiment, the expression vector of the invention encodes:
- a BiP-like peptide signal of SEQ ID NO:51,
- a MGMT protein of SEQ ID NO:4 or a SNAP protein of SEQ ID NO:2,
- a recombinant protein of interest,
- a proTEV peptidic cleavage site of SEQ ID NO:53,
- a poly-Histidine label, and,
- two spacer sequences having the amino acid sequence Glycine-Glycine-Glycine-Serine (GGGS).

Such vectors can for example comprise the sequence SEQ ID NO:19 (when the protein of interest is the nucleoprotein N of the RVF virus), SEQ ID NO:20 (when the protein of interest is the nucleoprotein N of the West Nile virus), SEQ ID NO:21 or 57 or 72 or 74 (when the protein of interest is IFNα), SEQ ID NO: 77, 79 or 81 (when the protein of interest is the cancer antigen SSX2), SEQ ID NO:55 (when the protein of interest is Granzyme M), SEQ ID NO:89 (when the protein of interest is FasL), SEQ ID NO:84 or 86 (when the protein of interest is the cancer antigen NERC-MSL), or SEQ ID NO:92 (when the protein of interest is the contacting CNTN4).

In a second aspect, the present invention also discloses a vector for expressing recombinant proteins in host cells, comprising a nucleotide sequence encoding in a single open reading frame, from 5' to 3':
a) a peptidic secretion signal,
b) a MGMT protein of SEQ ID NO:4 or a SNAP protein of SEQ ID NO:2,
c) at least one peptidic cleavage site,
d) a poly-Histidine label, and,
e) at least one spacer sequence.

In a preferred embodiment, said peptidic secretion signal is the BiP-like peptide signal of SEQ ID NO:50.

In a rather preferred embodiment, said vector comprises two proTEV peptidic cleavage sites of SEQ ID NO:52 and/or two spacer sequences having the amino acid sequence SEQ ID NO:63.

In a particularly preferred embodiment, said vector comprises the sequence SEQ ID NO:59 or SEQ ID NO:69, said sequences being referred to in this application as the universal DeSNAP cassette "DeSNAP Univ" and DeMGMT cassette "DeMGMT Univ" respectively.

These "DeSNAP Univ" (SEQ ID NO:59) and "DeMGMT Univ" (SEQ ID NO:69) are held as "universal" sequences since they can be inserted in any kind of vectors dedicated to transfect host cells in order to produce heterologous proteins, namely vertebrate vectors (such as pcDNA3 or pCI-neo vectors) as well non-vertebrate vectors (such as pMT/BiPN5-HisA which is useful in the DES system, see the examples below).

Examples of plasmid comprising said universal sequences are SEQ ID NO:64 (pUC57 comprising DeSNAP Univ) and SEQ ID NO:71 (pUC57 with DeMGMT Univ).

Once the heterologous sequence of a protein of interest is cloned herein, such a vector can be advantageously transfected in either vertebrate or non-vertebrate host cells, so as to produce the protein of interest in high amounts.

In a third aspect, the present invention targets the recombinant cell which is stably transfected by said DeSNAP Univ or DeMGMT Univ vector, i.e. by the expression vector comprising a nucleotide sequence encoding in a single open reading frame, from 5' to 3':
a) a peptidic secretion signal,
b) a MGMT protein of SEQ ID NO:4 or a SNAP protein of SEQ ID NO:2,
c) at least one peptidic cleavage site,
d) a poly-Histidine label, and,
e) at least one spacer sequence,
each component being as defined above.

It preferably comprises the plasmids of SEQ ID NO:64 (pUC57 comprising DeSNAP Univ) or SEQ ID NO:71 (pUC57 with DeMGMT Univ), or at least the nucleotide sequence SEQ ID NO: 59 (DeSNAP Univ) or SEQ ID NO:69 (DeMGMT Univ).

Preferably, in this aspect of the invention, said recombinant cell is a *E. Coli* cell.

This recombinant cell is used in order to amplify and purify the expression vectors of the invention, preferably those comprising DeSNAP Univ of SEQ ID NO:59 (such as SEQ ID NO:64) or DeMGMT Univ of SEQ ID NO:69 (such as SEQ ID NO:71).

The present invention therefore also targets the use of this recombinant cell for producing any expression vector of the invention (said vectors being as defined above).

The nucleotide expression vectors of the invention may also comprise a gene encoding a selection marker, and/or a terminator sequence.

Selection markers genes that can be included in the construct are typically those that confer selectable phenotypes such as resistance to antibiotics (e.g. blasticidin, ampicillin, kanamycin, hygromycin, puromycin, chloramphenicol).

In a fourth aspect, the present invention is drawn to a fusion polypeptide comprising a peptidic secretion signal which is functional in host cells, preferably in non-vertebrate or vertebrate cells, more preferably in insect cells, and the 6-methylguanine-DNA-methyltransferase enzyme (MGMT) (EC 2.1.1.63), mutant or catalytic domain thereof as defined above.

In this fusion polypeptide, said MGMT enzyme is preferably the protein of SEQ ID NO:4, the SNAP protein mutant of SEQ ID NO:2, or an homologous thereof.

This fusion polypeptide preferably further comprises a recombinant protein of interest as defined above, preferably located at the C terminal end of the MGMT enzyme or catalytic domain thereof, and/or a label, as defined above. This label is preferably a poly-histidine label, and is preferably located at the C terminal end of the recombinant protein of interest.

The fusion polypeptide of the invention can be the amino acid sequence of SEQ ID NO: 33 to 43, SEQ ID NO:56 or SEQ ID NO:58 (when the recombinant protein of interest is GrM), SEQ ID NO:73 or 75 (when the recombinant protein of interest is IFNα), SEQ ID NO:78 or 80 or 82 (when the recombinant protein of interest is the cancer antigen SSX2), SEQ ID NO: 85 or 87 (when the recombinant protein of interest is NERCMSL), SEQ ID NO:90 (when the recombinant protein of interest is FasL), or SEQ ID NO:93 (when the recombinant protein of interest is CNTN4).

Interestingly, the fusion proteins of the invention can be stored at 4° C. during several months without degradation. This in vitro stabilisation effect during storage could be the result of the scaffolding properties of the MGMT protein, and/or of the high concentration which is obtained thanks to the presence of the MGMT protein (typically at least 40 mg/mL).

More importantly, the association with MGMT stabilizes recombinant proteins during the purification process of the secreted proteins. It could thus be used for stabilising recombinant proteins in vivo once administered into a subject in need thereof. The coupling to MGMT would be a means for enhancing the life-span of such recombinant proteins in vivo. This in vivo stabilisation effect is currently under investigation.

In a fifth aspect, the present invention is drawn to a non-vertebrate recombinant host cell comprising the expression vector of the invention.

Non-vertebrate cells can be any cells from the Insect, Arachnida, Crustacea, Mollusca, Annelida, Cirripedia, Radiata, Coelenterata and Infusoria. In the context of the invention, non-vertebrate cells are preferably insect cells, such as *Drosophila* or Mosquito cells. They are more preferably a *Drosophila* S2 cells.

*Drosophila* S2 cells have been widely described. They are especially suited to high-yield production of protein, because they can be maintained in suspension cultures at room temperature (24±1° C.). Culture medium is M3 supplemented with between 5 and 10% (v/v) heat-inactivated fetal bovine serum (FBS). In the preferred embodiment of the invention, the culture medium contains 5% FBS. After induction, the cells are cultured in serum-free media. In this media, the S2 cells can be grown in suspension cultures, for example in 250 mL to 2000 mL spinner flasks, with stirring at 50-60 rpm. Cells densities are typically maintained between $10^6$ and $10^7$ cells per mL.

The present invention also targets recombinant S2 *Drosophila* cells comprising the expression vectors of the invention, said expression vectors comprising preferably the nucleotide sequence selected from the group consisting of:

the plasmid SEQ ID NO:64 (pUC57 with DeSNAP Univ) or the nucleotide sequence cloned in the cell which has been deposited according to the Budapest Treaty at the Centre National de Culture et de Microorganismes (CNCM), Institut Pasteur, 25 rue du Docteur Roux, 75724 Paris cedex 15, France, on Dec. 9, 2011, under the number CNCM I-4581, the vector comprising SEQ ID NO:19 or the nucleotide sequence cloned in the cell which has been deposited according to the Budapest Treaty at the Centre National de Culture et de Microorganismes (CNCM), Institut Pasteur, 25 rue du Docteur Roux, 75724 Paris cedex 15, France, on Aug. 19, 2010, under the number CNCM I-4357, the vector of the invention comprising SEQ ID NO:22, or the nucleotide sequence cloned in the cell which has been deposited at the Centre National de Culture et de Microorganismes (CNCM), Institut Pasteur, on Oct. 27, 2010 under the CNCM I-4381, the vector of the invention comprising SEQ ID NO:21 or the nucleotide sequence cloned in the cell which has been deposited at the Centre National de Culture et de Microorganismes (CNCM), Institut Pasteur, on Oct. 27, 2010, under the number CNCM I-4382, the vector of SEQ ID NO:9 or the nucleotide sequence cloned in the cell which has been deposited at the Centre National de Culture et de Microorganismes (CNCM), Institut Pasteur, on Sep. 29, 2010, under the number CNCM I-4368, and the vector of the invention comprising SEQ ID NO: 20 or the nucleotide sequence cloned in the cell which has been deposited at the Centre National de Culture et de Microorganismes (CNCM), Institut Pasteur, on Sep. 29, 2010, under the number CNCM I-4369, the vector of SEQ ID NO:71, the vector of the invention comprising SEQ ID NO:57 or 72 or 74 (when the protein of interest is IFNα), SEQ ID NO: 77, 79 or 81 (when the protein of interest is the cancer antigen SSX2), SEQ ID NO:55 (when the protein of interest is Granzyme M), SEQ ID NO:89 (when the protein of interest is FasL), SEQ ID NO:84 or 86 (when the protein of interest is the cancer antigen NERCMSL), or SEQ ID NO:92 (when the protein of interest is the contacting CNTN4) or SEQ ID NO:96 (when the protein of interest is hSULF-$2^{\Delta TMD}$).

The stably transfected S2 cells of the invention can also be selected from the group consisting of:

the cell which has been deposited at the Centre National de Culture et de Microorganismes (CNCM), Institut Pasteur, 25 rue du Docteur Roux, 75724 Paris cedex 15, France, on Aug. 19, 2010, under the number CNCM I-4357, the cell which has been deposited at the Centre National de Culture et de Microorganismes (CNCM), Institut Pasteur (25 rue du Docteur Roux, 75724 Paris cedex 15, France) on Oct. 27, 2010 under the CNCM 1-4381, the cell which has been deposited at the Centre National de Culture et de Microorganismes (CNCM), Institut Pasteur (25 rue du Docteur Roux, 75724 Paris cedex 15, France) on Oct. 27, 2010, under the number CNCM 1-4382, the cell which has been deposited at the Centre National de Culture et de Microorganismes (CNCM), Institut Pasteur (25 rue du Docteur Roux, 75724 Paris cedex 15, France) on Sep. 29, 2010, under the number CNCM 1-4368, the cell which has been deposited at the Centre National de Culture et de Microorganismes (CNCM), Institut Pasteur (25 rue du Docteur Roux, 75724 Paris cedex 15, France) on Sep. 29, 2010, under the number CNCM 1-4369, the cell which has been deposited at the Centre National de Culture et de Microorganismes (CNCM), Institut Pasteur (25 rue du Docteur Roux, 75724 Paris cedex 15, France) on Dec. 5, 2011, under the number CNCM 1-4565, the cell which has been deposited at the Centre National de Culture et de Microorganismes (CNCM), Institut Pasteur (25 rue du Docteur Roux, 75724 Paris cedex 15, France) on Dec. 5, 2011, under the number CNCM 1-4566, the cell which has been deposited at the Centre National de Culture et de Microorganismes (CNCM), Institut Pasteur (25 rue du Docteur Roux, 75724 Paris cedex 15, France) Dec. 5, 2011, under the number CNCM 1-4567, the cell which has been deposited at the Centre National de Culture et de Microorganismes (CNCM), Institut Pasteur (25 rue du Docteur Roux, 75724 Paris cedex 15, France) on Dec. 5, 2011, under the number CNCM 1-4568, the cell which has been deposited at the Centre National de Culture et de Microorganismes (CNCM), Institut Pasteur (25 rue du Docteur Roux, 75724 Paris cedex 15, France) on Dec. 5, 2011, under the number CNCM 1-4569, the cell which has been deposited at the Centre National de Culture et de Microorganismes (CNCM), Institut Pasteur (25 rue du Docteur Roux, 75724 Paris cedex 15, France) on Dec. 5, 2011, under the number CNCM 1-4570, the cell which has been deposited at the Centre National de Culture et de Microorganismes (CNCM), Institut Pasteur (25 rue du Docteur Roux, 75724 Paris cedex 15, France) on Dec. 5, 2011, under the number CNCM 1-4571, the cell which has been deposited at the Centre National de Culture et de Microorganismes (CNCM), Institut Pasteur (25 rue du Docteur Roux, 75724 Paris cedex 15, France) on Dec. 5, 2011, under the number CNCM 1-4572, the cell which has been deposited at the Centre National de Culture et de Microorganismes (CNCM), Institut Pasteur (25 rue du Docteur Roux, 75724 Paris cedex 15, France) on Dec. 8, 2011, under the number CNCM 1-4576, the cell which has been deposited at the Centre National de Culture et de Microorganismes (CNCM), Institut Pasteur (25 rue du Docteur Roux, 75724 Paris cedex 15, France) on Dec. 8, 2011, under the number CNCM 1-4577, the cell which has been deposited at the Centre National de Culture et de Microorganismes (CNCM), Institut Pasteur (25 rue du Docteur Roux, 75724 Paris cedex 15, France) on Dec. 8, 2011, under the number CNCM 1-4578, the cell which has been deposited at the Centre National de Culture et de Microorganismes (CNCM), Institut Pasteur (25 rue du Docteur Roux, 75724 Paris cedex 15, France) on Dec. 8, 2011, under the number CNCM 1-4579, the cell which has been deposited at the Centre National de Culture et de Microorganismes (CNCM), Institut Pasteur (25 rue du Docteur Roux, 75724 Paris cedex 15, France) on Dec. 8, 2011, under the number CNCM 1-4580, the cell which has been deposited at the Centre National de Culture et de Microorganismes (CNCM), Institut Pasteur (25 rue du Docteur Roux, 75724 Paris cedex 15, France) on Dec. 9, 2011, under the number CNCM 1-4582, the cell which has been deposited at the Centre National de Culture et de Microorganismes (CNCM), Institut Pasteur (25 rue du Docteur Roux, 75724 Paris cedex 15, France) on Dec. 9, 2011, under the number CNCM 1-4583, the cell which has been deposited at the Centre National de Culture et de Microorganismes (CNCM), Institut Pasteur (25 rue du Docteur Roux, 75724 Paris cedex 15, France) on Dec. 9, 2011, under the number CNCM 1-4584, the cell which has been deposited at the Centre National de Culture et de Microorganismes (CNCM), Institut Pasteur (25 rue du Docteur Roux, 75724 Paris cedex 15, France) on Dec. 9, 2011, under the number CNCM 1-4585, and the cell which has been deposited at the Centre National de Culture et de Microorganismes (CNCM), Institut Pasteur (25 rue du Docteur Roux, 75724 Paris cedex 15, France) on Dec. 9, 2011, under the number CNCM 1-4586.

The recombinant cell deposited under the number CNCM 1-4357 is the stable macrophage *Drosophila* cell line S2 comprising the plasmid vector of SEQ ID NO: 19 (pMT/BiP/SNAP-RVF.N/Histag), where RVF.N is the N antigen of the Rift Valley Fever virus (RVF) (see Brehin et al, *Virology* 371:185, 2008).

The recombinant cell deposited under the number CNCM 1-4381 is the stable macrophage *Drosophila* cell line S2 comprising a plasmid vector pMT/BiPN5-Histag in which the SEQ ID NO:22 (SNAP/WN.EDIII) has been inserted after the BiP sequence, where WN.EDIII is the III domain of the glycoprotein E of the West Nile virus.

The recombinant cell deposited under the number CNCM 1-4382 is the stable macrophage *Drosophila* cell line S2 comprising a plasmid vector pMTN5-Histag in which the SEQ ID NO:21 (BiP/SNAP/IFNαI) has been inserted. IFNα1 is the human alfa 1 interferon of SEQ ID NO:32 (Mokkim et al. *Protein expression purif.* 63:140, 2009).

The recombinant cell deposited at the CNCM 1-4369 is the stable macrophage *Drosophila* cell line S2 comprising a plasmid vector pMT/BiPN5-Histag containing the SEQ ID NO:20 (WN.sE/SNAP/histag), where WN.sE is the soluble form of the E envelope protein of the West Nile virus.

The recombinant cell deposited at the CNCM 1-4369 is the stable macrophage *Drosophila* cell line S2 comprising a plasmid vector pMT/BiPN5-Hi stag containing the SEQ ID NO:20 (WN. sE/SNAP/histag), where WN.sE is the soluble form of the E envelope protein of the West Nile virus.

The recombinant cell deposited at the CNCM 1-4565 is the stable macrophage *Drosophila* cell line S2 comprising a plasmid vector pMT/BiP/SNAP+DV1.EDIII/Hi stag, where DV1.EDIII encodes the EDIII protein of the Dengue virus 1, and has the sequence SEQ ID NO:27.

The recombinant cell deposited at the CNCM 1-4566 is the stable macrophage *Drosophila* cell line S2 comprising a plasmid vector pMT/BiP/SNAP+DV2.EDIII/Histag, where DV2.EDIII encodes the EDIII protein of the Dengue virus 2, and has the sequence SEQ ID NO:28.

The recombinant cell deposited at the CNCM 1-4567 is the stable macrophage *Drosophila* cell line S2 comprising a plasmid vector pMT/BiP/SNAP+DV3.EDIII/Histag, where DV3.EDIII encodes the EDIII protein of the Dengue virus 3, and has the sequence SEQ ID NO:29.

The recombinant cell deposited at the CNCM 1-4568 is the stable macrophage *Drosophila* cell line S2 comprising a plasmid vector pMT/BiP/SNAP+DV4.EDIII/Histag, where DV4.EDIII encodes the EDIII protein of the Dengue virus 4, and has the sequence SEQ ID NO:30.

The recombinant cell deposited at the CNCM 1-4569 is the stable macrophage *Drosophila* cell line S2 comprising a plasmid vector pMT/BiP/SNAP+YF.EDIII/Histag, where YF.EDIII encodes the EMI protein of the Yellow Fever virus, and has the sequence SEQ ID NO:31.

The recombinant cell deposited at the CNCM 1-4570 is the stable macrophage *Drosophila* cell line S2 comprising a plasmid vector pMT/BiP/SNAP+JE.EDIII/Histag, where JE.EDIII encodes the EDIII protein of the Japanese encephalitis virus, and has the sequence SEQ ID NO:25.

The recombinant cell deposited at the CNCM 1-4571 is the stable macrophage *Drosophila* cell line S2 comprising a plasmid vector pMT/BiP/SNAP+USU.EDIII/Histag, where USU.EDIII encodes the EDIII protein of the Usutu virus, and has the sequence SEQ ID NO:24.

The recombinant cell deposited at the CNCM 1-4572 is the stable macrophage *Drosophila* cell line S2 comprising a plasmid vector pMT/BiP/SNAP+TBE.EDIII/Histag, where TBE.EDIII encodes the EDIII protein of the Tick-borne encephalitis virus, and has the sequence SEQ ID NO:26.

The recombinant cell deposited at the CNCM 1-4576 is the stable macrophage *Drosophila* cell line S2 comprising a plasmid vector pMT/BiP/SNAP+MVE.EDIII/Histag, where MVE.EDIII encodes the EDIII protein of the Murray encephalitis virus.

The recombinant cell deposited at the CNCM 1-4577 is the stable macrophage *Drosophila* cell line S2 comprising a plasmid vector pMT/BiP/SNAP+Rocio.EDIII/Histag, where Rocio.EDIII encodes the EDIII protein of the Rocio virus.

The recombinant cell deposited at the CNCM 1-4578 is the stable macrophage *Drosophila* cell line S2 comprising a plasmid vector pMT/BiP/SNAP+SLE.EDIII/Histag, where SLE.EDIII encodes the EMI protein of the Saint-Louis encephalitis virus.

The recombinant cell deposited at the CNCM 1-4579 is the stable macrophage *Drosophila* cell line S2 comprising a plasmid vector pMT/BiP/SNAP+WSL.EDIII/Histag, where WSL.EDIII encodes the EDIII protein of the Wesselbron virus.

The recombinant cell deposited at the CNCM 1-4580 is the stable macrophage *Drosophila* cell line S2 comprising a plasmid vector pMT/BiP/SNAP+Zika.EDIII/Histag, where Zika.EDIII encodes the EDIII protein of the Zika virus.

The recombinant cell deposited at the CNCM 1-4583 is the stable macrophage *Drosophila* cell line S2 comprising a plasmid vector pMT/BiP/SNAP+SSX2/Histag, where SSX2 is of SEQ ID NO:76.

The recombinant cell deposited at the CNCM 1-4584 is the stable macrophage *Drosophila* cell line S2 comprising a plasmid vector pMT/BiP/SNAP+NERCMSL/Histag, where NERCMSL is of SEQ ID NO:83.

The recombinant cell deposited at the CNCM 1-4585 is the stable macrophage *Drosophila* cell line S2 comprising a plasmid vector pMT/BiP/SNAP+GrM/Histag, where GrM is of SEQ ID NO:54.

The recombinant cell deposited at the CNCM 1-4586 is the stable macrophage *Drosophila* cell line S2 comprising a plasmid vector pMT/BiP/ProTEV/Histag, where proTEV is of SEQ ID NO:52.

In a sixth aspect, the present invention targets also a vertebrate recombinant cell which is stably transfected by the expression vector of the invention.

Preferably, said vertebrate recombinant cell is a mammal cell, a preferably CHO, YB2/O, COS, HEK, NIH3T3, HeLa cell or derivatives thereof. More preferably, in this case, the expression vector of the invention comprises SEQ ID NO: 57 or 72 or 74 (when the protein of interest is IFNα), SEQ ID NO: 77, 79 or 81 (when the protein of interest is the cancer antigen SSX2), SEQ ID NO:55 (when the protein of interest is Granzyme M), SEQ ID NO:89 (when the protein of interest is FasL), SEQ ID NO:84 or 86 (when the protein of interest is the cancer antigen NERCMSL), SEQ ID NO:92 (when the protein of interest is the contacting CNTN4) or SEQ ID NO:96 (when the protein of interest is hSULF2$^{\Delta TMD}$). In a seventh aspect, the present invention is drawn to a method of enhancing expression of recombinant protein(s) comprising co-expressing said protein(s) with a peptidic secretion signal, together with the enzyme 6-methylguanine-DNA-methyltransferase (MGMT) (EC 2.1.1.63), a mutant or a catalytic domain thereof. Said co-expression is performed preferably in non-vertebrate cells, and, more preferably, insect cells.

More preferably, in this method, the MGMT enzyme is the protein of SEQ ID NO:4 or an homologous thereof, for example the SNAP protein of SEQ ID NO:2 or an homologous thereof.

In the context of the invention, the term "enhancing expression" of a heterologous protein means that the expression of said protein in the supernatant of the recombinant cells or within the cells themselves is improved by a factor of at least 2 fold, preferably 5 fold, more preferably 10 fold, and even more preferably 20 fold, as compared with the expression and/or secretion of said protein obtained with a recombinant vector of the prior art, that is, that does not co-express the protein with a MGMT or a SNAP protein. In a preferred embodiment, the term "enhancing expression" means that it is possible to recover from the supernatant of the host cells that have been transfected with the vector of the invention at least 40 mg/L, preferably at least 50 mg/L, more preferably at least 60 mg/L of a protein of interest.

The term "co-expressing" means that the DNA sequences encoding i) the recombinant protein, ii) the MGMT enzyme, mutant or catalytic domain thereof, and iii) the peptidic secretion signal, are operatively linked and regulated by the same expression control sequence (i.e. transcriptional and translational control sequences). The translation of the DNA sequences encoding the peptidic secretion signal, the heterologous protein of interest and the MGMT enzyme therefore leads to the formation of a fusion polypeptide, in which the proteins can be separated by a spacer sequence, and/or an enzyme cleavage site as defined above.

The "peptidic secretion signal" of the fusion polypeptide of the invention is a secretion signal which is preferably functional either in non-vertebrate cells, or in vertebrate cells, or both, and more preferably in insect cells, even more preferably in *Drosophila* S2 cells.

Examples of peptidic secretion signals which are functional in insect cells are: the insect ssBiP of SEQ ID NO:48, the BiP-like signal of SEQ ID NO:51 and any peptide signal present in an arbovirus, for example the envelop E protein of the West-Nile virus (SEQ ID NO: 15).

One example of a peptidic secretion signal which is functional in both vertebrate and non-vertebrate cells is the BiP-like signal of SEQ ID NO:51.

In a eighth aspect, the present invention is drawn to a method to improve the production of a recombinant protein of interest or to produce recombinant proteins in cell culture, comprising the use of the vector of the invention as described above, or the recombinant host cells as described above.

More precisely, said method to improve the production of a recombinant protein of interest, or to produce recombinant proteins in cell culture, comprises the steps of:

a) providing the nucleotide expression vector of the invention, encoding said protein of interest, b) introducing said expression vector into host cells, preferably non-vertebrate or vertebrate host cells, c) allowing for the expression of the nucleotide introduced in said host cells to produce said recombinant protein of interest.

Preferably, said non-vertebrate host cells are insect cells, for example Drosophila S2 cells.

Preferably, said vertebrate hosts cells are mammal cells, for example CHO, YB2/O, COS, HEK, NIH3T3, HeLa cells or derivatives thereof.

By using this method, the recombinant protein of interest is expressed at least at 40 mg/L of the recovered cell culture supernatant or greater.

The use of the Drosophila cell line S2 which secretes the gene product directly into the media is a preferred embodiment of the present invention (direct secretion into the media allows utilisation of an efficient one-step purification system).

In a ninth embodiment, the present invention is drawn to the use of the enzyme 6-methylguanine-DNA-methyltransferase (MGMT) (EC 2.1.1.63), mutant, or catalytic domain thereof, for enhancing the production level of recombinant protein(s) preferably in non-vertebrate and/or vertebrate host cells, more preferably in insect cells or mammal cells, infected with replicative or defective vectors.

The MGMT enzyme can be the human MGMT (referenced as NP_002403.2) of sequence SEQ ID NO:4, the mouse MGMT identified as NP_032624.1 (SEQ ID NO: 45), the rat MGMT identified as NP_036993.1 (SEQ ID NO:46), an homologous sequence thereof, or sub-fragments thereof.

Preferably, the MGMT mutant enzyme is the SNAP protein of SEQ ID NO:2 or is homologous thereof, i.e. it is at least identical at more than 80%, preferably 85%, more preferably 90% to the SNAP protein of sequence SEQ ID NO:2.

Said non-vertebrate cells are preferably insect cells, for example Drosophila S2 cells.

In a preferred embodiment, the present invention is drawn to the use of the enzyme 6-methylguanine-DNA-methyltransferase (MGMT) (EC 2.1.1.63), mutant, or catalytic domain thereof, for enhancing the production level of recombinant protein(s) in vertebrate cells, for example in mammal cells, infected with replicative or defective vectors.

Said vertebrate cells are preferably EBX, CHO, YB2/O, COS, HEK, NIH3T3 cells or derivatives thereof.

Also, the present invention is drawn to the use of a DNA sequence encoding an MGMT enzyme, mutant or catalytic domain thereof, for improving the production level of protein(s) of interest in recombinant cells.

The present invention is also drawn to the use of a DNA sequence encoding an MGMT enzyme, mutant or catalytic domain thereof, for i) stabilizing recombinant protein(s) of interest in vitro and in vivo, and thus ii) enhancing their life-span in vitro and in vivo.

Such DNA sequence is for example the human MGMT gene sequence NM 002412.3, gene ID 4255 (SEQ ID NO:3) or any homologous sequence thereof which encodes a functional MGMT enzyme, a mutant, or a catalytic domain thereof (preferably SEQ ID NO:1, SEQ NO: 47, SEQ ID NO: 67 or SEQ ID NO:68).

In particular, the present invention is drawn to the use of the 6-methylguanine-DNA-methyltransferase enzyme (MGMT, EC 2.1.1.63), mutants or catalytic domain thereof as protective polypeptide fused or linked to recombinant proteins to improve recombinant protein half-life in storage medium, in plasma or in buffer, to improve half-life of recombinant protein used as medicament or vaccine, or to improve half-life of recombinant protein used in diagnostic kits.

In the context of the invention, the term "improving the production level" or "enhancing the production level" of a heterologous protein means that the expression of said protein in the supernatant of said cells or inside the cells is improved by a factor of at least 2 fold, preferably 5 fold, more preferably 10 fold, and even more preferably 20 fold, as compared with the expression of said protein obtained with a recombinant vector of the prior art, that is, that does not comprise the vector of the invention. In a preferred embodiment, the term "improving the production" means that it is possible to recover from the supernatant of the host cells that have been transfected with the vector of the invention at least 40 mg/L, preferably at least 50 mg/L, more preferably at least 60 mg/L of a protein of interest.

In a preferred embodiment, said recombinant protein is chosen among: insulin, IFN, SSX2, Granzyme M, FasL, Mesotheline (NERMCSL), endosulfatase (hSULF) or contactins.

In a particular embodiment, the present invention is also drawn to a method for the production of a recombinant protein of interest, the method comprising the steps of:

(a) obtaining an heterologous DNA sequence encoding a recombinant protein of interest;

(b) inserting said heterologous DNA sequence into the nucleotide expression vector of the invention, said vector having for example the DNA sequence SEQ ID NO:9, SEQ ID NO:10, SEQ ID NO:64 or SEQ ID NO:71, (c) transfecting an host cell (preferably an insect cell or a mammal cell) with the polynucleotide obtained under step (b);

(d) allowing for the expression of said polynucleotide obtained under step (c) to produce the protein of interest;

(e) optionally, cleaving the MGMT polypeptide, (f) recovering the protein of interest, (g) optionally, purifying the protein of interest.

For performing the different steps of the method of the present invention, there may be employed conventional molecular biology, microbiology and recombinant DNA techniques within the skill of the art. Such techniques are explained fully in the literature. See, for example, Sambrook, Fitsch & Maniatis, Molecular Cloning: A Laboratory Manual, Second Edition (1989) Cold Spring Harbor Laboratory Press, Cold Spring Harbor, N.Y. (referred to herein as "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins, eds. 1984); Animal Cell Culture (R. I. Freshney, ed. 1986); Immobilized Cells and Enzymes (IRL Press, 1986); B. E. Perbal, A Practical Guide to Molecular Cloning (1984); F. M. Ausubel et al. (eds.), Current Protocols in Molecular Biology, John Wiley & Sons, Inc. (1994).

The term "transfection" means the introduction of a foreign nucleic acid into a eukaryotic host cell so that the host cell will express the introduced gene or sequence to produce a desired substance, in this invention a protein coded by the introduced gene or sequence. A host cell that receives and expresses introduced DNA or RNA has been "transfected" and is a "transfectant" or a "clone". The DNA or RNA introduced to a host cell can come from any source, including cells of the same genus or species as the host cell or cells of a different genus or species.

In the context of the invention, the transfection of the host cells with the polynucleotides can be performed by a classical method in the art, for example by transfection, infection, or electroporation. In another embodiment, the vector of the invention can be introduced in vivo by lipofection (as naked DNA), or with other transfection facilitating agents (peptides, polymers, etc.). Synthetic cationic lipids can be used to prepare liposomes for in vivo transfection of a gene encoding a marker (Feigner et al., Proc. Natl. Acad. Sci. U.S.A., 84:7413-7417, 1987). Useful lipid compounds and compositions for transfer of nucleic acids are described in WO 95/18863 and WO 96/17823, and in U.S. Pat. No. 5,459,127. Lipids may be chemically coupled to other molecules for the purpose of targeting (see, Mackey et al., Proc. Natl. Acad. Sci. U.S.A., 85:8027-8031, 1988). Targeted peptides, such as hormones or neurotransmitters, and proteins such as antibodies, or non-peptide molecules could be coupled to liposomes chemically. Other molecules are also useful for facilitating transfection of a nucleic acid in vivo, such as a cationic oligopeptides (see WO 95/21931), peptides derived from DNA binding proteins (see WO 96/25508), or a cationic polymer (see WO 95/21931). It is also possible to introduce the vector in vivo as a naked DNA plasmid. Naked DNA vectors for gene therapy can be introduced into the desired host cells by methods known in the art, such as electroporation, microinjection, cell fusion, DEAE dextran, calcium phosphate precipitation, use of a gene gun, or use of a DNA vector transporter (see, Wu et al., J. Biol. Chem., 267:963-967, 1992; Wu and Wu, J. Biol. Chem., 263:14621-14624, 1988; Williams et al., Proc. Natl. Acad. Sci. U.S.A., 88:2726-2730, 1991).

The term "allowing for the expression" of a polynucleotide herein means that the stimulus of the regulatory sequences that are present in the vector (e.g. the stimulus activating the inducible promoter), and all the required components are present in a sufficient amount for the translation of the polynucleotide to occur.

If need be, the cleaving of the MGMT/SNAP polypeptide of the produced fusion protein is obtained by adding a protease having a define cleavage site in the supernatant of or into the recombinant cells. For example, the cleavage of the enterokinase cleavage site DDDK/D is obtained by adding an enterokinase enzyme in the supernatant of the recombinant cells. Alternatively, the MGMT/SNAP polypeptide can be maintained so as to enhance the life-span of the recombinant proteins.

Moreover, the skilled artisan will appreciate that an expressed or secreted protein or polypeptide can be detected in the culture medium used to maintain or grow the present host cells. The culture medium can be separated from the host cells by known procedures, such as centrifugation or filtration. The protein or polypeptide can then be detected in the cell-free culture medium by taking advantage of known properties characteristic of the protein or polypeptide. Such properties can include the distinct immunological, enzymatic or physical properties of the protein or polypeptide. For example, if a protein or polypeptide has a unique enzyme activity an assay for that activity can be performed on the culture medium used by the host cells. Moreover, when antibodies reactive against a given protein or polypeptide are available, such antibodies can be used to detect the protein or polypeptide in any known immunological assay (for example as in Harlowe, et al., 1988, Antibodies: A Laboratory Manual, Cold Spring Harbor Laboratory Press).

Recovery of the protein of interest is mediated by the means well-known in the art, including, but not limited to, preparative disc-gel electrophoresis, isoelectric focusing, HPLC, reversed-phase HPLC, gel filtration, ion exchange and partition chromatography, precipitation and salting-out chromatography, extraction, and countercurrent distribution, and the like. As it is preferable to produce the protein of interest in the recombinant system of the invention linked with a label, said label will facilitate the recovery of the polypeptide from the crude lysate of the host cell by chromatography on an appropriate solid-phase matrix. Alternatively, antibodies produced against the protein or against peptides derived therefrom can be used as recovery reagents.

A further step (g) of purification may be achieved, but interestingly is not required.

A purified material may contain less than about 50%, preferably less than about 75%, and most preferably less than about 90%, of the cellular components with which it was originally associated. The "substantially pure" indicates the highest degree of purity which can be achieved using conventional purification techniques known in the art.

In an embodiment of the invention, the methods of the invention enable to obtain at least 40 mg/L, preferably at least 50 mg/L, more preferably at least 60 mg/L of the substantially pure protein of interest in the recovered cell culture supernatant.

The recombinant proteins of interest and the fusion proteins of the invention (i.e. the recombinant proteins coupled with the MGMT/SNAP polypeptide, which are more stable than the recombinant proteins alone) may be useful in a variety of products. For example, these recombinant and/or fusion proteins may be used in pharmaceutical compositions, for example for the treatment of viral infections.

In a preferred embodiment, said recombinant protein is chosen among: insulin, IFN, FasL, Granzyme M, SSX2, Mesotheline (NERMCSL), endosulfatase (hSULF) or contactins.

In another embodiment, the present invention provides infectious viral particles comprising the above-described nucleic acid vectors. Typically, such viral particles are produced by a process comprising the steps of:

(a) introducing the viral vector of the invention into a suitable cell line, (b) culturing said cell line under suitable conditions so as to allow the production of said infectious viral particle, (c) recovering the produced infectious viral particle from the culture of said cell line, and (d) optionally purifying said recovered infectious viral particle.

When the viral vector is defective, the infectious particles are usually produced in a complementation cell line or via the use of a helper virus, which supplies in trans the non functional viral genes. For example, suitable cell lines for complementing E1-deleted adenoviral vectors include the 293 cells as well as the PER-C6 cells. The infectious viral particles may be recovered from the culture supernatant or from the cells after lysis. They can be further purified according to standard techniques (chromatography, ultra-centrifugation in a cesium chloride gradient as described for example in WO96/27677, WO98/00524, WO98/22588, WO98/26048, WO00/40702, EP1016700 and WO00/50573).

The present invention is thus drawn to pharmaceutical compositions comprising the expression vector, the recombinant proteins, the fusion proteins, the host cells or the viral particles of the invention, or any combination thereof. Such pharmaceutical compositions comprise a therapeutic amount of the vector, particles, cells or proteins obtained by the method of the invention in admixture with a pharmaceutically acceptable carrier.

The composition can be systematically administered parenterally, intravenously or subcutaneously. When systematically administered, the therapeutic composition for use in this invention is in the form of a pyrogen-free, parenterally acceptable protein solution. The preparation of such parenterally acceptable protein solution, having due regard to pH, isotonicity, stability and the like, is within the skill of the art.

The dosage regimen will be determined by attending clinician, considering various factors which modify the action of drugs, e.g. the condition body weight, sew and diet of the patient, the severity of the infection, time of administration and other clinical factors. The pharmaceutical carrier and other components of a pharmaceutical composition would be selected by one of skill in the art.

Additionally the fusion and recombinant proteins of the present invention may be used as components of vaccines to inoculate mammalian subjects against viral infection for example. These proteins may be used either alone or with other recombinant proteins or therapeutic vaccinal agents. Components of such a vaccine would be determined by one of skill in the art.

The present invention also encompasses the use of the fusion proteins, the expression vectors, the infectious viral particles, the host cells or the pharmaceutical compositions of the invention for the preparation of a medicament, in particular a vaccine.

The present invention also provides a method for the treatment or the prevention of a human or animal organism, comprising administering to said organism a therapeutically effective amount of the fusion proteins, the expression vectors, the infectious viral particles, the host cells or the compositions of the invention.

Finally the proteins of the present invention, and especially the SNAP-protein of interest fusion, may be useful as diagnostic agents for the detection of the presence of cancer, viral infection or antibodies to viral proteins in biological fluids, such as blood, serum, saliva, and the like. These proteins may also be employed in methods to identify and/or isolate viral proteins in biological fluids and tissues. The proteins may thus be components in kits to perform such methods.

Thus, in another aspect, the present invention is also drawn to the use of recombinant proteins or MGMT- or SNAP-tagged recombinant proteins from pathogenic or non-pathogenic microorganisms obtained by any method of the invention for identifying the presence of said pathogenic or non-pathogenic microorganisms in a biological sample. In a preferred embodiment, said pathogenic microorganism is a virus, and the MGMT- or SNAP-tagged protein is a viral protein, such as EDIII from the Chikungunya, Dengue, Japanese encephalitis (JE), Tick-borne encephalitis (TBE), Yellow fever (YF), Usutu (USU) or West Nile viruses, or the nucleoprotein N from Rift Valley Fever or Toscana viruses.

In the context of the invention, said biological sample is meant to be a blood sample, an urine sample, or any biological sample which is possibly infected by the virus.

EXAMPLES

1. Plasmid(s) Construction 1.1. The plasmid pMT/BiPN5-His A was used. It contains 3642 nucleotides and contains the following features:

Metallothionein promoter: bases 412-778
Start of transcription: base 778
MT Forward priming site: bases 814-831
BiP signal sequence: bases 851-904 (SEQ ID NO:11)
Multiple cloning site: bases 906-999
V5 epitope tag: bases 1003-1044
Polyhistidine region: bases 1054-1074
BGH Reverse priming site: bases 1094-1111
SV40 late polyadenylation signal: bases 1267-1272
pUC origin: bases 1765-2438 (complementary strand)
bla promoter: bases 3444-3542 (complementary strand)
Ampicillin (bla) resistance gene ORF: bases 2583-3443 (complementary strand)

The pUC57 Amp vector can also be used for the purposes of the invention. This vector comprises:
The unique cloning site EcoR I
The Methallothionein promoter,
The 5' non-coding region of genomic RNA from West Nile virus strain IS-98-ST1,
An initiation codon of translation (ATG),
The signal peptide of the envelope E protein from West Nile virus strain IS-98-ST1 (SEQ ID NO: 15),
The 3' non-coding region of genomic RNA from West Nile virus strain IS-98-ST1 in which two repeat sequences and the 3'end stem-loop have been deleted,
The S40 polyA signal motif,
An unique cloning site Apa I.

1.2. SNAP Cloning

Amplification of the DNA encoding the SNAP protein sequence SEQ ID NO:2 was performed on template pMT/BiP/CHIK.sE2+SNAPtag by PCR using the couple of 5'-SNAP and 3'-MCS primers as described below.

```
Primer 5'-SNAP:
                                    (SEQ ID NO: 7)
5'-aaaaaagatctgacaaagactgcgaaatg-3'

Primer 3'-MCS:
                                    (SEQ ID NO: 8)
5'-gaggagagggttagggataggcttacc-3'
```

The PCR product was then digested by BglII and NotI and inserted between the unique BglII (at the 5' end of MCS) and NotI (at the 3' end of the MCS) sites of the linearized plasmid p/MT/BiP/V5-A in the DES system.

The resulting plasmid is the pMT/BiP/SNAP-Histag vector of SEQ ID NO:9, which comprises:
The insect ssBiP sequence of SEQ ID NO:11,
the SNAP DNA sequence of SEQ ID NO:1,
the enterokinase cleavage site of SEQ ID NO:12,
a EcoRV-SmaI restriction site,
the DNA encoding a His6tag (SEQ ID NO:14) located downstream of the restriction site, and
two DNA spacer sequences of SEQ ID NO:13 located i) between the enhancer sequence and the EcoRV-SmaI restriction site, and ii) between the EcoRV-SmaI restriction site and the DNA encoding a His6tag.

A pMT/BiP/SNAP-Histag vector can also be obtained from a pUC57 backbone and a vector having the sequence SEQ ID NO: 10 is obtained. This vector comprises:
The unique cloning site EcoR I
Methallothionin promoter
The 5' non-coding region of genomic RNA from West Nile virus strain IS-98-ST1,
An initiation codon of translation,
The signal peptide of the envelope E protein from West Nile virus strain IS-98-ST1 of SEQ ID NO:15, The SNAP DNA sequence of SEQ ID NO:47,
Unique cloning sites EcoR V et SmaI/Xma I for inserting in frame the foreign sequence,
The Enterokinase cleavage site of SEQ ID NO:12, located between the SNAP enhancer DNA and the cloning sites,
A DNA encoding a Hexa-histidin tag sequence (SEQ ID NO:14),
Two DNA spacer sequence of SEQ ID NO:13, located i) between the enhancer sequence and the EcoRV-SmaI restriction site, and ii) between the EcoRV-SmaI restriction site and the DNA encoding a His6tag.
Two stop codons of translation,
The 3' non-coding region of genomic RNA from West Nile virus strain IS-98-ST1 in which two repeat sequencse and the 3'end stem-loop have been deleted,
S40 polyA signal motifs and
Unique cloning site Apa I.

A pMT/BiP-like/SNAP-Hi stag vector can also be obtained from a pUC57 backbone in which the SEQ ID NO: 59 (see also FIG. 8) has been inserted between the unique sites Eco RV and Hind III. This vector has the sequence SEQ ID NO: 64. It comprises:
The unique cloning site EcoR I
Methallothionin promoter
The 5' non-coding region of genomic RNA from West Nile virus strain IS-98-ST1,
An initiation codon of translation,
The signal peptide of the envelope E protein from West Nile virus strain IS-98-ST1 of SEQ ID NO:15,
The SNAP DNA sequence of SEQ ID NO:47,
Unique cloning sites BamHI, EcoR V, ApaI and Xma I for inserting in frame the foreign sequence,
two proTEV cleavage sites of SEQ ID NO:52, located between the SNAP enhancer DNA and the HisTag,
A DNA encoding a Hexa-histidin tag sequence (SEQ ID NO:14),
Two DNA spacer sequences of SEQ ID NO:13, located i) between the enhancer sequence and the EcoRV-SmaI restriction site, and ii) between the ApaI restriction site and the DNA encoding a His6tag.
Two stop codons of translation,
The 3' non-coding region of genomic RNA from West Nile virus strain IS-98-ST1 in which two repeat sequences and the 3'end stem-loop have been deleted,
S40 polyA signal motifs and
Unique cloning site Apa I.

1.3. Cloning of a Gene of Interest
1.3.1. Nucleoprotein N of the Rift Valley Fever Virus (RVF-N)
Directed mutagenesis on a cDNA coding for the RFV-N protein sequence was performed by PCR using the couple of 5'-N and 3'-N' primers as listed below.

```
Primer 5'-N:
                                     (SEQ ID NO: 17)
5'-aaaaaggcgcgccaggggtggcggatctgacaactatcaagag cttcgagtccagtttgctgctc-3'

Primer 3'-N:
                                     (SEQ ID NO: 18)
5'-aaaaaaccggtcaatgatgatgatgatgatgacttccaccgccg gctgctgtcttgtaagcctgagcgg-3'
```

1.3.2. Non-viral protein, for example interferon IFNα1 or Granzyme M
The human IFNα1 protein sequence of SEQ ID NO:32 can also be used.
The human Granzyme M protein sequence of SEQ ID NO:54 can also be used. Granzyme M is a chymotrypsin-like serine protease that preferentially cuts its substrates after Met or Leu. It is constitutively expressed in activated innate effector natural killer cells. This protease also has anti-viral and anti-tumor properties (van Domselaar R. et al, *The Journal of Immunology* 2010; Hu D. et al, *The Journal of Biological Chemistry* 2010).

1.4. Insertion of a protein-encoding gene into the pMT/BiP/SNAP-Histag or pMT/BiP like/SNAP-Histag vector, so as to obtain pMT/BiP/SNAP-PROTEIN-Histag or pMT/BiPlike/SNAP-PROTEIN-Histag vectors 1.4.1. RVF.N
The PCR products obtained in point 1.3.1. were digested by BssHII and AgeI and inserted between the unique BssHII (at the 3'end of SNAP gene) and AgeI (at the 3'end of the MCS of shuttle vector) sites of the linearized plasmid p/MT/BiP/SNAP-Histag obtained in point 1.2.
The resulting plasmid is for example pMT/BiP/SNAP-RVF.N/Histag (SEQ ID NO:19).

1.4.2. ED III proteins of different flaviviruses
To enhance the specificity of ELISA or immunoblotting tests based on recombinant flaviviral antigens, the antigenic domain III of the E protein (ED III) appears to be a promising approach (Ludolfs et al. 2007). The production of recombinant EDIII from West Nile (WN), Usutu (USU), Japanese encephalitis (JE), tick-borne encephalitis (TBE), dengues serotypes 1 to 4 (DEN-1, -2, -3, -4) and Yellow fever (YF) virus have been tested with the method of the invention. Zoonotic WN, USU, and JE viruses belong to the JE serocomplex. The *Drosophila* S2 inducible expression system (DES, Invitrogen), has been chosen for the mass production of individual EDIII from flaviviruses in non-vertebrate cells. The synthetic genes coding for the full-length domain III of the E proteins from flaviviruses WN, USU, JE, TBE, DEN-1 to DEN-4 and YF are listed in SEQ ID NO: 23 to SEQ ID NO: 31. The ED III sequences were fused in frame to the C-terminus of the SNAP protein in the plasmid pMT/BiP/SNAP-Histag obtained in 1.2. to generate the fusions proteins SNAP-EDIII.

1.4.3. IFNα
A plasmid pMT/BiP/SNAP-IFN-Histag (see FIG. 4) and pMT/BiP-like/SNAP-IFN-Histag has been obtained (see details on FIG. 8).

1.4.4. Granzyme M
A plasmid pMT/BiP/SNAP-GrM-Histag has been obtained (see details on FIG. 6).

2. Transfection into Host Cells 2.1. Transfection into S2 cells
The resulting plasmids pMT/BiP/SNAP-PROTEIN-His$_{tag}$ that allows the production of SNAP-tagged proteins as secreted fusion proteins ended by the His$_{tag}$, were co-transfected with selection marker pCo-Blast into S2 cells to generate the stable S2/sSNAP-PROTEIN-His$_{tag}$ cell line showing resistance to Ampicilline.
Stable S2 cell lines grown in spinner (1000 ml) were stimulated 10 days with heavy metal cadmium (Cd2+) and proteins from extracellular medium were concentrated and purified.

Accumulation of secreted SNAP-tagged protein was observed in the supernatants of stable S2/sSNAP-PROTEIN-Histag cells after 10 days of induction with heavy metal cadmium.

Immunoblot assays enable to detect extracellular SNAP-tagged proteins using goat serum anti-Histag (see FIGS. 2B, 3B, 4B, 6C).

2.2. Transfection into HeLa Cells

The plasmid pMT/BiPlike/SNAP-IFN-His$_{tag}$ was transfected into HeLa cells.

Immunoblot assays enable to detect extracellular SNAP-tagged IFN using anti-SNAP antibodies (see FIG. 7B).

3. Purification of Recombinant Proteins

Extracellular His-tagged and SNAP-tagged proteins were purified using metal-chelating resin and HLPC method.

3.1. RVF-N and TOS-N

RVF-N

In collaboration with the Plate-Forme 5 Production de Protéines recombinantes et d'Anticorps (Institut Pasteur), as high as 97 mg of highly purified SNAP-tagged RVF.N protein have been obtained from 2 liters of S2/sSNAP-RVFV.N-$His_{tag}$ cell supernatants 10 days after stimulation with $Cd^{2+}$.

TOS-N

In collaboration with the Plate-Forme 5 Production de Protéines recombinantes et d'Anticorps (Institut Pasteur) as high as 41 mg of highly purified SNAP-tagged RVF.N protein have been obtained from 2 liters of S2/sSNAP-TOS.N-$His_{tag}$ cell supematants 10 days after stimulation with $Cd^{2+}$.

Summary of the Production Levels:

| Viral antigens | Plasmids | Stable cell lines | Purified proteins | Concentration (/2 L) |
|---|---|---|---|---|
| N gene from RVF | pMT/BiP/SNAP+RVF.N | S2/SNAP+RVF.N | SNAP-RVF.N | 97 mg |
| N gene from TOS | pMT/BiP/SNAP+TOS.N | S2/SNAP+TOS.N | SNAP-TOS.N | 41 mg |

3.2. Soluble IFNα1

The soluble IFNα1 proteins has been released from the SNAP tag by cleaving with the enterokinase enzyme (Novagen kit).

3.3. Antigens from Different Flaviviruses

Stocks of secreted SNAP-tagged proteins using *Drosophila* expression system

| Viral antigens | Plasmids | Purified proteins | Production per liter of cell culture | Concentration of purified proteins |
|---|---|---|---|---|
| EDIII from DEN-1 | pMT/BiP/SNAP+DV1.EDIII | sSNAP-DV1.EDIII | 132 mg | 4.93 mg/ml |
| EDIII from DEN-2 | pMT/BiP/SNAP+DV2.EDIII | sSNAP-DV2.EDIII | 59 mg | 2.67 mg/ml |
| EDIII from DEN-3 | pMT/BiP/SNAP+DV3.EDIII | sSNAP-DV3.EDIII | 124 mg | 3.54 mg/ml |
| EDIII from DEN-4 | pMT/BiP/SNAP+DV4.EDIII | sSNAP-DV4.EDIII | 43 mg | 1.67 mg/ml |
| EDIII from WN | pMT/BiP/SNAP+WN.EDIII | sSNAP-WN.EDIII | 176 mg | 4.2 mg/ml |
| EDIII from JE | pMT/BiP/SNAP+JE.EDIII | sSNAP-JE.EDIII | 223 mg | 6.38 mg/ml |
| EDIII from USU | pMT/BiP/SNAP+USU.EDIII | sSNAP-USU.EDIII | 182 mg | 4.8 mg/ml |
| EDIII from TBE | pMT/BiP/SNAP+TBE.EDIII | sSNAP-TBE.EDIII | 180 mg | 5.13 mg/ml |
| EDIII from YF | pMT/BiP/SNAP+YF.EDIII | sSNAP-YF.EDIII | 120 mg | 3.46 mg/ml |
| EDIII from MVE | pMT/BIP/SNAP+MVE.EDIII | sSNAP-MVE.EDIII | 87 mg | |
| EDIII from ROCIO | pMT/BIP/SNAP+Rocio.EDIII | sSNAP-Rocio.EDIII | 79 mg | |
| EDIII from WSL | pMT/BIP/SNAP+WSL.EDIII | sSNAP-WSL.EDIII | 63 mg | 2 mg/ml |
| EDIII from ZIKA | pMT/BIP/SNAP+Zika.EDIII | sSNAP-ZIKA.EDIII | 152 mg | 3.8 mg/ml |
| SNAP-DV1ectoM | pMT/BiP/SNAP−DV1ectoM | SNAP-DV1ectoM | 49 mg | 1.4 mg/ml |
| N gene from RVF | pMT/BiP/SNAP+N.RVF | sSNAP-N.RVF | 97 mg | 1.3 mg/ml |
| N gene from TOS | pMT/BiP/SNAP+N.TOS | sSNAP-N.TOS | 41 mg | 1.65 mg/ml |
| SNAP | pMT/BiP/SNAP | SNAP | 13 mg | 1 mg/ml |
| sE from WN | pMT/BiP/WN.sE+SNAP | WN.sE+SNAP | 40 mg | 2.3 mg/ml |
| sE2 from CHIK | pMT/BiP/CHIK.sE2+SNAP | CHIK.sE2-SNAPtag | 90 mg | 1.2 mg/ml |
| SNAP-EKS-IFNA1 | pMT/BiP/SNAP−EKS-IFNA1 | SNAP-EKS-IFNA1 | 49 mg | 3.5 mg/ml |

EDIII: domain antigenic III from flavivirus E proteins (Dengue [DEN], West Nile [WN], Japanese encephalitis [JE], Usutu [USU], Tick-borne encephalitis [TBE], Yellow Fever [YF], Murray Encephalitis [MVE], Wesselbron [WSL], Rocio, Zika)

ectoM: ectodomain of the M protein from dengue virus type 1

N gene from RVF: the nucleoprotein N of the Rift Valley Fever Virus (major viral antigen)

N gene from TOS: the nucleoprotein N of the Toscana Virus (major viral antigen)

sE from WN: soluble form of the envelope E protein from West Nile virus sE2 from CHIK: soluble form of the envelope E2 protein from Chikungunya SNAP-IFNAI: interferon-alpha 1 in fusion with SNAP.

3.4. Production of Granzyme M 10 mg of SNAP-GrM protein per liter of culture supernatant have been recovered in 7 days.

After purification steps, three forms of SNAP-GrM have been detected (see FIG. 6C) which correspond to the cleavage of the SNAP protein by the coupled GrM enzyme.

This clearly means that the human protease is active after being produced by the method of the invention (see below).

4. Control of the SNAP-Tagged Proteins

Immunoblots assays using specific antibodies (recognizing the protein of interest and/or to the Histag label) detected a substantial production of extracellular SNAP-tagged proteins:

Immunoblot assay detected extracellular SNAP-tagged RVF.N protein using goat serum anti-His$_{tag}$ (FIG. 2B). Human and mouse immune sera against RVF.N specifically recognize recombinant SNAP-tagged RVF.N protein.

Immunoblot assays showed no cross-reactivity between recombinant WN and USU EDIII using specific mouse polyclonal sera despite the high level of sequence similarity. Thus, the secreted soluble SNAP-EDIII from WNV, JE, USU are suitable as recombinant viral antigens for the specific diagnosis of members of JE serocomplex since USU and, in a lesser extent, JE viruses have recently been identified as potential emerging arboviruses in Europe.

5. Activity of SNAP-Tagged Recombinant Proteins

Soluble Recombinant SNAP-IFNαI Secreted from Induced S2/SNAP-IFNαI Cells Exhibits Potent Antiviral Effect Against CHIKV.

Supernatants (5 ml) of $Cd^{2+}$-stimulated S2/SNAP-IFNαI (#5×10^6 cells/ml) were collected 10 days post-induction. Accumulation of soluble SNAP-IFNαI protein was observed on cell supernatant by immunoblot using anti-Histag antibody (see below). Antiviral activity of SNAP-IFNαI was assessed on HeLa cells infected with Chikungunya virus expressing the luciferase (Luc) gene. Luc activity was determined 6 h post-infection. IFN alphacon 1 (Infergen) was used as an internal assay knowing its potent antiviral effect against CHIKV in HeLa cells. Supernatant of $Cd^{2+}$-stimulated S2/SNAP-Tos.N (the N protein from Toscana virus) served as a negative control. The graph depicted on FIG. 4C demonstrates that 1 µl of secreted SNAP-IFNαI or 0.1 µg of Infergen could suppress CHIKV replication inside the infected host cells. A dose-dependent effect of SNAP-IFNα is shown in the graph. Twenty percent of Luc activity was still observed with 0.1 µl of soluble SNAP-IFNαI or 0.01 µg of Infergen. No antiviral effect was observed using SNAP-TOS-N at the higher dose tested.

Granzyme M is Active Once it is Produced in the Supernatant of the S2 Cells

As mentioned previously, three forms of SNAP-GrM have been detected in the supernatant of S2 cells transfected with the vector pMT/BiP/SNAP-GrM-Histag (see FIG. 6C).

These three forms correspond to the cleavage of the SNAP protein by the coupled GrM enzyme. SNAP indeed contains three potential cleavage sites of GrM (see FIG. 6B). Immunoassays with either anti-His or anti-SNAP antibodies have revealed that these three forms are indeed fragments of the secreted fusion protein SNAP-GrM.

The smaller form (35 kDa) corresponds to GrM which has been deleted with the major part of SNAP during the purification process.

These results clearly show that the GrM protease which has been produced by the system of the invention is active, although it is coupled with the SNAP protein.

This is really interesting since active human proteases are known to be very difficult to produce recombinantly.

hSULF-2$^{\Delta TMD}$ is Active Once it is Produced in the Supernatant of HEK 293 Cells hSULF-2$^{\Delta TMD}$ has been expressed and purified from HEK-293 cells transfected with a recombinant plasmid pcDNA3/De SNAPuniv-hSULF-2$^{\Delta TMD}$ (see FIG. 13A).

The enzymatic activity of the hSULF-2$^{\Delta TMD}$ polypeptide obtained in the supernatant has been assessed as follows:

HEK 293 cells were transiently transfected with pcDNA3/DeSNAP-hSULF2ΔTMDs. After two days, an aliquote of cell supernatant was incubated with the Non-fluorescent pseudo-substrate 4-Methyl Umbelliferone (4-MUS) at 20 mM in 50 mM Tris pH7.5, 20 mM MgCl2 was incubated (1:1, V/V) with the enzyme (in conditioned medium) for 2-4 hours at 37° C. in a 96-well plate. The enzymatic reaction was stopped by addition (1:1 v/v) of 1.5 M NaHCO3/Na2CO3 pH 10.5 and generation of 4-Methyl Umbelliferone fluorescent product was monitored by fluorimetry (excitation: 360 nm). The values of the SULF activity in cell supernatant are measured in optical density (OD) at 460 nm.

Interestingly, the secreted protein (coupled with SNAP?) is active as shown on FIG. 13B.

6. Stability of SNAP-Tagged Recombinant Proteins

It has been surprisingly observed that the fusion proteins comprising the SNAP peptide are far more stable in vitro than in its absence.

Highly purified CHIK.sE2-SNAP, SNAP-WN.EDIII and SNAP-IFNAI proteins at the non-saturating concentrations of 0.1 mg/ml (Vol: 0.1 ml) in sterile PBS were incubated either 4 days at −80° C., 4° C., 25° C. or 37° C., or two months at the same temperature.

Protein samples (1 µg) were separated in SDS-PAGE 4-12% and visualized with Coomassie Brillant Blue G-250 dye using PageBlue Protein Staining solution (Fermentas).

Figure 10:
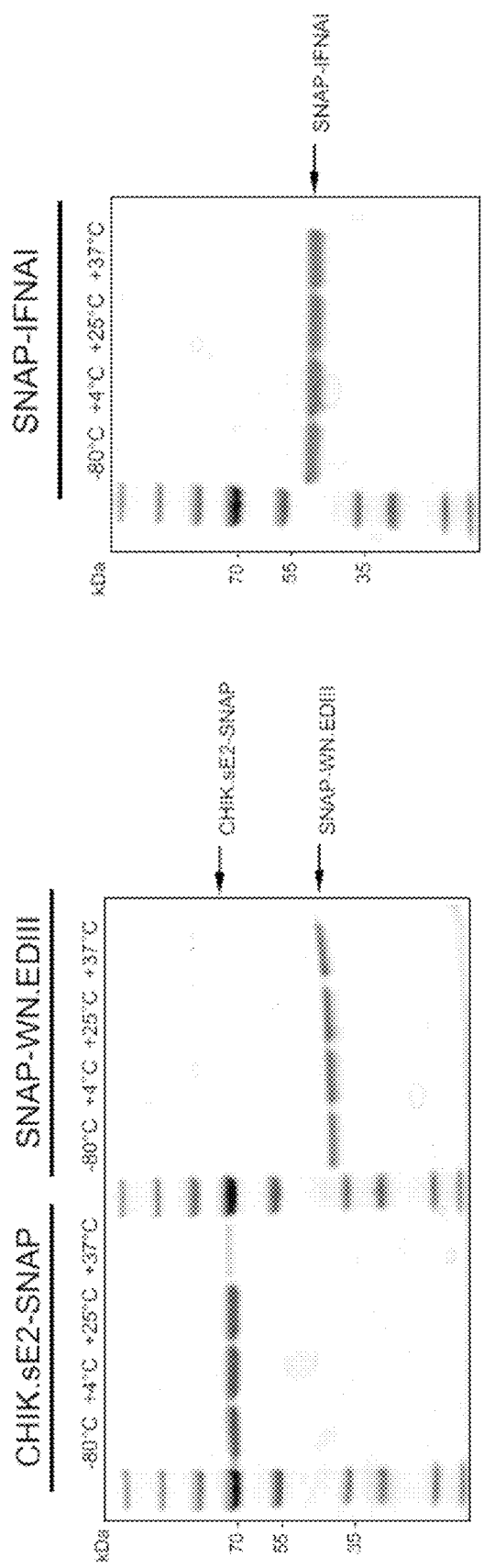
Figure 10:
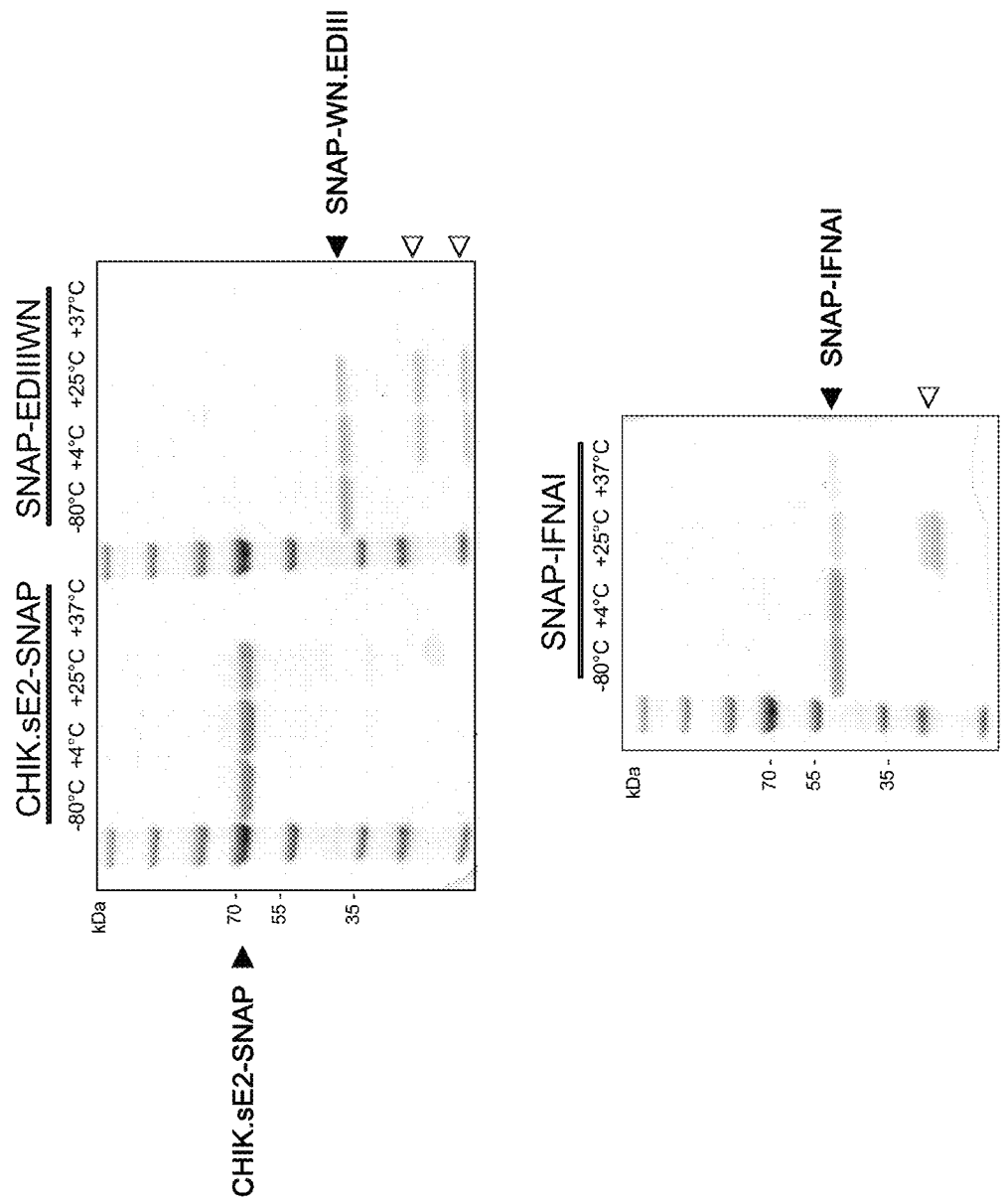

FIGS. 10 A and B discloses theresults obtained by comparing the stability of three different fusion proteins in vitro.

Importantly, all the fusion proteins appeared to be intact after two months at 4° C., and also after four days incubation at room temperature (25° C.) or at 37° C.

In particular, IFN is not affected after 4 days at body temperature (37° C.), and is still observed after two months at 37° C., so that in vivo stability is likely to be highly increased through its coupling to SNAP.

7. In Vitro Detection of SNAP-RVF.N Produced by S2 Cells

SNAP-RVF.N fusion proteins which have been produced according to the above-mentioned protocols were used as diagnostic tool for detecting anti-RVF.N antibodies in the sera of infected ovines.

These fusion proteins have been tested and compared with commercial kits of detection (RVF IgG detection kit from BDSL and RVF multi-species from IdVet).

The tests have been conducted on 46 sheeps sera, the sheeps being immunised by RVF vaccines. SNAP-RVF.N fusion proteins were directly coated on the bottom of the wells, or were biotinylated and added to streptavidin coated wells.

Anti-RVF antibodies were detected by indirect ELISA method using microtitration 96-well plaques directly coated with 0.2 µg of highly purified recombinant antigen SNAP-RVF.N in PBS (concentration: 2 µs protein/ml) for overnight at 4° C. After saturation, diluted sera were incubated with SNAP-RVF.N. Peroxidase-conjugated goat anti-IgG was used as secondary antibody. ELISA was performed with peroxidase substrate system and optical density (OD) was measured at 450 nm. Sample sera were considered to be positive if the OD were twice the OD from non immune sera.

Interestingly, the results show that the SNAP-RVF.N fusion proteins give the same sensitivity and specificity than the commercial proteins when directly coated onto the wells (not shown). The results are less reproducible when the proteins are biotinylated, The same results have been obtained on sera obtained from naturally immunised bovines (data not shown).

These results show that the fusion proteins of the invention can be used as diagnostic tools for identifying viral infection or bacterial infections in biological samples.

8. Multiplex Bead-Based Immunoassay

In the context of the invention, a multiplex bead-based immunoassay was developed for rapid and simultaneous detection of antibodies to arboviruses in biological fluids. The system is based on the xMAP technology (Luminex corporation) and uses a mixture of antigen-coated microspheres as capture reagents for specific human immunoglobulins. Distinct sets of microspheres (Magplex, Luminex corporation) were coupled with purified MGMT fusion proteins, namely the SNAP-tagged viral recombinant proteins described in section 3.3: sSNAP-DV1.EDIII, sSNAP-DV2.EDIII, sSNAP-DV3.EDIII, sSNAP-DV4.EDIII, sSNAP-WN.EDIII, sSNAP-JE.EDIII, sSNAP-USU.EDIII, sSNAP-TBE.EDIII, sSNAP-YF.EDIII, sSNAP-MVE.EDIII, sSNAP-Rocio.EDIII, sSNAP-WSL.EDIII, sSNAP-ZIKA.EDIII SNAP-DV1ectoM, sSNAP-N.RVF, sSNAP-N.TOS, and CHIK.sE2-SNAP.

Recombinant antigens were covalently coupled to the carboxyl microsphere surface using a substrate of the MGMT protein as linker (BG-PEG-NH2, New England Biolabs), thereby enhancing antibody capture efficiency as compared to standard amine coupling procedures.

Technical validation using anti-SNAP-tag antibodies and specific mouse monoclonal antibodies confirmed coupling efficiency and demonstrated long-term antigen stability (up to six month). This application is not limited to viral antigens as any peptide or polypeptide can be used for bead coating and subsequent antibody capture.

BIBLIOGRAPHIC REFERENCES

Ausubel F. M. et al. (eds.), *Current Protocols in Molecular Biology*, John Wiley & Sons, Inc. (1994).

Bond B. J. et al, *Mol. Cell. Biol.* 6:2080 (1986)

Brehin et al, *Virology* 371:185, 2008

Brinster et al., *Nature,* 296:39-42, 1982

Cheever et al, *Clinical Cancer Research,* 2009, 15:5323-5337

Dai et al, the Journal of Biological Chemistry, 2005, vol. 280. no 48, pp. 40066-40073

Daniels D. S. et al, *EMBO J.* 19: 1719-1730, 2000

Feigner et al., *Proc. Natl. Acad. Sci. U.S.A.,* 84:7413-7417, 1987

Harlowe, et al., 1988, Antibodies: A Laboratory Manual, Cold Spring Harbor Laboratory Press Hellwig S et al, *Nature Biotechnology*, no 11, vol. 22, 2004

Hu D. et al, 2010 *The Journal of Biological Chemistry*, vol. 285, no 24, pp18326-18335

Juillerat A. et al, *Chemistry & Biology*, vol. 10, 313-317, 2003

Lastowski-Perry et al, *J. Biol. Chem.* 260:1527 (1985)

Lim A. et al, *EMBO J* 15: 4050-4060, 1996

Ludolfs et al, 2007 *Eur J Clin Microbiol Infect Dis.* 2007 July; 26(7):467-73

Ma J K C et al, *Nature Genetics*, Review 2004, 794-800

Mackey et al., *Proc. Natl. Acad. Sci. U.S.A.,* 85:8027-8031, 1988

Miller and Rosman, *BioTechniques,* 7:980-990, 1992

Mokkim et al. *protein expression purif.* 63:140, 2009.

Pegg A. E. et al, *Mutat. Res.* 2000; 462, 82-100

Perbal B. E., *A Practical Guide to Molecular Cloning* (1984);

Sambrook, Fitsch & Maniatis, *Molecular Cloning*: A Laboratory Manual, Second Edition (1989) Cold Spring Harbor Laboratory Press, Cold Spring Harbor, N.Y. (referred to herein as "Sambrook et al., 1989");

Shimoda Y. and Watanabe K., *Cell adhesion and migration,* 2009, 3:1, 64-70 van Domselaar R. et al, *The Journal of Immunology,* 2010

Wibley et al, *Nucleic acid research* 2000

Williams et al., *Proc. Natl. Acad. Sci. U.S.A.,* 88:2726-2730, 1991

Wu and Wu, *J. Biol. Chem.,* 263:14621-14624, 1988;

Wu et al., *J. Biol. Chem.,* 267:963-967, 1992;

DNA Cloning: A Practical Approach, Volumes I and II (D. N. Glover ed. 1985);

Oligonucleotide Synthesis (M. J. Gait ed. 1984);

Nucleic Acid Hybridization (B. D. Hames & S. J. Higgins, eds. 1984);

Animal Cell Culture (R. I. Freshney, ed. 1986);

Immobilized Cells and Enzymes (IRL Press, 1986);

The invention claimed is:

1. A vector for expressing recombinant proteins in host cells, comprising a nucleotide sequence encoding in a single open reading frame, from 5' to 3':
    a) a peptidic secretion signal which is functional in said host cells,
    b) a 6-methylguanine-DNA-methyltransferase enzyme (MGMT) or a mutant thereof,
    wherein said MGMT enzyme or MGMT mutant is the protein of SEQ ID NO:4, or a homologous sequence thereof that is at least 75% identical to SEQ ID NO:4, and
    c) a recombinant protein.

2. The expression vector according to claim 1, wherein said MGMT enzyme or MGMT mutant is the protein of SEQ ID NO:4, or a homologous sequence thereof that is at least 80% identical to SEQ ID NO:4.

3. The expression vector according to claim 1, wherein said open reading frame is operatively associated with an inducible promoter which is functional in the same host cell as the peptidic signal.

4. The expression vector according to claim 3, wherein said secretion peptidic signal and said inducible promoter are functional in non-vertebrate cells.

5. The expression vector according to claim 3, wherein said secretion peptidic signal and said inducible promoter are functional in vertebrate cells.

6. The expression vector according to claim 1, wherein the recombinant protein is selected from the group consisting of:
    bacterial or viral immunogenic proteins selected from the EDIII protein from Dengue, Japanese encephalitis (JE), Tick-borne encephalitis (TBE), Yellow fever (YF), Usutu (USU), Rocio, Murray Encephalitis (MVE), Wesselbron (WSL), Zika and West Nile (WN) viruses, the nucleoprotein N from Rift Valley Fever (RVF) and Toscana (TOS) viruses, the soluble form of the E2 envelope protein from the Chikungunya virus, and the soluble form of the E envelope protein of the West-Nile virus
    blood factors, anticoagulants, growth factors, hormones, therapeutic enzymes and monoclonal antibodies and cytokines,
    anti-tumoral proteins,
    microbial, viral and/or parasite polypeptides, and antigens.

7. The expression vector according to claim 1, wherein said recombinant protein is selected from the group consisting of Interferon α (IFNα), Granzyme M, FasL, SSX2, NERCMSL, hSULF2$^{ATMD}$ and CNTN4.

8. The expression vector according to claim 1, wherein said MGMT enzyme is encoded by the DNA sequence of SEQ ID NO:3, or SEQ ID NO:68.

9. The expression vector according to claim 1, further encoding at least one peptidic cleavage site, which is preferably located between the MGMT enzyme, or a mutant or catalytic domain thereof, and the recombinant protein.

10. The vector according to claim 1, encoding in frame from 5' to 3':
    a peptidic BiP insect signal or a BiP-like peptide signal,
    a MGMT protein of SEQ ID NO: 4,
    at least one enterokinase cleavage site or proTEV peptidic cleavage site,
    a poly-Histidine label, and,
    two spacer sequences having the amino acid sequence Glycine-Glycine-Glycine-Serine (GGGS).

11. A fusion polypeptide encoded by the vector of claim 1.

12. The fusion polypeptide according to claim 11, further comprising a label located at the C terminal end of the recombinant protein.

13. An isolated non-vertebrate recombinant cell which is stably transfected by the expression vector of claim 1.

14. The stably transfected cell according to claim 13, wherein it is an insect cell.

15. The stably transfected cell according to claim 13, wherein it is a *Drosophila melanogaster* cell.

16. An isolated vertebrate recombinant cell which is stably transfected by the expression vector of claim 1.

17. The stably transfected cell according to claim 16, wherein it is a mammalian cell.

18. A method of enhancing expression of recombinant protein(s) comprising expressing the vector of claim 1 in non-vertebrate cells.

19. The method according to claim 18, wherein said MGMT enzyme or MGMT mutant enzyme is the protein of SEQ ID NO:4, or a homologous sequence thereof that is at least 80% identical to SEQ ID NO:4.

20. A method to produce recombinant protein in cell culture, comprising the steps of:
    a) providing the expression vector of claim 1,
    b) introducing said expression vector into host cells,
    c) allowing for the expression of the nucleotide introduced in said host cells to produce the recombinant protein.

21. The expression vector according to claim 4, wherein said secretion peptidic signal is a BiP insect signal or a BiP-like peptide.

22. The expression vector according to claim 10, further encoding a recombinant protein comprised between the MGMT protein and the cleavage site, said protein being preferably selected from the group consisting of Interferon α (IFNα), Granzyme M, FasL, SSX2, NERCMSL, hSULF2$^{\Delta TMD}$ and CNTN4.

* * * * *

SEQUENCE LISTING

```
<160> NUMBER OF SEQ ID NOS: 97

<210> SEQ ID NO 1
<211> LENGTH: 579
<212> TYPE: DNA
<213> ORGANISM: Artificial Sequence
<220> FEATURE:
<223> OTHER INFORMATION: DNA of SNAP (mutant of hMGT)

<400> SEQUENCE: 1
agatctgaca aagactgcga aatgaagcgc accaccctgg atagccctct gggcaagctg      60
gaactgtctg ggtgcgaaca gggcctgcac gagatcaagc tgctgggcaa aggaacatct     120
```

```
gccgccgacg ccgtggaagt gcctgcccca gccgccgtgc tgggcggacc agagccactg    180
atgcaggcca ccgcctggct caacgcctac tttcaccagc ctgaggccat cgaggagttc    240
cctgtgccag ccctgcacca cccagtgttc cagcaggaga gctttacccg ccaggtgctg    300
tggaaactgc tgaaagtggt gaagttcgga gaggtcatca gctaccagca gctggccgcc    360
ctggccggca tcccgccgc accgccgcc gtgaaaaccg ccctgagcgg aaatcccgtg    420
cccattctga tcccctgcca ccgggtggtg tctagctctg gcgccgtggg gggctacgag    480
ggcgggctcg ccgtgaaaga gtggctgctg gcccacgagg ccacagact gggcaagcct    540 gggctgggtc ctgcaggtat aggcgcgcca gggtcccta                           579

<210> SEQ ID NO 2
<211> LENGTH: 193
<212> TYPE: PRT
<213> ORGANISM: Artificial Sequence
<220> FEATURE:
<223> OTHER INFORMATION: Amino acid sequence of SNAP

<400> SEQUENCE: 2

Arg Ser Asp Lys Asp Cys Glu Met Lys Arg Thr Thr Leu Asp Ser Pro
 1               5                  10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu

<210> SEQ ID NO 3
<211> LENGTH: 1265
<212> TYPE: DNA
<213> ORGANISM: homo sapiens

<400> SEQUENCE: 3
ctcggccccg ccccgcgcc cggatatgc tgggacagcc cgcgcccta gaacgctttg        60 cgtcccgacg cccgcaggtc ctcgcggtgc gcaccgtttg cgacttggta cttgaaaaaa    120
tggacaagga ttgtgaaatg aaacgcacca cactggacag cccttgggg aagctggagc    180
```

```
tgtctggttg tgagcagggt ctgcacgaaa taaagctcct gggcaagggg acgtctgcag    240
ctgatgccgt ggaggtccca gcccccgctg cggttctcgg aggtccggag ccctgatgc    300
agtgcacagc ctggctgaat gcctatttcc accagcccga ggctatcgaa gagttccccg    360
tgccggctct tcaccatccc gttttccagc aagagtcgtt caccagacag gtgttatgga    420
agctgctgaa ggttgtgaaa ttcggagaag tgatttctta ccagcaatta gcagccctgg    480
caggcaaccc caaagccgcg cgagcagtgg gaggagcaat gagaggcaat cctgtcccca    540
tcctcatccc gtgccacaga gtggtctgca gcagcggagc cgtgggcaac tactccggag    600
gactggccgt gaaggaatgg cttctggccc atgaaggcca ccggttgggg aagccaggct    660
tgggagggag ctcaggtctg cagggggcct ggctcaaggg agcgggagct acctcgggct    720
ccccgcctgc tggccgaaac tgagtatgtg cagtaggatg gatgtttgag cgacacacac    780
gtgtaacact gcatcggatg cggggcgtgg aggcaccgct gtattaaagg aagtggcagt    840
gtcctgggaa caagcgtgtc tgccctttct gtttccatat tttacagcag gatgagttca    900
gacgcccgcg gtcctgcaca catttgtttc cttctctaac gctgcccttg ctctattttt    960
catgtccatt aaaacaggcc aagtgagtgt ggaaggcctg gctcatgttg gccacagcc   1020
caggatgggg cagtctggca ccctcaggcc acagacggct gccatagccg ctgtccaggg   1080
ccagctaagg cccatcccag gccgtccaca ctagaaagct ggccctgccc catcccacc   1140
atgcctccct tcctggctgt gtccatggct gtgatgcat tctccactca gcagttccta   1200
gcatcccaca cccaggtctc actgaaagaa aggggaacag gccatggcag tcagtgctta   1260
cagag                                                              1265
```

<210> SEQ ID NO 4
<211> LENGTH: 238
<212> TYPE: PRT
<213> ORGANISM: homo sapiens

<400> SEQUENCE: 4

```
Met Leu Gly Gln Pro Ala Pro Leu Glu Arg Phe Ala Ser Arg Arg Pro
1               5                   10                  15

Gln Val Leu Ala Val Arg Thr Val Cys Asp Leu Val Leu Gly Lys Met
            20                  25                  30

Asp Lys Asp Cys Glu Met Lys Arg Thr Thr Leu Asp Ser Pro Leu Gly
        35                  40                  45

Lys Leu Glu Leu Ser Gly Cys Glu Gln Gly Leu His Glu Ile Lys Leu
    50                  55                  60

Leu Gly Lys Gly Thr Ser Ala Ala Asp Ala Val Glu Val Pro Ala Pro
65                  70                  75                  80

Ala Ala Val Leu Gly Gly Pro Glu Pro Leu Met Gln Cys Thr Ala Trp
                85                  90                  95

Leu Asn Ala Tyr Phe His Gln Pro Glu Ala Ile Glu Glu Phe Pro Val
            100                 105                 110

Pro Ala Leu His His Pro Val Phe Gln Gln Glu Ser Phe Thr Arg Gln
        115                 120                 125

Val Leu Trp Lys Leu Leu Lys Val Val Lys Phe Gly Glu Val Ile Ser
    130                 135                 140

Tyr Gln Gln Leu Ala Ala Leu Ala Gly Asn Pro Lys Ala Ala Arg Ala
145                 150                 155                 160

Val Gly Gly Ala Met Arg Gly Asn Pro Val Pro Ile Leu Ile Pro Cys
                165                 170                 175
```

```
His Arg Val Val Cys Ser Ser Gly Ala Val Gly Asn Tyr Ser Gly Gly
            180                 185                 190

Leu Ala Val Lys Glu Trp Leu Leu Ala His Glu Gly His Arg Leu Gly
        195                 200                 205

Lys Pro Gly Leu Gly Gly Ser Ser Gly Leu Ala Gly Ala Trp Leu Lys
    210                 215                 220

Gly Ala Gly Ala Thr Ser Gly Ser Pro Pro Ala Gly Arg Asn
225                 230                 235

<210> SEQ ID NO 5
<211> LENGTH: 713
<212> TYPE: DNA
<213> ORGANISM: Artificial Sequence
<220> FEATURE:
<223> OTHER INFORMATION: DNA sequence of BiP + SNAP+ enterokinase site +
      EcoRV/XmaI+Histag

<400> SEQUENCE: 5
atgaagttat gcatattact ggccgtcgtg gcctttgttg gcctctcgct cgggagatct      60
gacaaagact gcgaaatgaa gcgcaccacc ctggatagcc tctgggcaa gctggaactg     120 tctgggtgcg aacagggcct gcacgagatc aagctgctgg caaaggaac atctgccgcc     180 gacgccgtgg aagtgcctgc cccagccgcc gtgctgggcg accagagcc actgatgcag     240 gccaccgcct ggctcaacgc ctactttcac cagcctgagg ccatcgagga gttccctgtg     300
ccagccctgc accccagt gttccagcag agagcttta cccgccaggt gctgtggaaa        360
ctgctgaaag tggtgaagtt cggagaggtc atcagctacc agcagctggc cgccctggcc     420
ggcaatcccg ccgccaccgc cgccgtgaaa accgccctga gcggaaatcc cgtgcccatt     480
ctgatcccct gccaccgggt ggtgtctagc tctggcgccg tgggggcta cgagggcggg     540 ctcgccgtga aagagtggct gctggcccac gagggccaca gactgggcaa gcctgggctg     600
ggtcctgcag gtataggcgc gccagggtcc ctaggtggcg atctgatga cgatgataaa     660 gatatcaaaa acccgggcgg tggaagtcat catcatcatc atcattgacc ggt            713

<210> SEQ ID NO 6
<211> LENGTH: 614
<212> TYPE: DNA
<213> ORGANISM: Artificial Sequence
<220> FEATURE:
<223> OTHER INFORMATION: DNA sequence of SNAP+Histag

<400> SEQUENCE: 6
agatctgaca aagactgcga atgaagcgc accaccctgg atagccctct gggcaagctg      60
gaactgtctg ggtgcgaaca gggcctgcac gagatcaagc tgctgggcaa ggaacatct     120 gccgccgacg ccgtggaagt gcctgcccca gccgccgtgc tgggcggacc agagccactg     180
atgcaggcca ccgcctggct caacgcctac tttcaccagc ctgaggccat cgaggagttc     240
cctgtgccag ccctgcacca ccagtgttc cagcaggaga gctttacccg ccaggtgctg    300
tggaaactgc tgaaagtggt gaagttcgga gaggtcatca gctaccagca gctggccgcc    360
ctggccggca atcccgccgc caccgccgcc gtgaaaaccg ccctgagcgg aaatcccgtg    420
cccattctga tccctgcca ccgggtggtg tctagtctg cgccgtggg gggctacgag       480 ggcgggctcg ccgtgaaaga gtggctgctg gcccacgagg ccacagact gggcaagcct    540 gggctggtc ctgcaggtat aggcgcgcca gggtccctgg agcatcatca tcatcatcat    600
tgatgagcgg ccgc                                                     614
```

<210> SEQ ID NO 7
<211> LENGTH: 29
<212> TYPE: DNA
<213> ORGANISM: Artificial Sequence
<220> FEATURE:
<223> OTHER INFORMATION: Primer 5'-SNAP

<400> SEQUENCE: 7
aaaaaagatc tgacaaagac tgcgaaatg                                29

<210> SEQ ID NO 8
<211> LENGTH: 27
<212> TYPE: DNA
<213> ORGANISM: Artificial Sequence
<220> FEATURE:
<223> OTHER INFORMATION: Primer 3'-MCS (SNAP)

<400> SEQUENCE: 8
gaggagaggg ttagggatag gcttacc                                  27

<210> SEQ ID NO 9
<211> LENGTH: 4181
<212> TYPE: DNA
<213> ORGANISM: Artificial Sequence
<220> FEATURE:
<223> OTHER INFORMATION: DNA sequence of the vector of invention
      (DeSNAP1)

<400> SEQUENCE: 9
tcgcgcgttt cggtgatgac ggtgaaaacc tctgacacat gcagctcccg gagacggtca      60
cagcttgtct gtaagcggat gccggagca gacaagcccg tcagggcgcg tcagcgggtg      120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgccag tgaattttaa cgttgcagga      420
caggatgtgg tgcccgatgt gactagctct ttgctgcagg ccgtcctatc ctctggttcc      480
gataagagac ccagaactcc ggcccccac cgcccaccgc cacccccata catatgtggt      540
acgcaagtaa gagtgcctgc gcatgcccca tgtgccccac caagagtttt gcatcccata      600
caagtcccca agtggagaa ccgaaccaat tcttcgcggg cagaacaaaa gcttctgcac      660
acgtctccac tcgaatttgg agccggccgg cgtgtgcaaa agaggtgaat cgaacgaaag      720
acccgtgtgt aaagccgcgt ttccaaaatg tataaaaccg agagcatctg gccaatgtgc      780
atcagttgtg gtcagcagca aaatcaagtg aatcatctca gtgcaactaa agggggggatc      840 cgatctcaat atgaagttat gcatattact ggccgtcgtg gcctttgttg gcctctcgct      900
cgggagatct gacaaagact gcgaaatgaa gcgcaccacc ctggatagcc ctctgggcaa      960
gctggaactg tctgggtgcg aacagggcct gcacgagatc aagctgctgg gcaaaggaac      1020
atctgccgcc gacgccgtgg aagtgcctgc cccagccgcc gtgctgggcg accagagcc      1080 actgatgcag gccaccgcct ggctcaacgc ctactttcac cagcctgagg ccatcgagga      1140
gttccctgtg ccagccctgc accacccagt gttccagcag agagctttta cccgccaggt      1200
gctgtggaaa ctgctgaaag tggtgaagtt cggagaggtc atcagctacc agcagctggc      1260
cgccctggcc ggcaatcccg ccgccaccgc cgccgtgaaa accgccctga gcggaaatcc      1320

```
cgtgcccatt ctgatcccct gccaccgggt ggtgtctagc tctggcgccg tggggggcta    1380
cgagggcggg ctcgccgtga aagagtggct gctggcccac gagggccaca gactgggcaa    1440
gcctgggctg gtcctgcag gtataggcgc gccagggtcc ctggagcatc atcatcatca    1500
tcattgatga gcgccgctc gagtctagag ggcccttcga aggtaagcct atccctaacc    1560
ctctcctcgg tctcgattct acgcgtaccg gtcatcatca ccatcaccat tgagtttaaa    1620
cccgctgatc agcctcgact gtgccttcta aggcctgagc tcgctgatca gcctcgatcg    1680
aggatccaga catgataaga tacattgatg agtttggaca aaccacaact agaatgcagt    1740
gaaaaaaatg ctttatttgt gaaatttgtg atgctattgc tttatttgta accattataa    1800
gctgcaataa acaagttaac aacaacaatt gcattcattt tatgtttcag gttcaggggg    1860
aggtgtggga ggttttttaa agcaagtaaa acctctacaa atgtggtatg gctgattatg    1920
atcagtcgac ctgcaggcat gcaagcttgg cgtaatcatg gtcatagctg tttcctgtgt    1980
gaaattgtta tccgctcaca attccacaca acatacgagc cggaagcata aagtgtaaag    2040
cctggggtgc ctaatgagtg agctaactca cattaattgc gttgcgctca ctgcccgctt    2100
tccagtcggg aaacctgtcg tgccagctgc attaatgaat cggccaacgc gcgggagag    2160
gcggtttgcg tattgggcgc tcttccgctt cctcgctcac tgactcgctg cgctcggtcg    2220
ttcggctgcg gcgagcggta tcagctcact caaaggcggt aatacggtta tccacagaat    2280
caggggataa cgcaggaaag aacatgtgag caaaaggcca gcaaaaggcc aggaaccgta    2340
aaaaggccgc gttgctggcg ttttccata ggctccgccc ccctgacgag catcacaaaa    2400
atcgacgctc aagtcagagg tggcgaaacc cgacaggact ataaagatac caggcgtttc    2460
cccctggaag ctccctcgtg cgctctcctg ttccgaccct gccgcttacc ggatacctgt    2520
ccgcctttct cccttcggga agcgtggcgc tttctcatag ctcacgctgt aggtatctca    2580
gttcggtgta ggtcgttcgc tccaagctgg gctgtgtgca cgaaccccc gttcagcccg    2640
accgctgcgc cttatccggt aactatcgtc ttgagtccaa cccggtaaga cacgacttat    2700
cgccactggc agcagccact ggtaacagga ttagcagagc gaggtatgta ggcggtgcta    2760
cagagttctt gaagtggtgg cctaactacg gctacactag aaggacagta tttggtatct    2820
gcgctctgct gaagccagtt accttcggaa aaagagttgg tagctcttga tccggcaaac    2880
aaaccaccgc tggtagcggt ggtttttttg tttgcaagca gcagattacg cgcagaaaaa    2940
aaggatctca agaagatcct ttgatctttt ctacggggtc tgacgctcag tggaacgaaa    3000
actcacgtta agggattttg gtcatgagat tatcaaaaag gatcttcacc tagatccttt    3060
taaattaaaa atgaagtttt aaatcaatct aaagtatata tgagtaaact tggtctgaca    3120
gttaccaatg cttaatcagt gaggcaccta tctcagcgat ctgtctattt cgttcatcca    3180
tagttgcctg actccccgtc gtgtagataa ctacgatacg ggagggctta ccatctggcc    3240
ccagtgctgc aatgataccg cgagacccac gctcaccggc tccagattta tcagcaataa    3300
accagccagc cggaagggcc gagcgcagaa gtggtcctgc aactttatcc gcctccatcc    3360
agtctattaa ttgttgccgg gaagctagag taagtagttc gccagttaat agtttgcgca    3420
acgttgttgc cattgctaca ggcatcgtgg tgtcacgctc gtcgtttggt atggcttcat    3480
tcagctccgg ttcccaacga tcaaggcgag ttacatgatc ccccatgttg tgcaaaaaag    3540
cggttagctc cttcggtcct ccgatcgttg tcagaagtaa gttggccgca gtgttatcac    3600
tcatggttat ggcagcactg cataattctc ttactgtcat gccatccgta agatgctttt    3660
ctgtgactgg tgagtactca accaagtcat tctgagaata gtgtatgcgg cgaccgagtt    3720
```

```
gctcttgccc ggcgtcaata cgggataata ccgcgccaca tagcagaact ttaaaagtgc    3780
tcatcattgg aaaacgttct tcggggcgaa aactctcaag gatcttaccg ctgttgagat    3840
ccagttcgat gtaacccact cgtgcaccca actgatcttc agcatctttt actttcacca    3900
gcgtttctgg gtgagcaaaa acaggaaggc aaaatgccgc aaaaaaggga ataagggcga    3960
cacggaaatg ttgaatactc atactcttcc tttttcaata ttattgaagc atttatcagg    4020
gttattgtct catgagcgga tacatatttg aatgtattta gaaaaataaa caaatagggg    4080
ttccgcgcac atttccccga aaagtgccac ctgacgtcta agaaaccatt attatcatga    4140
cattaaccta taaaaatagg cgtatcacga ggccctttcg t                       4181

<210> SEQ ID NO 10
<211> LENGTH: 1720
<212> TYPE: DNA
<213> ORGANISM: Artificial Sequence
<220> FEATURE:
<223> OTHER INFORMATION: DNA sequence of the DeSNAP2 vector of the
      invention

<400> SEQUENCE: 10
gaattcgttg caggacagga tgtggtgccc gatgtgacta gctctttgct gcaggccgtc      60
ctatcctctg gttccgataa gagacccaga actccggccc ccaccgccc accgccaccc     120 ccatacatat gtggtacgca agtaagagtg cctgcgcatg ccccatgtgc cccaccaaga     180
gttttgcatc ccatacaagt ccccaaagtg gagaaccgaa ccaattcttc gcgggcagaa     240
caaaagcttc tgcacacgtc tccactcgaa tttggagccg gccggcgtgt gcaaaagagg     300
tgaatcgaac gaaagacccg tgtgtaaagc gcgtttcca aaatctataa aaccgagagc     360
atctggacca tgtgcatcag ttgtggtcag cagcaaaatc aagtgaatca tctcagtgca     420
actaaagggg ggatccgatc tcaatgcgag ctgtttctta gcacgaagat ctcgatgtct     480
aagaaaccag gagggccggg caagagccgg ctgtcaata ccatggttgt gtttgtcgtg     540
ctattgcttt tggtggcccc agcttacagc cttgatattg aatttacaga caaagactgc     600
gaaatgaaaa gaactacatt ggattcacca cttgggaagt tggaactgag tggatgcgag     660
caaggattgc atgaaattaa gcttctggga aaaggaactt ctgcagctga tgcagttgaa     720
gttccagcac cagcagctgt tcttggaggt cctgagcccc tcatgcaagc cacagcctgg     780
cttaacgcat atttccacca gcctgaggcc attgaggaat tccagtccc gcccttcac      840 catcctgtgt tcagcagga aagcttcacc cgccaggtcc tgtggaaatt gctgaaggtg     900
gtcaagtttg gtgaagtgat tcatatcag caacttgctg cattggccgg taaccccgca     960
gctacagctg ccgtgaaaac tgctctcagc ggaaatcctg tgcccatcct gatcccttgt    1020
cacagagtcg tttcatcttc cggagctgta ggtggctatg aaggaggact ggcagttaag    1080
gagtggctgc tggctcatga aggtcataga cttggaaaac ctggttgggg aggtggcgga    1140
tctgatgacg atgataaaga tatcatatac ccgggcggtg aagtcatca tcaccatcac    1200 cactgataaa tatttaatca attgtaaata gacaatataa gtatgcataa aagtgtagtt    1260
ttatagtagt atttagtggt gttagtgtaa atagttaaga aaattttgag gagaaagtca    1320
ggccgggaag ttcccgccac cggaagttga gtagacggtg ctgcctgcga ctcaaccca    1380 ggaggactgg gtgaacaaag ccgcgaagtg atccatgtaa gccctcagaa ccgtctcgga    1440
aggaggaccc cacatgttgt aacttcaaag cccaatgtca gaccacgcta cggcgtgcta    1500
ctctgcggag agtgcagtct gcgatagtgt aacaaaggca aatcaacgcc ccacgcggcc    1560
```

```
ctagccccgg taatggtgtt aaccagggcg aaaggactag aggttagagg agaccccgcg    1620
gtttaaagtg cacggcccag cctggctgaa gctgtaggtc aggggtggag accccgtgcc    1680
acaaaacacc acaacaaaac agcataaata aacagggccc                         1720
```

<210> SEQ ID NO 11
<211> LENGTH: 54
<212> TYPE: DNA
<213> ORGANISM: Artificial Sequence
<220> FEATURE:
<223> OTHER INFORMATION: DNA sequence encoding the ssBiP sequence

<400> SEQUENCE: 11

```
atgaagttat gcatattact ggccgtcgtg gcctttgttg gcctctcgct cggg          54
```

<210> SEQ ID NO 12
<211> LENGTH: 18
<212> TYPE: DNA
<213> ORGANISM: Artificial Sequence
<220> FEATURE:
<223> OTHER INFORMATION: DNA sequence encoding the enterokinase cleaving
      site

<400> SEQUENCE: 12

```
gatgacgatg ataaagat                                                  18
```

<210> SEQ ID NO 13
<211> LENGTH: 12
<212> TYPE: DNA
<213> ORGANISM: Artificial Sequence
<220> FEATURE:
<223> OTHER INFORMATION: DNA spacer sequence

<400> SEQUENCE: 13

```
ggtggcggat ct                                                        12
```

<210> SEQ ID NO 14
<211> LENGTH: 18
<212> TYPE: DNA
<213> ORGANISM: Artificial Sequence
<220> FEATURE:
<223> OTHER INFORMATION: DNA sequence encoding the His tag

<400> SEQUENCE: 14

```
catcatcatc atcatcat                                                  18
```

<210> SEQ ID NO 15
<211> LENGTH: 17
<212> TYPE: PRT
<213> ORGANISM: West Nile virus strain IS-98-ST1

<400> SEQUENCE: 15

```
Met Val Val Phe Val Val Le

| | |
|---|---|
| agatctgaca aagactgcga aatgaagcgc accaccctgg atagccctct gggcaagctg | 60 |
| gaactgtctg ggtgcgaaca gggcctgcac gagatcaagc tgctgggcaa aggaacatct | 120 |
| gccgccgacg ccgtggaagt gcctgcccca gccgccgtgc tgggcggacc agagccactg | 180 |
| atgcaggcca ccgcctggct caacgcctac tttcaccagc ctgaggccat cgaggagttc | 240 |
| cctgtgccag ccctgcacca cccagtgttc cagcaggaga gctttacccg ccaggtgctg | 300 |
| tggaaactgc tgaaagtggt gaagttcgga gaggtcatca gctaccagca gctggccgcc | 360 |
| ctggccggca atcccgccgc caccgccgcc gtgaaaaccg ccctgagcgg aaatcccgtg | 420 |
| cccattctga tccectgcca ccgggtggtg tctagctctg cgccgtgggg gggctacgag | 480 |
| ggcgggctcg ccgtgaaaga gtggctgctg gcccacgagg ccacagact gggcaagcct | 540 |
| gggctgggtc ctgcaggtat aggcgcgcca gggtccctag gtggcggatc tgacaactat | 600 |
| caagagcttc gagtccagtt tgctgctcaa gcagtggacc gcaatgagat tgaacagtgg | 660 |
| gtccgagagt ttgcttatca agggtttgat gcccgtagag ttatcgaact cttaaagcag | 720 |
| tatggtgggg ctgactggga aaggatgcc aagaaaatga ttgttctggc tctaactcgt | 780 |
| ggcaacaagc ccaggaggat gatgatgaaa atgtcgaaag aaggcaaagc aactgtggag | 840 |
| gctctcatca acaagtataa gctaaaggaa gggaatcctt cccgggatga gttgactcta | 900 |
| tcacgagttg ctgccgcctt ggctggctgg acatgccagg cttttggtcgt cttgagtgag | 960 |
| tggcttcctg tcactgggac taccatggac ggcctatccc ctgcataccc gaggcatatg | 1020 |
| atgcacccca gctttgctgg catggtggat ccttctctac caggagacta tctaagggca | 1080 |
| atattagatg ctcactctct gtatctgctg cagttctccc gggtcatcaa cccaaacctc | 1140 |
| cgaggtagaa caaaagagga ggttgctgca acgttcacgc agccaatgaa tgcagcagtg | 1200 |
| aatagcaact ttataagcca tgagaagagg agagaattct tgaaagcctt tggacttgtg | 1260 |
| gattccaatg ggaagccgtc agctgctgtc atggcagccg ctcaggctta caagacagca | 1320 |
| gccggcggtg aagtcatca tcatcatcat cattgaccgg t | 1361 |

<210> SEQ ID NO 17
<211> LENGTH: 66
<212> TYPE: DNA
<213> ORGANISM: Artificial Sequence
<220> FEATURE:
<223> OTHER INFORMATION: Primer 5'N (for cloning RVF-N)

<400> SEQUENCE: 17

| | |
|---|---|
| aaaaaggcgc gccaggggt ggcggatctg acaactatca agagcttcga gtccagtttg | 60 |
| ctgctc | 66 |

<210> SEQ ID NO 18
<211> LENGTH: 69
<212> TYPE: DNA
<213> ORGANISM: Artificial Sequence
<220> FEATURE:
<223> OTHER INFORMATION: Primer 3'N (for cloning RVF-N)

<400> SEQUENCE: 18

| | |
|---|---|
| aaaaaaccgg tcaatgatga tgatgatgat gacttccacc gccggctgct gtcttgtaag | 60 |
| cctgagcgg | 69 |

<210> SEQ ID NO 19
<211> LENGTH: 4854
<212> TYPE: DNA
<213> ORGANISM: Artificial Sequence
<220> FEATURE:
<223> OTHER INFORMATION: DNA sequence of pMT/BiP/SNAP-RVF.N/Histag

<400> SEQUENCE: 19

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgccag tgaattttaa cgttgcagga    420
caggatgtgg tgcccgatgt gactagctct ttgctgcagg ccgtcctatc ctctggttcc    480
gataagagac ccagaactcc ggccccccac cgcccaccgc cacccccata catatgtggt    540
acgcaagtaa gagtgcctgc gcatgcccca tgtgccccac caagagtttt gcatcccata    600
caagtcccca aagtggagaa ccgaaccaat tcttcgcggg cagaacaaaa gcttctgcac    660
acgtctccac tcgaatttgg agccggccgg cgtgtgcaaa agaggtgaat cgaacgaaag    720
acccgtgtgt aaagccgcgt ttccaaaatg tataaaaccg agagcatctg gccaatgtgc    780
atcagttgtg gtcagcagca aaatcaagtg aatcatctca gtgcaactaa aggggggatc    840
cgatctcaat atgaagttat gcatattact ggccgtcgtg gcctttgttg gcctctcgct    900
cgggagatct gacaaagact gcgaaatgaa gcgcaccacc ctggatagcc ctctgggcaa    960
gctggaactg tctgggtgcg aacagggcct gcacgagatc aagctgctgg gcaaaggaac   1020
atctgccgcc gacgccgtgg aagtgcctgc cccagccgcc gtgctgggcg gaccagagcc   1080
actgatgcag gccaccgcct ggctcaacgc ctactttcac cagcctgagg ccatcgagga   1140
gttccctgtg ccagccctgc accacccagt gttccagcag gagagcttta cccgccaggt   1200
gctgtggaaa ctgctgaaag tggtgaagtt cggagaggtc atcagctacc agcagctggc   1260
cgccctggcc ggcaatcccg ccgccaccgc cgccgtgaaa accgccctga gcggaaatcc   1320
cgtgcccatt ctgatcccct gccaccgggt ggtgtctagc tctggcgccg tggggggcta   1380
cgagggcggg ctcgccgtga aagagtggct gctggcccac gagggccaca gactgggcaa   1440
gcctgggctg ggtcctgcag gtataggcgc gccagggtcc ctaggtggcg gatctgacaa   1500
ctatcaagag cttcgagtcc agtttgctgc tcaagcagtg gaccgcaatg agattgaaca   1560
gtgggtccga gagtttgctt atcaagggtt tgatgcccgt agagttatcg aactcttaaa   1620
gcagtatggt ggggctgact gggagaagga tgccaagaaa atgattgttc tggctctaac   1680
tcgtggcaac aagcccagga ggatgatgat gaaaatgtcg aaagaaggca aagcaactgt   1740
ggaggctctc atcaacaagt ataagctaaa ggaagggaat ccttcccggg atgagttgac   1800
tctatcacga gttgctgccg ccttggctgg ctggacatgc caggctttgg tcgtcttgag   1860
tgagtggctt cctgtcactg ggactaccat ggacggccta tcccctgcat acccgaggca   1920
tatgatgcac cccagctttg ctggcatggt ggatccttct ctaccaggag actatctaag   1980
ggcaatatta gatgctcact ctctgtatct gctgcagttc tcccgggtca tcaacccaaa   2040
cctccgaggt agaacaaaag aggaggttgc tgcaacgttc acgcagccaa tgaatgcagc   2100
agtgaatagc aactttataa gccatgagaa gaggagagaa ttcttgaaag cctttggact   2160
tgtggattcc aatgggaagc cgtcagctgc tgtcatggca gccgctcagg cttacaagac   2220
```

-continued

```
agcagccggc ggtggaagtc atcatcatca tcatcattga ccggtcatca tcaccatcac    2280
cattgagttt aaacccgctg atcagcctcg actgtgcctt ctaaggcctg agctcgctga    2340
tcagcctcga tcgaggatcc agacatgata agatacattg atgagtttgg acaaaccaca    2400
actagaatgc agtgaaaaaa atgctttatt tgtgaaattt gtgatgctat tgctttattt    2460
gtaaccatta taagctgcaa taaacaagtt aacaacaaca attgcattca ttttatgttt    2520
caggttcagg gggaggtgtg ggaggttttt taaagcaagt aaaacctcta caaatgtggt    2580
atggctgatt atgatcagtc gacctgcagg catgcaagct tggcgtaatc atggtcatag    2640
ctgtttcctg tgtgaaattg ttatccgctc acaattccac acaacatacg agccggaagc    2700
ataaagtgta aagcctgggg tgcctaatga gtgagctaac tcacattaat tgcgttgcgc    2760
tcactgcccg ctttccagtc gggaaacctg tcgtgccagc tgcattaatg aatcggccaa    2820
cgcgcgggga gaggcggttt gcgtattggg cgctcttccg cttcctcgct cactgactcg    2880
ctgcgctcgg tcgttcggct gcggcgagcg gtatcagctc actcaaaggc ggtaatacgg    2940
ttatccacag aatcagggga taacgcagga aagaacatgt gagcaaaagg ccagcaaaag    3000
gccaggaacc gtaaaaaggc cgcgttgctg gcgtttttcc ataggctccg cccccctgac    3060
gagcatcaca aaaatcgacg ctcaagtcag aggtggcgaa acccgacagg actataaaga    3120
taccaggcgt ttccccctgg aagctccctc gtgcgctctc ctgttccgac cctgccgctt    3180
accggatacc tgtccgcctt tctcccttcg ggaagcgtgg cgctttctca tagctcacgc    3240
tgtaggtatc tcagttcggt gtaggtcgtt cgctccaagc tgggctgtgt gcacgaaccc    3300
cccgttcagc ccgaccgctg cgccttatcc ggtaactatc gtcttgagtc aacccggta    3360 agacacgact tatcgccact ggcagcagcc actggtaaca ggattagcag agcgaggtat    3420
gtaggcggtg ctacagagtt cttgaagtgg tggcctaact acggctacac tagaaggaca    3480
gtatttggta tctgcgctct gctgaagcca gttaccttcg gaaaaagagt tggtagctct    3540
tgatccggca acaaaccacc gctggtagc ggtggttttt tgtttgcaa gcagcagatt    3600 acgcgcagaa aaaaaggatc tcaagaagat cctttgatct tttctacggg gtctgacgct    3660
cagtggaacg aaaactcacg ttaagggatt ttggtcatga gattatcaaa aaggatcttc    3720
acctagatcc ttttaaatta aaaatgaagt tttaaatcaa tctaaagtat atatgagtaa    3780
acttggtctg acagttacca atgcttaatc agtgaggcac ctatctcagc gatctgtcta    3840
tttcgttcat ccatagttgc ctgactcccc gtcgtgtaga taactacgat acgggagggc    3900
ttaccatctg gccccagtgc tgcaatgata ccgcgagacc cacgctcacc ggctccagat    3960
ttatcagcaa taaaccagcc agccggaagg gccgagcgca gaagtggtcc tgcaacttta    4020
tccgcctcca tccagtctat taattgttgc cgggaagcta gagtaagtag ttcgccagtt    4080
aatagtttgc gcaacgttgt tgccattgct acaggcatcg tggtgtcacg ctcgtcgttt    4140
ggtatggctt cattcagctc cggttcccaa cgatcaaggc gagttacatg atcccccatg    4200
ttgtgcaaaa aagcggttag ctccttcggt cctccgatcg ttgtcagaag taagttggcc    4260
gcagtgttat cactcatggt tatggcagca ctgcataatt ctcttactgt catgccatcc    4320
gtaagatgct tttctgtgac tggtgagtac tcaaccaagt cattctgaga atagtgtatg    4380
cggcgaccga gttgctcttg cccggcgtca atacgggata taccgcgcc acatagcaga    4440 actttaaaag tgctcatcat tggaaaacgt tcttcggggc gaaaactctc aaggatctta    4500
ccgctgttga gatccagttc gatgtaaccc actcgtgcac ccaactgatc ttcagcatct    4560
tttactttca ccagcgtttc tgggtgagca aaaacaggaa ggcaaaatgc cgcaaaaaag    4620
```

```
ggaataaggg cgacacggaa atgttgaata ctcatactct tccttttca atattattga    4680 agcatttatc agggttattg tctcatgagc ggatacatat ttgaatgtat ttagaaaaat    4740
aaacaaatag gggttccgcg cacatttccc cgaaaagtgc cacctgacgt ctaagaaacc    4800
attattatca tgacattaac ctataaaaat aggcgtatca cgaggccctt tcgt          4854
```

<210> SEQ ID NO 20
<211> LENGTH: 1957
<212> TYPE: DNA
<213> ORGANISM: Artificial Sequence
<220> FEATURE:
<223> OTHER INFORMATION: DNA sequence of WNsE/SNAP/Histag

<400> SEQUENCE: 20

```
agatctttca actgccttgg aatgagcaac agagacttct tggaaggagt gtctggagca      60
acatgggtgg atttggttct cgaaggcgac agctgcgtga ctatcatgtc taaggacaag     120
cctaccatcg atgtgaagat gatgaatatg gaggcggcca acctggcaga ggtccgcagt     180
tattgctatt tggctaccgt cagcgatctc tccaccaaag ctgcgtgccc gaccatggga     240
gaagctcaca atgacaaacg tgctgaccca gcttttgtgt gcagacaagg agtagtggac     300
aggggctggg gcaacggctg cggactattt ggcaaaggaa gcattgacac atgcgccaaa     360
tttgcctgct ctaccaaggc aataggaaga accatcttga aagagaatat caagtacgaa     420
gtggccattt ttgtccatgg accaactact gtggagtcgc acggaaacta ctccacacag     480
gttggagcca ctcaggcagg agattcagc atcactcctg cggcgccttc atacacacta     540
aagcttggag aatatggaga ggtgacagtg gactgtgaac cacggtcagg gattgacacc     600
aatgcatact acgtgatgac tgttggaaca aagacgttct tggtccatcg tgagtggttc     660
atggacctca acctcccttg gagcagtgct ggaagtactg tgtggaggaa cagagagacg     720
ttaatggagt ttgaggaacc acacgccacg aagcagtctg tgatagcatt gggctcacaa     780
gagggagctc tgcatcaagc tttggctgga gccattcctg tggaattttc aagcaacact     840
gtcaagttga cgtcgggtca tttgaagtgt agagtgaaga tggaaaaatt gcagttgaag     900
ggaacaacct atggcgtctg ttcaaaggct ttcaagtttc ttgggactcc cgcagacaca     960
ggtcacggca ctgtggtgtt ggaattgcag tacactggca cggatggacc ttgcaaagtt    1020
cctatctcgt cagtggcttc attgaacgac ctaacgccag tgggcagatt ggtcactgtc    1080
aacccttttg tttcagtggc cacggccaac gctaaggtcc tgattgaatt ggaaccaccc    1140 tttgagagact catacatagt ggtgggcaga ggagaacaac agattaatca ccattggcac    1200
aagtctggaa gcagcattgg caaagccttt acaaccaccc tcaaaggagc gcagagacta    1260
gccgctctag agacacagc ttgggacttt ggatcagttg gagggtgtt cacctcagtt    1320 gggaaggctg tgcggccgct gggcggaggt agcaaagact gcgaaatgaa gcgcaccacc    1380
ctggatagcc ctctgggcaa gctggaactg tctgggtgcg aacagggcct gcacgagatc    1440
aagctgctgg gcaaaggaac atctgccgcc gacgccgtgg aagtgcctgc cccagccgcc    1500
gtgctgggcg gaccagagcc actgatgcag gccaccgcct ggctcaacgc ctactttcac    1560
cagcctgagg ccatcgagga gttccctgtg ccagccctgc accaccagt gttccagcag    1620 gagagcttta cccgccaggt gctgtggaaa ctgctgaaag tggtgaagtt cggagaggtc    1680
atcagctacc agcagctggc cgccctggcc ggcaatcccg ccgccaccgc cgccgtgaaa    1740
accgccctga gcggaaatcc cgtgcccatt ctgatcccct gccaccgggt ggtgtctagc    1800
```

| | |
|---|---|
| tctggcgccg tggggggcta cgagggcggg ctcgccgtga aagagtggct gctggcccac | 1860 |
| gagggccaca gactgggcaa gcctgggctg ggtcctgcag gtataggcgc gccagggtcc | 1920 |
| ctggagcatc atcatcatca tcattgatga cgggccc | 1957 |

<210> SEQ ID NO 21
<211> LENGTH: 960
<212> TYPE: DNA
<213> ORGANISM: Artificial Sequence
<220> FEATURE:
<223> OTHER INFORMATION: DNA sequence of BiP/SNAP-IFN/Histag

<400> SEQUENCE: 21

| | |
|---|---|
| atgaagttat gcatattact ggccgtcgtg gcctttgttg gcctctcgct cgggagatct | 60 |
| gacaaagact gcgaaatgaa gcgcaccacc ctggatagcc ctctgggcaa gctggaactg | 120 |
| tctgggtgcg aacagggcct gcacgagatc aagctgctgg gcaaaggaac atctgccgcc | 180 |
| gacgccgtgg aagtgcctgc ccagccgcc gtgctgggcg accagagcc actgatgcag | 240 |
| gccaccgcct ggctcaacgc ctactttcac cagcctgagg ccatcgagga gttccctgtg | 300 |
| ccagccctgc accacccagt gttccagcag gagagctta cccgccaggt gctgtggaaa | 360 |
| ctgctgaaag tggtgaagtt cggagaggtc atcagctacc agcagctggc cgccctggcc | 420 |
| ggcaatcccg ccgccaccgc cgccgtgaaa accgccctga gcggaaatcc cgtgcccatt | 480 |
| ctgatcccct gccaccgggt ggtgtctagc tctggcgccg tgggggctaa cgagggcggg | 540 |
| ctcgccgtga aagagtggct gctggcccac gagggccaca gactgggcaa gcctgggctg | 600 |
| ggtcctgcag gtataggcgc gccagggtcc ctaggtggcg atctgatga cgatgataaa | 660 |
| gatatctgtg atctccctga cccacagcc ctggataaca ggaggacctt gatgctcctg | 720 |
| gcacaaatga gcagaatctc tccttcctcc tgtctgatgg acagacatga ctttggattt | 780 |
| ccccaggagg agtttgatgg caaccagttc agaaggctc agccatctc tgtcctccat | 840 |
| gagctgatcc agcagatctt caacctcttt accacaaaag attcatcgc tgcttgggat | 900 |
| gaggacctcc tagacaaatt ctgcaccgaa ctctaccagc agctgaatga cttggaagcc | 960 |

<210> SEQ ID NO 22
<211> LENGTH: 957
<212> TYPE: DNA
<213> ORGANISM: Artificial Sequence
<220> FEATURE:
<223> OTHER INFORMATION: DNA sequence of SNAP-EDIIIWN/Histag

<400> SEQUENCE: 22

| | |
|---|---|
| agatctgaca aagactgcga aatgaagcgc accaccctgg atagccctct gggcaagctg | 60 |
| gaactgtctg ggtgcgaaca gggcctgcac gagatcaagc tgctgggcaa aggaacatct | 120 |
| gccgccgacg ccgtggaagt gcctgcccca gccgccgtgc tgggcggacc agagccactg | 180 |
| atgcaggcca ccgcctggct caacgcctac tttcaccagc ctgaggccat cgaggagttc | 240 |
| cctgtgccag ccctgcacca cccagtgttc agcaggaga gctttacccg ccaggtgctg | 300 |
| tggaaactgc tgaaagtggt gaagttcgga gaggtcatca gctaccagca gctggccgcc | 360 |
| ctggccggca atcccgccgc caccgccgcc gtgaaaaccg ccctgagcgg aaatcccgtg | 420 |
| cccattctga tcccctgcca ccgggtggtg tctagctctg gcgccgtggg gggctacgag | 480 |
| ggcgggctcg ccgtgaaaga gtggctgctg gccacgagg ccacagact gggcaagcct | 540 |
| gggctgggtc ctgcaggtat aggcgcgcca ggaggtggcg gtctcagtt gaagggaaca | 600 |
| acctatggcg tctgttcaaa ggctttcaag tttcttggga ctcccgcaga cacaggtcac | 660 |

```
ggcactgtgg tgttggaatt gcagtacact ggcacggatg gaccttgcaa agttcctatc    720
tcgtcagtgg cttcattgaa cgacctaacg ccagtgggca gattggtcac tgtcaaccct    780
tttgtttcag tggccacggc caacgctaag gtcctgattg aattggaacc acccttttgga   840 gactcataca tagtggtggg cagaggagaa caacagatca tcaccattg gcacaagtct     900 ggaagcagca ttggcaaagg aggtggccat caccatcacc atcactgatg accggtt       957
```

<210> SEQ ID NO 23
<211> LENGTH: 398
<212> TYPE: DNA
<213> ORGANISM: west nile virus
<220> FEATURE:
<221> NAME/KEY: misc_feature
<223> OTHER INFORMATION: DNA sequence of the ED III protein from the WN virus

<400> SEQUENCE: 23

```
taggcgcgcc aggaggtggc gggtctcagt tgaagggaac aacctatggc gtctgttcaa     60
aggctttcaa gtttcttggg actcccgcag acacaggtca cggcactgtg gtgttggaat   120
tgcagtacac tggcacggat ggaccttgca agttcctat ctcgtcagtg gcttcattga    180
acgacctaac gccagtgggc agattggtca ctgtcaaccc ttttgtttca gtggccacgg   240
ccaacgctaa ggtcctgatt gaattggaac cacccttggg agactcatac atagtggtgg   300
gcagaggaga acaacagatc aatcaccatt ggcacaagtc tggaagcagc attggcaaag   360
gaggtggcca tcaccatcac catcactgat gaccggtt                           398
```

<210> SEQ ID NO 24
<211> LENGTH: 398
<212> TYPE: DNA
<213> ORGANISM: Usutu virus isolate USU629-05
<220> FEATURE:
<221> NAME/KEY: misc_feature
<223> OTHER INFORMATION: DNA sequence of the ED III protein from the USU virus

<400> SEQUENCE: 24

```
taggcgcgcc aggaggtggc gggtctacac taaaaggcac cacctacggc atgtgcacgg     60
aaaagttttc ttttgcaaaa aatccggctg acacgggtca cggcactgtg gtccttgaac   120
tgcagtacac gggatctgac ggaccttgca aaatcccaat ttccattgtg catcactttt   180
ccgatctcac ccccattggt agaatggtta cagcaaaccc ttatgtggct tcatccgaag   240
ccaacgcgaa agtgttggtt gagatggaac caccatttgg agattcatac attgtggttg   300
gaagagggga taagcagata aaccatcact ggcacaaagc aggaagttcc attggaaaag   360
gtggaggcca ccatcaccat caccattgat gaccggtt                           398
```

<210> SEQ ID NO 25
<211> LENGTH: 410
<212> TYPE: DNA
<213> ORGANISM: Japanese encephalitis virus strain GP05
<220> FEATURE:
<221> NAME/KEY: misc_feature
<223> OTHER INFORMATION: DNA sequence of the ED III protein from the JE virus

<400> SEQUENCE: 25

```
taggcgcgcc agggtccctg gagggaggtg gcgggtctgc tctgaaaggc acaacctatg     60
gcatgtgtac agaaaaattc tcgttcgcga aaaatccggc ggacactggt cacggaacag   120
```

```
ttgtcattga actctcctac tctgggagtg atggccctg caaaattccg attgtctccg      180
tcgcgagcct caatgacatg actcctgttg ggcggctggt gacagtgaac ccctttgtcg      240
cggcttccag tgccaactca aggtgctgg tcgagatgga acccccttc ggagactcct       300 atatcgtggt tggaagggga gacaagcaga tcaaccacca ttggcacaga gctggaagca     360
cgctgggcaa gggaggtggc catcaccatc accatcactg atgaccggtt                410
```

<210> SEQ ID NO 26
<211> LENGTH: 398
<212> TYPE: DNA
<213> ORGANISM: Tick-borne encephalitis virus Kumlinge strain A 52
<220> FEATURE:
<221> NAME/KEY: misc_feature
<223> OTHER INFORMATION: DNA sequence of the ED III protein from the TBE
      virus

<400> SEQUENCE: 26

```
taggcgcgcc agggtccctg gagggaggtg gcgggtctct ggaaaaactg aagatgaaag      60
gtcttacgta cacaatgtgt gacaaaacaa agttcacatg gaagagagct ccaacagata     120
gtgggcatga cacagtggtc atggaagtca cattctctgg aacaaagccc tgtaggatcc     180
cagtcagggc agtggcacat ggatctccag atgtgaacgt ggccatgctg ataacgccaa     240
accctacaat tgaaaacaat ggaggtggct tcatagagat gcagctgccc caggggata     300 acatcatcta tgttggggaa ctgagtcacc aatggttcca aaagggagc agcattggag      360 gaggtggcca tcaccatcac catcactgat gaccggtt                             398
```

<210> SEQ ID NO 27
<211> LENGTH: 404
<212> TYPE: DNA
<213> ORGANISM: Dengue virus type 1 strain FGA/NA d1d
<220> FEATURE:
<221> NAME/KEY: misc_feature
<223> OTHER INFORMATION: DNA sequence of the ED III protein from the
      DEN-1 virus

<400> SEQUENCE: 27

```
taggcgcgcc agggtccctg gagggaggtg gcgggtctct gactttaaaa gggatgtcat      60
atgtgatgtg cacaggctca tttaagctag agaaggaagt ggctgagacc cagcatggaa     120
ctgtcctagt gcaggttaaa tacgaaggaa cagatgcgcc atgcaagatc ccctttgcga    180
cccaagatga gaaggagtg acccagaatg ggagattgat aacagccaat cccatagtta     240
ctgacaaaga aaaccaatc aacattgaga cagaaccacc ttttggtgag agctacatca     300
tagtaggggc aggtgaaaaa gctttgaaac taagctggtt caagaaagga agcagcatag    360
ggaaaggagg tggccatcac catcaccatc actgatgacc ggtt                      404
```

<210> SEQ ID NO 28
<211> LENGTH: 404
<212> TYPE: DNA
<213> ORGANISM: Dengue virus 2
<220> FEATURE:
<221> NAME/KEY: misc_feature
<223> OTHER INFORMATION: DNA sequence of the ED III protein from the
      DEN-2 virus

<400> SEQUENCE: 28

```
taggcgcgcc agggtccctg gagggaggtg gcgggtctct acagctcaaa ggaatgtcat      60
attctatgtg tacaggaaag tttaaagttg tgaaggaaat agcagaaaca caacatggaa     120
caatagttct cagagtacaa tatgaagggg acggttctcc gtgcaagatc ccttttgaaa    180
```

```
taatggattt ggaaaaaaga catgtcttag gtcgcttgat cacagtcaac ccaattgtta      240
cagaaataga cagcccagtc aacatagaag cagaacctcc attcggagac agctacatca      300
ttataggagt agaaccggga caactgaagc tcagctggtt taagaaagga agttccattg      360
gccaaggagg tggccatcac catcaccatc actgatgacc ggtt                       404
```

<210> SEQ ID NO 29
<211> LENGTH: 401
<212> TYPE: DNA
<213> ORGANISM: Dengue virus 3
<220> FEATURE:
<221> NAME/KEY: misc_feature
<223> OTHER INFORMATION: DNA sequence of the ED III protein from the
      DEN-3 virus

<400> SEQUENCE: 29

```
taggcgcgcc agggtccctg gagggaggtg gcgggtctga actcaagggg atgagctatg       60
caatgtgctt gaatacccttt gtgttgaaga aagaagtctc cgaaacgcag catgggacaa     120
tactcattaa ggttgagtac aaggggaag atgcaccttg caagattcct ttctccacag      180
aggatggaca agggaaagcc acaatggta gactgatcac agccaaccca gtggttacta       240
agaaggagga gcctgtcaac attgaggctg aacctccttt tggggaaagc aacatagtga      300
ttggagttgg agacaaagcc ttgaaaatta ctggtacaa gagggaagc tcgattggga       360 agggaggtgg ccatcaccat caccatcact gatgaccggt t                          401
```

<210> SEQ ID NO 30
<211> LENGTH: 401
<212> TYPE: DNA
<213> ORGANISM: Dengue virus 4
<220> FEATURE:
<221> NAME/KEY: misc_feature
<223> OTHER INFORMATION: DNA sequence of the ED III protein from the
      DEN-4 virus

<400> SEQUENCE: 30

```
taggcgcgcc agggtccctg gagggaggtg gcgggtctag aatcaaggga atgtcataca       60
cgatgtgctc aggaaagttc tcaattgaca aagagatggc agaaacacag catgggacaa     120
cagtggtgaa agtcaagtat gaaggtgctg gagctccgtg taaagtcccc atagagatac      180
gagatgtaaa taaggaaaaa gtggttgggc gtgtcatctc atccacccct ctagctgaga      240
ataccaacag tgtgaccaac atagaactgg aaccccccctt tggggacagt tacatagtca      300
taggtgttgg gaacagtgca ttgacactcc attggttcag gaaggaagt tctattggca       360 agggaggtgg ccatcaccat caccatcact gatgaccggt t                          401
```

<210> SEQ ID NO 31
<211> LENGTH: 410
<212> TYPE: DNA
<213> ORGANISM: Yellow fever virus strain ASIBI
<220> FEATURE:
<221> NAME/KEY: misc_feature
<223> OTHER INFORMATION: DNA sequence of the ED III protein from the
      YF Asibi virus

<400> SEQUENCE: 31

```
taggcgcgcc agggtccctg gagggaggtg gcgggtcttc agctttgaca ctcaagggga       60
catcctacaa aatgtgcact gacaaaatgt cttttgtcaa gaacccaact gacactggcc     120
atggcactgt tgtgatgcag gtgaaagtgc caaaaggagc ccctgcaag attccagtga      180
```

```
tagtagctga tgatcttaca gcggcaatca ataaaggcat tttggttaca gttaacccca    240
tcgcctcaac caatgatgat gaagtgctga ttgaggtgaa cccacctttt ggagacagct    300
acattatcgt tggacagga gattcacgtc tcacttacca gtggcacaaa gagggaagct     360
caataggaaa gggaggtggc catcaccatc accatcactg atgaccggtt               410
```

```
<210> SEQ ID NO 32
<211> LENGTH: 595
<212> TYPE: DNA
<213> ORGANISM: Artificial Sequence
<220> FEATURE:
<223> OTHER INFORMATION: DNA sequence of the Synthetic IFNAI gene

<400> SEQUENCE: 32
gcgcgccagg gtccctaggt ggcggatctg atgacgatga taaagatatc tgtgatctcc     60
ctgagaccca cagcctggat aacaggagga ccttgatgct cctggcacaa atgagcagaa    120
tctctccttc ctcctgtctg atggacagac atgactttgg atttccccag gaggagtttg    180
atggcaacca gttccagaag ctccagcca tctctgtcct ccatgagctg atccagcaga    240
tcttcaacct ctttaccaca aaagattcat ctgctgcttg ggatgaggac ctcctagaca    300
aattctgcac cgaactctac cagcagctga atgacttgga agcctgtgtg atgcaggag     360 agagggtggg agaaactccc ctgatgaatg cggactccat cttggctgtg aagaaatact    420
tccgaagaat cactctctat ctgacagaga gaaatacag cccttgtgcc tgggaggttg     480
tcagagcaga aatcatgaga tccctctctt tatcaacaaa cttgcaagaa agattaagga    540
ggaaggaagg caagtggggc ggtggaagtc atcatcatca tcatcattga ccggt         595
```

```
<210> SEQ ID NO 33
<211> LENGTH: 469
<212> TYPE: PRT
<213> ORGANISM: Artificial Sequence
<220> FEATURE:
<223> OTHER INFORMATION: amino acid sequence of the fusion protein
      BiP-SNAP-spacer-RVF-N + spacer-(His)6tag

<400> SEQUENCE: 33

Met Lys Leu Cys Ile Leu Leu Ala Val Val Ala Phe Val Gly Leu Ser
1               5                   10                  15

Leu G

```
Leu Ile Pro Cys His Arg Val Val Ser Ser Gly Ala Val Gly Gly
                165                 170                 175

Tyr Glu Gly Gly Leu Ala Val Lys Glu Trp Leu Leu Ala His Glu Gly
            180                 185                 190

His Arg Leu Gly Lys Pro Gly Leu Gly Pro Ala Gly Ile Gly Ala Pro
        195                 200                 205

Gly Ser Leu Gly Gly Ser Asp Asn Tyr Gln Glu Leu Arg Val Gln
    210                 215                 220

Phe Ala Ala Gln Ala Val Asp Arg Asn Glu Ile Glu Gln Trp Val Arg
225                 230                 235                 240

Glu Phe Ala Tyr Gln Gly Phe Asp Ala Arg Arg Val Ile Glu Leu Leu
                245                 250                 255

Lys Gln Tyr Gly Gly Ala Asp Trp Glu Lys Asp Ala Lys Lys Met Ile
            260                 265                 270

Val Leu Ala Leu Thr Arg Gly Asn Lys Pro Arg Arg Met Met Met Lys
        275                 280                 285

Met Ser Lys Glu Gly Lys Ala Thr Val Glu Ala Leu Ile Asn Lys Tyr
    290                 295                 300

Lys Leu Lys Glu Gly Asn Pro Ser Arg Asp Glu Leu Thr Leu Ser Arg
305                 310                 315                 320

Val Ala Ala Ala Leu Ala Gly Trp Thr Cys Gln Ala Leu Val Val Leu
                325                 330                 335

Ser Glu Trp Leu Pro Val Thr Gly Thr Thr Met Asp Gly Leu Ser Pro
            340                 345                 350

Ala Tyr Pro Arg His Met Met His Pro Ser Phe Ala Gly Met Val Asp
        355                 360                 365

Pro Ser Leu Pro Gly Asp Tyr Leu Arg Ala Ile Leu Asp Ala His Ser
    370                 375                 380

Leu Tyr Leu Leu Gln Phe Ser Arg Val Ile Asn Pro Asn Leu Arg Gly
385                 390                 395                 400

Arg Thr Lys Glu Glu Val Ala Ala Thr Phe Thr Gln Pro Met Asn Ala
                405                 410                 415

Ala Val Asn Ser Asn Phe Ile Ser His Glu Lys Arg Arg Glu Phe Leu
            420                 425                 430

Lys Ala Phe Gly Leu Val Asp Ser Asn Gly Lys Pro Ser Ala Ala Val
        435                 440                 445

Met Ala Ala Ala Gln Ala Tyr Lys Thr Ala Ala Gly Gly Ser His
    450                 455                 460

His His His His
465

<210> SEQ ID NO 34
<211> LENGTH: 398
<212> TYPE: PRT
<213> ORGANISM: Artificial Sequence
<220> FEATURE:
<223> OTHER INFORMATION: amino acid sequence of the fusion protein BiP-
      SNAP-spacer - IFNa + spacer- (His)6tag

<400> SEQUENCE: 34

Met Lys Leu Cys Ile Leu Leu Ala Val Val Ala Phe Val Gly Leu Ser
1               5                   10                  15

Leu Gly Arg Ser Asp Lys Asp Cys Glu Met Lys Arg Thr Thr Leu Asp
            20                  25                  30

Ser Pro Leu Gly Lys Leu Glu Leu Ser Gly Cys Glu Gln Gly Leu His
        35                  40                  45
```

Glu Ile Lys Leu Leu Gly Lys Gly Thr Ser Ala Ala Asp Ala Val Glu
 50                  55                  60

Val Pro Pro Ala Ala Val Leu Gly Gly Pro Glu Pro Leu Met Gln Ala
 65                  70                  75                  80

Thr Ala Trp Leu Asn Ala Tyr Phe His Gln Pro Glu Ala Ile Glu Glu
                 85                  90                  95

Phe Pro Pro Ala Leu His His Pro Val Phe Gln Gln Glu Ser Phe Thr
                100                 105                 110

Arg Gln Val Leu Trp Lys Leu Leu Lys Val Val Lys Phe Gly Glu Val
            115                 120                 125

Ile Ser Tyr Gln Gln Leu Ala Ala Leu Ala Gly Asn Pro Ala Ala Thr
130                 135                 140

Ala Ala Val Lys Thr Ala Leu Ser Gly Asn Pro Val Pro Ile Leu Ile
145                 150                 155                 160

Pro Cys His Arg Val Ser Ser Gly Ala Val Gly Gly Tyr Glu Gly
                165                 170                 175

Gly Leu Ala Val Lys Glu Trp Leu Leu Ala His Glu Gly His Arg Leu
            180                 185                 190

Gly Lys Pro Gly Leu Gly Pro Ala Gly Ile Gly Ala Pro Gly Ser Leu
            195                 200                 205

Gly Gly Gly Ser Asp Asp Asp Lys Asp Ile Cys Asp Leu Pro Glu
210                 215                 220

Thr His Ser Leu Asp Asn Arg Arg Thr Leu Met Leu Leu Ala Gln Met
225                 230                 235                 240

Ser Arg Ile Ser Pro Ser Ser Cys Leu Met Asp Arg His Asp Phe Gly
                245                 250                 255

Phe Pro Gln Glu Glu Phe Asp Gly Asn Gln Phe Gln Lys Ala Pro Ala
                260                 265                 270

Ile Ser Val Leu His Glu Leu Ile Gln Gln Ile Phe Asn Leu Phe Thr
            275                 280                 285

Thr Lys Asp Ser Ser Ala Ala Trp Asp Glu Asp Leu Leu Asp Lys Phe
        290                 295                 300

Cys Thr Glu Leu Tyr Gln Gln Leu Asn Asp Leu Glu Ala Cys Val Met
305                 310                 315                 320

Gln Glu Glu Arg Val Gly Glu Thr Pro Leu Met Asn Ala Asp Ser Ile
                325                 330                 335

Leu Ala Val Lys Lys Tyr Phe Arg Arg Ile Thr Leu Tyr Leu Thr Glu
            340                 345                 350

Lys Lys Tyr Ser Pro Cys Ala Trp Glu Val Val Arg Ala Glu Ile Met
            355                 360                 365

Arg Ser Leu Ser Leu Ser Thr Asn Leu Gln Glu Arg Leu Arg Arg Lys
370                 375                 380

Glu Gly Lys Trp Gly Gly Gly Ser His His His His His
385                 390                 395

<210> SEQ ID NO 35
<211> LENGTH: 333
<212> TYPE: PRT
<213> ORGANISM: Artificial Sequence
<220> FEATURE:
<223> OTHER INFORMATION: amino acid sequence of the fusion protein
      BiP-SNAP-spacer - EDIII WN+ spacer- (His)6tag

<400> SEQUENCE: 35

Met Lys Leu Cys Ile Leu Leu Ala Val Val Ala Phe Val Gly Leu Ser

-continued

```
              1               5                  10                 15
            Leu Gly Arg Ser Asp Lys Asp Cys Glu Met Lys Arg Thr Thr Leu Asp
                            20                 25                 30

Ser Pro Leu Gly Lys Leu Glu Leu Ser Gly Cys Glu Gln Gly Leu His
                            35                 40                 45

Glu Ile Lys Leu Leu Gly Lys Gly Thr Ser Ala Ala Asp Ala Val Glu
                            50                 55                 60

Val Pro Ala Pro Ala Ala Val Leu Gly Gly Pro Glu Pro Leu Met Gln
             65                 70                 75                 80

Ala Thr Ala Trp Leu Asn Ala Tyr Phe His Gln Pro Glu Ala Ile Glu
                                85                 90                 95

Glu Phe Pro Val Pro Ala Leu His His Pro Val Phe Gln Gln Glu Ser
                           100                105                110

Phe Thr Arg Gln Val Leu Trp Lys Leu Leu Lys Val Val Lys Phe Gly
                           115                120                125

Glu Val Ile Ser Tyr Gln Gln Leu Ala Ala Leu Ala Gly Asn Pro Ala
                           130                135                140

Ala Thr Ala Ala Val Lys Thr Ala Leu Ser Gly Asn Pro Val Pro Ile
            145                150                155                160

Leu Ile Pro Cys His Arg Val Val Ser Ser Gly Ala Val Gly Gly
                               165                170                175

Tyr Glu Gly Gly Leu Ala Val Lys Glu Trp Leu Leu Ala His Glu Gly
                           180                185                190

His Arg Leu Gly Lys Pro Gly Leu Pro Ala Gly Ile Gly Ala Pro
                           195                200                205

Gly Gly Gly Gly Ser Gln Leu Lys Gly Thr Thr Tyr Gly Val Cys Ser
            210                215                220

Lys Ala Phe Lys Phe Leu Gly Thr Pro Ala Asp Thr Gly His Gly Thr
            225                230                235                240

Val Val Leu Glu Leu Gln Tyr Thr Gly Thr Asp Gly Pro Cys Lys Val
                               245                250                255

Pro Ile Ser Ser Val Ala Ser Leu Asn Asp Leu Thr Pro Val Gly Arg
                           260                265                270

Leu Val Thr Val Asn Pro Phe Val Ser Val Ala Thr Ala Asn Ala Lys
                           275                280                285

Val Leu Ile Glu Leu Glu Pro Pro Phe Gly Asp Ser Tyr Ile Val Val
                           290                295                300

Gly Arg Gly Glu Gln Gln Ile Asn His His Trp His Lys Ser Gly Ser
            305                310                315                320

Ser Ile Gly Lys Gly Gly His His His His
                           325                330
```

<210> SEQ ID NO 36
<211> LENGTH: 335
<212> TYPE: PRT
<213> ORGANISM: Artificial Sequence
<220> FEATURE:
<223> OTHER INFORMATION: amino acid sequence of the fusion protein
      BiP-SNAP-spacer - EDIII DEN-1 + spacer- (His)6tag

<400> SEQUENCE: 36

```
              1               5                  10                 15
            Met Lys Leu Cys Ile Leu Leu Ala Val Val Ala Phe Val Gly Leu Ser
            1               5                  10                 15

Leu Gly Arg Ser Asp Lys Asp Cys Glu Met Lys Arg Thr Thr Leu Asp
                            20                 25                 30
```

```
Ser Pro Leu Gly Lys Leu Glu Leu Ser Gly Cys Glu Gln Gly Leu His
        35                  40                  45

Glu Ile Lys Leu Leu Gly Lys Gly Thr Ser Ala Ala Asp Ala Val Glu
 50                  55                  60

Val Pro Ala Pro Ala Ala Val Leu Gly Gly Pro Glu Pro Leu Met Gln
 65                  70                  75                  80

Ala Thr Ala Trp Leu Asn Ala Tyr Phe His Gln Pro Glu Ala Ile Glu
                 85                  90                  95

Glu Phe Pro Val Pro Ala Leu His His Pro Val Phe Gln Gln Glu Ser
             100                 105                 110

Phe Thr Arg Gln Val Leu Trp Lys Leu Leu Lys Val Val Lys Phe Gly
         115                 120                 125

Glu Val Ile Ser Tyr Gln Gln Leu Ala Ala Leu Ala Gly Asn Pro Ala
     130                 135                 140

Ala Thr Ala Ala Val Lys Thr Ala Leu Ser Gly Asn Pro Val Pro Ile
145                 150                 155                 160

Leu Ile Pro Cys His Arg Val Val Ser Ser Gly Ala Val Gly Gly
                 165                 170                 175

Tyr Glu Gly Gly Leu Ala Val Lys Glu Trp Leu Leu Ala His Glu Gly
                 180                 185                 190

His Arg Leu Gly Lys Pro Gly Leu Gly Pro Ala Gly Ile Gly Ala Pro
         195                 200                 205

Gly Ser Leu Glu Gly Gly Gly Ser Leu Thr Leu Lys Gly Met Ser
     210                 215                 220

Tyr Val Met Cys Thr Gly Ser Phe Lys Leu Glu Lys Glu Val Ala Glu
225                 230                 235                 240

Thr Gln His Gly Thr Val Leu Val Gln Val Lys Tyr Glu Gly Thr Asp
                 245                 250                 255

Ala Pro Cys Lys Ile Pro Phe Ser Thr Gln Asp Glu Lys Gly Val Thr
             260                 265                 270

Gln Asn Gly Arg Leu Ile Thr Ala Asn Pro Ile Val Thr Asp Lys Glu
         275                 280                 285

Lys Pro Ile Asn Ile Glu Thr Glu Pro Pro Phe Gly Glu Ser Tyr Ile
     290                 295                 300

Ile Val Gly Ala Gly Glu Lys Ala Leu Lys Leu Ser Trp Phe Lys Lys
305                 310                 315                 320

Gly Ser Ser Ile Gly Lys Gly Gly His His His His His
                 325                 330                 335

<210> SEQ ID NO 37
<211> LENGTH: 335
<212> TYPE: PRT
<213> ORGANISM: Artificial Sequence
<220> FEATURE:
<223> OTHER INFORMATION: amino acid sequence of the fusion protein
      BiP-SNAP-spacer - EDIII DEN-2 + spacer- (His)6tag

<400> SEQUENCE: 37

Met Lys Leu Cys Ile Leu Leu Ala Val Val Ala Phe Val Gly Leu Ser
 1               5                  10                  15

Leu Gly Arg Ser Asp Lys Asp Cys Glu Met Lys Arg Thr Thr Leu Asp
             20                  25                  30

Ser Pro Leu Gly Lys Leu Glu Leu Ser Gly Cys Glu Gln Gly Leu His
         35                  40                  45

Glu Ile Lys Leu Leu Gly Lys Gly Thr Ser Ala Ala Asp Ala Val Glu
 50                  55                  60
```

```
Val Pro Ala Pro Ala Ala Val Leu Gly Gly Pro Glu Pro Leu Met Gln
 65                  70                  75                  80

Ala Thr Ala Trp Leu Asn Ala Tyr Phe His Gln Pro Glu Ala Ile Glu
                 85                  90                  95

Glu Phe Pro Val Pro Ala Leu His His Pro Val Phe Gln Gln Glu Ser
            100                 105                 110

Phe Thr Arg Gln Val Leu Trp Lys Leu Leu Lys Val Val Lys Phe Gly
        115                 120                 125

Glu Val Ile Ser Tyr Gln Gln Leu Ala Ala Leu Ala Gly Asn Pro Ala
    130                 135                 140

Ala Thr Ala Ala Val Lys Thr Ala Leu Ser Gly Asn Pro Val Pro Ile
145                 150                 155                 160

Leu Ile Pro Cys His Arg Val Val Ser Ser Ser Gly Ala Val Gly Gly
                165                 170                 175

Tyr Glu Gly Gly Leu Ala Val Lys Glu Trp Leu Leu Ala His Glu Gly
            180                 185                 190

His Arg Leu Gly Lys Pro Gly Leu Gly Pro Ala Gly Ile Gly Ala Pro
        195                 200                 205

Gly Ser Leu Glu Gly Gly Gly Ser Leu Gln Leu Lys Gly Met Ser
    210                 215                 220

Tyr Ser Met Cys Thr Gly Lys Phe Lys Val Val Lys Glu Ile Ala Glu
225                 230                 235                 240

Thr Gln His Gly Thr Ile Val Leu Arg Val Gln Tyr Glu Gly Asp Gly
                245                 250                 255

Ser Pro Cys Lys Ile Pro Phe Glu Ile Met Asp Leu Glu Lys Arg His
            260                 265                 270

Val Leu Gly Arg Leu Ile Thr Val Asn Pro Ile Val Thr Glu Ile Asp
        275                 280                 285

Ser Pro Val Asn Ile Glu Ala Glu Pro Pro Phe Gly Asp Ser Tyr Ile
    290                 295                 300

Ile Ile Gly Val Glu Pro Gly Gln Leu Lys Leu Ser Trp Phe Lys Lys
305                 310                 315                 320

Gly Ser Ser Ile Gly Gln Gly Gly Gly His His His His His
                325                 330                 335
```

<210> SEQ ID NO 38
<211> LENGTH: 334
<212> TYPE: PRT
<213> ORGANISM: Artificial Sequence
<220> FEATURE:
<223> OTHER INFORMATION: amino acid sequence of the fusion protein
      BiP-SNAP-spacer - EDIII DEN-3 + spacer- (His)6tag

<400> SEQUENCE: 38

```
Met Lys Leu Cys Ile Leu Leu Ala Val Val Ala Phe Val Gly Leu Ser
 1               5                  10                  15

Leu Gly Arg Ser Asp Lys Asp Cys Glu Met Lys Arg Thr Thr Leu Asp
                 20                  25                  30

Ser Pro Leu Gly Lys Leu Glu Leu Ser Gly Cys Glu Gln Gly Leu His
            35                  40                  45

Glu Ile Lys Leu Leu Gly Lys Gly Thr Ser Ala Ala Asp Ala Val Glu
    50                  55                  60

Val Pro Ala Pro Ala Ala Val Leu Gly Gly Pro Glu Pro Leu Met Gln
 65                  70                  75                  80

Ala Thr Ala Trp Leu Asn Ala Tyr Phe His Gln Pro Glu Ala Ile Glu
```

```
                    85                  90                  95
Glu Phe Pro Val Pro Ala Leu His His Pro Val Phe Gln Gln Glu Ser
                100                 105                 110

Phe Thr Arg Gln Val Leu Trp Lys Leu Leu Lys Val Lys Phe Gly
            115                 120                 125

Glu Val Ile Ser Tyr Gln Gln Leu Ala Ala Leu Ala Gly Asn Pro Ala
            130                 135                 140

Ala Thr Ala Ala Val Lys Thr Ala Leu Ser Gly Asn Pro Val Pro Ile
145                 150                 155                 160

Leu Ile Pro Cys His Arg Val Val Ser Ser Gly Ala Val Gly Gly
                165                 170                 175

Tyr Glu Gly Gly Leu Ala Val Lys Glu Trp Leu Leu Ala His Glu Gly
                180                 185                 190

His Arg Leu Gly Lys Pro Gly Leu Gly Pro Ala Gly Ile Gly Ala Pro
                195                 200                 205

Gly Ser Leu Glu Gly Gly Gly Ser Glu Leu Lys Gly Met Ser Tyr
210                 215                 220

Ala Met Cys Leu Asn Thr Phe Val Leu Lys Lys Glu Val Ser Glu Thr
225                 230                 235                 240

Gln His Gly Thr Ile Leu Ile Lys Val Glu Tyr Lys Gly Glu Asp Ala
                245                 250                 255

Pro Cys Lys Ile Pro Phe Ser Thr Glu Asp Gly Gln Gly Lys Ala His
                260                 265                 270

Asn Gly Arg Leu Ile Thr Ala Asn Pro Val Val Thr Lys Lys Glu Glu
                275                 280                 285

Pro Val Asn Ile Glu Ala Glu Pro Pro Phe Gly Glu Ser Asn Ile Val
                290                 295                 300

Ile Gly Val Gly Asp Lys Ala Leu Lys Ile Asn Trp Tyr Lys Lys Gly
305                 310                 315                 320

Ser Ser Ile Gly Lys Gly Gly His His His His His His
                325                 330

<210> SEQ ID NO 39
<211> LENGTH: 334
<212> TYPE: PRT
<213> ORGANISM: Artificial Sequence
<220> FEATURE:
<223> OTHER INFORMATION: amino acid sequence of the fusion protein
      BiP-SNAP-spacer - EDIII DEN-4 + spacer- (His)6tag

<400> SEQUENCE: 39

Met Lys Leu Cys Ile Leu Leu Ala Val Val Ala Phe Val Gly Leu Ser
1               5                   10                  15

Leu Gly Arg Ser Asp Lys Asp Cys Glu Met Lys Arg Thr Thr Leu Asp
                20                  25                  30

Ser Pro Leu Gly Lys Leu Glu Leu Ser Gly Cys Glu Gln Gly Leu His
            35                  40                  45

Glu Ile Lys Leu Leu Gly Lys Gly Thr Ser Ala Ala Asp Ala Val Glu
            50                  55                  60

Val Pro Ala Pro Ala Ala Val Leu Gly Gly Pro Glu Pro Leu Met Gln
65                  70                  75                  80

Ala Thr Ala Trp Leu Asn Ala Tyr Phe His Gln Pro Glu Ala Ile Glu
                85                  90                  95

Glu Phe Pro Val Pro Ala Leu His His Pro Val Phe Gln Gln Glu Ser
                100                 105                 110
```

-continued

```
Phe Thr Arg Gln Val Leu Trp Lys Leu Leu Lys Val Lys Phe Gly
            115                 120                 125
Glu Val Ile Ser Tyr Gln Gln Leu Ala Ala Leu Ala Gly Asn Pro Ala
        130                 135                 140
Ala Thr Ala Ala Val Lys Thr Ala Leu Ser Gly Asn Pro Val Pro Ile
145                 150                 155                 160
Leu Ile Pro Cys His Arg Val Val Ser Ser Gly Ala Val Gly Gly
                165                 170                 175
Tyr Glu Gly Gly Leu Ala Val Lys Glu Trp Leu Leu Ala His Glu Gly
            180                 185                 190
His Arg Leu Gly Lys Pro Gly Leu Gly Pro Ala Gly Ile Gly Ala Pro
        195                 200                 205
Gly Ser Leu Glu Gly Gly Gly Ser Arg Ile Lys Gly Met Ser Tyr
            210                 215                 220
Thr Met Cys Ser Gly Lys Phe Ser Ile Asp Lys Glu Met Ala Glu Thr
225                 230                 235                 240
Gln His Gly Thr Thr Val Val Lys Val Lys Tyr Glu Gly Ala Gly Ala
                245                 250                 255
Pro Cys Lys Val Pro Ile Glu Ile Arg Asp Val Asn Lys Glu Lys Val
            260                 265                 270
Val Gly Arg Val Ile Ser Ser Thr Pro Leu Ala Glu Asn Thr Asn Ser
        275                 280                 285
Val Thr Asn Ile Glu Leu Glu Pro Pro Phe Gly Asp Ser Tyr Ile Val
    290                 295                 300
Ile Gly Val Gly Asn Ser Ala Leu Thr Leu His Trp Phe Arg Lys Gly
305                 310                 315                 320
Ser Ser Ile Gly Lys Gly Gly His His His His His His
                325                 330
```

<210> SEQ ID NO 40
<211> LENGTH: 338
<212> TYPE: PRT
<213> ORGANISM: Artificial Sequence
<220> FEATURE:
<223> OTHER INFORMATION: amino acid sequence of the fusion protein
      BiP-SNAP-spacer - EDIII JE + spacer- (His)6tag

<400> SEQUENCE: 40

```
Met Lys Leu Cys Ile Leu Leu Ala Val Val Ala Phe Val Gly Leu Ser
1               5                   10                  15
Leu Gly Arg Ser Asp Lys Asp Cys Glu Met Lys Arg Thr Thr Leu Asp
            20                  25                  30
Ser Pro Leu Gly Lys Leu Glu Leu Ser Gly Cys Glu Gln Gly Leu His
        35                  40                  45
Glu Ile Lys Leu Leu Gly Lys Gly Thr Ser Ala Ala Asp Ala Val Glu
    50                  55                  60
Val Pro Ala Pro Ala Ala Val Leu Gly Gly Pro Glu Pro Leu Met Gln
65                  70                  75                  80
Ala Thr Ala Trp Leu Asn Ala Tyr Phe His Gln Pro Glu Ala Ile Glu
                85                  90                  95
Glu Phe Pro Val Pro Ala Leu His His Pro Val Phe Gln Gln Glu Ser
            100                 105                 110
Phe Thr Arg Gln Val Leu Trp Lys Leu Leu Lys Val Lys Phe Gly
        115                 120                 125
Glu Val Ile Ser Tyr Gln Gln Leu Ala Ala Leu Ala Gly Asn Pro Ala
    130                 135                 140
```

```
Ala Thr Ala Ala Val Lys Thr Ala Leu Ser Gly Asn Pro Val Pro Ile
145                 150                 155                 160

Leu Ile Pro Cys His Arg Val Val Ser Ser Gly Ala Val Gly Gly
                165                 170                 175

Tyr Glu Gly Gly Leu Ala Val Lys Glu Trp Leu Leu Ala His Glu Gly
            180                 185                 190

His Arg Leu Gly Lys Pro Gly Leu Gly Pro Ala Gly Ile Gly Ala Pro
            195                 200                 205

Gly Ser Leu Glu Gly Gly Gly Ser Ser Ala Leu Lys Gly Thr Thr
        210                 215                 220

Tyr Gly Met Cys Thr Glu Lys Phe Ser Phe Ala Lys Asn Pro Ala Asp
225                 230                 235                 240

Thr Gly His Gly Thr Val Val Ile Glu Leu Ser Tyr Ser Gly Ser Asp
                245                 250                 255

Gly Pro Cys Lys Ile Pro Ile Val Ser Val Ala Ser Leu Asn Asp Met
            260                 265                 270

Thr Pro Val Gly Arg Leu Val Thr Val Asn Pro Phe Val Ala Ala Ser
            275                 280                 285

Ser Ala Asn Ser Lys Val Leu Val Glu Met Glu Pro Pro Phe Gly Asp
        290                 295                 300

Ser Tyr Ile Val Val Gly Arg Gly Asp Lys Gln Ile Asn His His Trp
305                 310                 315                 320

His Arg Ala Gly Ser Thr Leu Gly Lys Gly Gly His His His
                325                 330                 335

His His

<210> SEQ ID NO 41
<211> LENGTH: 333
<212> TYPE: PRT
<213> ORGANISM: Artificial Sequence
<220> FEATURE:
<223> OTHER INFORMATION: amino acid sequence of the fusion protein
      BiP-SNAP-spacer - EDIII TBE + spacer- (His)6tag

<400> SEQUENCE: 41

Met Lys Leu Cys Ile Leu Leu Ala Val Val Ala Phe Val Gly Leu Ser
1               5                   10                  15

Leu Gly Arg Ser Asp Lys Asp Cys Glu Met Lys Arg Thr Thr Leu Asp
            20                  25                  30

Ser Pro Leu Gly Lys Leu Glu Leu Ser Gly Cys Glu Gln Gly Leu His
            35                  40                  45

Glu Ile Lys Leu Leu Gly Lys Gly Thr Ser Ala Ala Asp Ala Val Glu
    50                  55                  60

Val Pro Ala Pro Ala Ala Val Leu Gly Gly Pro Glu Pro Leu Met Gln
65                  70                  75                  80

Ala Thr Ala Trp Leu Asn Ala Tyr Phe His Gln Pro Glu Ala Ile Glu
                85                  90                  95

Glu Phe Pro Val Pro Ala Leu His His Pro Val Phe Gln Gln Glu Ser
            100                 105                 110

Phe Thr Arg Gln Val Leu Trp Lys Leu Leu Lys Val Val Lys Phe Gly
            115                 120                 125

Glu Val Ile Ser Tyr Gln Gln Leu Ala Ala Leu Ala Gly Asn Pro Ala
    130                 135                 140

Ala Thr Ala Ala Val Lys Thr Ala Leu Ser Gly Asn Pro Val Pro Ile
145                 150                 155                 160
```

```
Leu Ile Pro Cys His Arg Val Val Ser Ser Gly Ala Val Gly Gly
            165                 170                 175

Tyr Glu Gly Gly Leu Ala Val Lys Glu Trp Leu Leu Ala His Glu Gly
        180                 185                 190

His Arg Leu Gly Lys Pro Gly Leu Gly Pro Ala Gly Ile Gly Ala Pro
        195                 200                 205

Gly Ser Leu Glu Gly Gly Gly Ser Leu Glu Lys Leu Lys Met Lys
    210                 215                 220

Gly Leu Thr Tyr Thr Met Cys Asp Lys Thr Lys Phe Thr Trp Lys Arg
225                 230                 235                 240

Ala Pro Thr Asp Ser Gly His Asp Thr Val Val Met Glu Val Thr Phe
            245                 250                 255

Ser Gly Thr Lys Pro Cys Arg Ile Pro Val Arg Ala Val Ala His Gly
        260                 265                 270

Ser Pro Asp Val Asn Val Ala Met Leu Ile Thr Pro Asn Pro Thr Ile
    275                 280                 285

Glu Asn Asn Gly Gly Gly Phe Ile Glu Met Gln Leu Pro Pro Gly Asp
        290                 295                 300

Asn Ile Ile Tyr Val Gly Glu Leu Ser His Gln Trp Phe Gln Lys Gly
305                 310                 315                 320

Ser Ser Ile Gly Gly Gly Gly His His His His His His
            325                 330

<210> SEQ ID NO 42
<211> LENGTH: 337
<212> TYPE: PRT
<213> ORGANISM: Artificial Sequence
<220> FEATURE:
<223> OTHER INFORMATION: amino acid sequence of the fusion protein
      BiP-SNAP-spacer - EDIII USU + spacer- (His)6tag

<400> SEQUENCE: 42

Met Lys Leu Cys Ile Leu Leu Ala Val Val Ala Phe Val Gly Leu Ser
1               5                   10                  15

Leu Gly Arg Ser Asp Lys Asp Cys Glu Met Lys Arg Thr Thr Leu Asp
            20                  25                  30

Ser Pro Leu Gly Lys Leu Glu Leu Ser Gly Cys Glu Gln Gly Leu His
        35                  40                  45

Glu Ile Lys Leu Leu Gly Lys Gly Thr Ser Ala Ala Asp Ala Val Glu
    50                  55                  60

Val Pro Ala Pro Ala Ala Val Leu Gly Gly Pro Glu Pro Leu Met Gln
65                  70                  75                  80

Ala Thr Ala Trp Leu Asn Ala Tyr Phe His Gln Pro Glu Ala Ile Glu
                85                  90                  95

Glu Phe Pro Val Pro Ala Leu His His Pro Val Phe Gln Gln Glu Ser
            100                 105                 110

Phe Thr Arg Gln Val Leu Trp Lys Leu Leu Lys Val Val Lys Phe Gly
        115                 120                 125

Glu Val Ile Ser Tyr Gln Gln Leu Ala Ala Leu Ala Gly Asn Pro Ala
    130                 135                 140

Ala Thr Ala Ala Val Lys Thr Ala Leu Ser Gly Asn Pro Val Pro Ile
145                 150                 155                 160

Leu Ile Pro Cys His Arg Val Val Ser Ser Gly Ala Val Gly Gly
            165                 170                 175

Tyr Glu Gly Gly Leu Ala Val Lys Glu Trp Leu Leu Ala His Glu Gly
```

```
                180                 185                 190
His Arg Leu Gly Lys Pro Gly Leu Gly Pro Ala Gly Ile Gly Ala Pro
            195                 200                 205
Gly Ser Leu Glu Gly Gly Gly Ser Thr Leu Lys Gly Thr Thr Tyr
            210                 215                 220
Gly Met Cys Thr Glu Lys Phe Ser Phe Ala Lys Asn Pro Ala Asp Thr
225                 230                 235                 240
Gly His Gly Thr Val Val Leu Glu Leu Gln Tyr Thr Gly Ser Asp Gly
                245                 250                 255
Pro Cys Lys Ile Pro Ile Ser Ile Val Ala Ser Leu Ser Asp Leu Thr
            260                 265                 270
Pro Ile Gly Arg Met Val Thr Ala Asn Pro Tyr Val Ala Ser Ser Glu
            275                 280                 285
Ala Asn Ala Lys Val Leu Val Glu Met Glu Pro Phe Gly Asp Ser
            290                 295                 300
Tyr Ile Val Val Gly Arg Gly Asp Lys Gln Ile Asn His His Trp His
305                 310                 315                 320
Lys Ala Gly Ser Ser Ile Gly Lys Gly Gly His His His His
                325                 330                 335
His

<210> SEQ ID NO 43
<211> LENGTH: 337
<212> TYPE: PRT
<213> ORGANISM: Artificial Sequence
<220> FEATURE:
<223> OTHER INFORMATION: amino acid sequence of the fusion protein
      BiP-SNAP-spacer - EDIII YF + spacer- (His)6tag

<400> SEQUENCE: 43

Met Lys Leu Cys Ile Leu Leu Ala Val Val Ala Phe Val Gly Leu Ser
1                   5                   10                  15
Leu Gly Arg Ser Asp Lys Asp Cys Glu Met Lys Arg Thr Thr Leu Asp
                20                  25                  30
Ser Pro Leu Gly Lys Leu Glu Leu Ser Gly Cys Glu Gln Gly Leu His
            35                  40                  45
Glu Ile Lys Leu Leu Gly Lys Gly Thr Ser Ala Ala Asp Ala Val Glu
        50                  55                  60
Val Pro Ala Pro Ala Ala Val Leu Gly Gly Pro Glu Pro Leu Met Gln
65                  70                  75                  80
Ala Thr Ala Trp Leu Asn Ala Tyr Phe His Gln Pro Glu Ala Ile Glu
                85                  90                  95
Glu Phe Pro Val Pro Ala Leu His His Pro Val Phe Gln Gln Glu Ser
            100                 105                 110
Phe Thr Arg Gln Val Leu Trp Lys Leu Leu Lys Val Val Lys Phe Gly
        115                 120                 125
Glu Val Ile Ser Tyr Gln Gln Leu Ala Ala Leu Ala Gly Asn Pro Ala
    130                 135                 140
Ala Thr Ala Ala Val Lys Thr Ala Leu Ser Gly Asn Pro Val Pro Ile
145                 150                 155                 160
Leu Ile Pro Cys His Arg Val Val Ser Ser Gly Ala Val Gly Gly
                165                 170                 175
Tyr Glu Gly Gly Leu Ala Val Lys Glu Trp Leu Leu Ala His Glu Gly
            180                 185                 190
His Arg Leu Gly Lys Pro Gly Leu Gly Pro Ala Gly Ile Gly Ala Pro
```

```
                195                 200                 205
Gly Ser Leu Glu Gly Gly Gly Ser Ser Ala Leu Thr Leu Lys Gly
    210                 215                 220

Thr Ser Tyr Lys Met Cys Thr Asp Lys Met Ser Phe Val Lys Asn Pro
225                 230                 235                 240

Thr Asp Thr Gly His Gly Thr Val Val Met Gln Val Lys Val Pro Lys
                245                 250                 255

Gly Ala Pro Cys Lys Ile Pro Val Ile Val Ala Asp Asp Leu Thr Ala
                260                 265                 270

Ala Ile Asn Lys Gly Ile Leu Val Thr Val Asn Pro Ile Ala Ser Thr
                275                 280                 285

Asn Asp Asp Glu Val Leu Ile Glu Val Asn Pro Pro Phe Gly Asp Ser
                290                 295                 300

Tyr Ile Ile Val Gly Thr Gly Asp Ser Arg Leu Thr Tyr Gln Trp His
305                 310                 315                 320

Lys Glu Gly Ser Ser Ile Gly Lys Gly Gly His His His His
                325                 330                 335

His

<210> SEQ ID NO 44
<211> LENGTH: 234
<212> TYPE: PRT
<213> ORGANISM: Artificial Sequence
<220> FEATURE:
<223> OTHER INFORMATION: Amino acid sequence of the fusion polypeptide:
      BiP signal peptide + SNAP+ enterokinase site+EcoRV/XmaI+Histag

<400> SEQUENCE: 44

Met Lys Leu Cys Ile Leu Leu Ala Val Val Ala Phe Val Gly Leu Ser
1               5                   10                  15

Leu Gly Arg Ser Asp Lys Asp Cys Glu Met Lys Arg Thr Thr Leu Asp
                20                  25                  30

Ser Pro Leu Gly Lys Leu Glu Leu Ser Gly Cys Glu Gln Gly Leu His
                35                  40                  45

Glu Ile Lys Leu Leu Gly Lys Gly Thr Ser Ala Ala Asp Ala Val Glu
    50                  55                  60

Val Pro Ala Pro Ala Ala Val Leu Gly Gly Pro Glu Pro Leu Met Gln
65                  70                  75                  80

Ala Thr Ala Trp Leu Asn Ala Tyr Phe His Gln Pro Glu Ala Ile Glu
                85                  90                  95

Glu Phe Pro Val Pro Ala Leu His His Pro Val Phe Gln Gln Glu Ser
                100                 105                 110

Phe Thr Arg Gln Val Leu Trp Lys Leu Leu Lys Val Val Lys Phe Gly
                115                 120                 125

Glu Val Ile Ser Tyr Gln Gln Leu Ala Ala Leu Ala Gly Asn Pro Ala
    130                 135                 140

Ala Thr Ala Ala Val Lys Thr Ala Leu Ser Gly Asn Pro Val Pro Ile
145                 150                 155                 160

Leu Ile Pro Cys His Arg Val Val Ser Ser Gly Ala Val Gly Gly
                165                 170                 175

Tyr Glu Gly Gly Leu Ala Val Lys Glu Trp Leu Leu Ala His Glu Gly
                180                 185                 190

His Arg Leu Gly Lys Pro Gly Leu Gly Pro Ala Gly Ile Gly Ala Pro
                195                 200                 205

Gly Ser Leu Gly Gly Gly Ser Asp Asp Asp Asp Lys Asp Ile Lys Asn
```

```
                    210                 215                 220
Pro Gly Gly Gly Ser His His His His
225                 230

<210> SEQ ID NO 45
<211> LENGTH: 211
<212> TYPE: PRT
<213> ORGANISM: mus musculus

<400> SEQUENCE: 45

Met Ala Glu Thr Cys Lys Met Lys Tyr Ser Val Leu Asp Ser Pro Leu
1               5                   10                  15

Gly Lys Met Glu Leu Ser Gly Cys Glu Arg Gly Leu His Gly Ile Arg
                20                  25                  30

Leu Leu Ser Gly Lys Thr Pro Asn Thr Asp Pro Thr Glu Ala Pro Ala
            35                  40                  45

Thr Pro Glu Val Leu Gly Gly Pro Gly Val Pro Glu Pro Leu Val
        50                  55                  60

Gln Cys Thr Ala Trp Leu Glu Ala Tyr Phe Arg Glu Pro Ala Ala Thr
65                  70                  75                  80

Glu Gly Leu Pro Leu Pro Ala Leu His His Pro Val Phe Gln Gln Asp
                85                  90                  95

Ser Phe Thr Arg Gln Val Leu Trp Lys Leu Leu Lys Val Val Lys Phe
            100                 105                 110

Gly Glu Thr Val Ser Tyr Gln Gln Leu Ala Ala Leu Ala Gly Asn Pro
        115                 120                 125

Lys Ala Ala Arg Ala Val Gly Gly Ala Met Arg Ser Asn Pro Val Pro
130                 135                 140

Ile Leu Ile Pro Cys His Arg Val Val Arg Ser Asp Gly Ala Ile Gly
145                 150                 155                 160

His Tyr Ser Gly Gly Gly Gln Ala Val Lys Glu Trp Leu Leu Ala His
                165                 170                 175

Glu Gly Ile Pro Thr Gly Gln Pro Ala Ser Lys Gly Leu Gly Leu Thr
            180                 185                 190

Gly Thr Trp Leu Lys Ser Ser Phe Glu Ser Thr Ser Glu Pro Ser
        195                 200                 205

Gly Arg Asn
    210

<210> SEQ ID NO 46
<211> LENGTH: 209
<212> TYPE: PRT
<213> ORGANISM: ratus norvegicus

<400> SEQUENCE: 46

Met Ala Glu Ile Cys Lys Met Lys Tyr Thr Val Leu Asp Ser Pro Leu
1               5                   10                  15

Gly Lys Ile Glu Leu Ser Gly Cys Glu Arg Gly Leu His Gly Ile Arg
                20                  25                  30

Phe Leu Ser Gly Lys Thr Pro Asn Thr Asp Pro Thr Glu Ala Pro Ala
            35                  40                  45

Cys Pro Glu Val Leu Gly Gly Pro Glu Gly Val Pro Glu Pro Leu Val
        50                  55                  60

Gln Cys Thr Ala Trp Leu Glu Ala Tyr Phe His Glu Pro Ala Ala Thr
65                  70                  75                  80

Glu Gly Leu Pro Leu Pro Ala Leu His His Pro Val Phe Gln Gln Asp
```

```
                85                  90                  95

Ser Phe Thr Arg Gln Val Leu Trp Lys Leu Leu Lys Val Val Lys Phe
            100                 105                 110

Gly Glu Met Val Ser Tyr Gln Gln Leu Ala Ala Leu Ala Gly Asn Pro
        115                 120                 125

Lys Ala Ala Arg Ala Val Gly Gly Ala Met Arg Ser Asn Pro Val Pro
    130                 135                 140

Ile Leu Ile Pro Cys His Arg Val Ile Arg Ser Asp Gly Ala Ile Gly
145                 150                 155                 160

Asn Tyr Ser Gly Gly Gly Gln Thr Val Lys Glu Trp Leu Leu Ala His
                165                 170                 175

Glu Gly Ile Pro Thr Gly Gln Pro Ala Ser Lys Gly Leu Gly Leu Ile
            180                 185                 190

Gly Ser Trp Leu Lys Pro Ser Phe Glu Ser Ser Ser Pro Lys Pro Ser
        195                 200                 205

Gly
```

<210> SEQ ID NO 47
<211> LENGTH: 555
<212> TYPE: DNA
<213> ORGANISM: Artificial Sequence
<220> FEATURE:
<223> OTHER INFORMATION: DNA encoding SNAP G/C low content

<400> SEQUENCE: 47

```
attgaattta cagacaaaga ctgcgaaatg aaaagaacta cattggattc accacttggg     60
aagttggaac tgagtggatg cgagcaagga ttgcatgaaa ttaagcttct gggaaaagga    120
acttctgcag ctgatgcagt tgaagttcca gcaccagcag ctgttcttgg aggtcctgag    180
cccctcatgc aagccacagc ctggcttaac gcatatttcc accagcctga ggccattgag    240
gaatttccag tccccgccct tcaccatcct gtgtttcagc aggaaagctt cacccgccag    300
gtcctgtgga aattgctgaa ggtggtcaag tttggtgaag tgatttcata tcagcaactt    360
gctgcattgg ccggtaaccc cgcagctaca gctgccgtga aaactgctct cagcggaaat    420
cctgtgccca tcctgatccc ttgtcacaga gtcgtttcat cttccggagc tgtaggtggc    480
tatgaaggag gactggcagt taaggagtgg ctgctggctc atgaaggtca tagacttgga    540
aaacctggtt tggga                                                     555
```

<210> SEQ ID NO 48
<211> LENGTH: 18
<212> TYPE: PRT
<213> ORGANISM: Artificial Sequence
<220> FEATURE:
<223> OTHER INFORMATION: amino acid sequence of BiP

<400> SEQUENCE: 48

```
Met Lys Leu Cys Ile Leu Leu Ala Val Val Ala Phe Val Gly Leu Ser
1               5                   10                  15

Leu Gly
```

<210> SEQ ID NO 49
<211> LENGTH: 738
<212> TYPE: DNA
<213> ORGANISM: TOSCANA virus

<400> SEQUENCE: 49

```
atggacaact atcaagagct tcgagtccag tttgctgctc aagcagtgga ccgcaatgag     60
```

```
attgaacagt gggtccgaga gtttgcttat caagggtttg atgcccgtag agttatcgaa    120
ctcttaaagc agtatggtgg ggctgactgg gagaaggatg ccaagaaaat gattgttctg    180
gctctaactc gtggcaacaa gcccaggagg atgatgatga aaatgtcgaa agaaggcaaa    240
gcaactgtgg aggctctcat caacaagtat aagctaaagg aagggaatcc ttcccgggat    300
gagttgactc tatcacgagt tgctgccgcc ttggctggct ggacatgcca ggctttggtc    360
gtcttgagtg agtggcttcc tgtcactggg actaccatgg acggcctatc ccctgcatac    420
ccgaggcata tgatgcaccc cagctttgct ggcatggtgg atccttctct accaggagac    480
tatctaaggg caatattaga tgctcactct ctgtatctgc tgcagttctc ccgggtcatc    540
aacccaaacc tccgaggtag aacaaaagag gaggttgctg caacgttcac gcagccaatg    600
aatgcagcag tgaatagcaa ctttataagc catgagaaga ggagagaatt cttgaaagcc    660
tttggacttg tggattccaa tgggaagccg tcagctgctg tcatggcagc cgctcaggct    720
tacaagacag cagcctaa                                                   738
```

<210> SEQ ID NO 50
<211> LENGTH: 66
<212> TYPE: DNA
<213> ORGANISM: Artificial Sequence
<220> FEATURE:
<223> OTHER INFORMATION: BiP-like signal : extended insect BiP signal
      peptide for mammalian cells

<400> SEQUENCE: 50

```
atgaaactat gtattctact tgcagttgtt gcgttcgtag gattgtcctt acctacagct    60
ctggca                                                                66
```

<210> SEQ ID NO 51
<211> LENGTH: 22
<212> TYPE: PRT
<213> ORGANISM: Artificial Sequence
<220> FEATURE:
<223> OTHER INFORMATION: BiP-like signal : extended insect BiP signal
      peptide for mammalian cells

<400> SEQUENCE: 51

```
Met Lys Leu Cys Ile Leu Leu Ala Val Val Ala Phe Val Gly Leu Ser
1               5                   10                  15

Leu Pro Thr Ala Leu Ala
            20
```

<210> SEQ ID NO 52
<211> LENGTH: 21
<212> TYPE: DNA
<213> ORGANISM: Tobacco etch virus

<400> SEQUENCE: 52

```
gaaaacctgt acttccagag c                                               21
```

<210> SEQ ID NO 53
<211> LENGTH: 7
<212> TYPE: PRT
<213> ORGANISM: Tobacco etch virus

<400> SEQUENCE: 53

```
Glu Asn Leu Tyr Phe Gln Ser
1               5
```

<210> SEQ ID NO 54
<211> LENGTH: 699
<212> TYPE: DNA
<213> ORGANISM: Homo sapiens

<400> SEQUENCE: 54

| | | | | | |
|---|---|---|---|---|---|
| gatatcatag | gaggtcgaga | agttattccc | cactcacgcc | cttacatggc | atcacttcag | 60 |
| agaaatggtt | cccacctatg | cggtggtgta | ctagttcacc | caaagtgggt | tctaacggca | 120 |
| gctcactgcc | ttgcccagcg | gatggctcag | ctaaggcttg | tacttggact | tcacacccta | 180 |
| gacagccccg | gtctcacctt | ccacatcaag | gcagctatcc | agcaccctcg | atacaagcca | 240 |
| gtacctgcac | ttgagaacga | cctagctcta | cttcagctag | acggtaaagt | aaagcctagc | 300 |
| cggaccatcc | gaccgttggc | tctacctagt | aagcgccagg | tagttgcagc | aggtactcgg | 360 |
| tgcagcatgg | caggctgggg | acttacccac | cagggtggac | gcctttcccg | agtacttcgg | 420 |
| gagctagacc | ttcaagtact | ggacacccgc | atgtgtaaca | acagccgctt | ttggaacgga | 480 |
| agcctatccc | caagcatggt | ttgcctagca | gctgactcca | aggaccaggc | tccctgcaag | 540 |
| ggtgactcgg | gtggaccct | ggtttgtggc | aaaggccggg | tgttagccgg | agttctttcc | 600 |
| ttcagctcca | gggtatgcac | tgacatcttc | aagcctccag | ttgcaaccgc | tgttgcacct | 660 |
| tacgtttcct | ggatcaggaa | ggtcaccggt | cgatcggcc | | | 699 |

Figure 6:
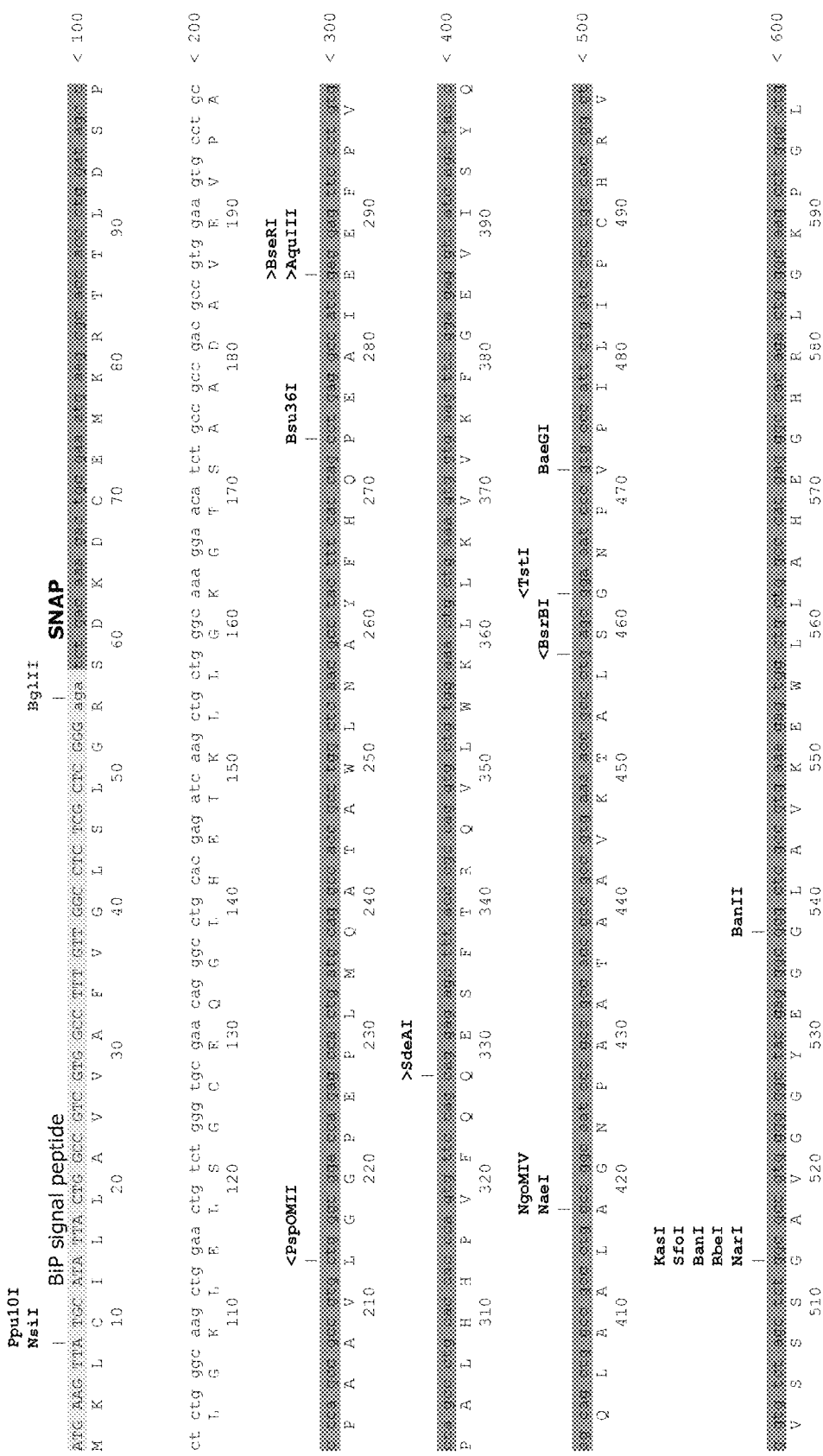
Figure 6:
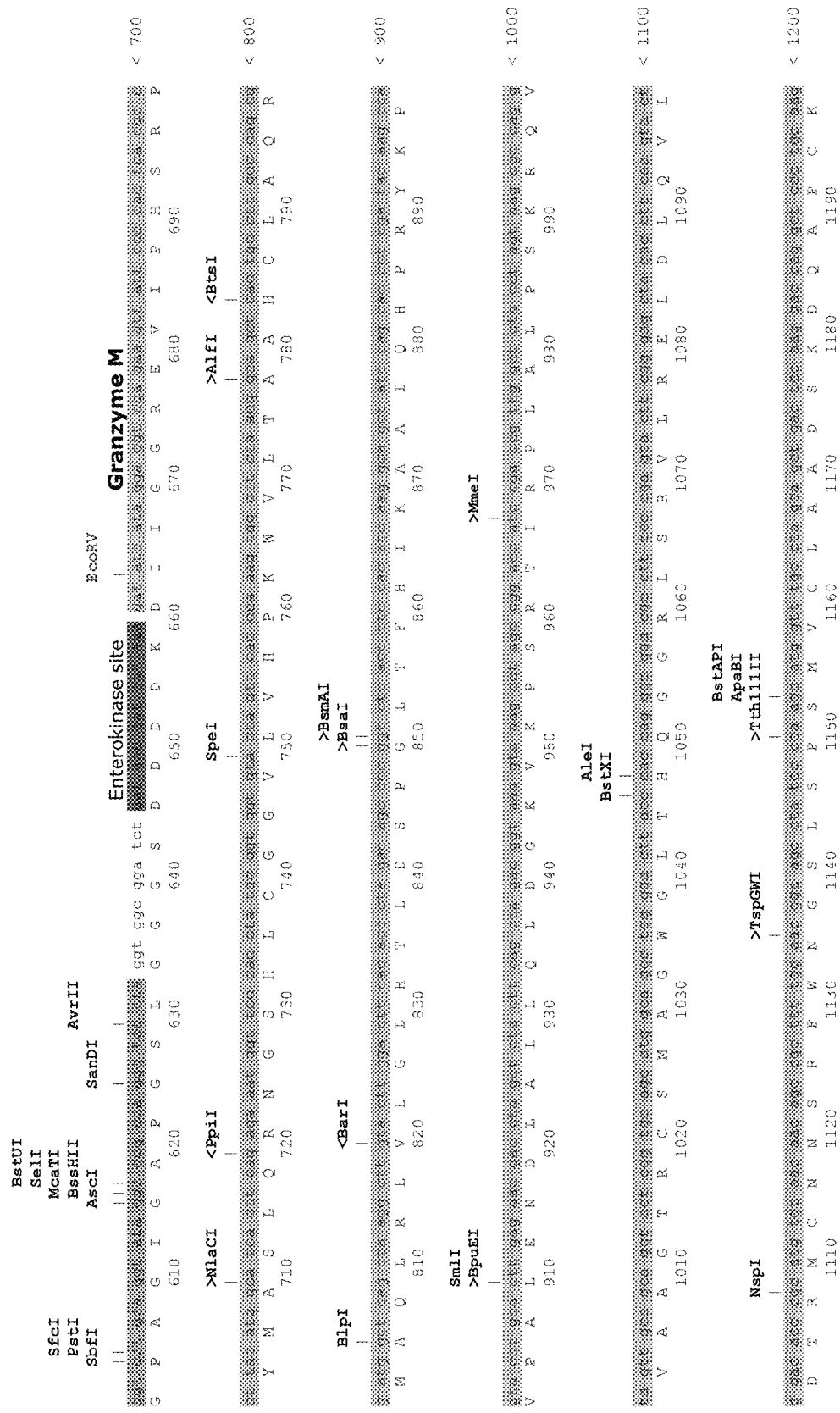
Figure 6:
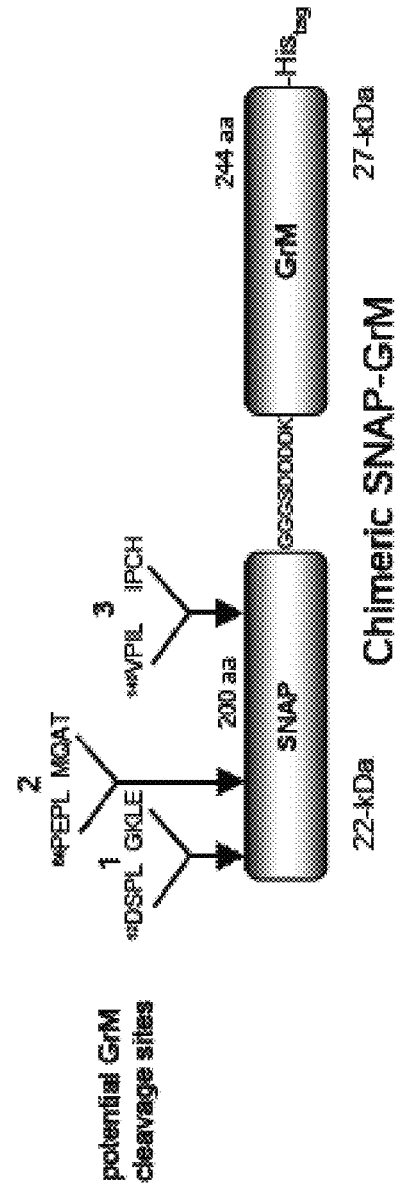
Figure 6:
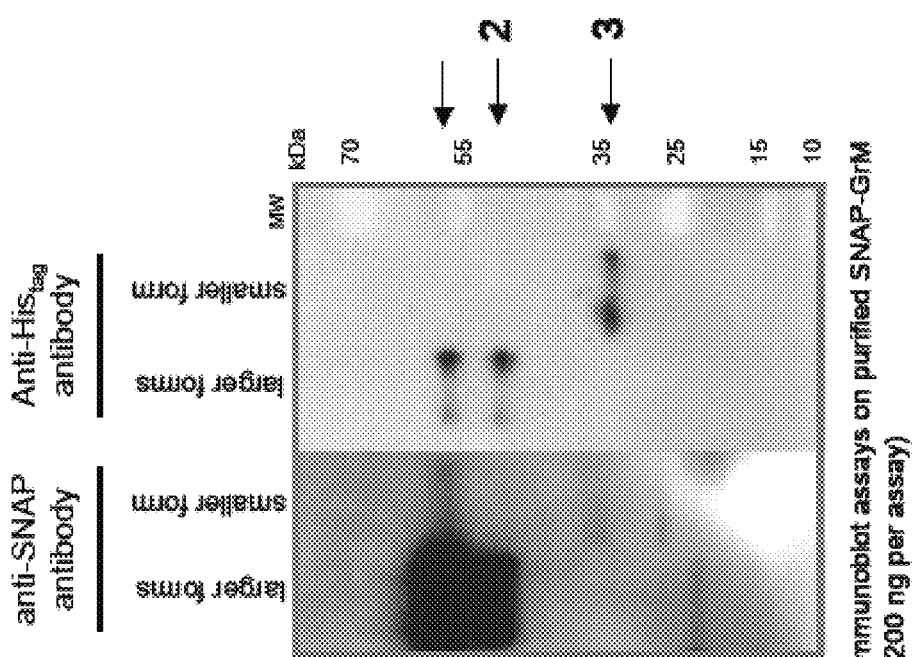

<210> SEQ ID NO 55
<211> LENGTH: 1400
<212> TYPE: DNA
<213> ORGANISM: Artificial Sequence
<220> FEATURE:
<223> OTHER INFORMATION: DNA sequence of insect BiP-like/SNAP/
      enteroKinase/GrM/Histag for S2 cells (fig 6)

<400> SEQUENCE: 55

| | | | | | |
|---|---|---|---|---|---|
| atgaagttat | gcatattact | ggccgtcgtg | gcctttgttg | gcctctcgct | cggagatct | 60 |
| gacaaagact | gcgaaatgaa | gcgcaccacc | ctggatagcc | ctctgggcaa | gctgaactg | 120 |
| tctgggtgcg | aacagggcct | gcacgagatc | aagctgctgg | gcaaaggaac | atctgccgcc | 180 |
| gacgccgtgg | aagtgcctgc | cccagccgcc | gtgctgggcg | gaccagagcc | actgatgcag | 240 |
| gccaccgcct | ggctcaacgc | ctactttcac | cagcctgagg | ccatcgagga | gttccctgtg | 300 |
| ccagccctgc | accacccagt | gttccagcag | gagagcttta | cccgccaggt | gctgtggaaa | 360 |
| ctgctgaaag | tggtgaagtt | cggagaggtc | atcagctacc | agcagctggc | cgccctggcc | 420 |
| ggcaatcccg | ccgccaccgc | cgccgtgaaa | accgccctga | gcggaaatcc | cgtgcccatt | 480 |
| ctgatcccct | gccaccgggt | ggtgtctagc | tctggcgccg | tgggggcta | cgagggcggg | 540 |
| ctcgccgtga | aagagtggct | gctggcccac | gagggccaca | gactgggcaa | gcctgggctg | 600 |
| ggtcctgcag | gtataggcgc | gccagggtcc | ctaggtggcg | gatctgatga | cgatgataaa | 660 |
| gatatcatag | gaggtcgaga | agttattccc | cactcacgcc | cttacatggc | atcacttcag | 720 |
| agaaatggtt | cccacctatg | cggtggtgta | ctagttcacc | caaagtgggt | tctaacggca | 780 |
| gctcactgcc | ttgcccagcg | gatggctcag | ctaaggcttg | tacttggact | tcacacccta | 840 |
| gacagccccg | gtctcacctt | ccacatcaag | gcagctatcc | agcaccctcg | atacaagcca | 900 |
| gtacctgcac | ttgagaacga | cctagctcta | cttcagctag | acggtaaagt | aaagcctagc | 960 |
| cggaccatcc | gaccgttggc | tctacctagt | aagcgccagg | tagttgcagc | aggtactcgg | 1020 |
| tgcagcatgg | caggctgggg | acttacccac | cagggtggac | gcctttcccg | agtacttcgg | 1080 |
| gagctagacc | ttcaagtact | ggacacccgc | atgtgtaaca | acagccgctt | ttggaacgga | 1140 |

-continued

```
agcctatccc caagcatggt ttgcctagca gctgactcca aggaccaggc tccctgcaag    1200
ggtgactcgg gtggacccct ggtttgtggc aaaggccggg tgttagccgg agttctttcc    1260
ttcagctcca gggtatgcac tgacatcttc aagcctccag ttgcaaccgc tgttgcacct    1320
tacgtttcct ggatcaggaa ggtcaccggt cgatcggccc cgggcggtgg aagtcatcat    1380
catcatcatc attgaccggt                                                1400
```

```
<210> SEQ ID NO 56
<211> LENGTH: 434
<212> TYPE: PRT
<213> ORGANISM: Artificial Sequence
<220> FEATURE:
<223> OTHER INFORMATION: Amino acid sequence of BiP-like/SNAP/
      enteroKinase/GrM/Histag for S2 cells (fig 6)

<400> SEQUENCE: 56
```

| | | | | | | | | | | | | | | |
|---|---|---|---|---|---|---|---|---|---|---|---|---|---|---|
| Met | Lys | Leu | Cys | Ile | Leu | Leu | Ala | Val | Val | Ala | Phe | Val | Gly | Leu | Ser |
| 1 | | | | 5 | | | | | 10 | | | | | 15 | |

Leu Gly Arg Ser Asp Lys Asp Cys Glu Met Lys Arg Thr Thr Leu Asp
            20                  25                  30

Ser Pro Leu Gly Lys Leu Glu Leu Ser Gly Cys Glu Gln Gly Leu His
        35                  40                  45

Glu Ile Lys Leu Leu Gly Lys Gly Thr Ser Ala Ala Asp Ala Val Glu
    50                  55                  60

Val Pro Ala Pro Ala Ala Val Leu Gly Gly Pro Glu Pro Leu Met Gln
65                  70                  75                  80

Ala Thr Ala Trp Leu Asn Ala Tyr Phe His Gln Pro Glu Ala Ile Glu
                85                  90                  95

Glu Phe Pro Val Pro Ala Leu His His Pro Val Phe Gln Gln Glu Ser
            100                 105                 110

Phe Thr Arg Gln Val Leu Trp Lys Leu Leu Lys Val Val Lys Phe Gly
        115                 120                 125

Glu Val Ile Ser Tyr Gln Gln Leu Ala Ala Leu Ala Gly Asn Pro Ala
    130                 135                 140

Ala Thr Ala Ala Val Lys Thr Ala Leu Ser Gly Asn Pro Val Pro Ile
145                 150                 155                 160

Leu Ile Pro Cys His Arg Val Val Ser Ser Gly Ala Val Gly Gly
                165                 170                 175

Tyr Glu Gly Gly Leu Ala Val Lys Glu Trp Leu Leu Ala His Glu Gly
            180                 185                 190

His Arg Leu Gly Lys Pro Gly Leu Gly Pro Ala Gly Ile Gly Ala Pro
        195                 200                 205

Gly Ser Leu Gly Gly Ser Asp Asp Asp Lys Asp Ile Ile Gly
    210                 215                 220

Gly Arg Glu Val Ile Pro His Ser Arg Pro Tyr Met Ala Ser Leu Gln
225                 230                 235                 240

Arg Asn Gly Ser His Leu Cys Gly Gly Val Leu Val His Pro Lys Trp
                245                 250                 255

Val Leu Thr Ala Ala His Cys Leu Ala Gln Arg Met Ala Gln Leu Arg
            260                 265                 270

Leu Val Leu Gly Leu His Thr Leu Asp Ser Pro Gly Leu Thr Phe His
        275                 280                 285

Ile Lys Ala Ala Ile Gln His Pro Arg Tyr Lys Pro Val Pro Ala Leu
    290                 295                 300

```
Glu Asn Asp Leu Ala Leu Leu Gln Leu Asp Gly Lys Val Lys Pro Ser
305                 310                 315                 320
Arg Thr Ile Arg Pro Leu Ala Leu Pro Ser Lys Arg Gln Val Val Ala
            325                 330                 335
Ala Gly Thr Arg Cys Ser Met Ala Gly Trp Gly Leu Thr His Gln Gly
            340                 345                 350
Gly Arg Leu Ser Arg Val Leu Arg Glu Leu Asp Leu Gln Val Leu Asp
            355                 360                 365
Thr Arg Met Cys Asn Asn Ser Arg Phe Trp Asn Gly Ser Leu Ser Pro
    370                 375                 380
Ser Met Val Cys Leu Ala Ala Asp Ser Lys Asp Gln Ala Pro Cys Lys
385                 390                 395                 400
Gly Asp Ser Gly Gly Pro Leu Val Cys Gly Lys Gly Arg Val Leu Ala
                405                 410                 415
Gly Val Leu Ser Phe Ser Ser Arg Val Cys Thr Asp Ile Phe Lys Pro
                420                 425                 430
Pro Val

<210> SEQ ID NO 57
<211> LENGTH: 1243
<212> TYPE: DNA
<213> ORGANISM: Artificial Sequence
<220> FEATURE:
<223> OTHER INFORMATION: DNA sequence of BiP-like/SNAP-like/proTEV/IFN/
      Histag for mammalian cells such as HeLa cells (fig 7)

<400> SEQUENCE: 57
gctagcacca tgaagttatg catattactg gccgtcgtgg cctttgttgg cctctcgctc      60
ccaacagctc tggcagacaa agactgcgaa atgaaaagaa ctacattgga ttcaccactt     120
gggaagttgg aactgagtgg atgcgagcaa ggattgcatg aaattaagct actgggaaaa     180
ggaacttctg ctgctgatgc agttgaagtt ccagcaccag cagctgttct tggaggtcct     240
gagcccctca tgcaagccac agcctggctt aacgcatatt tccaccagcc tgaggccatt     300
gaggaatttc cagtccccgc ccttcaccat cctgtgtttc agcaggagag cttcacccgc     360
caggtcctgt ggaaattgct gaaggtggtc aagtttggtg aagtgatttc atatcagcaa     420
cttgctgcat tggccggtaa ccccgcagct acagctgccg tgaaaactgc tctcagcgga     480
aatcctgtgc ccatcctgat cccttgtcac agagtcgttt catcttccgg agctgtaggt     540
ggctatgaag gaggactggc agttaaggag tggctgctgg ctcatgaagg tcatagactt     600
ggaaagcctg gctgggtcc tgctggtata ggcgcgccag gtccctagg tggcggatct      660 gaaaacctgt acttccagag cgatatctgt gatctccctg agacccacag cctggataac     720
aggaggacct tgatgctcct ggcacaaatg agcagaatct tccttcctc ctgtctgatg      780 gacagacatg actttggatt tccccaggag gagtttgatg caaccagtt ccagaaggct      840 ccagccatct ctgtcctcca tgagctgatc agcagattt caacctctt taccacaaaa      900 gattcatctg ctgcttggga tgaggacctc ctagacaaat tctgcaccga actctaccag    960
cagctgaatg acttggaagc ctgtgtgatg caggaggaga gggtgggaga aactcccctg    1020
atgaatgcgg actccatctt ggctgtgaag aaatacttcc gaagaatcac tctctatctg   1080
acagagaaga aatacagccc ttgtgcctgg gaggttgtca gagcagaaat catgagatcc   1140
ctctctttat caacaaactt gcaagaaaga ttaaggagga aggaaggcaa gtggcccggg   1200
ggtggaagtc atcatcatca tcatcattga agcttgcggc cgc                       1243
```

-continued

<210> SEQ ID NO 58
<211> LENGTH: 406
<212> TYPE: PRT
<213> ORGANISM: Artificial Sequence
<220> FEATURE:
<223> OTHER INFORMATION: Amino acid sequence of BiP-like/SNAP-like/
      proTEV/IFN/Histag for mammalian cells such as HeLa cells (fig 7)

<400> SEQUENCE: 58

```
Met Lys Leu Cys Ile Leu Ala Val Ala Phe Val Gly Leu Ser
1               5                   10                  15

Leu Pro Thr Ala Leu Ala Asp Lys Asp Cys Glu Met Lys Arg Thr Thr
            20                  25                  30

Leu Asp Ser Pro Leu Gly Lys Leu Glu Leu Ser Gly Cys Glu Gln Gly
        35                  40                  45

Leu His Glu Ile Lys Leu Leu Gly Lys Gly Thr Ser Ala Ala Asp Ala
    50                  55                  60

Val Glu Val Pro Ala Pro Ala Ala Val Leu Gly Gly Pro Glu Pro Leu
65                  70                  75                  80

Met Gln Ala Thr Ala Trp Leu Asn Ala Tyr Phe His Gln Pro Glu Ala
                85                  90                  95

Ile Glu Glu Phe Pro Val Pro Ala Leu His His Pro Val Phe Gln Gln
            100                 105                 110

Glu Ser Phe Thr Arg Gln Val Leu Trp Lys Leu Leu Lys Val Val Lys
        115                 120                 125

Phe Gly Glu Val Ile Ser Tyr Gln Gln Leu Ala Ala Leu Ala Gly Asn
    130                 135                 140

Pro Ala Ala Thr Ala Ala Val Lys Thr Ala Leu Ser Gly Asn Pro Val
145                 150                 155                 160

Pro Ile Leu Ile Pro Cys His Arg Val Val Ser Ser Gly Ala Val
                165                 170                 175

Gly Gly Tyr Glu Gly Gly Leu Ala Val Lys Glu Trp Leu Leu Ala His
            180                 185                 190

Glu Gly His Arg Leu Gly Lys Pro Gly Leu Gly Pro Ala Gly Ile Gly
        195                 200                 205

Ala Pro Gly Ser Leu Gly Gly Gly Ser Glu Asn Leu Tyr Phe Gln Ser
    210                 215                 220

Asp Ile Cys Asp Leu Pro Glu Thr His Ser Leu Asp Asn Arg Arg Thr
225                 230                 235                 240

Leu Met Leu Leu Ala Gln Met Ser Arg Ile Ser Pro Ser Ser Cys Leu
                245                 250                 255

Met Asp Arg His Asp Phe Gly Phe Pro Gln Glu Glu Phe Asp Gly Asn
            260                 265                 270

Gln Phe Gln Lys Ala Pro Ala Ile Ser Val Leu His Glu Leu Ile Gln
        275                 280                 285

Gln Ile Phe Asn Leu Phe Thr Thr Lys Asp Ser Ser Ala Ala Trp Asp
    290                 295                 300

Glu Asp Leu Leu Asp Lys Phe Cys Thr Glu Leu Tyr Gln Gln Leu Asn
305                 310                 315                 320

Asp Leu Glu Ala Cys Val Met Gln Glu Glu Arg Val Gly Glu Thr Pro
                325                 330                 335

Leu Met Asn Ala Asp Ser Ile Leu Ala Val Lys Lys Tyr Phe Arg Arg
            340                 345                 350

Ile Thr Leu Tyr Leu Thr Glu Lys Lys Tyr Ser Pro Cys Ala Trp Glu
        355                 360                 365
```

Val Val Arg Ala Glu Ile Met Arg Ser Leu Ser Leu Ser Thr Asn Leu
        370                 375                 380

Gln Glu Arg Leu Arg Arg Lys Glu Gly Lys Trp Pro Gly Gly Gly Ser
385                 390                 395                 400

His His His His His His
            405

Figure 8:
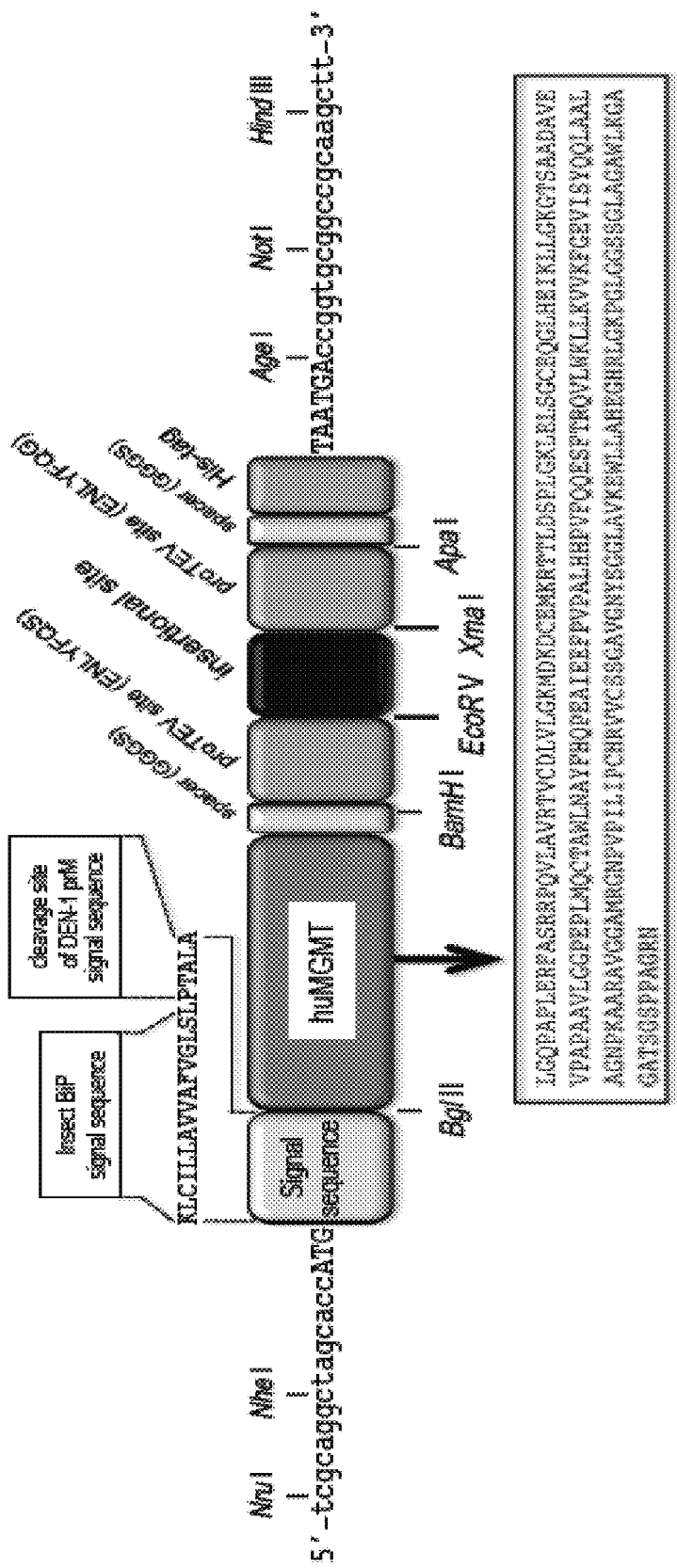

<210> SEQ ID NO 59
<211> LENGTH: 798
<212> TYPE: DNA
<213> ORGANISM: Artificial Sequence
<220> FEATURE:
<223> OTHER INFORMATION: DNA sequence of deSNAP Univ : BiP-like/SNAP-
      like/proTEV/MCS/proTEV/Histag (fig 8)

<400> SEQUENCE: 59
gatcgcgagc tagcaccatg aaactatgta ttctacttgc agttgttgcg ttcgtaggat      60
tgtccttacc tacagctctg gcaagatctg acaaagactg cgaaatgaaa agaactacat    120
tggattcacc acttgggaag ttggaactga gtggatgcga gcaaggattg catgaaatta    180
agctactggg aaaaggaact tctgctgctg atgcagttga agttccagca ccagcagctg    240
ttcttggagg tcctgagccc ctcatgcaag ccacagcctg gcttaacgca tatttccacc    300
agcctgaggc cattgaggaa tttccagtcc ccgcccttca ccatcctgtg tttcagcagg    360
agagcttcac ccgccaggtc ctgtggaaat tgctgaaggt ggtcaagttt ggtgaagtga    420
tttcatatca gcaacttgct gcattggccg gtaaccccgc agctacagct gccgtgaaaa    480
ctgctctcag cggaaatcct gtgcccatcc tgatcccttg tcacagagtc gtttcatctt    540
ccggagctgt aggtggctat gaaggaggac tggcagttaa ggagtggctg ctggctcatg    600
aaggtcatag acttggaaag cctgggctgg gtcctgctgg tataggcgcg ccagggtccc    660
taggtggcgg atccgaaaac ctgtacttcc agagcgatat cggaggtgga ggcccgggag    720
agaatctata ttttcaaggg cccggcggag gtagtcacca tcatcaccat cactaatgac    780
cggtgcggcc gcaagctt                                                   798

<210> SEQ ID NO 60
<211> LENGTH: 252
<212> TYPE: PRT
<213> ORGANISM: Artificial Sequence
<220> FEATURE:
<223> OTHER INFORMATION: Amino acid sequence of deSNAP Univ :
      BiP-like/SNAP-like/proTEV/MCS/ proTEV/Histag (fig 8)

<400> SEQUENCE: 60

Met Lys Leu Cys Ile Leu Leu Ala Val Val Ala Phe Val Gly Leu Ser
1               5                   10                  15

Leu Pro Thr Ala Leu Ala Arg Ser Asp Lys Asp Cys Glu Met Lys Arg
            20                  25                  30

Thr Thr Leu Asp Ser Pro Leu Gly Lys Leu Glu Leu Ser Gly Cys Glu
        35                  40                  45

Gln Gly Leu His Glu Ile Lys Leu Leu Gly Lys Gly Thr Ser Ala Ala
    50                  55                  60

Asp Ala Val Glu Val Pro Ala Pro Ala Ala Val Leu Gly Gly Pro Glu
65                  70                  75                  80

Pro Leu Met Gln Ala Thr Ala Trp Leu Asn Ala Tyr Phe His Gln Pro
                85                  90                  95

Glu Ala Ile Glu Glu Phe Pro Val Pro Ala Leu His His Pro Val Phe

```
                      100                 105                 110
Gln Gln Glu Ser Phe Thr Arg Gln Val Leu Trp Lys Leu Leu Lys Val
        115                 120                 125

Val Lys Phe Gly Glu Val Ile Ser Tyr Gln Gln Leu Ala Ala Leu Ala
    130                 135                 140

Gly Asn Pro Ala Ala Thr Ala Ala Val Lys Thr Ala Leu Ser Gly Asn
145                 150                 155                 160

Pro Val Pro Ile Leu Ile Pro Cys His Arg Val Val Ser Ser Ser Gly
                165                 170                 175

Ala Val Gly Gly Tyr Glu Gly Gly Leu Ala Val Lys Glu Trp Leu Leu
            180                 185                 190

Ala His Glu Gly His Arg Leu Gly Lys Pro Gly Leu Gly Pro Ala Gly
        195                 200                 205

Ile Gly Ala Pro Gly Ser Leu Gly Gly Ser Glu Asn Leu Tyr Phe
    210                 215                 220

Gln Ser Asp Ile Gly Gly Gly Pro Gly Glu Asn Leu Tyr Phe Gln
225                 230                 235                 240

Gly Pro Gly Gly Gly Ser His His His His His His
                245                 250

<210> SEQ ID NO 61
<211> LENGTH: 5
<212> TYPE: PRT
<213> ORGANISM: Artificial Sequence
<220> FEATURE:
<223> OTHER INFORMATION: Amino acid cleavage site of the membrane
      precursor prM from Dengue virus serotype 1

<400> SEQUENCE: 61

Pro Thr Ala Leu Ala
1               5

<210> SEQ ID NO 62
<211> LENGTH: 6
<212> TYPE: PRT
<213> ORGANISM: Artificial Sequence
<220> FEATURE:
<223> OTHER INFORMATION: Amino acid cleavage site of enterokinase

<400> SEQUENCE: 62

Asp Asp Asp Asp Lys Asp
1               5

<210> SEQ ID NO 63
<211> LENGTH: 4
<212> TYPE: PRT
<213> ORGANISM: Artificial Sequence
<220> FEATURE:
<223> OTHER INFORMATION: Amino acid spacer sequence

<400> SEQUENCE: 63

Gly Gly Gly Ser
1

<210> SEQ ID NO 64
<211> LENGTH: 3461
<212> TYPE: DNA
<213> ORGANISM: Artificial Sequence
<220> FEATURE:
<223> OTHER INFORMATION: DeSNAP-Universal sequence inserted into pUC57
      plasmid

<400> SEQUENCE: 64
```

-continued

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgagctcggt acctcgcgaa   420
tgcatctaga ttcgcgagct agcaccatga aactatgtat tctacttgca gttgttgcgt   480
tcgtaggatt gtccttacct acagctctgg caagatctga caaagactgc gaaatgaaaa   540
gaactacatt ggattcacca cttgggaagt tggaactgag tggatgcgag caaggattgc   600
atgaaattaa gctactggga aaaggaactt ctgctgctga tgcagttgaa gttccagcac   660
cagcagctgt tcttggaggt cctgagcccc tcatgcaagc cacagcctgg cttaacgcat   720
atttccacca gcctgaggcc attgaggaat ttccagtccc cgcccttcac catcctgtgt   780
ttcagcagga gagcttcacc cgccaggtcc tgtggaaatt gctgaaggtg gtcaagtttg   840
gtgaagtgat ttcatatcag caacttgctg cattggccgg taaccccgca gctacagctg   900
ccgtgaaaac tgctctcagc ggaaatcctg tgcccatcct gatcccttgt cacagagtcg   960
tttcatcttc cggagctgta ggtggctatg aaggaggact ggcagttaag gagtggctgc  1020
tggctcatga aggtcataga cttggaaagc ctggctgggg tcctgctggt ataggcgcgc  1080
cagggtccct aggtggcgga tccgaaaacc tgtacttcca gagcgatatc ggaggtggag  1140
gcccgggaga gaatctatat ttcaagggc cggcggagg tagtcaccat catcaccatc  1200
actaatgacc ggtgcggccg caagcttggc gtaatcatgg tcatagctgt ttcctgtgtg  1260
aaattgttat ccgctcacaa ttccacacaa catacgagcc ggaagcataa agtgtaaagc  1320
ctggggtgcc taatgagtga gctaactcac attaattgcg ttgcgctcac tgcccgcttt  1380
ccagtcggga aacctgtcgt gccagctgca ttaatgaatc ggccaacgcg cggggagagg  1440
cggtttgcgt attgggcgct cttccgcttc ctcgctcact gactcgctgc gctcggtcgt  1500
tcggctgcgg cgagcggtat cagctcactc aaaggcggta atacggttat ccacagaatc  1560
aggggataac gcaggaaaga acatgtgagc aaaaggccag caaaaggcca ggaaccgtaa  1620
aaaggccgcg ttgctggcgt ttttccatag gctccgcccc cctgacgagc atcacaaaaa  1680
tcgacgctca agtcagaggt ggcgaaaccc gacaggacta taaagatacc aggcgtttcc  1740
ccctggaagc tccctcgtgc gctctcctgt tccgaccctg ccgcttaccg gatacctgtc  1800
cgcctttctc ccttcgggaa gcgtggcgct ttctcatagc tcacgctgta ggtatctcag  1860
ttcggtgtag gtcgttcgct ccaagctggg ctgtgtgcac gaaccccccg ttcagcccga  1920
ccgctgcgcc ttatccggta actatcgtct tgagtccaac ccggtaagac acgacttatc  1980
gccactggca gcagccactg gtaacaggat tagcagagcg aggtatgtag cggtgctac   2040 agagttcttg aagtggtggc ctaactacgg ctacactaga agaacagtat ttggtatctg  2100
cgctctgctg aagccagtta ccttcggaaa aagagttggt agctcttgat ccggcaaaca  2160
aaccaccgct ggtagcggtg gttttttgt ttgcaagcag cagattacgc gcagaaaaaa  2220
aggatctcaa gaagatcctt tgatctttc tacgggtct gacgctcagt ggaacgaaaa  2280
ctcacgttaa gggattttgg tcatgagatt atcaaaaagg atcttcacct agatcctttt  2340
```

```
aaattaaaaa tgaagtttta aatcaatcta aagtatatat gagtaaactt ggtctgacag    2400
ttaccaatgc ttaatcagtg aggcacctat ctcagcgatc tgtctatttc gttcatccat    2460
agttgcctga ctccccgtcg tgtagataac tacgatacgg gagggcttac catctggccc    2520
cagtgctgca atgataccgc gagacccacg ctcaccggct ccagatttat cagcaataaa    2580
ccagccagcc ggaagggccg agcgcagaag tggtcctgca actttatccg cctccatcca    2640
gtctattaat tgttgccggg aagctagagt aagtagttcg ccagttaata gtttgcgcaa    2700
cgttgttgcc attgctacag gcatcgtggt gtcacgctcg tcgtttggta tggcttcatt    2760
cagctccggt tcccaacgat caaggcgagt tacatgatcc cccatgttgt gcaaaaaagc    2820
ggttagctcc ttcggtcctc cgatcgttgt cagaagtaag ttggccgcag tgttatcact    2880
catggttatg gcagcactgc ataattctct tactgtcatg ccatccgtaa gatgcttttc    2940
tgtgactggt gagtactcaa ccaagtcatt ctgagaatag tgtatgcggc gaccgagttg    3000
ctcttgcccg gcgtcaatac gggataatac cgcgccacat agcagaactt taaaagtgct    3060
catcattgga aaacgttctt cggggcgaaa actctcaagg atcttaccgc tgttgagatc    3120
cagttcgatg taacccactc gtgcacccaa ctgatcttca gcatctttta ctttcaccag    3180
cgtttctggg tgagcaaaaa caggaaggca aaatgccgca aaaagggaa taagggcgac    3240 acggaaatgt tgaatactca tactcttcct ttttcaatat tattgaagca tttatcaggg    3300
ttattgtctc atgagcggat acatatttga atgtatttag aaaaataaac aatagggggt    3360
tccgcgcaca tttccccgaa aagtgccacc tgacgtctaa gaaaccatta ttatcatgac    3420
attaacctat aaaaataggc gtatcacgag gccctttcgt c                       3461
```

<210> SEQ ID NO 65
<211> LENGTH: 7
<212> TYPE: PRT
<213> ORGANISM: Tobacco etch virus

<400> SEQUENCE: 65

Glu Asn Leu Tyr Phe Gln Gly
1               5

<210> SEQ ID NO 66
<211> LENGTH: 21
<212> TYPE: DNA
<213> ORGANISM: Tobacco etch virus

<400> SEQUENCE: 66
gaaaacctgt acttccaggg g                                               21

<210> SEQ ID NO 67
<211> LENGTH: 530
<212> TYPE: DNA
<213> ORGANISM: Artificial Sequence
<220> FEATURE:
<223> OTHER INFORMATION: DNA sequence of SNAP-like sequence

<400> SEQUENCE: 67

```
gacaaagact gcgaaatgaa aagaactaca ttggattcac cacttgggaa gttggaactg     60
agtggatgcg agcaaggatt gcatgaaatt aagctactgg aaaaggaac ttctgctgct    120 gatgcagttg aagttccagc accagcagct gttcttggag tcctgagcc cctcatgcaa    180 gccacagcct ggcttaacgc atatttccac cagcctgagg ccattgagga atttccagtc    240
cccgcccttc accatcctgt gtttcagcag gagagcttca cccgccaggt cctgtggaaa    300
```

| | |
|---|---:|
| ttgctgaagg tggtcaagtt tggtgaagtg atttcatatc agcaacttgc tgcattggcc | 360 |
| ggtaaccccg cagctacagc tgccgtgaaa actgctctca gcggaaatcc tgtgcccatc | 420 |
| ctgatccctt gtcacagagt cgtttcatct tccggagctg taggtggcta tgaaggagga | 480 |
| ctggcagtta aggagtggct gctggctcat gaaggtcata gacttggaaa | 530 |

<210> SEQ ID NO 68
<211> LENGTH: 711
<212> TYPE: DNA
<213> ORGANISM: Artificial Sequence
<220> FEATURE:
<223> OTHER INFORMATION: DNA sequence of modified MGMT sequence

<400> SEQUENCE: 68

| | |
|---|---:|
| ctaggacaac ctgctccact agaacgattt gcttcacgac gtccacaggt ccttgcagta | 60 |
| cgtactgttt gtgatttagt acttggaaaa atggacaaag actgcgaaat gaaaagaact | 120 |
| acattggatt caccacttgg gaagttggaa ctgagtggat gcgagcaagg attgcatgaa | 180 |
| attaagctac tgggaaaagg aacttctgct gctgatgcag ttgaagttcc agcaccagca | 240 |
| gctgttcttg gaggtcctga gcccctcatg caatgtacag catggcttaa cgcatatttc | 300 |
| caccagcctg aggccattga ggaatttcca gtccccgccc ttcaccatcc tgtgtttcag | 360 |
| caggagagct tcacccgcca ggtcctgtgg aaattgctga aggtggtcaa gtttggtgaa | 420 |
| gtgatttcat atcagcaact tgctgcattg gccggtaacc ctaaagccgc gcgagcagtg | 480 |
| ggaggagcaa tgagaggcaa tcctgtgccc atcctgatcc cttgtcacag agtcgtttgt | 540 |
| tcttccggag ctgtaggcaa ctattctgga ggactggcag ttaaggagtg gctgctggct | 600 |
| catgaaggac atcgattagg caaaccaggt ttaggaggta gttcaggtct agcaggtgca | 660 |
| tggcttaagg gagcaggagc tacatctgga tcaccacctg ctggacgaaa t | 711 |

<210> SEQ ID NO 69
<211> LENGTH: 900
<212> TYPE: DNA
<213> ORGANISM: Artificial Sequence
<220> FEATURE:
<223> OTHER INFORMATION: DNA sequence of DeMGMT Univ (BIPlike/MGMT/
      proTEVx2/HIStag) (figure 9)

<400> SEQUENCE: 69

| | |
|---|---:|
| atgaaactat gtattctact tgcagttgtt gcgttcgtag gattgtcctt acctacagct | 60 |
| ctggcaagat ctctaggaca acctgctcca ctagaacgat ttgcttcacg acgtccacag | 120 |
| gtccttgcag tacgtactgt ttgtgattta gtacttggaa aaatggacaa agactgcgaa | 180 |
| atgaaaagaa ctacattgga ttcaccactt gggaagttgg aactgagtgg atgcgagcaa | 240 |
| ggattgcatg aaattaagct actgggaaaa ggaacttctg ctgctgatgc agttgaagtt | 300 |
| ccagcaccag cagctgttct tggaggtcct gagcccctca tgcaatgtac agcatggctt | 360 |
| aacgcatatt tccaccagcc tgaggccatt gaggaatttc agtccccgc ccttcaccat | 420 |
| cctgtgtttc agcaggagag cttcacccgc caggtcctgt ggaaattgct gaaggtggtc | 480 |
| aagtttggtg aagtgatttc atatcagcaa cttgctgcat tggccggtaa ccctaaagcc | 540 |
| gcgcgagcag tgggaggagc aatgagaggc aatcctgtgc ccatcctgat cccttgtcac | 600 |
| agagtcgttt gttcttccgg agctgtaggc aactattctg gaggactggc agttaaggag | 660 |
| tggctgctgg ctcatgaagg acatcgatta ggcaaaccag gtttaggagg tagttcaggt | 720 |
| ctagcaggtg catggcttaa gggagcagga gctacatctg gatcaccacc tgctggacga | 780 | aatggtggcg atccgaaaaa cctgtacttc cagagcgata tcggaggtgg aggcccggga    840 gagaatctat attttcaagg gcccggcgga ggtagtcacc atcatcacca tcactaatga    900

<210> SEQ ID NO 70
<211> LENGTH: 297
<212> TYPE: PRT
<213> ORGANISM: Artificial Sequence
<220> FEATURE:
<223> OTHER INFORMATION: Amino acid sequence of DeMGMT Univ (BIPlike/
      MGMT/proTEVx2/HIStag) (figure 9)

<400> SEQUENCE: 70

Met Lys Leu Cys Ile Leu Leu Ala Val Ala Phe Val Gly Leu Ser
1               5                   10                  15

Leu Pro Thr Ala Leu Ala Arg Ser Leu Gly Gln Pro Ala Pro Leu Glu
            20                  25                  30

Arg Phe Ala Ser Arg Arg Pro Gln Val Leu Ala Val Arg Thr Val Cys
        35                  40                  45

Asp Leu Val Leu Gly Lys Met Asp Lys Asp Cys Glu Met Lys Arg Thr
50                  55                  60

Thr Leu Asp Ser Pro Leu Gly Lys Leu Glu Ser Gly Cys Glu Gln Gly
65                  70                  75                  80

Leu His Glu Ile Lys Leu Leu Gly Lys Gly Thr Ser Ala Ala Asp Ala
                85                  90                  95

Val Glu Val Pro Ala Pro Ala Ala Val Leu Gly Gly Pro Glu Pro Leu
            100                 105                 110

Met Gln Cys Thr Ala Trp Leu Asn Ala Tyr Phe His Gln Pro Glu Ala
        115                 120                 125

Ile Glu Glu Phe Pro Val Pro Ala Leu His His Pro Val Phe Gln Gln
    130                 135                 140

Glu Ser Phe Thr Arg Gln Val Leu Trp Lys Leu Leu Lys Val Val Lys
145                 150                 155                 160

Phe Gly Glu Val Ile Ser Tyr Gln Gln Leu Ala Ala Leu Ala Gly Asn
                165                 170                 175

Pro Lys Ala Ala Arg Ala Val Gly Gly Ala Met Arg Gly Asn Pro Val
            180                 185                 190

Pro Ile Leu Ile Pro Cys His Arg Val Val Cys Ser Ser Gly Ala Val
        195                 200                 205

Gly Asn Tyr Ser Gly Gly Leu Ala Val Lys Glu Trp Leu Leu Ala His
    210                 215                 220

Glu Gly His Arg Leu Gly Lys Pro Gly Leu Gly Gly Ser Ser Gly Leu
225                 230                 235                 240

Ala Gly Ala Trp Leu Lys Gly Ala Gly Ala Thr Ser Gly Ser Pro Pro
                245                 250                 255

Ala Gly Arg Asn Gly Gly Ser Glu Asn Leu Tyr Phe Gln Ser Asp
            260                 265                 270

Ile Gly Gly Gly Gly Pro Gly Glu Asn Leu Tyr Phe Gln Gly Pro Gly
        275                 280                 285

Gly Gly Ser His His His His His His
    290                 295

<210> SEQ ID NO 71
<211> LENGTH: 3581
<212> TYPE: DNA
<213> ORGANISM: Artificial Sequence
<220> FEATURE:
<223> OTHER INFORMATION: DNA sequence of shuttle vector pUC57/DeMGMT (DeMGMT sequence inserted between Nru I and Hind III from pUC57)

<400> SEQUENCE: 71

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acctcgcgag     420
ctagcaccat gaaactatgt attctacttg cagttgttgc gttcgtagga ttgtccttac     480
ctacagctct ggcaagatct ctaggacaac ctgctccact agaacgattt gcttcacgac     540
gtccacaggt ccttgcagta cgtactgttt gtgatttagt acttggaaaa atggacaaag     600
actgcgaaat gaaagaact acattggatt caccacttgg gaagttggaa ctgagtggat      660
gcgagcaagg attgcatgaa attaagctac tgggaaaagg aacttctgct gctgatgcag     720
ttgaagttcc agcaccagca gctgttcttg gaggtcctga gcccctcatg caatgtacag     780
catggcttaa cgcatatttc caccagcctg aggccattga ggaatttcca gtccccgccc     840
ttcaccatcc tgtgtttcag caggagagct tcacccgcca ggtcctgtgg aaattgctga     900
aggtggtcaa gtttggtgaa gtgatttcat atcagcaact tgctgcattg gccggtaacc     960
ctaaagccgc gcgagcagtg ggaggagcaa tgagaggcaa tcctgtgccc atcctgatcc    1020
cttgtcacag agtcgtttgt tcttccggag ctgtaggcaa ctattctgga ggactggcag    1080
ttaaggagtg gctgctggct catgaaggac atcgattagg caaaccaggt ttaggaggta    1140
gttcaggtct agcaggtgca tggcttaagg gagcaggagc tacatctgga tcaccacctg    1200
ctggacgaaa tggtggcgga tccgaaaacc tgtacttcca gagcgatatc ggaggtggag    1260
gcccgggaga gaatctatat tttcaagggc ccggcggagg tagtcaccat catcaccatc    1320
actaatgacc ggtgcggccg caagcttggc gtaatcatgg tcatagctgt ttcctgtgtg    1380
aaattgttat ccgctcacaa ttccacacaa catacgagcc ggaagcataa agtgtaaagc    1440
ctggggtgcc taatgagtga gctaactcac attaattgcg ttgcgctcac tgcccgcttt    1500
ccagtcggga aacctgtcgt gccagctgca ttaatgaatc ggccaacgcg cggggagagg    1560
cggtttgcgt attgggcgct cttccgcttc ctcgctcact gactcgctgc gctcggtcgt    1620
tcggctgcgg cgagcggtat cagctcactc aaaggcggta atacggttat ccacagaatc    1680
agggataac gcaggaaaga acatgtgagc aaaaggccag caaaaggcca ggaaccgtaa     1740
aaaggccgcg ttgctggcgt ttttccatag gctccgcccc cctgacgagc atcacaaaaa    1800
tcgacgctca gtcagaggt ggcgaaaccc gacaggacta taaagatacc aggcgtttcc     1860
ccctggaagc tccctcgtgc gctctcctgt tccgaccctg ccgcttaccg gatacctgtc    1920
cgcctttctc ccttcgggaa gcgtggcgct ttctcatagc tcacgctgta ggtatctcag    1980
ttcggtgtag tcgttcgct ccaagctggg ctgtgtgcac gaaccccccg ttcagcccga     2040
ccgctgcgcc ttatccggta actatcgtct tgagtccaac ccggtaagac acgacttatc    2100
gccactggca gcagccactg gtaacaggat tagcagagcg aggtatgtag gcggtgctac    2160
agagttcttg aagtggtggc ctaactacgg ctacactaga agaacagtat ttggtatctg    2220
cgctctgctg aagccagtta ccttcggaaa aagagttggt agctcttgat ccggcaaaca    2280
```

| | | |
|---|---|---|
| aaccaccgct ggtagcggtg gttttttgt ttgcaagcag cagattacgc gcagaaaaaa | 2340 |
| aggatctcaa gaagatcctt tgatcttttc tacggggtct gacgctcagt ggaacgaaaa | 2400 |
| ctcacgttaa gggattttgg tcatgagatt atcaaaaagg atcttcacct agatccttt | 2460 |
| aaattaaaaa tgaagtttta aatcaatcta agtatatat gagtaaactt ggtctgacag | 2520 |
| ttaccaatgc ttaatcagtg aggcacctat ctcagcgatc tgtctatttc gttcatccat | 2580 |
| agttgcctga ctccccgtcg tgtagataac tacgatacgg gagggcttac catctggccc | 2640 |
| cagtgctgca atgataccgc gagacccacg ctcaccggct ccagatttat cagcaataaa | 2700 |
| ccagccagcc ggaagggccg agcgcagaag tggtcctgca actttatccg cctccatcca | 2760 |
| gtctattaat tgttgccggg aagctagagt aagtagttcg ccagttaata gtttgcgcaa | 2820 |
| cgttgttgcc attgctacag gcatcgtggt gtcacgctcg tcgtttggta tggcttcatt | 2880 |
| cagctccggt tcccaacgat caaggcgagt tacatgatcc cccatgttgt gcaaaaaagc | 2940 |
| ggttagctcc ttcggtcctc cgatcgttgt cagaagtaag ttggccgcag tgttatcact | 3000 |
| catggttatg gcagcactgc ataattctct tactgtcatg ccatccgtaa gatgctttc | 3060 |
| tgtgactggt gagtactcaa ccaagtcatt ctgagaatag tgtatgcggc gaccgagttg | 3120 |
| ctcttgcccg gcgtcaatac gggataatac cgcgccacat agcagaactt taaaagtgct | 3180 |
| catcattgga aaacgttctt cggggcgaaa actctcaagg atcttaccgc tgttgagatc | 3240 |
| cagttcgatg taacccactc gtgcacccaa ctgatcttca gcatcttta ctttcaccag | 3300 |
| cgtttctggg tgagcaaaaa caggaaggca aaatgccgca aaaagggaa taagggcgac | 3360 |
| acggaaatgt tgaatactca tactcttcct ttttcaatat tattgaagca tttatcaggg | 3420 |
| ttattgtctc atgagcggat acatatttga atgtatttag aaaaataaac aaataggggt | 3480 |
| tccgcgcaca tttccccgaa aagtgccacc tgacgtctaa gaaaccatta ttatcatgac | 3540 |
| attaacctat aaaaataggc gtatcacgag gcccttttcgt c | 3581 |

<210> SEQ ID NO 72
<211> LENGTH: 1285
<212> TYPE: DNA
<213> ORGANISM: Artificial Sequence
<220> FEATURE:
<223> OTHER INFORMATION: DNA sequence of DeSNAP Univ + IFN

<400> SEQUENCE: 72

| | | |
|---|---|---|
| tcgcgagcta gcaccatgaa actatgtatt ctacttgcag ttgttgcgtt cgtaggattg | 60 |
| tccttaccta cagctctggc aagatctgac aaagactgcg aaatgaaaag aactacattg | 120 |
| gattcaccac ttgggaagtt ggaactgagt ggatgcgagc aaggattgca tgaaattaag | 180 |
| ctactgggaa aaggaacttc tgctgctgat gcagttgaag ttccagcacc agcagctgtt | 240 |
| cttggaggtc ctgagcccct catgcaagcc acagcctggc ttaacgcata tttccaccag | 300 |
| cctgaggcca ttgaggaatt ccagtcccc gccttcacc atcctgtgtt tcagcaggag | 360 |
| agcttcaccc gccaggtcct gtggaaattg ctgaaggtgg tcaagtttgg tgaagtgatt | 420 |
| tcatatcagc aacttgctgc attggccggt aaccccgcag ctacagctgc cgtgaaaact | 480 |
| gctctcagcg gaaatcctgt gcccatcctg atcccttgtc acagagtcgt ttcatcttcc | 540 |
| ggagctgtag gtggctatga aggaggactg gcagttaagg agtggctgct ggctcatgaa | 600 |
| ggtcatagac ttgaaagcc tgggctgggt cctgctggta taggcgcgcc agggtcccta | 660 |
| ggtggcggat ccgaaaacct gtacttccag agcgatatct gtgatctccc tgagacccac | 720 |

```
agcctggata acaggaggac cttgatgctc ctggcacaaa tgagcagaat ctctccttcc      780
tcctgtctga tggacagaca tgactttgga tttccccagg aggagtttga tggcaaccag      840
ttccagaagg ctccagccat ctctgtcctc catgagctga tccagcagat tttcaacctc      900
tttaccacaa aagattcatc tgctgcttgg gatgaggacc tcctagacaa attctgcacc      960
gaactctacc agcagctgaa tgacttggaa gcctgtgtga tgcaggagga gagggtggga     1020
gaaactcccc tgatgaatgc ggactccatc ttggctgtga agaaatactt ccgaagaatc     1080
actctctatc tgacagagaa gaaatacagc ccttgtgcct gggaggttgt cagagcagaa     1140
atcatgagat ccctctcttt atcaacaaac ttgcaagaaa gattaaggag gaaggaaggc     1200
ccgggagaga atctatattt tcaagggccc ggcggaggta gtcaccatca tcaccatcac     1260
taatgaccgg tgcggccgca agctt                                           1285
```

<210> SEQ ID NO 73
<211> LENGTH: 414
<212> TYPE: PRT
<213> ORGANISM: Artificial Sequence
<220> FEATURE:
<223> OTHER INFORMATION: Amino acid sequence of De SNAP Univ + IFN

<400> SEQUENCE: 73

```
Met Lys Leu Cys Ile Leu Leu Ala Val Val Ala Phe Val Gly Leu Ser
1               5                   10                  15

Leu Pro Thr Ala Leu Ala Arg Ser Asp Lys Asp Cys Glu Met Lys Arg
            20                  25                  30

Thr Thr Leu Asp Ser Pro Leu Gly Lys Leu Glu Leu Ser Gly Cys Glu
        35                  40                  45

Gln Gly Leu His Glu Ile Lys Leu Leu Gly Lys Gly Thr Ser Ala Asp
    50                  55                  60

Ala Val Glu Val Pro Ala Pro Ala Ala Val Leu Gly Gly Pro Glu Pro
65                  70                  75                  80

Leu Met Gln Ala Thr Ala Trp Leu Asn Ala Tyr Phe His Gln Pro Glu
                85                  90                  95

Ala Ile Glu Glu Phe Pro Val Pro Ala Leu His His Pro Val Phe Gln
            100                 105                 110

Gln Glu Ser Phe Thr Arg Gln Val Leu Trp Lys Leu Leu Lys Val Val
        115                 120                 125

Lys Phe Gly Glu Val Ile Ser Tyr Gln Gln Leu Ala Ala Leu Ala Gly
    130                 135                 140

Asn Pro Ala Ala Thr Ala Ala Val Lys Thr Ala Leu Ser Gly Asn Pro
145                 150                 155                 160

Val Pro Ile Leu Ile Pro Cys His Arg Val Val Ser Ser Ser Gly Ala
                165                 170                 175

Val Gly Gly Tyr Glu Gly Gly Leu Ala Val Lys Glu Trp Leu Leu Ala
            180                 185                 190

His Glu Gly His Arg Leu Gly Lys Pro Gly Leu Gly Pro Ala Gly Ile
        195                 200                 205

Gly Ala Pro Gly Ser Leu Gly Gly Ser Glu Asn Leu Tyr Phe Gln
    210                 215                 220

Ser Asp Ile Cys Asp Leu Pro Glu Thr His Ser Leu Asp Asn Arg Arg
225                 230                 235                 240

Thr Leu Met Leu Leu Ala Gln Met Ser Arg Ile Ser Pro Ser Ser Cys
                245                 250                 255

Leu Met Asp Arg His Asp Phe Gly Phe Pro Gln Glu Glu Phe Asp Gly
```

-continued

```
            260                 265                 270

Asn Gln Phe Gln Lys Ala Pro Ala Ile Ser Val Leu His Glu Leu Ile
        275                 280                 285

Gln Gln Ile Phe Asn Leu Phe Thr Thr Lys Asp Ser Ser Ala Ala Trp
    290                 295                 300

Asp Glu Asp Leu Leu Asp Lys Phe Cys Thr Glu Leu Tyr Gln Gln Leu
305                 310                 315                 320

Asn Asp Leu Glu Ala Cys Val Met Gln Glu Glu Arg Val Gly Glu Thr
                325                 330                 335

Pro Leu Met Asn Ala Asp Ser Ile Leu Ala Val Lys Lys Tyr Phe Arg
            340                 345                 350

Arg Ile Thr Leu Tyr Leu Thr Glu Lys Lys Tyr Ser Pro Cys Ala Trp
        355                 360                 365

Glu Val Val Arg Ala Glu Ile Met Arg Ser Leu Ser Leu Ser Thr Asn
    370                 375                 380

Leu Gln Glu Arg Leu Arg Arg Lys Glu Gly Pro Gly Glu Asn Leu Tyr
385                 390                 395                 400

Phe Gln Gly Pro Gly Gly Gly Ser His His His His His His
                405                 410

<210> SEQ ID NO 74
<211> LENGTH: 1423
<212> TYPE: DNA
<213> ORGANISM: Artificial Sequence
<220> FEATURE:
<223> OTHER INFORMATION: DNA sequence of DeMGMT Univ + IFN

<400> SEQUENCE: 74
tcgcgagcta gcaccatgaa actatgtatt ctacttgcag ttgttgcgtt cgtaggattg     60
tccttaccta cagctctggc aagatctcta ggacaacctg ctccactaga acgatttgct    120
tcacgacgtc cacaggtcct tgcagtacgt actgtttgtg atttagtact tggaaaaatg    180
gacaaagact gcgaaatgaa aagaactaca ttggattcac cacttgggaa gttggaactg    240
agtggatgcg agcaaggatt gcatgaaatt aagctactgg gaaaaggaac ttctgctgct    300
gatgcagttg aagttccagc accagcagct gttcttggag gtcctgagcc cctcatgcaa    360
tgtacagcat ggcttaacgc atatttccac cagcctgagg ccattgagga atttccagtc    420
cccgcccttc accatcctgt gtttcagcag gagagcttca cccgccaggt cctgtggaaa    480
ttgctgaagg tggtcaagtt tggtgaagtg atttcatatc agcaacttgc tgcattggcc    540
ggtaacccta aagccgcgcg agcagtggga ggagcaatga gaggcaatcc tgtgcccatc    600
ctgatccctt gtcacagagt cgtttgttct tccggagctg taggcaacta ttctggagga    660
ctggcagtta aggagtggct gctggctcat gaaggacatc gattaggcaa accaggttta    720
ggaggtagtt caggtctagc aggtgcatgg cttaagggag caggagctac atctggatca    780
ccacctgctg gacgaaatgg tggcggatcc gaaaacctgt acttccagag cgatatctgt    840
gatctccctg agacccacag cctggataac aggaggacct tgatgctcct ggcacaaatg    900
agcagaatct ctccttcctc ctgtctgatg gacagacatg actttggatt tccccaggag    960
gagtttgatg gcaaccagtt ccagaaggct ccagccatct ctgtcctcca tgagctgatc   1020
cagcagattt tcaacctctt taccacaaaa gattcatctg ctgcttggga tgaggacctc   1080
ctagacaaat tctgcaccga actctaccag cagctgaatg acttggaagc ctgtgtgatg   1140
caggaggaga gggtgggaga aactcccctg atgaatgcgg actccatctt ggctgtgaag   1200
```

```
aaatacttcc gaagaatcac tctctatctg acagagaaga aatacagccc ttgtgcctgg    1260
gaggttgtca gagcgaaaat catgagatcc ctctctttat caacaaactt gcaagaaaga    1320
ttaaggagga aggaaggccc gggagagaat ctatattttc aagggccggg cggaggtagt    1380
caccatcatc accatcacta atgaccggtg cggccgcaag ctt                      1423
```

<210> SEQ ID NO 75
<211> LENGTH: 415
<212> TYPE: PRT
<213> ORGANISM: Artificial Sequence
<220> FEATURE:
<223> OTHER INFORMATION: Amino acid sequence of DeMGMT Univ + IFN

<400> SEQUENCE: 75

```
Met Lys Leu Cys Ile Leu Leu Ala Val Val Ala Phe Val Gly Leu Ser
1               5                   10                  15

Leu Pro Thr Ala Leu Ala Arg Ser Asp Lys Asp Cys Glu Met Lys Arg
            20                  25                  30

Thr Thr Leu Asp Ser Pro Leu Gly Lys Leu Glu Leu Ser Gly Cys Glu
        35                  40                  45

Gln Gly Leu His Glu Ile Lys Leu Leu Gly Lys Gly Thr Ser Ala Ala
    50                  55                  60

Asp Ala Val Glu Val Pro Ala Pro Ala Ala Val Leu Gly Gly Pro Glu
65                  70                  75                  80

Pro Leu Met Gln Ala Thr Ala Trp Leu Asn Ala Tyr Phe His Gln Pro
                85                  90                  95

Glu Ala Ile Glu Glu Phe Pro Val Pro Ala Leu His His Pro Val Phe
            100                 105                 110

Gln Gln Glu Ser Phe Thr Arg Gln Val Leu Trp Lys Leu Leu Lys Val
        115                 120                 125

Val Lys Phe Gly Glu Val Ile Ser Tyr Gln Gln Leu Ala Ala Leu Ala
    130                 135                 140

Gly Asn Pro Ala Ala Thr Ala Ala Val Lys Thr Ala Leu Ser Gly Asn
145                 150                 155                 160

Pro Val Pro Ile Leu Ile Pro Cys His Arg Val Val Ser Ser Ser Gly
                165                 170                 175

Ala Val Gly Gly Tyr Glu Gly Gly Leu Ala Val Lys Glu Trp Leu Leu
            180                 185                 190

Ala His Glu Gly His Arg Leu Gly Lys Pro Gly Leu Gly Pro Ala Gly
        195                 200                 205

Ile Gly Ala Pro Gly Ser Leu Gly Gly Ser Glu Asn Leu Tyr Phe
    210                 215                 220

Gln Ser Asp Ile Cys Asp Leu Pro Glu Thr His Ser Leu Asp Asn Arg
225                 230                 235                 240

Arg Thr Leu Met Leu Leu Ala Gln Met Ser Arg Ile Ser Pro Ser Ser
                245                 250                 255

Cys Leu Met Asp Arg His Asp Phe Gly Phe Pro Gln Glu Glu Phe Asp
            260                 265                 270

Gly Asn Gln Phe Gln Lys Ala Pro Ala Ile Ser Val Leu His Glu Leu
        275                 280                 285

Ile Gln Gln Ile Phe Asn Leu Phe Thr Thr Lys Asp Ser Ser Ala Ala
    290                 295                 300

Trp Asp Glu Asp Leu Leu Asp Lys Phe Cys Thr Glu Leu Tyr Gln Gln
305                 310                 315                 320

Leu Asn Asp Leu Glu Ala Cys Val Met Gln Glu Glu Arg Val Gly Glu
```

325                 330                 335
Thr Pro Leu Met Asn Ala Asp Ser Ile Leu Ala Val Lys Lys Tyr Phe
                340                 345                 350

Arg Arg Ile Thr Leu Tyr Leu Thr Glu Lys Lys Tyr Ser Pro Cys Ala
            355                 360                 365

Trp Glu Val Val Arg Ala Glu Ile Met Arg Ser Leu Ser Leu Ser Thr
        370                 375                 380

Asn Leu Gln Glu Arg Leu Arg Arg Lys Glu Gly Pro Gly Glu Asn Leu
385                 390                 395                 400

Tyr Phe Gln Gly Pro Gly Gly Ser His His His His His
                405                 410                 415

<210> SEQ ID NO 76
<211> LENGTH: 570
<212> TYPE: PRT
<213> ORGANISM: Homo sapiens

<400> SEQUENCE: 76

Gly Ala Thr Ala Thr Cys Ala Ala Cys Gly Gly Ala Gly Ala Cys Gly
1               5                   10                  15

Ala Cys Gly Cys Cys Thr Thr Gly Cys Ala Ala Gly Ala Gly Ala Gly
            20                  25                  30

Ala Cys Cys Cys Ala Cys Gly Gly Thr Thr Gly Gly Thr Gly Cys Thr
        35                  40                  45

Cys Ala Ala Thr Ala Cys Cys Ala Gly Gly Ala Ala Gly Ala
    50                  55                  60

Thr Cys Ala Ala Ala Ala Gly Gly Cys Cys Thr Thr Cys Gly Ala
65                  70                  75                  80

Thr Gly Ala Thr Ala Thr Thr Gly Cys Cys Ala Ala Thr Ala Cys
                85                  90                  95

Thr Thr Cys Thr Cys Thr Ala Ala Gly Gly Ala Ala Gly Ala Gly Thr
            100                 105                 110

Gly Gly Gly Ala Ala Ala Ala Gly Ala Thr Gly Ala Ala Ala Gly Cys
        115                 120                 125

Cys Thr Cys Gly Gly Ala Gly Ala Ala Ala Ala Thr Cys Thr Thr Cys
    130                 135                 140

Thr Ala Thr Gly Thr Gly Thr Ala Thr Ala Thr Gly Ala Ala Gly Ala
145                 150                 155                 160

Gly Ala Ala Ala Gly Thr Ala Thr Gly Ala Gly Gly Cys Thr Ala Thr
                165                 170                 175

Gly Ala Cys Thr Ala Ala Ala Cys Thr Ala Gly Gly Thr Thr Thr Cys
            180                 185                 190

Ala Ala Gly Gly Cys Cys Ala Cys Cys Cys Thr Cys Cys Ala Cys
        195                 200                 205

Cys Thr Thr Thr Cys Ala Thr Gly Thr Gly Thr Ala Ala Thr Ala Ala
    210                 215                 220

Ala Cys Gly Gly Gly Cys Thr Cys Gly Ala Ala Gly Ala Cys Thr Cys
225                 230                 235                 240

Cys Ala Gly Gly Gly Gly Ala Ala Thr Gly Ala Thr Thr Gly Gly
                245                 250                 255

Ala Thr Ala Ala Thr Gly Ala Cys Cys Cys Thr Ala Ala Cys Cys Gly
            260                 265                 270

Thr Gly Gly Gly Ala Ala Thr Cys Ala Gly Gly Thr Thr Gly Ala Ala
        275                 280                 285

```
Cys Gly Thr Cys Cys Thr Cys Ala Gly Ala Thr Gly Ala Cys Thr Thr
    290                 295                 300
Thr Cys Gly Gly Cys Ala Gly Gly Cys Thr Cys Cys Ala Gly Gly Gly
305                 310                 315                 320
Ala Ala Thr Cys Thr Cys Cys Cys Gly Ala Ala Gly Ala Thr Cys
                325                 330                 335
Ala Thr Gly Cys Cys Ala Ala Gly Ala Ala Gly Cys Cys Ala Gly
            340                 345                 350
Cys Ala Gly Ala Gly Gly Ala Ala Gly Gly Ala Ala Thr Gly Ala
        355                 360                 365
Thr Thr Cys Gly Gly Ala Gly Gly Ala Ala Gly Thr Gly Cys Cys Ala
    370                 375                 380
Gly Ala Ala Gly Cys Ala Thr Cys Thr Gly Gly Cys Cys Cys Ala Cys
385                 390                 395                 400
Ala Ala Ala Ala Thr Gly Ala Thr Gly Gly Gly Ala Ala Gly Ala
                405                 410                 415
Gly Cys Thr Gly Thr Gly Cys Cys Cys Thr Cys Thr Gly Gly Ala
            420                 425                 430
Ala Ala Ala Cys Cys Ala Ala Cys Thr Ala Cys Thr Cys Thr Gly
        435                 440                 445
Ala Gly Ala Ala Gly Ala Thr Thr Cys Ala Cys Gly Ala Gly Ala Gly
    450                 455                 460
Ala Thr Cys Ala Gly Gly Ala Cys Cys Cys Ala Ala Ala Gly Gly
465                 470                 475                 480
Gly Gly Gly Gly Ala Cys Ala Thr Gly Cys Cys Thr Gly Gly Ala
                485                 490                 495
Cys Cys Cys Ala Cys Ala Gly Ala Cys Thr Gly Cys Gly Thr Gly Ala
            500                 505                 510
Gly Ala Gly Ala Ala Ala Cys Ala Gly Cys Thr Gly Gly Thr Gly
        515                 520                 525
Ala Thr Thr Thr Ala Thr Gly Ala Ala Gly Ala Gly Ala Thr Cys Ala
    530                 535                 540
Gly Cys Gly Ala Cys Cys Cys Thr Gly Ala Gly Gly Ala Ala Gly Ala
545                 550                 555                 560
Thr Gly Ala Cys Gly Ala Gly Thr Ala Cys
                565                 570
```

<210> SEQ ID NO 77
<211> LENGTH: 1369
<212> TYPE: DNA
<213> ORGANISM: Artificial Sequence
<220> FEATURE:
<223> OTHER INFORMATION: DNA sequence of DeSNAP Univ + SSX2

<400> SEQUENCE: 77

```
tcgcgagcta gcaccatgaa actatgtatt ctacttgcag ttgttgcgtt cgtaggattg      60
tccttaccta cagctctggc aagatctgac aaagactgcg aaatgaaaag aactacattg     120
gattcaccac ttgggaagtt ggaactgagt ggatgcgagc aaggattgca tgaaattaag     180
ctactgggaa aggaacttc tgctgctgat gcagttgaag ttccagcacc agcagctgtt     240
cttggaggtc ctgagcccct catgcaagcc acagcctggc ttaacgcata tttccaccag     300
cctgaggcca ttaggaatt tccagtcccc gccttcacc atcctgtgtt tcagcaggag     360
agcttcaccc gccaggtcct gtggaaattg ctgaaggtgg tcaagtttgg tgaagtgatt     420
tcatatcagc aacttgctgc attggccggt aaccccgcag ctacagctgc cgtgaaaact     480
```

```
gctctcagcg gaaatcctgt gcccatcctg atcccttgtc acagagtcgt tcatcttcc    540 ggagctgtag gtggctatga aggaggactg cagttaagg agtggctgct ggctcatgaa    600
ggtcatagac ttggaaagcc tgggctgggt cctgctggta taggcgcgcc agggtccta    660 ggtggcggat ccgaaaacct gtacttccag agcgatatca acggagacga cgcctttgca    720
aggagaccca cggttggtgc tcaaatacca gagaagatcc aaaaggcctt cgatgatatt    780
gccaaatact tctctaagga agagtgggaa aagatgaaag cctcggagaa aatcttctat    840
gtgtatatga agagaaagta tgaggctatg actaaactag gtttcaaggc cacctcccca    900
cctttcatgt gtaataaacg ggccgaagac ttccagggga tgatttgga taatgaccct    960 aaccgtggga atcaggttga acgtcctcag atgactttcg gcaggctcca gggaatctcc   1020
ccgaagatca tgcccaagaa gccagcagag aaggaaatg attcggagga agtgccagaa   1080
gcatctggcc cacaaaatga tgggaaagag ctgtgccctc ctggaaaacc aactacctct   1140
gagaagattc acgagagatc aggacccaaa agggggaac atgcctggac ccacagactg   1200
cgtgagagaa aacagctggt gatttatgaa gagatcagcg accctgagga agatgacgag   1260
tacgagaatc tatattttca aggcccggga gagaatctat attttcaagg gcccggcgga   1320
ggtagtcacc atcatcacca tcactaatga ccggtgcggc cgcaagctt               1369
```

<210> SEQ ID NO 78
<211> LENGTH: 415
<212> TYPE: PRT
<213> ORGANISM: Artificial Sequence
<220> FEATURE:
<223> OTHER INFORMATION: Amino acid sequence of DeSNAP Univ + SSX2

<400> SEQUENCE: 78

```
Met Lys Leu Cys Ile Leu Leu Ala Val Val Ala Phe Val Gly Leu Ser
1               5                   10                  15

Leu Pro Thr Ala Leu Ala Arg Ser Asp Lys Asp Cys Glu Met Lys Arg
            20                  25                  30

Thr Thr Leu Asp Ser Pro Leu Gly Lys Leu Glu Leu Ser Gly Cys Glu
        35                  40                  45

Gln Gly Leu His Glu Ile Lys Leu Leu Gly Lys Gly Thr Ser Ala Ala
    50                  55                  60

Asp Ala Val Glu Val Pro Ala Pro Ala Ala Val Leu Gly Gly Pro Glu
65                  70                  75                  80

Pro Leu Met Gln Ala Thr Ala Trp Leu Asn Ala Tyr Phe His Gln Pro
                85                  90                  95

Glu Ala Ile Glu Glu Phe Pro Val Pro Ala Leu His His Pro Val Phe
            100                 105                 110

Gln Gln Glu Ser Phe Thr Arg Gln Val Leu Trp Lys Leu Leu Lys Val
        115                 120                 125

Val Lys Phe Gly Glu Val Ile Ser Tyr Gln Gln Leu Ala Ala Leu Ala
    130                 135                 140

Gly Asn Pro Ala Ala Thr Ala Ala Val Lys Thr Ala Leu Ser Gly Asn
145                 150                 155                 160

Pro Val Pro Ile Leu Ile Pro Cys His Arg Val Val Ser Ser Gly
                165                 170                 175

Ala Val Gly Gly Tyr Glu Gly Gly Leu Ala Val Lys Glu Trp Leu Leu
            180                 185                 190

Ala His Glu Gly His Arg Leu Gly Lys Pro Gly Leu Gly Pro Ala Gly
        195                 200                 205
```

```
Ile Gly Ala Pro Gly Ser Leu Gly Gly Gly Ser Glu Asn Leu Tyr Phe
    210                 215                 220

Gln Ser Asp Ile Cys Asp Leu Pro Glu Thr His Ser Leu Asp Asn Arg
225                 230                 235                 240

Arg Thr Leu Met Leu Leu Ala Gln Met Ser Arg Ile Ser Pro Ser Ser
                245                 250                 255

Cys Leu Met Asp Arg His Asp Phe Gly Phe Pro Gln Glu Glu Phe Asp
                260                 265                 270

Gly Asn Gln Phe Gln Lys Ala Pro Ala Ile Ser Val Leu His Glu Leu
                275                 280                 285

Ile Gln Gln Ile Phe Asn Leu Phe Thr Thr Lys Asp Ser Ser Ala Ala
    290                 295                 300

Trp Asp Glu Asp Leu Leu Asp Lys Phe Cys Thr Glu Leu Tyr Gln Gln
305                 310                 315                 320

Leu Asn Asp Leu Glu Ala Cys Val Met Gln Glu Arg Val Gly Glu
                325                 330                 335

Thr Pro Leu Met Asn Ala Asp Ser Ile Leu Ala Val Lys Lys Tyr Phe
                340                 345                 350

Arg Arg Ile Thr Leu Tyr Leu Thr Glu Lys Lys Tyr Ser Pro Cys Ala
                355                 360                 365

Trp Glu Val Val Arg Ala Glu Ile Met Arg Ser Leu Ser Leu Ser Thr
370                 375                 380

Asn Leu Gln Glu Arg Leu Arg Arg Lys Glu Gly Pro Gly Glu Asn Leu
385                 390                 395                 400

Tyr Phe Gln Gly Pro Gly Gly Gly Ser His His His His His
                405                 410                 415

<210> SEQ ID NO 79
<211> LENGTH: 1369
<212> TYPE: DNA
<213> ORGANISM: Artificial Sequence
<220> FEATURE:
<223> OTHER INFORMATION: DNA sequence of DeMGMT Univ + SSX2

<400> SEQUENCE: 79
tcgcgagcta gcaccatgaa actatgtatt ctacttgcag ttgttgcgtt cgtaggattg      60
tccttaccta cagctctggc aagatctgac aaagactgcg aaatgaaaag aactacattg     120
gattcaccac ttgggaagtt ggaactgagt ggatgcgagc aaggattgca tgaaattaag     180
ctactgggaa aggaacttc tgctgctgat gcagttgaag ttccagcacc agcagctgtt     240
cttggaggtc ctgagcccct catgcaagcc acagcctggc ttaacgcata tttccaccag     300
cctgaggcca ttgaggaatt ccagtcccc gcccttcacc atcctgtgtt tcagcaggag     360
agcttcaccc gccaggtcct gtggaaattg ctgaaggtgg tcaagtttgg tgaagtgatt     420
tcatatcagc aacttgctgc attggccggt aaccccgcag ctacagctgc cgtgaaaact     480
gctctcagcg gaaatcctgt gcccatcctg atcccttgtc acagagtcgt tcatcttcc     540 ggagctgtag gtggctatga aggaggactg gcagttaagg agtggctgct ggctcatgaa     600
ggtcatagac ttgaaagcc tgggctgggt cctgctggta taggcgcgcc agggtcccta     660
ggtggcggat ccgaaaacct gtacttccag agcgatatca acggagacga cgcctttgca     720
aggagaccca cggttggtgc tcaaatacca gagaagatcc aaaaggcctt cgatgatatt     780
gccaaatact tctctaagga agagtgggaa aagatgaaag cctcggagaa aatcttctat     840
gtgtatatga agagaaagta tgaggctatg actaaactag gtttcaaggc caccctccca     900
```

```
cctttcatgt gtaataaacg ggccgaagac ttccagggga atgatttgga taatgaccct    960
aaccgtggga atcaggttga acgtcctcag atgactttcg gcaggctcca gggaatctcc   1020
ccgaagatca tgcccaagaa gccagcagag gaaggaaatg attcggagga agtgccagaa   1080
gcatctggcc cacaaaatga tgggaaagag ctgtgccctc ctggaaaacc aactacctct   1140
gagaagattc acgagagatc aggacccaaa agggggaac atgcctggac ccacagactg    1200
cgtgagagaa aacagctggt gatttatgaa gagatcagcg accctgagga agatgacgag   1260
tacgagaatc tatattttca aggcccggga gagaatctat attttcaagg cccggcgga   1320 ggtagtcacc atcatcacca tcactaatga ccggtgcggc cgcaagctt              1369
```

<210> SEQ ID NO 80
<211> LENGTH: 489
<212> TYPE: PRT
<213> ORGANISM: Artificial Sequence
<220> FEATURE:
<223> OTHER INFORMATION: Amino acid sequence of DeMGMT Univ + SSX2

<400> SEQUENCE: 80

```
Met Lys Leu Cys Ile Leu Leu Ala Val Val Ala Phe Val Gly Leu Ser
1               5                   10                  15

Leu Pro Thr Ala Leu Ala Arg Ser Leu Gly Gln Pro Ala Pro Leu Glu
            20                  25                  30

Arg Phe Ala Ser Arg Arg Pro Gln Val Leu Ala Val Arg Thr Val Cys
        35                  40                  45

Asp Leu Val Leu Gly Lys Met Asp Lys Asp Cys Glu Met Lys Arg Thr
    50                  55                  60

Thr Leu Asp Ser Pro Leu Gly Lys Leu Glu Leu Ser Gly Cys Glu Gln
65                  70                  75                  80

Gly Leu His Glu Ile Lys Leu Leu Gly Lys Gly Thr Ser Ala Ala Asp
                85                  90                  95

Ala Val Glu Val Pro Ala Pro Ala Ala Val Leu Gly Gly Pro Glu Pro
            100                 105                 110

Leu Met Gln Cys Thr Ala Trp Leu Asn Ala Tyr Phe His Gln Pro Glu
        115                 120                 125

Ala Ile Glu Glu Phe Pro Val Pro Ala Leu His His Pro Val Phe Gln
    130                 135                 140

Gln Glu Ser Phe Thr Arg Gln Val Leu Trp Lys Leu Leu Lys Val Val
145                 150                 155                 160

Lys Phe Gly Glu Val Ile Ser Tyr Gln Gln Leu Ala Ala Leu Ala Gly
                165                 170                 175

Asn Pro Lys Ala Ala Arg Ala Val Gly Gly Ala Met Arg Gly Asn Pro
            180                 185                 190

Val Pro Ile Leu Ile Pro Cys His Arg Val Val Cys Ser Ser Gly Ala
        195                 200                 205

Val Gly Asn Tyr Ser Gly Gly Leu Ala Val Lys Glu Trp Leu Leu Ala
    210                 215                 220

His Glu Gly His Arg Leu Gly Lys Pro Gly Leu Gly Gly Ser Ser Gly
225                 230                 235                 240

Leu Ala Gly Ala Trp Leu Lys Gly Ala Gly Ala Thr Ser Gly Ser Pro
                245                 250                 255

Pro Ala Gly Arg Asn Gly Gly Gly Ser Glu Asn Leu Tyr Phe Gln Ser
            260                 265                 270

Asp Ile Asn Gly Asp Asp Ala Phe Ala Arg Arg Pro Thr Val Gly Ala
```

```
                275                 280                 285
    Gln Ile Pro Glu Lys Ile Gln Lys Ala Phe Asp Asp Ile Ala Lys Tyr
        290                 295                 300
    Phe Ser Lys Glu Glu Trp Glu Lys Met Lys Ala Ser Glu Lys Ile Phe
    305                 310                 315                 320
    Tyr Val Tyr Met Lys Arg Lys Tyr Glu Ala Met Thr Lys Leu Gly Phe
                    325                 330                 335
    Lys Ala Thr Leu Pro Pro Phe Met Cys Asn Lys Arg Ala Glu Asp Phe
                340                 345                 350
    Gln Gly Asn Asp Leu Asp Asn Asp Pro Asn Arg Gly Asn Gln Val Glu
                355                 360                 365
    Arg Pro Gln Met Thr Phe Gly Arg Leu Gln Gly Ile Ser Pro Lys Ile
        370                 375                 380
    Met Pro Lys Lys Pro Ala Glu Glu Gly Asn Asp Ser Glu Glu Val Pro
    385                 390                 395                 400
    Glu Ala Ser Gly Pro Gln Asn Asp Gly Lys Glu Leu Cys Pro Pro Gly
                    405                 410                 415
    Lys Pro Thr Thr Ser Glu Lys Ile His Glu Arg Ser Gly Pro Lys Arg
                420                 425                 430
    Gly Glu His Ala Trp Thr His Arg Leu Arg Glu Arg Lys Gln Leu Val
                435                 440                 445
    Ile Tyr Glu Glu Ile Ser Asp Pro Glu Glu Asp Asp Glu Tyr Glu Asn
        450                 455                 460
    Leu Tyr Phe Gln Gly Pro Gly Glu Asn Leu Tyr Phe Gln Gly Pro Gly
    465                 470                 475                 480
    Gly Gly Ser His His His His His His
                    485

<210> SEQ ID NO 81
<211> LENGTH: 1299
<212> TYPE: DNA
<213> ORGANISM: Artificial Sequence
<220> FEATURE:
<223> OTHER INFORMATION: DNA sequence of ssBiP+SNAP+proTEV site + SSX2+
      proTEV + Histag

<400> SEQUENCE: 81
atgaagttat gcatattact ggccgtcgtg gcctttgttg gcctctcgct cgggagatct    60
gacaaagact gcgaaatgaa gcgcaccacc ctggatagcc ctctgggcaa gctggaactg   120
tctgggtgcg aacagggcct gcacgagatc aagctgctgg caaaggaac atctgccgcc   180 gacgccgtgg aagtgcctgc cccagccgcc gtgctgggcg accagagcc actgatgcag   240 gccaccgcct ggctcaacgc ctactttcac cagcctgagg ccatcgagga gttccctgtg   300
ccagccctgc accaccagt gttccagcag gagagcttta cccgccaggt gctgtggaaa   360
ctgctgaaag tggtgaagtt cggagaggtc atcagctacc agcagctggc cgccctggcc   420
ggcaatcccg ccgccaccgc cgccgtgaaa accgccctga gcggaaatcc cgtgcccatt   480
ctgatcccct gccaccgggt ggtgtctagc tctggcgccg tgggggcta cgagggcggg   540 ctcgccgtga agagtggct gctggcccac gagggccaca gactgggcaa gcctgggctg   600
ggtcctgcag gtataggcgc gccagggtcc ctaggtggcg atctgaaaa cctctacttc   660 cagagtgata tcaacggaga cgacgccttt gcaaggagac ccacggttgg tgctcaaata   720
ccagagaaga tccaaaaggc cttcgatgat attgccaaat acttctctaa ggaagagtgg   780 gaaagatga agcctcgga gaaaatcttc tatgtgtata tgaagagaaa gtatgaggct   840
```

-continued

```
atgactaaac taggtttcaa ggccaccctc ccacctttca tgtgtaataa acgggccgaa    900
gacttccagg ggaatgattt ggataatgac cctaaccgtg ggaatcaggt tgaacgtcct    960
cagatgactt tcggcaggct ccagggaatc tccccgaaga tcatgcccaa gaagccagca   1020
gaggaaggaa atgattcgga ggaagtgcca gaagcatctg gcccacaaaa tgatgggaaa   1080
gagctgtgcc ctcctggaaa accaactacc tctgagaaga ttcacgagag atcaggaccc   1140
aaaaggggg aacatgcctg gacccacaga ctgcgtgaga gaaaacagct ggtgatttat   1200
gaagagatca gcgaccctga ggaagatgac gagtacgaga atctatattt tcaaggcccg   1260
ggcggtggaa gtcaccatca tcaccatcac tgaccggta                           1299
```

<210> SEQ ID NO 82
<211> LENGTH: 430
<212> TYPE: PRT
<213> ORGANISM: Artificial Sequence
<220> FEATURE:
<223> OTHER INFORMATION: Amino acid sequence of ssBiP+SNAP+proTEV site
   + SSX2+ proTEV + Histag

<400> SEQUENCE: 82

```
Met Lys Leu Cys Ile Leu Leu Ala Val Val Ala Phe Val Gly Leu Ser
 1               5                  10                  15

Leu Gly Arg Ser Asp Lys Asp Cys Glu Met Lys Arg Thr Thr Leu Asp
            20                  25                  30

Ser Pro Leu Gly Lys Leu Glu Leu Ser Gly Cys Glu Gln Gly Leu His
        35                  40                  45

Glu Ile Lys Leu Leu Gly Lys Gly Thr Ser Ala Ala Asp Ala Val Glu
    50                  55                  60

Val Pro Ala Pro Ala Ala Val Leu Gly Gly Pro Glu Pro Leu Met Gln
65                  70                  75                  80

Ala Thr Ala Trp Leu Asn Ala Tyr Phe His Gln Pro Glu Ala Ile Glu
                85                  90                  95

Glu Phe Pro Val Pro Ala Leu His His Pro Val Phe Gln Gln Glu Ser
            100                 105                 110

Phe Thr Arg Gln Val Leu Trp Lys Leu Leu Lys Val Val Lys Phe Gly
        115                 120                 125

Glu Val Ile Ser Tyr Gln Gln Leu Ala Ala Leu Ala Gly Asn Pro Ala
    130                 135                 140

Ala Thr Ala Ala Val Lys Thr Ala Leu Ser Gly Asn Pro Val Pro Ile
145                 150                 155                 160

Leu Ile Pro Cys His Arg Val Val Ser Ser Gly Ala Val Gly Gly
                165                 170                 175

Tyr Glu Gly Gly Leu Ala Val Lys Glu Trp Leu Leu Ala His Glu Gly
            180                 185                 190

His Arg Leu Gly Lys Pro Gly Leu Gly Pro Ala Gly Ile Gly Ala Pro
        195                 200                 205

Gly Ser Leu Gly Gly Gly Ser Glu Asn Leu Tyr Phe Gln Ser Asp Ile
    210                 215                 220

Asn Gly Asp Asp Ala Phe Ala Arg Arg Pro Thr Val Gly Ala Gln Ile
225                 230                 235                 240

Pro Glu Lys Ile Gln Lys Ala Phe Asp Asp Ile Ala Lys Tyr Phe Ser
                245                 250                 255

Lys Glu Glu Trp Glu Lys Met Lys Ala Ser Glu Lys Ile Phe Tyr Val
            260                 265                 270
```

```
        Tyr Met Lys Arg Lys Tyr Glu Ala Met Thr Lys Leu Gly Phe Lys Ala
                    275                 280                 285

Thr Leu Pro Pro Phe Met Cys Asn Lys Arg Ala Glu Asp Phe Gln Gly
                    290                 295                 300

Asn Asp Leu Asp Asn Asp Pro Asn Arg Gly Asn Gln Val Glu Arg Pro
        305                 310                 315                 320

Gln Met Thr Phe Gly Arg Leu Gln Gly Ile Ser Pro Lys Ile Met Pro
                        325                 330                 335

Lys Lys Pro Ala Glu Glu Gly Asn Asp Ser Glu Val Pro Glu Ala
                        340                 345                 350

Ser Gly Pro Gln Asn Asp Gly Lys Glu Leu Cys Pro Gly Lys Pro
                    355                 360                 365

Thr Thr Ser Glu Lys Ile His Glu Arg Ser Gly Pro Lys Arg Gly Glu
                    370                 375                 380

His Ala Trp Thr His Arg Leu Arg Glu Arg Lys Gln Leu Val Ile Tyr
        385                 390                 395                 400

Glu Glu Ile Ser Asp Pro Glu Asp Asp Glu Tyr Glu Asn Leu Tyr
                        405                 410                 415

Phe Gln Gly Pro Gly Gly Ser His His His His His
                    420                 425                 430

<210> SEQ ID NO 83
<211> LENGTH: 798
<212> TYPE: DNA
<213> ORGANISM: Homo sapiens

<400> SEQUENCE: 83
tctctagctg gagaaacagg tcaagaagct gcacctcttg atggagtact agcaaatcca      60
cctaatattt caagtctatc acctcgacaa cttcttggat ttccatgtgc agaagtatct     120
ggactaagta cagaacgtgt tcgagaacta gctgtagcat tagcacagaa aaatgtaaaa     180
ctatcaacag acaacttcg atgtctagct catcgacttt ctgaaccacc tgaggatcta      240
gatgcacttc cattcgatct acttctattt ctaaatccag atgcattttc aggacctcaa     300
gcatgtactc gatttttttc tcgaattaca aaagcaaatg tcgatctact tccaaggaa      360 gcaccagaac gacaacgact actacctgca gctctagcat gttggggagt acgaggatct     420
ctacttagtg aagcagatgt acgagctcta ggaggtctag cttgtgatct acctggacga     480
tttgtagcag aatctgcaga agtactacta ccacgacttg ttagttgtcc tggacctcta     540
gatcaagatc aacaagaagc tgctagagca gctcttcaag tggtggacc tccttatgga      600 cctccatcaa catggtctgt atcaacaatg gatgcactac gaggacttct tcctgtacta     660
ggtcaaccta ttattcgaag tattccacaa ggtattgtag cagcatggcg acaacgatct     720
tctcgagatc catcttggcg acaacctgaa cgaactattc ttcgaccacg cccgggagag     780
aatctatatt ttcaaggg                                                   798

<210> SEQ ID NO 84
<211> LENGTH: 1558
<212> TYPE: DNA
<213> ORGANISM: Artificial Sequence
<220> FEATURE:
<223> OTHER INFORMATION: DNA sequence of DeSNAP Univ -NERCMSL

<400> SEQUENCE: 84
tcgcgagcta gcaccatgaa actatgtatt ctacttgcag ttgttgcgtt cgtaggattg      60
tccttaccta cagctctggc aagatctgac aaagactgcg aaatgaaaag aactacattg     120
```

-continued

```
gattcaccac ttgggaagtt ggaactgagt ggatgcgagc aaggattgca tgaaattaag      180
ctactgggaa aaggaacttc tgctgctgat gcagttgaag ttccagcacc agcagctgtt      240
cttggaggtc ctgagcccct catgcaagcc acagcctggc ttaacgcata tttccaccag      300
cctgaggcca ttgaggaatt ccagtcccc gcccttcacc atcctgtgtt tcagcaggag       360
agcttcaccc gccaggtcct gtggaaattg ctgaaggtgg tcaagtttgg tgaagtgatt      420
tcatatcagc aacttgctgc attggccggt aaccccgcag ctacagctgc cgtgaaaact      480
gctctcagcg gaaatcctgt gcccatcctg atccttgtc acagagtcgt ttcatcttcc       540
ggagctgtag gtggctatga aggaggactg gcagttaagg agtggctgct ggctcatgaa      600
ggtcatagac ttggaaagcc tgggctgggt cctgctggta taggcgcgcc agggtcccta      660
ggtggcggat ccgaaaacct gtacttccag agcgatatca ggtctctagc tggagaaaca      720
ggtcaagaag ctgcacctct tgatggagta ctagcaaatc cacctaatat ttcaagtcta      780
tcacctcgac aacttcttgg atttccatgt gcagaagtat ctggactaag tacagaacgt      840
gttcgagaac tagctgtagc attagcacag aaaaatgtaa aactatcaac agaacaactt     900
cgatgtctag ctcatcgact ttctgaacca cctgaggatc tagatgcact tccattcgat      960
ctacttctat ttctaaatcc agatgcattt tcaggacctc aagcatgtac tcgattttt      1020
tctcgaatta caaaagcaaa tgtcgatcta cttccaagag gagcaccaga acgacaacga     1080
ctactacctg cagctctagc atgttgggga gtacgaggat ctctacttag tgaagcagat     1140
gtacgagctc taggaggtct agcttgtgat ctacctggac gatttgtagc agaatctgca     1200
gaagtactac taccacgact tgttagttgt cctggaccct ctagatcaaga tcaacaagaa    1260
gctgctagag cagctcttca aggtggtgga cctcctttatg gacctccatc aacatggtct    1320
gtatcaacaa tggatgcact acgaggactt cttcctgtac taggtcaacc tattattcga    1380
agtattccac aaggtattgt agcagcatgg cgacaacgat cttctcgaga tccatcttgg    1440
cgacaacctg aacgaactat tcttcgacca cgcccgggag agaatctata ttttcaaggg    1500
cccggcggag gtagtcacca tcatcaccat cactaatgac cggtgcggcc gcaagctt     1558
```

<210> SEQ ID NO 85
<211> LENGTH: 504
<212> TYPE: PRT
<213> ORGANISM: Artificial Sequence
<220> FEATURE:
<223> OTHER INFORMATION: Amino acid sequence of DeSNAP Univ -NERCMSL

<400> SEQUENCE: 85

```
Met Lys Leu Cys Ile Leu Leu Ala Val Val Ala Phe Val Gly Leu Ser
1               5                   10                  15

Leu Pro Thr Ala Leu Ala Arg Ser Asp Lys Asp Cys Glu Met Lys Arg
                20                  25                  30

Thr Thr Leu Asp Ser Pro Leu Gly Lys Leu Glu Leu Ser Gly Cys Glu
            35                  40                  45

Gln Gly Leu His Glu Ile Lys Leu Leu Gly Lys Gly Thr Ser Ala Ala
        50                  55                  60

Asp Ala Val Glu Val Pro Ala Pro Ala Ala Val Leu Gly Gly Pro Glu
65                  70                  75                  80

Pro Leu Met Gln Ala Thr Ala Trp Leu Asn Ala Tyr Phe His Gln Pro
                85                  90                  95

Glu Ala Ile Glu Glu Phe Pro Val Pro Ala Leu His His Pro Val Phe
                100                 105                 110
```

```
Gln Gln Glu Ser Phe Thr Arg Gln Val Leu Trp Lys Leu Leu Lys Val
        115                 120                 125

Val Lys Phe Gly Glu Val Ile Ser Tyr Gln Gln Leu Ala Ala Leu Ala
130                 135                 140

Gly Asn Pro Ala Ala Thr Ala Ala Val Lys Thr Ala Leu Ser Gly Asn
145                 150                 155                 160

Pro Val Ile Leu Ile Pro Cys His Arg Val Val Ser Ser Ser Gly Ala
                165                 170                 175

Val Gly Gly Tyr Glu Gly Gly Leu Ala Val Lys Glu Trp Leu Leu Ala
            180                 185                 190

His Glu Gly His Arg Leu Gly Lys Pro Gly Leu Gly Pro Ala Gly Ile
        195                 200                 205

Gly Ala Pro Gly Ser Leu Gly Gly Ser Glu Asn Leu Tyr Phe Gln
    210                 215                 220

Ser Asp Ile Arg Ser Leu Ala Gly Glu Thr Gly Gln Glu Ala Ala Pro
225                 230                 235                 240

Leu Asp Gly Val Leu Ala Asn Pro Pro Asn Ile Ser Ser Leu Ser Pro
                245                 250                 255

Arg Gln Leu Leu Gly Phe Pro Cys Ala Glu Val Ser Gly Leu Ser Thr
            260                 265                 270

Glu Arg Val Arg Glu Leu Ala Val Ala Leu Ala Gln Lys Asn Val Lys
        275                 280                 285

Leu Ser Thr Glu Gln Leu Arg Cys Leu Ala His Arg Leu Ser Glu Pro
    290                 295                 300

Pro Glu Asp Leu Asp Ala Leu Pro Phe Asp Leu Leu Leu Phe Leu Asn
305                 310                 315                 320

Pro Asp Ala Phe Ser Gly Pro Gln Ala Cys Thr Arg Phe Phe Ser Arg
                325                 330                 335

Ile Thr Lys Ala Asn Val Asp Leu Leu Pro Arg Gly Ala Pro Glu Arg
            340                 345                 350

Gln Arg Leu Leu Pro Ala Ala Leu Ala Cys Trp Gly Val Arg Gly Ser
        355                 360                 365

Leu Leu Ser Glu Ala Asp Val Arg Ala Leu Gly Gly Leu Ala Cys Asp
    370                 375                 380

Leu Pro Gly Arg Phe Val Ala Glu Ser Ala Val Leu Leu Pro Arg Leu
385                 390                 395                 400

Val Ser Cys Pro Gly Pro Leu Asp Gln Asp Gln Gln Glu Ala Ala Arg
                405                 410                 415

Ala Ala Leu Gln Gly Gly Gly Pro Pro Tyr Gly Pro Pro Ser Thr Trp
            420                 425                 430

Ser Val Ser Thr Met Asp Ala Leu Arg Gly Leu Leu Pro Val Leu Gly
    435                 440                 445

Gln Pro Ile Ile Arg Ser Ile Pro Gln Gly Ile Val Ala Ala Trp Arg
450                 455                 460

Gln Arg Ser Ser Arg Asp Pro Ser Trp Arg Gln Pro Glu Arg Thr Ile
465                 470                 475                 480

Leu Arg Pro Arg Pro Gly Glu Asn Leu Tyr Phe Gln Gly Pro Gly Gly
                485                 490                 495

Gly Ser His His His His His His
            500

<210> SEQ ID NO 86
<211> LENGTH: 1558
```

```
<212> TYPE: DNA
<213> ORGANISM: Artificial Sequence
<220> FEATURE:
<223> OTHER INFORMATION: DNA sequence of DeMGMT Univ -NERCMSL

<400> SEQUENCE: 86
tcgcgagcta gcaccatgaa actatgtatt ctacttgcag ttgttgcgtt cgtaggattg      60
tccttaccta cagctctggc aagatctgac aaagactgcg aaatgaaaag aactacattg     120
gattcaccac ttgggaagtt ggaactgagt ggatgcgagc aaggattgca tgaaattaag     180
ctactgggaa aaggaacttc tgctgctgat gcagttgaag ttccagcacc agcagctgtt     240
cttggaggtc ctgagcccct catgcaagcc acagcctggc ttaacgcata tttccaccag     300
cctgaggcca ttgaggaatt ccagtcccc gcccttcacc atcctgtgtt tcagcaggag       360
agcttcaccc gccaggtcct gtggaaattg ctgaaggtgg tcaagtttgg tgaagtgatt     420
tcatatcagc aacttgctgc attggccggt aaccccgcag ctacagctgc cgtgaaaact     480
gctctcagcg aaatcctgt gcccatcctg atcccttgtc acagagtcgt ttcatcttcc      540
ggagctgtag gtggctatga aggaggactg gcagttaagg agtggctgct ggctcatgaa     600
ggtcatagac ttggaaagcc tgggctgggt cctgctggta taggcgcgcc agggtcccta     660
ggtggcggat ccgaaaaacct gtacttccag agcgatatca ggtctctagc tggagaaaca    720
ggtcaagaag ctgcacctct tgatggagta ctagcaaatc cacctaatat ttcaagtcta    780
tcacctcgac aacttcttgg atttccatgt gcagaagtat ctggactaag tacagaacgt     840
gttcgagaac tagctgtagc attagcacag aaaaatgtaa aactatcaac agaacaactt     900
cgatgtctag ctcatcgact ttctgaacca cctgaggatc tagatgcact tccattcgat     960
ctacttctat ttctaaatcc agatgcattt tcaggacctc aagcatgtac tcgattttt    1020
tctcgaatta caaaagcaaa tgtcgatcta cttccaagag gagcaccaga acgacaacga   1080
ctactacctg cagctctagc atgttgggga gtacgaggat ctctactag tgaagcagat    1140
gtacgagctc taggaggtct agcttgtgat ctacctggac gatttgtagc agaatctgca   1200
gaagtactac taccacgact tgttagttgt cctggacctc tagatcaaga tcaacaagaa   1260
gctgctagag cagctcttca aggtggtgga cctcctatg gacctccatc aacatggtct    1320
gtatcaacaa tggatgcact acgaggactt cttcctgtac taggtcaacc tattattcga   1380
agtattccac aaggtattgt agcagcatgg cgacaacgat cttctcgaga tccatcttgg   1440
cgacaacctg aacgaactat tcttcgacca cgcccgggag agaatctata ttttcaaggg    1500
cccggcggag gtagtcacca tcatcaccat cactaatgac cggtgcggcc gcaagctt     1558

<210> SEQ ID NO 87
<211> LENGTH: 551
<212> TYPE: PRT
<213> ORGANISM: Artificial Sequence
<220> FEATURE:
<223> OTHER INFORMATION: Amino acid sequence of DeMGMT Univ -NERCMSL

<400> SEQUENCE: 87

Met Lys Leu Cys Ile Leu Leu Ala Val Val Ala Phe Val Gly Leu Ser
1               5                   10                  15

Leu Pro Thr Ala Leu Ala Arg Ser Leu Gly Gln Pro Ala Pro Leu Glu
                20                  25                  30

Arg Phe Ala Ser Arg Arg Pro Gln Val Leu Ala Val Arg Thr Val Cys
            35                  40                  45

Asp Leu Val Leu Gly Lys Met Asp Lys Asp Cys Glu Met Lys Arg Thr
```

```
            50                  55                  60
Thr Leu Asp Ser Pro Leu Gly Lys Leu Glu Leu Ser Gly Cys Glu Gln
 65                  70                  75                  80

Gly Leu His Glu Ile Lys Leu Leu Gly Lys Gly Thr Ser Ala Ala Asp
                 85                  90                  95

Ala Val Glu Val Pro Ala Pro Ala Ala Val Leu Gly Gly Pro Glu Pro
                100                 105                 110

Leu Met Gln Cys Thr Ala Trp Leu Asn Ala Tyr Phe His Gln Pro Glu
                115                 120                 125

Ala Ile Glu Glu Phe Pro Val Pro Ala Leu His His Pro Val Phe Gln
                130                 135                 140

Gln Glu Ser Phe Thr Arg Gln Val Leu Trp Lys Leu Leu Lys Val Val
145                 150                 155                 160

Lys Phe Gly Glu Val Ile Ser Tyr Gln Gln Leu Ala Ala Leu Ala Gly
                165                 170                 175

Asn Pro Lys Ala Ala Arg Ala Val Gly Gly Ala Met Arg Gly Asn Pro
                180                 185                 190

Val Pro Ile Leu Ile Pro Cys His Arg Val Val Cys Ser Ser Gly Ala
                195                 200                 205

Val Gly Asn Tyr Ser Gly Gly Leu Ala Val Lys Glu Trp Leu Leu Ala
                210                 215                 220

His Glu Gly His Arg Gly Lys Pro Gly Leu Gly Gly Ser Ser Gly Leu
225                 230                 235                 240

Ala Gly Ala Trp Leu Lys Gly Ala Gly Ala Thr Ser Gly Ser Pro Pro
                245                 250                 255

Ala Gly Arg Asn Gly Gly Ser Glu Asn Leu Tyr Phe Gln Ser Asp
                260                 265                 270

Ile Arg Ser Leu Ala Gly Glu Thr Gly Gln Glu Ala Ala Pro Leu Asp
                275                 280                 285

Gly Val Leu Ala Asn Pro Pro Asn Ile Ser Ser Leu Ser Pro Arg Gln
                290                 295                 300

Leu Leu Gly Phe Pro Cys Ala Glu Val Ser Gly Leu Ser Thr Glu Arg
305                 310                 315                 320

Val Arg Glu Leu Ala Val Ala Leu Ala Gln Lys Asn Val Lys Leu Ser
                325                 330                 335

Thr Glu Gln Leu Arg Cys Leu Ala His Arg Leu Ser Glu Pro Pro Glu
                340                 345                 350

Asp Leu Asp Ala Leu Pro Phe Asp Leu Leu Leu Phe Leu Asn Pro Asp
                355                 360                 365

Ala Phe Ser Gly Pro Gln Ala Cys Thr Arg Phe Phe Ser Arg Ile Thr
                370                 375                 380

Lys Ala Asn Val Asp Leu Leu Pro Arg Gly Ala Pro Glu Arg Gln Arg
385                 390                 395                 400

Leu Leu Pro Ala Ala Leu Ala Cys Trp Gly Val Arg Gly Ser Leu Leu
                405                 410                 415

Ser Glu Ala Asp Val Arg Ala Leu Gly Gly Leu Ala Cys Asp Leu Pro
                420                 425                 430

Gly Arg Phe Val Ala Glu Ser Ala Glu Val Leu Leu Pro Arg Leu Val
                435                 440                 445

Ser Cys Pro Gly Pro Leu Asp Gln Asp Gln Gln Glu Ala Ala Arg Ala
                450                 455                 460

Ala Leu Gln Gly Gly Gly Pro Pro Tyr Gly Pro Pro Ser Thr Trp Ser
465                 470                 475                 480
```

```
Val Ser Thr Met Asp Ala Leu Arg Gly Leu Leu Pro Val Leu Gly Gln
            485                 490                 495

Pro Ile Ile Arg Ser Ile Pro Gln Gly Ile Val Ala Ala Trp Arg Gln
        500                 505                 510

Arg Ser Ser Arg Asp Pro Ser Trp Arg Gln Pro Glu Arg Thr Ile Leu
        515                 520                 525

Arg Pro Arg Pro Gly Glu Asn Leu Tyr Phe Gln Gly Pro Gly Gly Gly
    530                 535                 540

Ser His His His His His His
545                 550

<210> SEQ ID NO 88
<211> LENGTH: 543
<212> TYPE: DNA
<213> ORGANISM: Homo sapiens

<400> SEQUENCE: 88
gatatccagc tcttccacct acagaaggag ctggcagaac tccgagagtc taccagccag    60
atgcacacag catcatcttt ggagaagcaa ataggccacc ccagtccacc ccctgaaaaa   120
aaggagctga ggaaagtggc ccatttaaca ggcaagtcca actcaaggtc catgcctctg   180
gaatgggaag acacctatgg aattgtcctg ctttctggag tgaagtataa aagggtggc   240 cttgtgatca tgaaactggc tgtactttg tatattcca agtatacttt ccggggtcaa   300
tcttgcaaca acctgccccct gagccacaag gtctacatga ggaactctaa gtatccccag   360
gatctggtga tgatggaggg gaagatgatg agctactgca ctactgggca gatgtgggcc   420
cgcagcagct acctgggggc agtgttcaat cttaccagtg ctgatcattt atatgtcaac   480
gtatctgagc tctctctggt caattttgag aatctcaga cgttttttcgg cttatataag   540 ctc                                                                 543

<210> SEQ ID NO 89
<211> LENGTH: 1250
<212> TYPE: DNA
<213> ORGANISM: Artificial Sequence
<220> FEATURE:
<223> OTHER INFORMATION: DNA sequence of ssBiP-SNAP-proTEV site-sFasL

<400> SEQUENCE: 89
atgaagttat gcatattact ggccgtcgtg gcctttgttg gcctctcgct cgggagatct    60
gacaaagact gcgaaatgaa gcgcaccacc ctggatagcc ctctgggcaa gctggaactg   120
tctgggtgcg aacagggcct gcacgagatc aagctgctgg caaaggaac atctgccgcc   180 gacgccgtgg aagtgcctgc ccagccgcc gtgctgggcg accagagcc actgatgcag   240 gccaccgcct ggctcaacgc ctactttcac cagcctgagg ccatcgagga gttccctgtg   300
ccagccctgc accccagt gttccagcag gagagcttta cccgccaggt gctgtggaaa   360
ctgctgaaag tggtgaagtt cggagaggtc atcagctacc agcagctggc cgccctggcc   420
ggcaatcccg ccgccaccgc cgccgtgaaa accgccctga cggaaatcc cgtgcccatt   480 ctgatcccct gccaccgggt ggtgtctagc tctggcgccg tgggggggcta cgagggcggg   540 ctcgccgtga agagtggct gctggcccac gagggccaca actgggcaa gcctgggctg   600 ggtcctgcag gtataggcgc gccagggtcc ctaggtggcg gatctgaaaa cctctacttc   660
cagagtgata tccagctctt ccacctacag aaggagctgg cagaactccg agagtctacc   720
agccagatgc acacagcatc atctttggag aagcaaatag gccacccag tccacccct   780
```

```
gaaaaaaagg agctgaggaa agtggcccat ttaacaggca agtccaactc aaggtccatg    840
cctctggaat gggaagacac ctatggaatt gtcctgcttt ctggagtgaa gtataagaag    900
ggtggccttg tgatcaatga aactgggctg tactttgtat attccaaagt atacttccgg    960
ggtcaatctt gcaacaacct gcccctgagc cacaaggtct acatgaggaa ctctaagtat   1020
ccccaggatc tggtgatgat ggaggggaag atgatgagct actgcactac tgggcagatg   1080
tgggcccgca gcagctacct gggggcagtg ttcaatctta ccagtgctga tcatttatat   1140
gtcaacgtat ctgagctctc tctggtcaat tttgaggaat ctcagacgtt tttcggctta   1200
tataagctcc cgggcggtgg aagtcatcat catcatcatc attgaccggt              1250
```

<210> SEQ ID NO 90
<211> LENGTH: 414
<212> TYPE: PRT
<213> ORGANISM: Artificial Sequence
<220> FEATURE:
<223> OTHER INFORMATION: Amino acid sequence of ssBiP-SNAP-proTEV site-sFasL

<400> SEQUENCE: 90

```
Met Lys Leu Cys Ile Leu Leu Ala Val Val Ala Phe Val Gly Leu Ser
1               5                   10                  15

Leu Gly Arg Ser Asp Lys Asp Cys Glu Met Lys Arg Thr Thr Leu Asp
            20                  25                  30

Ser Pro Leu Gly Lys Leu Glu Leu Ser Gly Cys Glu Gln Gly Leu His
        35                  40                  45

Glu Ile Lys Leu Leu Gly Lys Gly Thr Ser Ala Ala Asp Ala Val Glu
    50                  55                  60

Val Pro Ala Pro Ala Ala Val Leu Gly Gly Pro Glu Pro Leu Met Gln
65                  70                  75                  80

Ala Thr Ala Trp Leu Asn Ala Tyr Phe His Gln Pro Glu Ala Ile Glu
                85                  90                  95

Glu Phe Pro Val Pro Ala Leu His His Pro Val Phe Gln Gln Glu Ser
            100                 105                 110

Phe Thr Arg Gln Val Leu Trp Lys Leu Leu Lys Val Val Lys Phe Gly
        115                 120                 125

Glu Val Ile Ser Tyr Gln Gln Leu Ala Ala Leu Ala Gly Asn Pro Ala
    130                 135                 140

Ala Thr Ala Ala Val Lys Thr Ala Leu Ser Gly Asn Pro Val Pro Ile
145                 150                 155                 160

Leu Ile Pro Cys His Arg Val Val Ser Ser Gly Ala Val Gly Gly
                165                 170                 175

Tyr Glu Gly Gly Leu Ala Val Lys Glu Trp Leu Leu Ala His Glu Gly
            180                 185                 190

His Arg Leu Gly Lys Pro Gly Leu Gly Pro Ala Gly Ile Gly Ala Pro
        195                 200                 205

Gly Ser Leu Gly Gly Gly Ser Glu Asn Leu Tyr Phe Gln Ser Asp Ile
    210                 215                 220

Gln Leu Phe His Leu Gln Lys Glu Leu Ala Glu Leu Arg Glu Ser Thr
225                 230                 235                 240

Ser Gln Met His Thr Ala Ser Ser Leu Glu Lys Gln Ile Gly His Pro
                245                 250                 255

Ser Pro Pro Pro Glu Lys Lys Glu Leu Arg Lys Val Ala His Leu Thr
            260                 265                 270
```

```
Gly Lys Ser Asn Ser Arg Ser Met Pro Leu Glu Trp Glu Asp Thr Tyr
            275                 280                 285
Gly Ile Val Leu Leu Ser Gly Val Lys Tyr Lys Gly Gly Leu Val
        290                 295                 300
Ile Asn Glu Thr Gly Leu Tyr Phe Val Tyr Ser Lys Val Tyr Phe Arg
305                 310                 315                 320
Gly Gln Ser Cys Asn Asn Leu Pro Leu Ser His Lys Val Tyr Met Arg
                325                 330                 335
Asn Ser Lys Tyr Pro Gln Asp Leu Val Met Met Glu Gly Lys Met Met
            340                 345                 350
Ser Tyr Cys Thr Thr Gly Gln Met Trp Ala Arg Ser Ser Tyr Leu Gly
        355                 360                 365
Ala Val Phe Asn Leu Thr Ser Ala Asp His Leu Tyr Val Asn Val Ser
        370                 375                 380
Glu Leu Ser Leu Val Asn Phe Glu Glu Ser Gln Thr Phe Phe Gly Leu
385                 390                 395                 400
Tyr Lys Leu Pro Gly Gly Gly Ser His His His His His
            405                 410
```

<210> SEQ ID NO 91
<211> LENGTH: 2976
<212> TYPE: DNA
<213> ORGANISM: Homo sapiens
<220> FEATURE:
<221> NAME/KEY: misc_feature
<223> OTHER INFORMATION: CNTN4 sequence from amino acid 19 to 990

<400> SEQUENCE: 91

```
agatctatga ggttgccatg ggaactgctg gtactgcaat cattcatttt gtgccttgca      60
gatgattcca cactgcatgg cccgattttt attcaagaac caagtcctgt aatgttccct     120
ttggattctg aggagaaaaa agtgaagctc aattgtgaag ttaaaggaaa tccaaaacct     180
catatcaggt ggaagttaaa tggaacagat gttgacactg gtatggattt ccgctacagt     240
gttgttgaag ggagcttgtt gatcaataac cccaataaaa cccaagatgc tggaacgtac     300
cagtgcacag cgacaaactc gtttggaaca attgttagca gagaagcaaa gctgcagttt     360
gcttatcttg acaactttaa aacaagaaca agaagcactg tgtctgtccg tcgaggtcaa     420
ggaatggtgc tactgtgtgg cccgccaccc cattctggag agctgagtta tgcctggatc     480
ttcaatgaat accttcctta tcaggataat cgccgctttg tttctcaaga gactgggaat     540
ctgtatattg ccaaagtaga aaatcagatg gttgggaatt atacctgtgt ggttaccaat     600
accgtgacaa accacaaggt cctggggcca cctacaccac taatattgag aaatgatgga     660
gtgatgggtg aatatgagcc caaaatagaa gtgcagttcc cagaaacagt tccgactgca     720
aaaggagcaa cggtgaagct ggaatgcttt gctttaggaa atccagtacc aactattatc     780
tggcgaagag ctgatggaaa gccaatagca aggaaagcca gaagcacaa gtcaaatgga     840
attcttgaga tccctaattt tcagcaggag gatgctggtt tatatgaatg tgtagctgaa     900
aattccagag ggaaaaatgt agcaagggga cagctaactt tctatgctca acctaattgg     960
attcaaaaaa taaatgatat tcacgtggcc atggaagaaa atgtcttttg ggaatgtaaa    1020
gcaaatggaa ggcctaagcc tacatacaag tggctaaaaa atgcgaacc tctgctaact    1080
cgggatagaa ttcaaattga gcaaggaaca ctcaacataa caatagtgaa cctctcagat    1140
gctggcatgt atcagtgttt ggcagagaat aaacatggag ttatctttcc aacgcagag    1200
cttagtgtta tagctgtagg tccagatttt tcaagaacac tcttgaaaag agtaactctt    1260
```

| | |
|---|---|
| gtcaaagtgg gaggtgaagt tgtcattgag tgtaagccaa aagcgtctcc aaaacctgtt | 1320 |
| tacacctgga agaaaggaag ggatatatta aagaaaatg aaagaattac catttctgaa | 1380 |
| gatggaaacc tcagaatcat caacgttact aaatcagacg ctgggagtta tacctgtata | 1440 |
| gccactaacc attttggaac tgctagcagt actggaaact tggtagtgaa agatccaaca | 1500 |
| agggtaatgg tacccccttc cagtatggat gtcactgttg agagagtat tgttttaccg | 1560 |
| tgccaggtaa cgcatgatca ctcgctagac atcgtgttta cttggtcatt taatggacac | 1620 |
| ctgatagact ttgacagaga tggggaccac tttgaaagag ttggagggca ggattcagct | 1680 |
| ggtgatttga tgatccgaaa catccaactg aagcatgctg gaaatatgt ctgcatggtc | 1740 |
| caaacaagtg tggacaggct atctgctgct gcagacctga ttgtaagagg tcctccaggt | 1800 |
| cccccagagg ctgtgacaat agacgaaatc acagatacca ctgctcagct ctcctggaga | 1860 |
| cccggtcctg acaaccacag ccccatcacc atgtatgtca ttcaagccag gactccattc | 1920 |
| tccgtgggct ggcaagcagt cagtacagtc ccagaactca ttgatgggaa gacattcaca | 1980 |
| gcgaccgtgg tgggtttgaa cccttgggtt gaatatgaat tccgcacagt tgcagccaac | 2040 |
| gtgattggga ttggggagcc cagccgcccc tcagagaaac ggagaacaga agaagctctc | 2100 |
| cccgaagtca caccagcgaa tgtcagtggt ggcggaggca gcaaatctga actggttata | 2160 |
| acctgggaga cggtccctga ggaattacag aatggtcgag ctttggtta tgtggtggcc | 2220 |
| ttccggccct acggtaaaat gatctggatg ctgacagtgc tggcctcagc tgatgcctct | 2280 |
| agatacgtgt tcaggaatga gagcgtgcac cccttctctc cctttgaggt taaagtaggt | 2340 |
| gtcttcaaca acaaaggaga aggcccttc agtcccacca cggtggtgta ttctgcagaa | 2400 |
| gaagaaccca ccaaaccacc agccagtatc tttgccagaa gtctttctgc cacagatatt | 2460 |
| gaagttttct gggcctcccc actggagaag aatagaggac gaatacaagg ttatgaggtt | 2520 |
| aaatattgga gacatgaaga caaagaagaa aatgctagaa aaatacgaac agttggaaat | 2580 |
| cagacatcaa caaaaatcac gaacttaaaa ggcagtgtgc tgtatcactt agctgtcaag | 2640 |
| gcatataatt ctgctgggac aggcccctct agtgcaacag tcaatgtgac aacccgaaag | 2700 |
| ccaccaccaa gtcaaccccc cggaaacatc atatggaatt catcagactc caaaattatc | 2760 |
| ctgaattggg atcaagtgaa ggccctggat aatgagtcgg aagtaaaagg atacaaagtc | 2820 |
| ttgtacagat ggaacagaca aagcagcaca tctgtcattg aaacaaataa acatcggtg | 2880 |
| gagctttctt tgcctttcga tgaagattat ataatagaaa ttaagccatt cagcgacgga | 2940 |
| ggagatggca gcagcagtga acaaattcga attccc | 2976 |

<210> SEQ ID NO 92
<211> LENGTH: 3688
<212> TYPE: DNA
<213> ORGANISM: Artificial Sequence
<220> FEATURE:
<223> OTHER INFORMATION: DNA sequence of BiP-CNTN419-990-SNAP-ProTEV-
      HisTag

<400> SEQUENCE: 92

| | |
|---|---|
| atgaagttat gcatattact ggccgtcgtg gcctttgttg cctctcgct cgggagatct | 60 |
| atgaggttgc catgggaact gctggtactg caatcattca ttttgtgcct tgcagatgat | 120 |
| tccacactgc atggcccgat ttttattcaa gaaccaagtc ctgtaatgtt ccctttggat | 180 |
| tctgaggaga aaaagtgaa gctcaattgt gaagttaaag aaatccaaa acctcatatc | 240 |
| aggtggaagt taaatggaac agatgttgac actggtatgg atttccgcta cagtgttgtt | 300 |

```
gaagggagct tgttgatcaa taaccccaat aaaacccaag atgctggaac gtaccagtgc    360
acagcgacaa actcgtttgg aacaattgtt agcagagaag caaagctgca gtttgcttat    420
cttgacaact ttaaaacaag aacaagaagc actgtgtctg tccgtcgagg tcaaggaatg    480
gtgctactgt gtggcccgcc accccattct ggagagctga gttatgcctg gatcttcaat    540
gaataccctt cctatcagga taatcgccgc tttgtttctc aagagactgg gaatctgtat    600
attgccaaag tagaaaaatc agatgttggg aattatacct gtgtggttac caataccgtg    660
acaaaccaca aggtcctggg gccacctaca ccactaatat tgagaaatga tggagtgatg    720
ggtgaatatg agcccaaaat agaagtgcag ttcccagaaa cagttccgac tgcaaaagga    780
gcaacggtga agctggaatg ctttgcttta ggaaatccag taccaactat tatctggcga    840
agagctgatg gaaagccaat agcaaggaaa gccagaagac acaagtcaaa tggaattctt    900
gagatcccta attttcagca ggaggatgct ggtttatatg aatgtgtagc tgaaaattcc    960
agagggaaaa atgtagcaag gggacagcta actttctatg ctcaacctaa ttggattcaa    1020
aaaataaatg atattcacgt ggccatggaa gaaaatgtct tttgggaatg taaagcaaat    1080
ggaaggccta agcctacata caagtggcta aaaaatggcg aacctctgct aactcgggat    1140
agaattcaaa ttgagcaagg aacactcaac ataacaatag tgaacctctc agatgctggc    1200
atgtatcagt gtttggcaga gaataaacat ggagttatct tttccaacgc agagcttagt    1260
gttatagctg taggtccaga ttttttcaaga acactcttga aaagagtaac tcttgtcaaa    1320
gtgggaggtg aagttgtcat tgagtgtaag ccaaaagcgt ctccaaaacc tgtttacacc    1380
tggaagaaag aagggatat attaaaagaa aatgaaagaa ttaccatttc tgaagatgga    1440
aacctcagaa tcatcaacgt tactaaatca gacgctggga gttatacctg tatagccact    1500
aaccattttg gaactgctag cagtactgga aacttggtag tgaaagatcc aacaagggta    1560
atggtacccc cttccagtat ggatgtcact gttggagaga gtattgtttt accgtgccag    1620
gtaacgcatg atcactcgct agacatcgtg tttacttggt catttaatgg acacctgata    1680
gactttgaca gagatgggga ccactttgaa agagttggag gcaggattc agctggtgat    1740
ttgatgatcc gaaacatcca actgaagcat gctgggaaat atgtctgcat ggtccaaaca    1800
agtgtggaca ggctatctgc tgctgcagac ctgattgtaa gaggtcctcc aggtccccca    1860
gaggctgtga caatagacga aatcacagat accactgctc agctctcctg gagacccggt    1920
cctgacaacc acagccccat caccatgtat gtcattcaag ccaggactcc attctccgtg    1980
ggctggcaag cagtcagtac agtcccagaa ctcattgatg gaagacattc acagcgacc    2040
gtggtgggtt tgaacccttg ggttgaatat gaattccgca cagttgcagc caacgtgatt    2100
gggattgggg agcccagccg cccctcagag aaacggagaa cagaagaagc tctccccgaa    2160
gtcacaccag cgaatgtcag tggtggcgga ggcagcaaat ctgaactggt tataacctgg    2220
gagacggtcc ctgaggaatt acagaatggt cgaggctttg gttatgtggt ggccttccgg    2280
ccctacggta aaatgatctg gatgctgaca gtgctggcct cagctgatgc ctctagatac    2340
gtgttcagga atgagagcgt gcaccccttc tctcccctttg aggttaaagt aggtgtcttc    2400
aacaacaaag gagaaggccc tttcagtccc accacggtgg tgtattctgc agaagaagaa    2460
cccaccaaac caccagccag tatctttgcc agaagtcttt ctgccacaga tattgaagtt    2520
ttctgggcct ccccactgga gaagaataga ggacgaatac aaggttatga ggttaaatat    2580
tggagacatg aagacaaaga agaaaatgct agaaaaatac gaacagttgg aaatcagaca    2640
```

-continued

```
tcaacaaaaa tcacgaactt aaaaggcagt gtgctgtatc acttagctgt caaggcatat    2700
aattctgctg ggacaggccc ctctagtgca acagtcaatg tgacaacccg aaagccacca    2760
ccaagtcaac cccccggaaa catcatatgg aattcatcag actccaaaat tatcctgaat    2820
tgggatcaag tgaaggccct ggataatgag tcggaagtaa aaggatacaa agtcttgtac    2880
agatggaaca gacaaagcag cacatctgtc attgaaacaa ataaaacatc ggtggagctt    2940
tctttgcctt tcgatgaaga ttatataata gaaattaagc cattcagcga cggaggagat    3000
ggcagcagca gtgaacaaat tcgaattccc gggggaggta gcaaagactg cgaaatgaag    3060
cgcaccaccc tggatagccc tctgggcaag ctggaactgt ctgggtgcga acagggcctg    3120
cacgagatca agctgctggg caaggaaca tctgccgccg acgccgtgga agtgcctgcc    3180
ccagccgccg tgctgggcgg accagagcca ctgatgcagg ccaccgcctg gctcaacgcc    3240
tactttcacc agcctgaggc catcgaggag ttccctgtgc agcccctgca ccacccagtg    3300
ttccagcagg agagctttac ccgccaggtg ctgtggaaac tgctgaaagt ggtgaagttc    3360
ggagaggtca tcagctacca gcagctggcc gccctggccg gcaatcccgc cgccaccgcc    3420
gccgtgaaaa ccgccctgag cggaaatccc gtgcccattc tgatcccctg ccaccgggtg    3480
gtgtctagct ctggcgccgt ggggggctac gagggcgggc tcgccgtgaa agagtggctg    3540
ctggcccacg agggccacag actgggcaag cctgggctgg gtcctgcagg tataggcgcg    3600
ccagggtccc tggagaatct atattttcaa agtggcggag gtagccatca tcatcatcat    3660
cattgatgac cggtaagctt gcggccgc                                        3688
```

<210> SEQ ID NO 93
<211> LENGTH: 1221
<212> TYPE: PRT
<213> ORGANISM: Artificial Sequence
<220> FEATURE:
<223> OTHER INFORMATION: Amino acid sequence of BiP-CNTN419-990-SNAP-ProTEV-HisTag

<400> SEQUENCE: 93

```
Met Lys Leu Cys Ile Leu Leu Ala Val Val Ala Phe Val Gly Leu Ser
1               5                   10                  15

Leu Gly Arg Ser Met Arg Leu Pro Trp Glu Leu Val Leu Gln Ser
            20                  25                  30

Phe Ile Leu Cys Leu Ala Asp Asp Ser Thr Leu His Gly Pro Ile Phe
        35                  40                  45

Ile Gln Glu Pro Ser Pro Val Met Phe Pro Leu Asp Ser Glu Glu Lys
    50                  55                  60

Lys Val Lys Leu Asn Cys Glu Val Lys Gly Asn Pro Lys Pro His Ile
65                  70                  75                  80

Arg Trp Lys Leu Asn Gly Thr Asp Val Asp Thr Gly Met Asp Phe Arg
                85                  90                  95

Tyr Ser Val Val Glu Gly Ser Leu Leu Ile Asn Asn Pro Asn Lys Thr
            100                 105                 110

Gln Asp Ala Gly Thr Tyr Gln Cys Thr Ala Thr Asn Ser Phe Gly Thr
        115                 120                 125

Ile Val Ser Arg Glu Ala Lys Leu Gln Phe Ala Tyr Leu Asp Asn Phe
    130                 135                 140

Lys Thr Arg Thr Arg Ser Thr Val Ser Val Arg Arg Gly Gln Gly Met
145                 150                 155                 160

Val Leu Leu Cys Gly Pro Pro His Ser Gly Glu Leu Ser Tyr Ala
                165                 170                 175
```

-continued

Trp Ile Phe Asn Glu Tyr Pro Ser Tyr Gln Asp Asn Arg Arg Phe Val
            180                 185                 190

Ser Gln Glu Thr Gly Asn Leu Tyr Ile Ala Lys Val Glu Lys Ser Asp
        195                 200                 205

Val Gly Asn Tyr Thr Cys Val Val Thr Asn Thr Val Thr Asn His Lys
    210                 215                 220

Val Leu Gly Pro Pro Thr Pro Leu Ile Leu Arg Asn Asp Gly Val Met
225                 230                 235                 240

Gly Glu Tyr Glu Pro Lys Ile Glu Val Gln Phe Pro Glu Thr Val Pro
                245                 250                 255

Thr Ala Lys Gly Ala Thr Val Lys Leu Glu Cys Phe Ala Leu Gly Asn
            260                 265                 270

Pro Val Pro Thr Ile Ile Trp Arg Arg Ala Asp Gly Lys Pro Ile Ala
        275                 280                 285

Arg Lys Ala Arg Arg His Lys Ser Asn Gly Ile Leu Glu Ile Pro Asn
    290                 295                 300

Phe Gln Gln Glu Asp Ala Gly Leu Tyr Glu Cys Val Ala Glu Asn Ser
305                 310                 315                 320

Arg Gly Lys Asn Val Ala Arg Gly Gln Leu Thr Phe Tyr Ala Gln Pro
                325                 330                 335

Asn Trp Ile Gln Lys Ile Asn Asp Ile His Val Ala Met Glu Glu Asn
            340                 345                 350

Val Phe Trp Glu Cys Lys Ala Asn Gly Arg Pro Lys Pro Thr Tyr Lys
        355                 360                 365

Trp Leu Lys Asn Gly Glu Pro Leu Leu Thr Arg Asp Arg Ile Gln Ile
    370                 375                 380

Glu Gln Gly Thr Leu Asn Ile Thr Ile Val Asn Leu Ser Asp Ala Gly
385                 390                 395                 400

Met Tyr Gln Cys Leu Ala Glu Asn Lys His Gly Val Ile Phe Ser Asn
                405                 410                 415

Ala Glu Leu Ser Val Ile Ala Val Gly Pro Asp Phe Ser Arg Thr Leu
            420                 425                 430

Leu Lys Arg Val Thr Leu Val Lys Val Gly Gly Glu Val Val Ile Glu
        435                 440                 445

Cys Lys Pro Lys Ala Ser Pro Lys Pro Val Tyr Thr Trp Lys Lys Gly
    450                 455                 460

Arg Asp Ile Leu Lys Glu Asn Glu Arg Ile Thr Ile Ser Glu Asp Gly
465                 470                 475                 480

Asn Leu Arg Ile Ile Asn Val Thr Lys Ser Asp Ala Gly Ser Tyr Thr
                485                 490                 495

Cys Ile Ala Thr Asn His Phe Gly Thr Ala Ser Ser Thr Gly Asn Leu
            500                 505                 510

Val Val Lys Asp Pro Thr Arg Val Met Val Pro Pro Ser Ser Met Asp
        515                 520                 525

Val Thr Val Gly Glu Ser Ile Val Leu Pro Cys Gln Val Thr His Asp
    530                 535                 540

His Ser Leu Asp Ile Val Phe Thr Trp Ser Phe Asn Gly His Leu Ile
545                 550                 555                 560

Asp Phe Asp Arg Asp Gly Asp His Phe Glu Arg Val Gly Gly Gln Asp
                565                 570                 575

Ser Ala Gly Asp Leu Met Ile Arg Asn Ile Gln Leu Lys His Ala Gly
            580                 585                 590

-continued

Lys Tyr Val Cys Met Val Gln Thr Ser Val Asp Arg Leu Ser Ala Ala
            595                 600                 605

Ala Asp Leu Ile Val Arg Gly Pro Gly Pro Pro Glu Ala Val Thr
    610                 615                 620

Ile Asp Glu Ile Thr Asp Thr Thr Ala Gln Leu Ser Trp Arg Pro Gly
625                 630                 635                 640

Pro Asp Asn His Ser Pro Ile Thr Met Tyr Val Ile Gln Ala Arg Thr
                645                 650                 655

Pro Phe Ser Val Gly Trp Gln Ala Val Ser Thr Val Pro Glu Leu Ile
                660                 665                 670

Asp Gly Lys Thr Phe Thr Ala Thr Val Gly Leu Asn Pro Trp Val
        675                 680                 685

Glu Tyr Glu Phe Arg Thr Val Ala Ala Asn Val Ile Gly Ile Gly Glu
    690                 695                 700

Pro Ser Arg Pro Ser Glu Lys Arg Thr Glu Ala Leu Pro Glu
705                 710                 715                 720

Val Thr Pro Ala Asn Val Ser Gly Gly Gly Ser Lys Ser Glu Leu
                725                 730                 735

Val Ile Thr Trp Glu Thr Val Pro Glu Glu Leu Gln Asn Gly Arg Gly
                740                 745                 750

Phe Gly Tyr Val Val Ala Phe Arg Pro Tyr Gly Lys Met Ile Trp Met
    755                 760                 765

Leu Thr Val Leu Ala Ser Ala Asp Ala Ser Arg Tyr Val Phe Arg Asn
    770                 775                 780

Glu Ser Val His Pro Phe Ser Pro Phe Glu Val Lys Val Gly Val Phe
785                 790                 795                 800

Asn Asn Lys Gly Glu Gly Pro Phe Ser Pro Thr Thr Val Val Tyr Ser
                805                 810                 815

Ala Glu Glu Pro Thr Lys Pro Pro Ala Ser Ile Phe Ala Arg Ser
                820                 825                 830

Leu Ser Ala Thr Asp Ile Glu Val Phe Trp Ala Ser Pro Leu Glu Lys
    835                 840                 845

Asn Arg Gly Arg Ile Gln Gly Tyr Glu Val Lys Tyr Trp Arg His Glu
    850                 855                 860

Asp Lys Glu Glu Asn Ala Arg Lys Ile Arg Thr Val Gly Asn Gln Thr
865                 870                 875                 880

Ser Thr Lys Ile Thr Asn Leu Lys Gly Ser Val Leu Tyr His Leu Ala
                885                 890                 895

Val Lys Ala Tyr Asn Ser Ala Gly Thr Gly Pro Ser Ser Ala Thr Val
    900                 905                 910

Asn Val Thr Thr Arg Lys Pro Pro Pro Ser Gln Pro Pro Gly Asn Ile
        915                 920                 925

Ile Trp Asn Ser Ser Asp Ser Lys Ile Ile Leu Asn Trp Asp Gln Val
    930                 935                 940

Lys Ala Leu Asp Asn Glu Ser Glu Val Lys Gly Tyr Lys Val Leu Tyr
945                 950                 955                 960

Arg Trp Asn Arg Gln Ser Ser Thr Ser Val Ile Glu Thr Asn Lys Thr
                965                 970                 975

Ser Val Glu Leu Ser Leu Pro Phe Asp Glu Asp Tyr Ile Ile Glu Ile
            980                 985                 990

Lys Pro Phe Ser Asp Gly Gly Asp  Gly Ser Ser Ser Glu  Gln Ile Arg
    995                 1000                 1005

Ile Pro  Gly Gly Gly Ser Lys  Asp Cys Glu Met Lys  Arg Thr Thr

```
                1010                1015                1020
Leu Asp Ser Pro Leu Gly Lys Leu Glu Leu Ser Gly Cys Glu Gln
    1025                1030                1035
Gly Leu His Glu Ile Lys Leu Leu Gly Lys Gly Thr Ser Ala Ala
    1040                1045                1050
Asp Ala Val Glu Val Pro Ala Pro Ala Ala Val Leu Gly Gly Pro
    1055                1060                1065
Glu Pro Leu Met Gln Ala Thr Ala Trp Leu Asn Ala Tyr Phe His
    1070                1075                1080
Gln Pro Glu Ala Ile Glu Glu Phe Pro Val Pro Ala Leu His His
    1085                1090                1095
Pro Val Phe Gln Gln Glu Ser Phe Thr Arg Gln Val Leu Trp Lys
    1100                1105                1110
Leu Leu Lys Val Val Lys Phe Gly Glu Val Ile Ser Tyr Gln Gln
    1115                1120                1125
Leu Ala Ala Leu Ala Gly Asn Pro Ala Ala Thr Ala Ala Val Lys
    1130                1135                1140
Thr Ala Leu Ser Gly Asn Pro Val Pro Ile Leu Ile Pro Cys His
    1145                1150                1155
Arg Val Val Ser Ser Ser Gly Ala Val Gly Gly Tyr Glu Gly Gly
    1160                1165                1170
Leu Ala Val Lys Glu Trp Leu Leu Ala His Glu Gly His Arg Leu
    1175                1180                1185
Gly Lys Pro Gly Leu Gly Pro Ala Gly Ile Gly Ala Pro Gly Ser
    1190                1195                1200
Leu Glu Asn Leu Tyr Phe Gln Ser Gly Gly Gly Ser His His His
    1205                1210                1215
His His His
    1220

<210> SEQ ID NO 94
<211> LENGTH: 2538
<212> TYPE: DNA
<213> ORGANISM: Homo sapiens

<400> SEQUENCE: 94
ttcctgtcgc accaccgcct gaaaggcagg tttcagaggg accgcaggaa catccgcccc      60
aacatcatcc tggtgctgac ggacgaccag gatgtggagc tgggttccat gcaggtgatg     120
aacaagaccc ggcgcatcat ggagcagggc ggggcgcact tcatcaacgc cttcgtgacc     180
acacccatgt gctgcccctc acgctcctcc atcctcactg gcaagtacgt ccacaaccac     240
aacacctaca ccaacaatga gaactgctcc tcgccctcct ggcaggcaca gcacgagagc     300
cgcacctttg ccgtgtacct caatagcact ggctaccgga cagctttctt cgggaagtat     360
cttaatgaat acaacggctc ctacgtgcca cccggctgga aggagtgggt cggactcctt     420
aaaaactccc gcttttataa ctacacgctg tgtcggaacg gggtgaaaga gaagcacggc     480
tccgactact ccaaggatta cctcacagac ctcatcacca tgacagcgt gagcttcttc     540 cgcacgtcca agaagatgta cccgcacagg ccagtcctca tggtcatcag ccatgcagcc     600
ccccacggcc ctgaggattc agccccacaa tattcacgcc tcttcccaaa cgcatctcag     660
cacatcacgc cgagctacaa ctacgcgccc aacccggaca acactggat catgcgctac     720 acggggccca tgaagcccat ccacatggaa ttcaccaaca tgctccagcg gaagcgcttg     780 cagacccctca tgtcggtgga cgactccatg gagacgattt acaacatgct ggttgagacg     840
```

```
ggcgagctgg acaacacgta catcgtatac accgccgacc acggttacca catcggccag    900
tttggcctgg tgaaagggaa atccatgcca tatgagtttg acatcagggt cccgttctac    960
gtgaggggcc ccaacgtgga agccggctgt ctgaatcccc acatcgtcct caacattgac   1020
ctggccccca ccatcctgga cattgcaggc ctggacatac ctgcggatat ggacgggaaa   1080
tccatcctca agctgctgga cacggagcgg ccggtgaatc ggtttcactt gaaaaagaag   1140
atgagggtct ggcgggactc cttcttggtg gagagaggca agctgctaca agagagac    1200
aatgacaagg tggacgccca ggaggagaac tttctgccca gtaccagcg tgtgaaggac   1260
ctgtgtcagc gtgctgagta ccagacgcg tgtgagcagc tgggacagaa gtggcagtgt   1320
gtggaggacg ccacggggaa gctgaagctg cataagtgca agggcccat gcggctgggc   1380
ggcagcagag ccctctccaa cctcgtgccc aagtactacg gcagggcag cgaggcctgc   1440
acctgtgaca gcggggacta caagctcagc ctggccggac gccggaaaaa actcttcaag   1500
aagaagtaca aggccagcta tgtccgcagt cgctccatcc gctcagtggc catcgaggtg   1560
gacggcaggg tgtaccacgt aggcctgggt gatgccgccc agccccgaaa cctcaccaag   1620
cggcactggc caggggcccc tgaggaccaa gatgacaagg atggtgggga cttcagtggc   1680
actggaggcc ttcccgacta ctcagccgcc aaccccatta agtgacaca tcggtgctac   1740
atcctagaga cgacacagt ccagtgtgac ctggacctgt acaagtccct gcaggcctgg   1800
aaagaccaca agctgcacat cgaccacgag attgaaaccc tgcagaacaa aattaagaac   1860
ctgagggaag tccgaggtca cctgaagaaa agcggccag aagaatgtga ctgtcacaaa   1920
atcagctacc acacccagca caaggccgc ctcaagcaca gaggctccag tctgcatcct   1980
ttcaggaagg gcctgcaaga aaggacaag gtgtggctgt tgcgggagca gaagcgcaag   2040
aagaaactcc gcaagctgct caagcgcctg cagaacaacg acacgtgcag catgccaggc   2100
ctcacgtgct tcacccacga caaccagcac tggcagacgg cgcctttctg gacactgggg   2160
cctttctgtg cctgcaccag cgccaacaat aacacgtact ggtgcatgag gaccatcaat   2220
gagactcaca atttcctctt ctgtgaattt gcaactggct tcctagagta ctttgatctc   2280
aacacagacc cctaccagct gatgaatgca gtgaacacac tggacaggga tgtcctcaac   2340
cagctacacg tacagctcat ggagctgagg agctgcaagg ttacaagca gtgtaacccc   2400
cggactcgaa acatggacct gggacttaaa gatggaggaa gctatgagca atacaggcag   2460
tttcagcgtc gaaagtggcc agaaatgaag agaccttctt ccaaatcact gggacaactg   2520
tgggaaggct gggaaggc                                                  2538
```

<210> SEQ ID NO 95
<211> LENGTH: 879
<212> TYPE: PRT
<213> ORGANISM: Homo sapiens

<400> SEQUENCE: 95

```
Gly His Arg Leu Gly Lys Pro Gly Leu Gly Pro Ala Gly Ile Gly Ala
1               5                   10                  15

Pro Gly Ser Leu Gly Gly Gly Ser Glu Asn Leu Tyr Phe Gln Ser Asp
            20                  25                  30

Ile Phe Leu Ser His His Arg Leu Lys Gly Arg Phe Gln Arg Asp Arg
        35                  40                  45

Arg Asn Ile Arg Pro Asn Ile Ile Leu Val Leu Thr Asp Asp Gln Asp
    50                  55                  60
```

```
Val Glu Leu Gly Ser Met Gln Val Met Asn Lys Thr Arg Arg Ile Met
 65                  70                  75                  80

Glu Gln Gly Gly Ala His Phe Ile Asn Ala Phe Val Thr Thr Pro Met
                 85                  90                  95

Cys Cys Pro Ser Arg Ser Ser Ile Leu Thr Gly Lys Tyr Val His Asn
            100                 105                 110

His Asn Thr Tyr Thr Asn Asn Glu Asn Cys Ser Ser Pro Ser Trp Gln
        115                 120                 125

Ala Gln His Glu Ser Arg Thr Phe Ala Val Tyr Leu Asn Ser Thr Gly
    130                 135                 140

Tyr Arg Thr Ala Phe Phe Gly Lys Tyr Leu Asn Glu Tyr Asn Gly Ser
145                 150                 155                 160

Tyr Val Pro Pro Gly Trp Lys Glu Trp Val Gly Leu Leu Lys Asn Ser
                165                 170                 175

Arg Phe Tyr Asn Tyr Thr Leu Cys Arg Asn Gly Val Lys Glu Lys His
            180                 185                 190

Gly Ser Asp Tyr Ser Lys Asp Tyr Leu Thr Asp Leu Ile Thr Asn Asp
        195                 200                 205

Ser Val Ser Phe Phe Arg Thr Ser Lys Lys Met Tyr Pro His Arg Pro
210                 215                 220

Val Leu Met Val Ile Ser His Ala Ala Pro His Gly Pro Glu Asp Ser
225                 230                 235                 240

Ala Pro Gln Tyr Ser Arg Leu Phe Pro Asn Ala Ser Gln His Ile Thr
                245                 250                 255

Pro Ser Tyr Asn Tyr Ala Pro Asn Pro Asp Lys His Trp Ile Met Arg
            260                 265                 270

Tyr Thr Gly Pro Met Lys Pro Ile His Met Glu Phe Thr Asn Met Leu
        275                 280                 285

Gln Arg Lys Arg Leu Gln Thr Leu Met Ser Val Asp Asp Ser Met Glu
    290                 295                 300

Thr Ile Tyr Asn Met Leu Val Glu Thr Gly Glu Leu Asp Asn Thr Tyr
305                 310                 315                 320

Ile Val Tyr Thr Ala Asp His Gly Tyr His Ile Gly Gln Phe Gly Leu
                325                 330                 335

Val Lys Gly Lys Ser Met Pro Tyr Glu Phe Asp Ile Arg Val Pro Phe
            340                 345                 350

Tyr Val Arg Gly Pro Asn Val Glu Ala Gly Cys Leu Asn Pro His Ile
        355                 360                 365

Val Leu Asn Ile Asp Leu Ala Pro Thr Ile Leu Asp Ile Ala Gly Leu
    370                 375                 380

Asp Ile Pro Ala Asp Met Asp Gly Lys Ser Ile Leu Lys Leu Leu Asp
385                 390                 395                 400

Thr Glu Arg Pro Val Asn Arg Phe His Leu Lys Lys Met Arg Val
                405                 410                 415

Trp Arg Asp Ser Phe Leu Val Arg Gly Lys Leu Leu His Lys Arg
            420                 425                 430

Asp Asn Asp Lys Val Asp Ala Gln Glu Glu Asn Phe Leu Pro Lys Tyr
        435                 440                 445

Gln Arg Val Lys Asp Leu Cys Gln Arg Ala Glu Tyr Gln Thr Ala Cys
    450                 455                 460

Glu Gln Leu Gly Gln Lys Trp Gln Cys Val Glu Asp Ala Thr Gly Lys
465                 470                 475                 480

Leu Lys Leu His Lys Cys Lys Gly Pro Met Arg Leu Gly Gly Ser Arg
```

```
                     485                 490                 495
Ala Leu Ser Asn Leu Val Pro Lys Tyr Tyr Gly Gln Gly Ser Glu Ala
                500                 505                 510

Cys Thr Cys Asp Ser Gly Asp Tyr Lys Leu Ser Leu Ala Gly Arg Arg
            515                 520                 525

Lys Lys Leu Phe Lys Lys Tyr Lys Ala Ser Tyr Val Arg Ser Arg
        530                 535                 540

Ser Ile Arg Ser Val Ala Ile Glu Val Asp Gly Arg Val Tyr His Val
545                 550                 555                 560

Gly Leu Gly Asp Ala Ala Gln Pro Arg Asn Leu Thr Lys Arg His Trp
                565                 570                 575

Pro Gly Ala Pro Glu Asp Gln Asp Asp Lys Asp Gly Gly Asp Phe Ser
            580                 585                 590

Gly Thr Gly Gly Leu Pro Asp Tyr Ser Ala Ala Asn Pro Ile Lys Val
        595                 600                 605

Thr His Arg Cys Tyr Ile Leu Glu Asn Asp Thr Val Gln Cys Asp Leu
            610                 615                 620

Asp Leu Tyr Lys Ser Leu Gln Ala Trp Lys Asp His Lys Leu His Ile
625                 630                 635                 640

Asp His Glu Ile Glu Thr Leu Gln Asn Lys Ile Lys Asn Leu Arg Glu
                645                 650                 655

Val Arg Gly His Leu Lys Lys Arg Pro Glu Glu Cys Asp Cys His
            660                 665                 670

Lys Ile Ser Tyr His Thr Gln His Lys Gly Arg Leu Lys His Arg Gly
        675                 680                 685

Ser Ser Leu His Pro Phe Arg Lys Gly Leu Gln Glu Lys Asp Lys Val
    690                 695                 700

Trp Leu Leu Arg Glu Gln Lys Arg Lys Lys Leu Arg Lys Leu Leu
705                 710                 715                 720

Lys Arg Leu Gln Asn Asn Asp Thr Cys Ser Met Pro Gly Leu Thr Cys
                725                 730                 735

Phe Thr His Asp Asn Gln His Trp Gln Thr Ala Pro Phe Trp Thr Leu
            740                 745                 750

Gly Pro Phe Cys Ala Cys Thr Ser Ala Asn Asn Thr Tyr Trp Cys
        755                 760                 765

Met Arg Thr Ile Asn Glu Thr His Asn Phe Leu Phe Cys Glu Phe Ala
    770                 775                 780

Thr Gly Phe Leu Glu Tyr Phe Asp Leu Asn Thr Asp Pro Tyr Gln Leu
785                 790                 795                 800

Met Asn Ala Val Asn Thr Leu Asp Arg Asp Val Leu Asn Gln Leu His
                805                 810                 815

Val Gln Leu Met Glu Leu Arg Ser Cys Lys Gly Tyr Lys Gln Cys Asn
            820                 825                 830

Pro Arg Thr Arg Asn Met Asp Leu Gly Leu Lys Asp Gly Ser Tyr
        835                 840                 845

Glu Gln Tyr Arg Gln Phe Gln Arg Arg Lys Trp Pro Glu Met Lys Arg
    850                 855                 860

Pro Ser Ser Lys Ser Leu Gly Gln Leu Trp Glu Gly Trp Glu Gly
865                 870                 875

<210> SEQ ID NO 96
<211> LENGTH: 3322
<212> TYPE: DNA
<213> ORGANISM: Artificial Sequence
```

<220> FEATURE:
<223> OTHER INFORMATION: DNA sequence of BiPLikeSNAP-hSULF2

<400> SEQUENCE: 96

```
tcgcgagcta gcaccatgaa actatgtatt ctacttgcag ttgttgcgtt cgtaggattg      60
tccttaccta cagctctggc aagatctgac aaagactgcg aaatgaaaag aactacattg     120
gattcaccac ttgggaagtt ggaactgagt ggatgcgagc aaggattgca tgaaattaag     180
ctactgggaa aaggaacttc tgctgctgat gcagttgaag ttccagcacc agcagctgtt     240
cttggaggtc ctgagcccct catgcaagcc acagcctggc ttaacgcata tttccaccag     300
cctgaggcca ttgaggaatt ccagtcccc gcccttcacc atcctgtgtt tcagcaggag     360
agcttcaccc gccaggtcct gtggaaattg ctgaaggtgg tcaagtttgg tgaagtgatt     420
tcatatcagc aacttgctgc attggccggt aaccccgcag ctacagctgc cgtgaaaact     480
gctctcagcg gaaatcctgt gcccatcctg atcccttgtc acagagtcgt ttcatcttcc     540
ggagctgtag gtggctatga aggaggactg gcagttaagg agtggctgct ggctcatgaa     600
ggtcatagac ttggaaagcc tgggctgggt cctgctggta taggcgcgcc agggtcccta     660
ggtggcggat ccgaaaaacct gtacttccag agcgatatct tcctgtcgca ccaccgcctg     720
aaaggcaggt ttcagaggga ccgcaggaac atccgcccca acatcatcct ggtgctgacg     780
gacgaccagg atgtggagct gggttccatg caggtgatga acaagacccg gcgcatcatg     840
gagcagggcg gggcgcactt catcaacgcc ttcgtgacca cacccatgtg ctgcccctca     900
cgctcctcca tcctcactgg caagtacgtc cacaaccaca cacctacac caacaatgag     960
aactgctcct cgccctcctg gcaggcacag cacgagagcc gcacctttgc cgtgtacctc    1020
aatagcactg gctaccggac agcttttcttc gggaagtatc ttaatgaata caacggctcc    1080
tacgtgccac ccggctggaa ggagtgggtc ggactcctta aaaactcccg cttttataac    1140
tacacgctgt gtcggaacgg ggtgaaagag aagcacggct ccgactactc caaggattac    1200
ctcacagacc tcatcaccaa tgacagcgtg agcttcttcc gcacgtccaa gaagatgtac    1260
ccgcacaggc cagtcctcat ggtcatcagc catgcagccc ccacggccc tgaggattca    1320
gccccacaat attcacgcct cttcccaaac gcatctcagc acatcacgcc gagctacaac    1380
tacgcgccca acccggacaa acactggatc atgcgctaca cgggccccat gaagcccatc    1440
cacatggaat tcaccaacat gctccagcgg aagcgcttgc agaccctcat gtcggtggac    1500
gactccatgg agacgattta caacatgctg gttgagacgg gcgagctgga caacacgtac    1560
atcgtataca ccgccgacca cggttaccac atcggccagt ttggcctggt gaaagggaaa    1620
tccatgccat atgagtttga catcagggtc ccgttctacg tgaggggccc caacgtggaa    1680
gccggctgtc tgaatcccca catcgtcctc aacattgacc tggcccccac catcctggac    1740
attgcaggcc tggacatacc tgcggatatg gacgggaaat ccatcctcaa gctgctggac    1800
acggagcggc cggtgaatcg gtttcacttg aaaaagaaga tgagggtctg gcgggactcc    1860
ttcttggtgg agagaggcaa gctgctacac aagagagaca atgacaaggt ggacgcccag    1920
gaggagaact ttctgcccca agtaccagcg tgtgaaggacc tgtgtcagcg tgctgagtac    1980
cagacggcgt gtgagcagct gggacagaag tggcagtgtg tggaggacgc cacggggaag    2040
ctgaagctgc ataagtgcaa gggccccatg cggctgggcg gcagcagagc cctctccaac    2100
ctcgtgccca gtactacgg gcagggcagc gaggcctgca cctgtgacag cggggactac    2160
aagctcagcc tggccggacg ccggaaaaaa ctcttcaaga agaagtacaa ggccagctat    2220
```

```
gtccgcagtc gctccatccg ctcagtggcc atcgaggtgg acggcagggt gtaccacgta    2280
ggcctgggtg atgccgccca gccccgaaac ctcaccaagc ggcactggcc aggggcccct    2340
gaggaccaag atgacaagga tggtggggac ttcagtggca ctggaggcct tcccgactac    2400
tcagccgcca acccattaa agtgacacat cggtgctaca tcctagagaa cgacacagtc    2460
cagtgtgacc tggacctgta caagtccctg caggcctgga agaccacaa gctgcacatc    2520 gaccacgaga ttgaaaccct gcagaacaaa attaagaacc tgagggaagt ccgaggtcac    2580
ctgaagaaaa agcggccaga agaatgtgac tgtcacaaaa tcagctacca cacccagcac    2640
aaaggccgcc tcaagcacag aggctccagt ctgcatcctt tcaggaaggg cctgcaagag    2700
aaggacaagg tgtggctgtt gcgggagcag aagcgcaaga agaaactccg caagctgctc    2760
aagcgcctgc agaacaacga cacgtgcagc atgccaggcc tcacgtgctt cacccacgac    2820
aaccagcact ggcagacggc gcctttctgg acactggggc ctttctgtgc ctgcaccagc    2880
gccaacaata acacgtactg gtgcatgagg accatcaatg agactcacaa tttcctcttc    2940
tgtgaatttg caactggctt cctagagtac tttgatctca acacagaccc ctaccagctg    3000
atgaatgcag tgaacacact ggacagggat gtcctcaacc agctacacgt acagctcatg    3060
gagctgagga gctgcaaggg ttacaagcag tgtaaccccc ggactcgaaa catggacctg    3120
ggacttaaag atggaggaag ctatgagcaa tacaggcagt ttcagcgtcg aaagtggcca    3180
gaaatgaaga gaccttcttc caaatcactg ggacaactgt gggaaggctg ggaaggcccg    3240
ggagagaatc tatattttca agggcccggc ggaggtagtc accatcatca ccatcactaa    3300
tgaccggtgc ggccgcaagc tt                                              3322
```

<210> SEQ ID NO 97
<211> LENGTH: 1094
<212> TYPE: PRT
<213> ORGANISM: Artificial Sequence
<220> FEATURE:
<223> OTHER INFORMATION: Amino acid sequence of BiPLikeSNAP-hSULF2

<400> SEQUENCE: 97

```
Met Lys Leu Cys Ile Leu Leu Ala Val Val Ala Phe Val Gly Leu Ser
1               5                   10                  15

Leu Pro Thr Ala Leu Ala Arg Ser Asp Lys Asp Cys Glu Met Lys Arg
                20                  25                  30

Thr Thr Leu Asp Ser Pro Leu Gly Lys Leu Glu Leu Ser Gly Cys Glu
            35                  40                  45

Gln Gly Leu His Glu Ile Lys Leu Leu Gly Lys Gly Thr Ser Ala Ala
        50                  55                  60

Asp Ala Val Glu Val Pro Ala Pro Ala Ala Val Leu Gly Gly Pro Glu
65                  70                  75                  80

Pro Leu Met Gln Ala Thr Ala Trp Leu Asn Ala Tyr Phe His Gln Pro
                85                  90                  95

Glu Ala Ile Glu Glu Phe Pro Val Pro Ala Leu His His Pro Val Phe
            100                 105                 110

Gln Gln Glu Ser Phe Thr Arg Gln Val Leu Trp Lys Leu Leu Lys Val
        115                 120                 125

Val Lys Phe Gly Glu Val Ile Ser Tyr Gln Gln Leu Ala Ala Leu Ala
    130                 135                 140

Gly Asn Pro Ala Ala Thr Ala Ala Val Lys Thr Ala Leu Ser Gly Asn
145                 150                 155                 160

Pro Val Pro Ile Leu Ile Pro Cys His Arg Val Val Ser Ser Ser Gly
```

-continued

```
                165                 170                 175
Ala Val Gly Gly Tyr Glu Gly Gly Leu Ala Val Lys Glu Trp Leu Leu
                180                 185                 190

Ala His Glu Gly His Arg Leu Gly Lys Pro Gly Leu Gly Pro Ala Gly
                195                 200                 205

Ile Gly Ala Pro Gly Ser Leu Gly Gly Ser Glu Asn Leu Tyr Phe
    210                 215                 220

Gln Ser Asp Ile Phe Leu Ser His His Arg Leu Lys Gly Arg Phe Gln
225                 230                 235                 240

Arg Asp Arg Arg Asn Ile Arg Pro Asn Ile Ile Leu Val Leu Thr Asp
                245                 250                 255

Asp Gln Asp Val Glu Leu Gly Ser Met Gln Val Met Asn Lys Thr Arg
                260                 265                 270

Arg Ile Met Glu Gln Gly Gly Ala His Phe Ile Asn Ala Phe Val Thr
                275                 280                 285

Thr Pro Met Cys Cys Pro Ser Arg Ser Ser Ile Leu Thr Gly Lys Tyr
                290                 295                 300

Val His Asn His Asn Thr Tyr Thr Asn Asn Glu Asn Cys Ser Ser Pro
305                 310                 315                 320

Ser Trp Gln Ala Gln His Glu Ser Arg Thr Phe Ala Val Tyr Leu Asn
                325                 330                 335

Ser Thr Gly Tyr Arg Thr Ala Phe Phe Gly Lys Tyr Leu Asn Glu Tyr
                340                 345                 350

Asn Gly Ser Tyr Val Pro Pro Gly Trp Lys Glu Trp Val Gly Leu Leu
                355                 360                 365

Lys Asn Ser Arg Phe Tyr Asn Tyr Thr Leu Cys Arg Asn Gly Val Lys
                370                 375                 380

Glu Lys His Gly Ser Asp Tyr Ser Lys Asp Tyr Leu Thr Asp Leu Ile
385                 390                 395                 400

Thr Asn Asp Ser Val Ser Phe Phe Arg Thr Ser Lys Lys Met Tyr Pro
                405                 410                 415

His Arg Pro Val Leu Met Val Ile Ser His Ala Ala Pro His Gly Pro
                420                 425                 430

Glu Asp Ser Ala Pro Gln Tyr Ser Arg Leu Phe Pro Asn Ala Ser Gln
                435                 440                 445

His Ile Thr Pro Ser Tyr Asn Tyr Ala Pro Asn Pro Asp Lys His Trp
                450                 455                 460

Ile Met Arg Tyr Thr Gly Pro Met Lys Pro Ile His Met Glu Phe Thr
465                 470                 475                 480

Asn Met Leu Gln Arg Lys Arg Leu Gln Thr Leu Met Ser Val Asp Asp
                485                 490                 495

Ser Met Glu Thr Ile Tyr Asn Met Leu Val Glu Thr Gly Glu Leu Asp
                500                 505                 510

Asn Thr Tyr Ile Val Tyr Thr Ala Asp His Gly Tyr His Ile Gly Gln
                515                 520                 525

Phe Gly Leu Val Lys Gly Lys Ser Met Pro Tyr Glu Phe Asp Ile Arg
                530                 535                 540

Val Pro Phe Tyr Val Arg Gly Pro Asn Val Glu Ala Gly Cys Leu Asn
545                 550                 555                 560

Pro His Ile Val Leu Asn Ile Asp Leu Ala Pro Thr Ile Leu Asp Ile
                565                 570                 575

Ala Gly Leu Asp Ile Pro Ala Asp Met Asp Gly Lys Ser Ile Leu Lys
                580                 585                 590
```

-continued

```
Leu Leu Asp Thr Glu Arg Pro Val Asn Arg Phe His Leu Lys Lys Lys
            595                 600                 605
Met Arg Val Trp Arg Asp Ser Phe Leu Val Glu Arg Gly Lys Leu Leu
            610                 615                 620
His Lys Arg Asp Asn Asp Lys Val Asp Ala Gln Glu Glu Asn Phe Leu
625                 630                 635                 640
Pro Lys Tyr Gln Arg Val Lys Asp Leu Cys Gln Arg Ala Glu Tyr Gln
            645                 650                 655
Thr Ala Cys Glu Gln Leu Gly Gln Lys Trp Gln Cys Val Glu Asp Ala
            660                 665                 670
Thr Gly Lys Leu Lys Leu His Lys Cys Lys Gly Pro Met Arg Leu Gly
            675                 680                 685
Gly Ser Arg Ala Leu Ser Asn Leu Val Pro Lys Tyr Tyr Gly Gln Gly
            690                 695                 700
Ser Glu Ala Cys Thr Cys Asp Ser Gly Asp Tyr Lys Leu Ser Leu Ala
705                 710                 715                 720
Gly Arg Arg Lys Lys Leu Phe Lys Lys Lys Tyr Lys Ala Ser Tyr Val
            725                 730                 735
Arg Ser Arg Ser Ile Arg Ser Val Ala Ile Glu Val Asp Gly Arg Val
            740                 745                 750
Tyr His Val Gly Leu Gly Asp Ala Ala Gln Pro Arg Asn Leu Thr Lys
            755                 760                 765
Arg His Trp Pro Gly Ala Pro Glu Asp Gln Asp Lys Asp Gly Gly
            770                 775                 780
Asp Phe Ser Gly Thr Gly Leu Pro Asp Tyr Ser Ala Ala Asn Pro
785                 790                 795                 800
Ile Lys Val Thr His Arg Cys Tyr Ile Leu Glu Asn Asp Thr Val Gln
            805                 810                 815
Cys Asp Leu Asp Leu Tyr Lys Ser Leu Gln Ala Trp Lys Asp His Lys
            820                 825                 830
Leu His Ile Asp His Glu Ile Glu Thr Leu Gln Asn Lys Ile Lys Asn
            835                 840                 845
Leu Arg Glu Val Arg Gly His Leu Lys Lys Lys Arg Pro Glu Glu Cys
            850                 855                 860
Asp Cys His Lys Ile Ser Tyr His Thr Gln His Lys Gly Arg Leu Lys
865                 870                 875                 880
His Arg Gly Ser Ser Leu His Pro Phe Arg Lys Gly Leu Gln Glu Lys
                    885                 890                 895
Asp Lys Val Trp Leu Leu Arg Glu Gln Lys Arg Lys Lys Lys Leu Arg
            900                 905                 910
Lys Leu Leu Lys Arg Leu Gln Asn Asn Asp Thr Cys Ser Met Pro Gly
            915                 920                 925
Leu Thr Cys Phe Thr His Asp Asn Gln His Trp Gln Thr Ala Pro Phe
            930                 935                 940
Trp Thr Leu Gly Pro Phe Cys Ala Cys Thr Ser Ala Asn Asn Asn Thr
945                 950                 955                 960
Tyr Trp Cys Met Arg Thr Ile Asn Glu Thr His Asn Phe Leu Phe Cys
            965                 970                 975
Glu Phe Ala Thr Gly Phe Leu Glu Tyr Phe Asp Leu Asn Thr Asp Pro
            980                 985                 990
Tyr Gln Leu Met Asn Ala Val Asn  Thr Leu Asp Arg Asp  Val Leu Asn
            995                 1000                1005
```

-continued

```
Gln Leu His Val Gln Leu Met Glu Leu Arg Ser Cys Lys Gly Tyr
    1010            1015            1020

Lys Gln Cys Asn Pro Arg Thr Arg Asn Met Asp Leu Gly Leu Lys
    1025            1030            1035

Asp Gly Gly Ser Tyr Glu Gln Tyr Arg Gln Phe Gln Arg Arg Lys
    1040            1045            1050

Trp Pro Glu Met Lys Arg Pro Ser Ser Lys Ser Leu Gly Gln Leu
    1055            1060            1065

Trp Glu Gly Trp Glu Gly Pro Gly Glu Asn Leu Tyr Phe Gln Gly
    1070            1075            1080

Pro Gly Gly Gly Ser His His His His His His
    1085            1090
```